(12) United States Patent
Baber et al.

(10) Patent No.: US 10,881,401 B2
(45) Date of Patent: Jan. 5, 2021

(54) STAPLE FIRING MEMBER COMPRISING A MISSING CARTRIDGE AND/OR SPENT CARTRIDGE LOCKOUT

(71) Applicant: Ethicon Endo-Surgery, LLC, Guaynabo, PR (US)

(72) Inventors: Daniel L. Baber, West Chester, OH (US); Nicholas Fanelli, Morrow, OH (US); Frederick E. Shelton, IV, Hillsboro, OH (US); Gregory J. Bakos, Mason, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 414 days.

(21) Appl. No.: 15/385,904

(22) Filed: Dec. 21, 2016

(65) Prior Publication Data

US 2018/0168605 A1 Jun. 21, 2018

(51) Int. Cl.
*A61B 17/072* (2006.01)
*A61B 17/068* (2006.01)
(Continued)

(52) U.S. Cl.
CPC .... *A61B 17/07207* (2013.01); *A61B 17/0644* (2013.01); *A61B 34/30* (2016.02); *A61B 90/03* (2016.02); *A61B 2017/00017* (2013.01); *A61B 2017/0046* (2013.01); *A61B 2017/00398* (2013.01); *A61B 2017/00477* (2013.01);
(Continued)

(58) Field of Classification Search
CPC ........... A61B 2017/07285; A61B 2017/00017; A61B 2017/07242; A61B 2017/2936; A61B 2017/07278; A61B 2017/07235; A61B 2017/2933; A61B 2017/07207; A61B 2017/07271; A61B 2017/2927; A61B 2017/00398; A61B 2017/0046; A61B 2090/034; A61B 2090/0811; A61B 2090/037; A61B 2090/0808; A61B 2090/0814; A61B 34/30; A61B 90/03; A61B 17/0644; A61B 2017/00477; A61B 2017/00991
See application file for complete search history.

(56) References Cited

U.S. PATENT DOCUMENTS 66,052 A 6/1867 Smith
662,587 A 11/1900 Blake
(Continued)

FOREIGN PATENT DOCUMENTS

AU 2011218702 B2 6/2013
AU 2012200178 B2 7/2013
(Continued)

OTHER PUBLICATIONS

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
(Continued)

*Primary Examiner* — Thomas M Wittenschlaeger

(57) ABSTRACT

Surgical stapling instruments are disclosed comprising missing staple cartridge and/or spent cartridge lockouts. In various instances, such lockouts are positioned in a shaft of the surgical stapling instruments.

19 Claims, 51 Drawing Sheets

(51) Int. Cl.
*A61B 34/30* (2016.01)
*A61B 90/00* (2016.01)
*A61B 17/064* (2006.01)
*A61B 17/00* (2006.01)
*A61B 17/29* (2006.01)

(52) U.S. Cl.
CPC ............ *A61B 2017/00991* (2013.01); *A61B 2017/07235* (2013.01); *A61B 2017/07242* (2013.01); *A61B 2017/07271* (2013.01); *A61B 2017/07278* (2013.01); *A61B 2017/07285* (2013.01); *A61B 2017/2927* (2013.01); *A61B 2017/2933* (2013.01); *A61B 2017/2936* (2013.01); *A61B 2090/034* (2016.02); *A61B 2090/037* (2016.02); *A61B 2090/0808* (2016.02); *A61B 2090/0811* (2016.02); *A61B 2090/0814* (2016.02)

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,188,721 A | 6/1916 | Bittner |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,441,096 A | 5/1948 | Happe |
| 2,448,741 A | 9/1948 | Scott et al. |
| 2,450,527 A | 10/1948 | Smith |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,981,051 A | 9/1976 | Brumlik |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |

(56) References Cited

U.S. PATENT DOCUMENTS

| | | |
|---|---|---|
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |

(56) References Cited

U.S. PATENT DOCUMENTS

| | | |
|---|---|---|
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A * | 1/1990 | Fox .............. A61B 17/068 227/120 |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,973,274 A | 11/1990 | Hirukawa |
| 4,973,302 A | 11/1990 | Armour et al. |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,002,543 A | 3/1991 | Bradshaw et al. |
| 5,002,553 A | 3/1991 | Shiber |

(56) References Cited

U.S. PATENT DOCUMENTS

| | | | |
|---|---|---|---|
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |

(56) References Cited

U.S. PATENT DOCUMENTS

| | | |
|---|---|---|
| 5,293,024 A | 3/1994 | Sugahara et al. |
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |

(56) References Cited

U.S. PATENT DOCUMENTS

| | | |
|---|---|---|
| 5,441,483 A | 8/1995 | Avitall |
| 5,441,494 A | 8/1995 | Ortiz |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |

(56) References Cited

U.S. PATENT DOCUMENTS

| | | |
|---|---|---|
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |

(56) References Cited

U.S. PATENT DOCUMENTS

| | | |
|---|---|---|
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,765,565 A | 6/1998 | Adair |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |

(56) References Cited

U.S. PATENT DOCUMENTS

| | | |
|---|---|---|
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |

(56) References Cited

U.S. PATENT DOCUMENTS

| | | |
|---|---|---|
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |

(56) References Cited

U.S. PATENT DOCUMENTS

| | | |
|---|---|---|
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,457,625 B1 | 10/2002 | Tormala et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |

(56) References Cited

U.S. PATENT DOCUMENTS

| | | |
|---|---|---|
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,802,822 B1 | 10/2004 | Dodge |
| 6,802,843 B2 | 10/2004 | Truckai et al. |
| 6,802,844 B2 | 10/2004 | Ferree |

(56) References Cited

U.S. PATENT DOCUMENTS

| | | |
|---|---|---|
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |

(56) References Cited

U.S. PATENT DOCUMENTS

| | | |
|---|---|---|
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,133 B2 | 1/2007 | Evans et al. |

(56) References Cited

U.S. PATENT DOCUMENTS

| | | |
|---|---|---|
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,368,124 B2 | 5/2008 | Chun et al. |

(56) References Cited

U.S. PATENT DOCUMENTS

| | | |
|---|---|---|
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |

(56) References Cited

U.S. PATENT DOCUMENTS

| | | |
|---|---|---|
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| D605,201 S | 12/2009 | Lorenz et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |

(56) References Cited

U.S. PATENT DOCUMENTS

| | | |
|---|---|---|
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |

(56) References Cited

U.S. PATENT DOCUMENTS

| | | |
|---|---|---|
| 7,896,897 B2 | 3/2011 | Gresham et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,941,865 B2 | 5/2011 | Seman, Jr. et al. |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |

(56) References Cited

U.S. PATENT DOCUMENTS

| | | |
|---|---|---|
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |

(56) References Cited

U.S. PATENT DOCUMENTS

| | | |
|---|---|---|
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |

(56) References Cited

U.S. PATENT DOCUMENTS

| | | |
|---|---|---|
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,381,828 B2 | 2/2013 | Whitman et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |

(56) References Cited

U.S. PATENT DOCUMENTS

| | | |
|---|---|---|
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |

(56) References Cited

U.S. PATENT DOCUMENTS

| | | |
|---|---|---|
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,851,215 B2 | 10/2014 | Goto |
| 8,851,354 B2 | 10/2014 | Swensgard et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |

(56) References Cited

U.S. PATENT DOCUMENTS

| | | |
|---|---|---|
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |

(56) References Cited

U.S. PATENT DOCUMENTS

| | | |
|---|---|---|
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,099,863 B2 | 8/2015 | Smith et al. |
| 9,099,877 B2 | 8/2015 | Banos et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,761 B2 | 1/2016 | Burbank |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,244,524 B2 | 1/2016 | Inoue et al. |
| D748,668 S | 2/2016 | Kim et al. |
| D749,623 S | 2/2016 | Gray et al. |
| D750,122 S | 2/2016 | Shardlow et al. |
| D750,129 S | 2/2016 | Kwon |

(56) References Cited

U.S. PATENT DOCUMENTS

| | | |
|---|---|---|
| 9,254,131 B2 | 2/2016 | Soltz et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| D758,433 S | 6/2016 | Lee et al. |
| D759,063 S | 6/2016 | Chen |
| 9,358,003 B2 | 6/2016 | Hail et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |

(56) References Cited

U.S. PATENT DOCUMENTS

| | | |
|---|---|---|
| 9,427,223 B2 | 8/2016 | Park et al. |
| 9,427,231 B2 | 8/2016 | Racenet et al. |
| D767,624 S | 9/2016 | Lee et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Overes et al. |
| 9,451,958 B2 | 9/2016 | Shelton, IV et al. |
| D768,152 S | 10/2016 | Gutierrez et al. |
| D768,156 S | 10/2016 | Frincke |
| D769,315 S | 10/2016 | Scotti |
| D769,930 S | 10/2016 | Agrawal |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,521 B2 | 11/2016 | Deutmeyer et al. |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| D776,683 S | 1/2017 | Gobinski et al. |
| D777,773 S | 1/2017 | Shi |
| 9,532,783 B2 | 1/2017 | Swayze et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,013 B2 | 2/2017 | Tsuchiya |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,111 B2 | 5/2017 | Wenchell |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |

(56) References Cited

U.S. PATENT DOCUMENTS

| | | |
|---|---|---|
| 9,655,616 B2 | 5/2017 | Aranyi |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,675,344 B2 | 6/2017 | Combrowski et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| 9,717,498 B2 | 8/2017 | Aranyi et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |

(56) References Cited

U.S. PATENT DOCUMENTS

| | | |
|---|---|---|
| D806,108 S | 12/2017 | Day |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,382 B2 | 1/2018 | Smith et al. |
| 9,861,446 B2 | 1/2018 | Lang |
| 9,867,612 B2 | 1/2018 | Parihar et al. |
| 9,867,615 B2 | 1/2018 | Fanelli et al. |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,723 B2 | 1/2018 | Hall et al. |
| D810,099 S | 2/2018 | Riedel |
| 9,883,843 B2 | 2/2018 | Garlow |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,095 B2 | 6/2018 | Chowaniec et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,022,125 B2 | 7/2018 | (Prommersberger) Stopek et al. |
| 10,024,407 B2 | 7/2018 | Aranyi et al. |

(56) References Cited

U.S. PATENT DOCUMENTS

| | | |
|---|---|---|
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,748 B2 | 10/2018 | Morgan et al. |
| 10,085,749 B2 | 10/2018 | Cappola et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,638 B2 | 10/2018 | Viola et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,106,932 B2 | 10/2018 | Anderson et al. |
| 10,111,657 B2 | 10/2018 | McCuen |
| 10,111,679 B2 | 10/2018 | Baber et al. |
| 10,111,698 B2 | 10/2018 | Scheib et al. |
| 10,111,702 B2 | 10/2018 | Kostrzewski |
| 10,117,649 B2 | 11/2018 | Baxter et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,154,841 B2 | 12/2018 | Weaner et al. |
| 10,159,482 B2 | 12/2018 | Swayze et al. |
| 10,159,483 B2 | 12/2018 | Beckman et al. |
| 10,163,589 B2 | 12/2018 | Zergiebel et al. |
| D837,244 S | 1/2019 | Kuo et al. |
| D837,245 S | 1/2019 | Kuo et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,188,385 B2 | 1/2019 | Kerr et al. |
| 10,188,393 B2 | 1/2019 | Smith et al. |
| 10,188,394 B2 | 1/2019 | Shelton, IV et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,910 B2 | 2/2019 | Shelton, IV et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |

(56) References Cited

U.S. PATENT DOCUMENTS

| | | |
|---|---|---|
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,058 B2 | 4/2019 | Omori et al. |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,582 B2 | 6/2019 | Shelton, IV et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,939 B2 | 7/2019 | Shelton, IV et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| 10,363,045 B2 | 7/2019 | Whitfield et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,867 B2 | 8/2019 | Harris et al. |
| 10,368,892 B2 | 8/2019 | Stulen et al. |
| 10,376,262 B2 | 8/2019 | Zemlok et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D860,219 S | 9/2019 | Rasmussen et al. |
| 10,398,433 B2 | 9/2019 | Boudreaux et al. |

(56) References Cited

U.S. PATENT DOCUMENTS

| | | |
|---|---|---|
| 10,398,434 B2 | 9/2019 | Shelton, IV et al. |
| 10,398,436 B2 | 9/2019 | Shelton, IV et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,552 B2 | 9/2019 | Shelton, IV et al. |
| 10,420,553 B2 | 9/2019 | Shelton, IV et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D864,388 S | 10/2019 | Barber |
| 10,426,463 B2 | 10/2019 | Shelton, IV et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,768 B2 | 11/2019 | Harris et al. |
| 10,470,769 B2 | 11/2019 | Shelton, IV et al. |
| 10,471,576 B2 | 11/2019 | Totsu |
| 10,471,607 B2 | 11/2019 | Butt et al. |
| 10,478,181 B2 | 11/2019 | Shelton, IV et al. |
| 10,478,182 B2 | 11/2019 | Taylor |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Privitera |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,918 B2 | 12/2019 | Schellin et al. |
| 10,500,309 B2 | 12/2019 | Shah et al. |
| 10,512,461 B2 | 12/2019 | Gupta et al. |
| 10,517,590 B2 | 12/2019 | Giordano et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0034530 A1 | 10/2001 | Malackowski et al. |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0116063 A1 | 8/2002 | Giannetti et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0040670 A1 | 2/2003 | Govari |
| 2003/0045835 A1 | 3/2003 | Anderson et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0121586 A1 | 7/2003 | Mitra et al. |
| 2003/0139741 A1 | 7/2003 | Goble et al. |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0164172 A1 | 9/2003 | Chumas et al. |

(56) References Cited

U.S. PATENT DOCUMENTS

| | | |
|---|---|---|
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232200 A1* | 11/2004 | Shelton, IV ..... A61B 17/07207 227/176.1 |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |

(56) References Cited

U.S. PATENT DOCUMENTS

| | | |
|---|---|---|
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0102475 A1* | 5/2007 | Ortiz et al. ...... A61B 17/07207 227/175.2 |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0262592 A1 | 11/2007 | Hwang et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |

(56) References Cited

U.S. PATENT DOCUMENTS

| | | |
|---|---|---|
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0112234 A1 | 4/2009 | Crainich et al. |
| 2009/0118762 A1 | 5/2009 | Crainch et al. |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1* | 8/2009 | Weisenburgh, II ............ A61B 17/07207 227/175.2 |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0278406 A1 | 11/2009 | Hoffman |
| 2009/0290016 A1 | 11/2009 | Suda |
| 2009/0292283 A1 | 11/2009 | Odom |
| 2009/0302090 A1* | 12/2009 | Shah ............... A61B 17/07207 227/180.1 |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0051668 A1 | 3/2010 | Milliman et al. |
| 2010/0057118 A1 | 3/2010 | Dietz et al. |
| 2010/0065604 A1* | 3/2010 | Weng ............... A61B 17/07207 227/175.2 |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100123 A1 | 4/2010 | Bennett |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0137990 A1 | 6/2010 | Apatsidis et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0241137 A1 | 9/2010 | Doyle et al. |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0108605 A1* | 5/2011 | Sapienza .......... A61B 17/07207 227/180.1 |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |

(56) References Cited

U.S. PATENT DOCUMENTS

| | | |
|---|---|---|
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0225105 A1 | 9/2011 | Scholer et al. |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0283707 A1 | 11/2012 | Giordano et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0105552 A1 | 5/2013 | Weir et al. |
| 2013/0106352 A1 | 5/2013 | Nagamine |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172878 A1 | 7/2013 | Smith |
| 2013/0175317 A1 | 7/2013 | Yates et al. |
| 2013/0214025 A1 | 8/2013 | Zemlok et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1* | 10/2013 | Fernandez ............ A61B 17/068 227/175.2 |
| 2013/0306704 A1 | 11/2013 | Balbierz et al. |
| 2013/0317753 A1 | 11/2013 | Kamen et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012299 A1 | 1/2014 | Stoddard et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107640 A1 | 4/2014 | Yates et al. |
| 2014/0115229 A1 | 4/2014 | Kothamasu et al. |
| 2014/0131418 A1 | 5/2014 | Kostrzewski |
| 2014/0135832 A1 | 5/2014 | Park et al. |
| 2014/0151433 A1 | 6/2014 | Shelton, IV et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0188091 A1 | 7/2014 | Vidal et al. |
| 2014/0188159 A1 | 7/2014 | Steege |
| 2014/0207124 A1 | 7/2014 | Aldridge et al. |
| 2014/0207125 A1 | 7/2014 | Applegate et al. |
| 2014/0209658 A1 | 7/2014 | Skalla et al. |
| 2014/0224857 A1 | 8/2014 | Schmid |
| 2014/0228867 A1 | 8/2014 | Thomas et al. |
| 2014/0239041 A1* | 8/2014 | Zerkle ............ A61B 17/07207 227/176.1 |
| 2014/0239047 A1 | 8/2014 | Hodgkinson et al. |
| 2014/0243865 A1 | 8/2014 | Swayze et al. |

(56) References Cited

U.S. PATENT DOCUMENTS

| | | |
|---|---|---|
| 2014/0246475 A1 | 9/2014 | Hall et al. |
| 2014/0248167 A1 | 9/2014 | Sugimoto et al. |
| 2014/0249557 A1 | 9/2014 | Koch et al. |
| 2014/0249573 A1 | 9/2014 | Arav |
| 2014/0252061 A1 | 9/2014 | Estrella et al. |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0038961 A1 | 2/2015 | Clark et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0122870 A1 | 5/2015 | Zemlok et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0222212 A1 | 8/2015 | Iwata |
| 2015/0223868 A1 | 8/2015 | Brandt et al. |
| 2015/0231409 A1 | 8/2015 | Racenet et al. |
| 2015/0238118 A1 | 8/2015 | Legassey et al. |
| 2015/0238186 A1* | 8/2015 | Aronhalt ............... B29C 55/00 227/175.2 |
| 2015/0272557 A1 | 10/2015 | Overmyer et al. |
| 2015/0272571 A1 | 10/2015 | Leimbach et al. |
| 2015/0272576 A1* | 10/2015 | Cappola ............... A61B 17/072 227/175.2 |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297233 A1 | 10/2015 | Huitema et al. |
| 2015/0297234 A1 | 10/2015 | Schellin et al. |
| 2015/0302539 A1 | 10/2015 | Mazar et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0336249 A1 | 11/2015 | Iwata et al. |
| 2015/0352699 A1 | 12/2015 | Sakai et al. |
| 2015/0366585 A1 | 12/2015 | Lemay et al. |
| 2015/0372265 A1 | 12/2015 | Morisaku et al. |
| 2015/0374369 A1 | 12/2015 | Yates et al. |
| 2015/0374371 A1 | 12/2015 | Richard et al. |
| 2015/0374372 A1 | 12/2015 | Zergiebel et al. |
| 2015/0374378 A1 | 12/2015 | Giordano et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0023342 A1 | 1/2016 | Koenig et al. |
| 2016/0030042 A1 | 2/2016 | Heinrich et al. |
| 2016/0058443 A1 | 3/2016 | Yates et al. |
| 2016/0066815 A1 | 3/2016 | Mei et al. |
| 2016/0066913 A1 | 3/2016 | Swayze et al. |
| 2016/0069449 A1 | 3/2016 | Kanai et al. |
| 2016/0074040 A1 | 3/2016 | Widenhouse et al. |
| 2016/0074103 A1 | 3/2016 | Sartor |
| 2016/0082161 A1 | 3/2016 | Zilberman et al. |
| 2016/0089137 A1 | 3/2016 | Hess et al. |
| 2016/0089198 A1 | 3/2016 | Arya et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120545 A1 | 5/2016 | Shelton, IV et al. |
| 2016/0135835 A1 | 5/2016 | Onuma |
| 2016/0166248 A1 | 6/2016 | Deville et al. |
| 2016/0166256 A1 | 6/2016 | Baxter, III et al. |
| 2016/0174974 A1 | 6/2016 | Schmid et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192916 A1 | 7/2016 | Shelton, IV et al. |
| 2016/0192918 A1 | 7/2016 | Shelton, IV et al. |
| 2016/0192960 A1 | 7/2016 | Bueno et al. |
| 2016/0192977 A1 | 7/2016 | Manwaring et al. |
| 2016/0199063 A1 | 7/2016 | Mandakolathur Vasudevan et al. |
| 2016/0199089 A1 | 7/2016 | Hess et al. |
| 2016/0199956 A1 | 7/2016 | Shelton, IV et al. |
| 2016/0206314 A1 | 7/2016 | Scheib et al. |
| 2016/0235404 A1 | 8/2016 | Shelton, IV |
| 2016/0235409 A1 | 8/2016 | Shelton, IV et al. |
| 2016/0235494 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249922 A1 | 9/2016 | Morgan et al. |
| 2016/0256071 A1 | 9/2016 | Shelton, IV et al. |
| 2016/0256154 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0262921 A1 | 9/2016 | Balbierz et al. |
| 2016/0270780 A1 | 9/2016 | Hall et al. |
| 2016/0278765 A1 | 9/2016 | Shelton, IV et al. |
| 2016/0278771 A1 | 9/2016 | Shelton, IV et al. |
| 2016/0287279 A1 | 10/2016 | Bovay et al. |
| 2016/0310143 A1 | 10/2016 | Bettuchi |
| 2016/0345976 A1 | 12/2016 | Gonzalez et al. |
| 2016/0346034 A1 | 12/2016 | Arya et al. |
| 2016/0354088 A1 | 12/2016 | Cabrera et al. |
| 2016/0367122 A1 | 12/2016 | Ichimura et al. |

(56) References Cited

U.S. PATENT DOCUMENTS

| | | |
|---|---|---|
| 2016/0374678 A1 | 12/2016 | Becerra et al. |
| 2017/0007236 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0027573 A1 | 2/2017 | Nalagatla et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0055986 A1 | 3/2017 | Harris et al. |
| 2017/0056000 A1 | 3/2017 | Nalagatla et al. |
| 2017/0056002 A1 | 3/2017 | Nalagatla et al. |
| 2017/0056005 A1 | 3/2017 | Shelton, IV et al. |
| 2017/0079642 A1 | 3/2017 | Overmyer et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086838 A1 | 3/2017 | Harris et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0105733 A1 | 4/2017 | Scheib et al. |
| 2017/0119388 A1 | 5/2017 | Kostrzewski |
| 2017/0119397 A1 | 5/2017 | Harris et al. |
| 2017/0150965 A1 | 6/2017 | Williams |
| 2017/0172382 A1 | 6/2017 | Nir et al. |
| 2017/0172550 A1 | 6/2017 | Mukherjee et al. |
| 2017/0172662 A1 | 6/2017 | Panescu et al. |
| 2017/0172672 A1 | 6/2017 | Bailey et al. |
| 2017/0182211 A1 | 6/2017 | Raxworthy et al. |
| 2017/0196554 A1 | 7/2017 | Rousseau et al. |
| 2017/0196558 A1 | 7/2017 | Morgan et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196648 A1 | 7/2017 | Ward et al. |
| 2017/0196649 A1 | 7/2017 | Yates et al. |
| 2017/0202571 A1 | 7/2017 | Shelton, IV et al. |
| 2017/0202596 A1 | 7/2017 | Shelton, IV et al. |
| 2017/0202770 A1 | 7/2017 | Friedrich et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0215943 A1 | 8/2017 | Allen, IV |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224339 A1 | 8/2017 | Huang et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265774 A1 | 9/2017 | Johnson et al. |
| 2017/0265856 A1 | 9/2017 | Shelton, IV et al. |
| 2017/0281164 A1 | 10/2017 | Harris et al. |
| 2017/0281166 A1 | 10/2017 | Morgan et al. |
| 2017/0281167 A1 | 10/2017 | Shelton, IV et al. |
| 2017/0281169 A1 | 10/2017 | Harris et al. |
| 2017/0281171 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281183 A1 | 10/2017 | Miller et al. |
| 2017/0281184 A1 | 10/2017 | Shelton, IV et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290584 A1 | 10/2017 | Jasemian et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0325813 A1 | 11/2017 | Aranyi et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0354415 A1 | 12/2017 | Casasanta, Jr. et al. |
| 2017/0358052 A1 | 12/2017 | Yuan |
| 2017/0360439 A1 | 12/2017 | Chen et al. |
| 2017/0360441 A1 | 12/2017 | Sgroi |
| 2017/0360442 A1 | 12/2017 | Shelton, IV et al. |
| 2017/0364183 A1 | 12/2017 | Xiao |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367699 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049819 A1 | 2/2018 | Harris et al. |
| 2018/0049824 A1 | 2/2018 | Harris et al. |
| 2018/0049883 A1 | 2/2018 | Moskowitz et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070942 A1 | 3/2018 | Shelton, IV et al. |
| 2018/0078248 A1 | 3/2018 | Swayze et al. |
| 2018/0078268 A1 | 3/2018 | Messerly et al. |
| 2018/0085116 A1 | 3/2018 | Yates et al. |
| 2018/0085117 A1 | 3/2018 | Shelton, IV et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |

(56) References Cited

U.S. PATENT DOCUMENTS

| | | |
|---|---|---|
| 2018/0125481 A1 | 5/2018 | Yates et al. |
| 2018/0125484 A1 | 5/2018 | Kostrzewski |
| 2018/0125487 A1 | 5/2018 | Beardsley |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0125594 A1 | 5/2018 | Beardsley |
| 2018/0126504 A1 | 5/2018 | Shelton, IV et al. |
| 2018/0132845 A1 | 5/2018 | Schmid et al. |
| 2018/0132849 A1 | 5/2018 | Miller et al. |
| 2018/0132850 A1 | 5/2018 | Leimbach et al. |
| 2018/0132851 A1 | 5/2018 | Hall et al. |
| 2018/0132926 A1 | 5/2018 | Asher et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0150153 A1 | 5/2018 | Yoon et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168584 A1 | 6/2018 | Harris et al. |
| 2018/0168585 A1 | 6/2018 | Shelton, IV et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168621 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168643 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168715 A1 | 6/2018 | Strobl |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0242962 A1 | 8/2018 | Walen et al. |
| 2018/0250001 A1 | 9/2018 | Aronhalt et al. |
| 2018/0250020 A1 | 9/2018 | Carusillo |
| 2018/0250086 A1 | 9/2018 | Grubbs |
| 2018/0271520 A1 | 9/2018 | Shelton, IV et al. |
| 2018/0273597 A1 | 9/2018 | Stimson |
| 2018/0280020 A1 | 10/2018 | Hess et al. |
| 2018/0286274 A1 | 10/2018 | Kamiguchi et al. |
| 2018/0289369 A1 | 10/2018 | Shelton, IV et al. |
| 2018/0296211 A1 | 10/2018 | Timm et al. |
| 2018/0296215 A1 | 10/2018 | Baxter, III et al. |
| 2018/0296216 A1 | 10/2018 | Shelton, IV et al. |
| 2018/0296217 A1 | 10/2018 | Moore et al. |
| 2018/0303481 A1 | 10/2018 | Shelton, IV et al. |
| 2018/0303482 A1 | 10/2018 | Shelton, IV et al. |
| 2018/0310931 A1 | 11/2018 | Hall et al. |
| 2018/0311002 A1 | 11/2018 | Giordano et al. |
| 2018/0317907 A1 | 11/2018 | Kostrzewski |
| 2018/0317916 A1 | 11/2018 | Wixey |
| 2018/0317917 A1 | 11/2018 | Huang et al. |
| 2018/0317918 A1 | 11/2018 | Shelton, IV |
| 2018/0317919 A1 | 11/2018 | Shelton, IV et al. |
| 2018/0325528 A1 | 11/2018 | Windolf et al. |
| 2018/0325611 A1 | 11/2018 | Robinson et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353170 A1 | 12/2018 | Overmyer et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360443 A1 | 12/2018 | Shelton, IV et al. |
| 2018/0360445 A1 | 12/2018 | Shelton, IV et al. |
| 2018/0360446 A1 | 12/2018 | Shelton, IV et al. |
| 2018/0360447 A1 | 12/2018 | Shelton, IV et al. |
| 2018/0360448 A1 | 12/2018 | Harris et al. |
| 2018/0360449 A1 | 12/2018 | Shelton, IV |
| 2018/0360450 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360455 A1 | 12/2018 | Shelton, IV et al. |
| 2018/0360456 A1 | 12/2018 | Shelton, IV et al. |
| 2018/0360471 A1 | 12/2018 | Parfett et al. |
| 2018/0360472 A1 | 12/2018 | Harris et al. |
| 2018/0360473 A1 | 12/2018 | Shelton, IV et al. |
| 2018/0360549 A1 | 12/2018 | Hares et al. |
| 2018/0368822 A1 | 12/2018 | Shelton, IV et al. |
| 2018/0368833 A1 | 12/2018 | Shelton, IV et al. |
| 2018/0368837 A1 | 12/2018 | Morgan et al. |
| 2018/0368838 A1 | 12/2018 | Shelton, IV et al. |
| 2018/0368839 A1 | 12/2018 | Shelton, IV et al. |
| 2018/0368840 A1 | 12/2018 | Shelton, IV et al. |
| 2018/0368841 A1 | 12/2018 | Shelton, IV et al. |
| 2018/0368842 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |

(56) References Cited

U.S. PATENT DOCUMENTS

| | | |
|---|---|---|
| 2018/0368846 A1 | 12/2018 | Shelton, IV et al. |
| 2018/0368847 A1 | 12/2018 | Shelton, IV et al. |
| 2019/0000446 A1 | 1/2019 | Shelton, IV et al. |
| 2019/0000448 A1 | 1/2019 | Shelton, IV et al. |
| 2019/0000450 A1 | 1/2019 | Shelton, IV et al. |
| 2019/0000454 A1 | 1/2019 | Swayze et al. |
| 2019/0000456 A1 | 1/2019 | Shelton, IV et al. |
| 2019/0000457 A1 | 1/2019 | Shelton, IV et al. |
| 2019/0000458 A1 | 1/2019 | Shelton, IV et al. |
| 2019/0000459 A1 | 1/2019 | Shelton, IV et al. |
| 2019/0000460 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000463 A1 | 1/2019 | Shelton, IV et al. |
| 2019/0000464 A1 | 1/2019 | Shelton, IV et al. |
| 2019/0000465 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000468 A1 | 1/2019 | Adams et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000473 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000528 A1 | 1/2019 | Yates et al. |
| 2019/0000530 A1 | 1/2019 | Yates et al. |
| 2019/0000531 A1 | 1/2019 | Messerly et al. |
| 2019/0000534 A1 | 1/2019 | Messerly et al. |
| 2019/0000538 A1 | 1/2019 | Widenhouse et al. |
| 2019/0000555 A1 | 1/2019 | Schings et al. |
| 2019/0000565 A1 | 1/2019 | Shelton, IV et al. |
| 2019/0003292 A1 | 1/2019 | Balan et al. |
| 2019/0008509 A1 | 1/2019 | Shelton, IV et al. |
| 2019/0008511 A1 | 1/2019 | Kerr et al. |
| 2019/0015096 A1 | 1/2019 | Shelton, IV et al. |
| 2019/0015102 A1 | 1/2019 | Baber et al. |
| 2019/0015165 A1 | 1/2019 | Giordano et al. |
| 2019/0029675 A1 | 1/2019 | Yates et al. |
| 2019/0029676 A1 | 1/2019 | Yates et al. |
| 2019/0029677 A1 | 1/2019 | Yates et al. |
| 2019/0029678 A1 | 1/2019 | Shelton, IV et al. |
| 2019/0029681 A1 | 1/2019 | Swayze et al. |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038292 A1 | 2/2019 | Zhang |
| 2019/0038371 A1 | 2/2019 | Wixey et al. |
| 2019/0046181 A1 | 2/2019 | McCuen |
| 2019/0046187 A1 | 2/2019 | Yates et al. |
| 2019/0059886 A1 | 2/2019 | Shelton, IV et al. |
| 2019/0090870 A1 | 3/2019 | Shelton, IV et al. |
| 2019/0090871 A1 | 3/2019 | Shelton, IV et al. |
| 2019/0091183 A1 | 3/2019 | Tomat et al. |
| 2019/0099177 A1 | 4/2019 | Yates et al. |
| 2019/0099178 A1 | 4/2019 | Leimbach et al. |
| 2019/0099179 A1 | 4/2019 | Leimbach et al. |
| 2019/0099180 A1 | 4/2019 | Leimbach et al. |
| 2019/0099181 A1 | 4/2019 | Shelton, IV et al. |
| 2019/0099182 A1 | 4/2019 | Bakos et al. |
| 2019/0099183 A1 | 4/2019 | Leimbach et al. |
| 2019/0099184 A1 | 4/2019 | Setser et al. |
| 2019/0099224 A1 | 4/2019 | Leimbach et al. |
| 2019/0099229 A1 | 4/2019 | Spivey et al. |
| 2019/0102930 A1 | 4/2019 | Leimbach et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105038 A1 | 4/2019 | Schmid et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0105049 A1 | 4/2019 | Moore et al. |
| 2019/0110791 A1 | 4/2019 | Shelton, IV et al. |
| 2019/0110792 A1 | 4/2019 | Shelton, IV et al. |
| 2019/0110793 A1 | 4/2019 | Parihar et al. |
| 2019/0117216 A1 | 4/2019 | Overmyer et al. |
| 2019/0117217 A1 | 4/2019 | Overmyer et al. |
| 2019/0117222 A1 | 4/2019 | Shelton, IV et al. |
| 2019/0117224 A1 | 4/2019 | Setser et al. |
| 2019/0117225 A1 | 4/2019 | Moore et al. |
| 2019/0125343 A1 | 5/2019 | Wise et al. |
| 2019/0125344 A1 | 5/2019 | DiNardo et al. |
| 2019/0125345 A1 | 5/2019 | Baber et al. |
| 2019/0125365 A1 | 5/2019 | Parfett et al. |
| 2019/0125380 A1 | 5/2019 | Hunter et al. |
| 2019/0125475 A1 | 5/2019 | Wise et al. |
| 2019/0133585 A1 | 5/2019 | Smith et al. |
| 2019/0142421 A1 | 5/2019 | Shelton, IV |
| 2019/0183490 A1 | 6/2019 | Shelton, IV et al. |
| 2019/0183491 A1 | 6/2019 | Shelton, IV et al. |
| 2019/0183492 A1 | 6/2019 | Shelton, IV et al. |
| 2019/0183493 A1 | 6/2019 | Shelton, IV et al. |
| 2019/0183494 A1 | 6/2019 | Shelton, IV et al. |
| 2019/0183495 A1 | 6/2019 | Shelton, IV et al. |
| 2019/0183496 A1 | 6/2019 | Shelton, IV et al. |
| 2019/0183497 A1 | 6/2019 | Shelton, IV et al. |
| 2019/0183498 A1 | 6/2019 | Shelton, IV et al. |
| 2019/0183499 A1 | 6/2019 | Shelton, IV et al. |
| 2019/0183500 A1 | 6/2019 | Shelton, IV et al. |
| 2019/0183501 A1 | 6/2019 | Shelton, IV et al. |
| 2019/0183502 A1 | 6/2019 | Shelton, IV et al. |
| 2019/0183503 A1 | 6/2019 | Shelton, IV et al. |
| 2019/0183504 A1 | 6/2019 | Shelton, IV et al. |
| 2019/0183505 A1 | 6/2019 | Vendely et al. |
| 2019/0183592 A1 | 6/2019 | Shelton, IV et al. |
| 2019/0183594 A1 | 6/2019 | Shelton, IV et al. |
| 2019/0183597 A1 | 6/2019 | Shelton, IV et al. |
| 2019/0192137 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192144 A1 | 6/2019 | Parfett et al. |
| 2019/0192145 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192156 A1 | 6/2019 | Simms et al. |
| 2019/0192157 A1 | 6/2019 | Scott et al. |
| 2019/0192158 A1 | 6/2019 | Scott et al. |
| 2019/0192159 A1 | 6/2019 | Simms et al. |
| 2019/0192227 A1 | 6/2019 | Shelton, IV et al. |
| 2019/0192235 A1 | 6/2019 | Harris et al. |
| 2019/0192236 A1 | 6/2019 | Shelton, IV et al. |
| 2019/0200895 A1 | 7/2019 | Shelton, IV et al. |
| 2019/0200991 A1 | 7/2019 | Moore et al. |
| 2019/0200992 A1 | 7/2019 | Moore et al. |
| 2019/0200993 A1 | 7/2019 | Moore et al. |
| 2019/0200994 A1 | 7/2019 | Moore et al. |
| 2019/0201028 A1 | 7/2019 | Shelton, IV et al. |
| 2019/0209164 A1 | 7/2019 | Timm et al. |
| 2019/0209165 A1 | 7/2019 | Timm et al. |
| 2019/0209171 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |

(56) References Cited

U.S. PATENT DOCUMENTS

| | | | |
|---|---|---|---|
| 2019/0216558 A1 | 7/2019 | Giordano et al. | |
| 2019/0223865 A1 | 7/2019 | Shelton, IV et al. | |
| 2019/0223871 A1 | 7/2019 | Moore et al. | |
| 2019/0261991 A1 | 8/2019 | Beckman et al. | |
| 2019/0267403 A1 | 8/2019 | Li et al. | |
| 2019/0269400 A1 | 9/2019 | Mandakolathur Vasudevan et al. | |
| 2019/0269402 A1 | 9/2019 | Murray et al. | |
| 2019/0269403 A1 | 9/2019 | Baxter, III et al. | |
| 2019/0269407 A1 | 9/2019 | Swensgard et al. | |
| 2019/0269428 A1 | 9/2019 | Allen et al. | |
| 2019/0290263 A1 | 9/2019 | Morgan et al. | |
| 2019/0290264 A1 | 9/2019 | Morgan et al. | |
| 2019/0290265 A1 | 9/2019 | Shelton, IV et al. | |
| 2019/0290274 A1 | 9/2019 | Shelton, IV | |
| 2019/0321040 A1 | 10/2019 | Shelton, IV | |
| 2019/0321041 A1 | 10/2019 | Shelton, IV | |
| 2019/0350582 A1 | 11/2019 | Shelton, IV et al. | |
| 2019/0365384 A1 | 12/2019 | Baxter et al. | |

FOREIGN PATENT DOCUMENTS

| | | |
|---|---|---|
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101378791 A | 3/2009 |
| CN | 101522120 A | 9/2009 |
| CN | 101669833 A | 3/2010 |
| CN | 101721236 A | 6/2010 |
| CN | 101828940 A | 9/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 102217961 A | 10/2011 |
| CN | 102217963 A | 10/2011 |
| CN | 101779977 B | 12/2011 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 202489990 U | 10/2012 |
| CN | 102228387 B | 11/2012 |
| CN | 102835977 A | 12/2012 |
| CN | 202568350 U | 12/2012 |
| CN | 103690212 A | 4/2014 |
| CN | 203564285 U | 4/2014 |
| CN | 203564287 U | 4/2014 |
| CN | 203597997 U | 5/2014 |
| CN | 103829981 A | 6/2014 |
| CN | 103829983 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 203815517 U | 9/2014 |
| CN | 102783741 B | 10/2014 |
| CN | 102973300 B | 10/2014 |
| CN | 104337556 A | 2/2015 |
| CN | 204158440 U | 2/2015 |
| CN | 204158441 U | 2/2015 |
| CN | 102469995 B | 3/2015 |
| CN | 204636451 U | 9/2015 |
| CN | 103860225 B | 3/2016 |
| CN | 103750872 B | 5/2016 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004063606 A1 | 7/2006 |
| DE | 202007003114 U1 | 6/2007 |
| DE | 102010013150 A1 | 9/2011 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |

(56) References Cited

FOREIGN PATENT DOCUMENTS

| | | | |
|---|---|---|---|
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2842500 A1 | 3/2015 |
| EP | 2853220 A1 | 4/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 2789299 B1 | 5/2017 |
| EP | 3225190 A2 | 10/2017 |
| EP | 3363378 A1 | 8/2018 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S63270040 A | 11/1988 |
| JP | H0129503 B2 | 6/1989 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H06237937 A | 8/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000271141 A | 10/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006346445 A | 12/2006 |
| JP | 2008220032 A | 9/2008 |
| JP | 2009507526 A | 2/2009 |
| JP | 200990113 A | 4/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 2011524199 A | 9/2011 |
| JP | 2012143283 A | 8/2012 |
| JP | 5154710 B1 | 2/2013 |
| JP | 2014121599 A | 7/2014 |
| JP | 2016512057 A | 4/2016 |
| KR | 20100110134 A | 10/2010 |
| KR | 20110003229 A | 1/2011 |
| RU | 1814161 A1 | 5/1993 |
| RU | 1814161 C | 5/1993 |
| RU | 2008830 C1 | 3/1994 |
| RU | 2052979 C1 | 1/1996 |
| RU | 2066128 C1 | 9/1996 |

(56) References Cited

FOREIGN PATENT DOCUMENTS

| | | |
|---|---|---|
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2015032797 A1 | 3/2015 |
| WO | WO-2015138760 A1 | 9/2015 |
| WO | WO-2015187107 A1 | 12/2015 |

OTHER PUBLICATIONS

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Young, "Microcellular foams via phase separation," Journal of Vacuum Science & Technology A 4(3), (May/Jun. 1986).

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1 &SRETRY=0; [online] accessed: Sep. 22, 2008 (2 pages).

Disclosed Anonymously, "Motor-Driven Surgical Stapler Improvements," Research Disclosure Database No. 526041, Published: Feb. 2008.

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

(56) References Cited

OTHER PUBLICATIONS

ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Solorio et al., "Gelatin Microspheres Crosslinked with Genipin for Local Delivery of Growth Factors," J. Tissue Eng. Regen. Med. (2010), 4(7): pp. 514-523.
Pitt et al., "Attachment of Hyaluronan to Metallic Surfaces," J. Biomed. Mater. Res. 68A: pp. 95-106, 2004.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Covidien Brochure "iDrive™ Ultra Powered Stapling System," (6 pages).
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.

Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press Ltd, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the

(56) References Cited

OTHER PUBLICATIONS https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "*Demystifying UHF Gen 2 RFID, HF RFID,*" Online Article, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications,*" Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry—II: Second Year Diploma in Pharmacy, Nirali Prakashan, p. 339, 2007.
Forum discussion regarding "Speed Is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).

\* cited by examiner

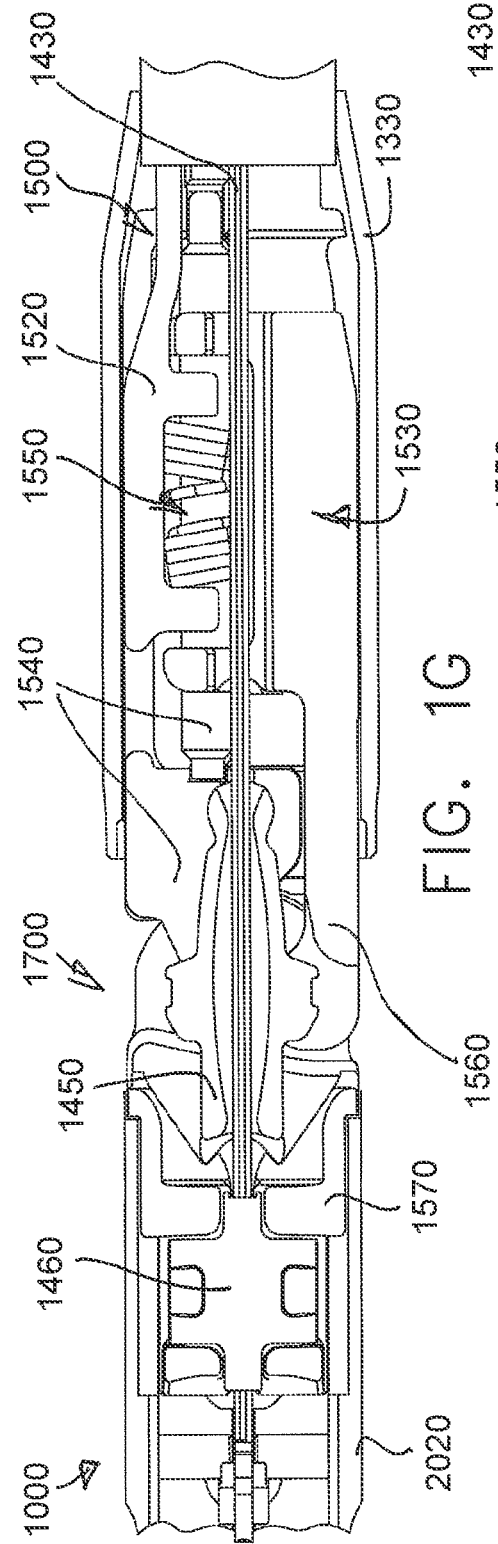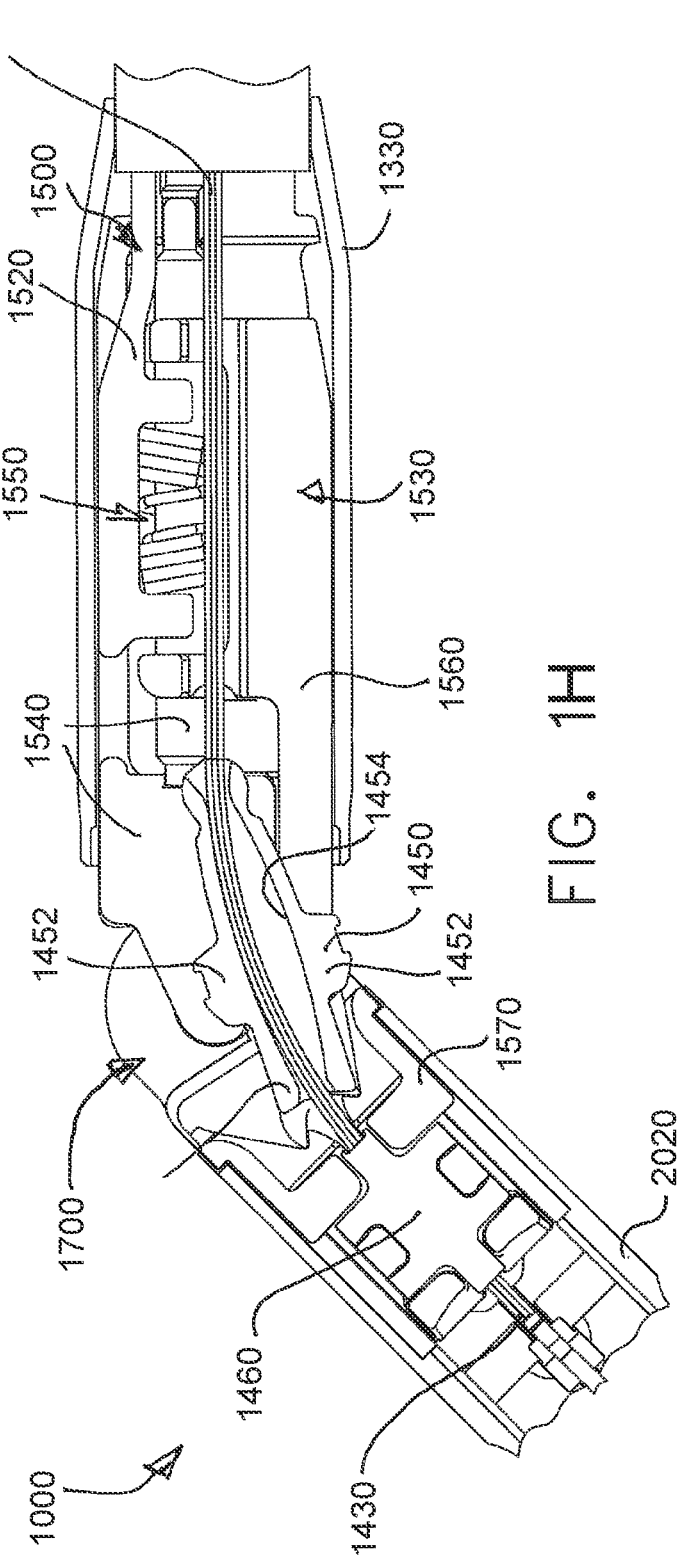

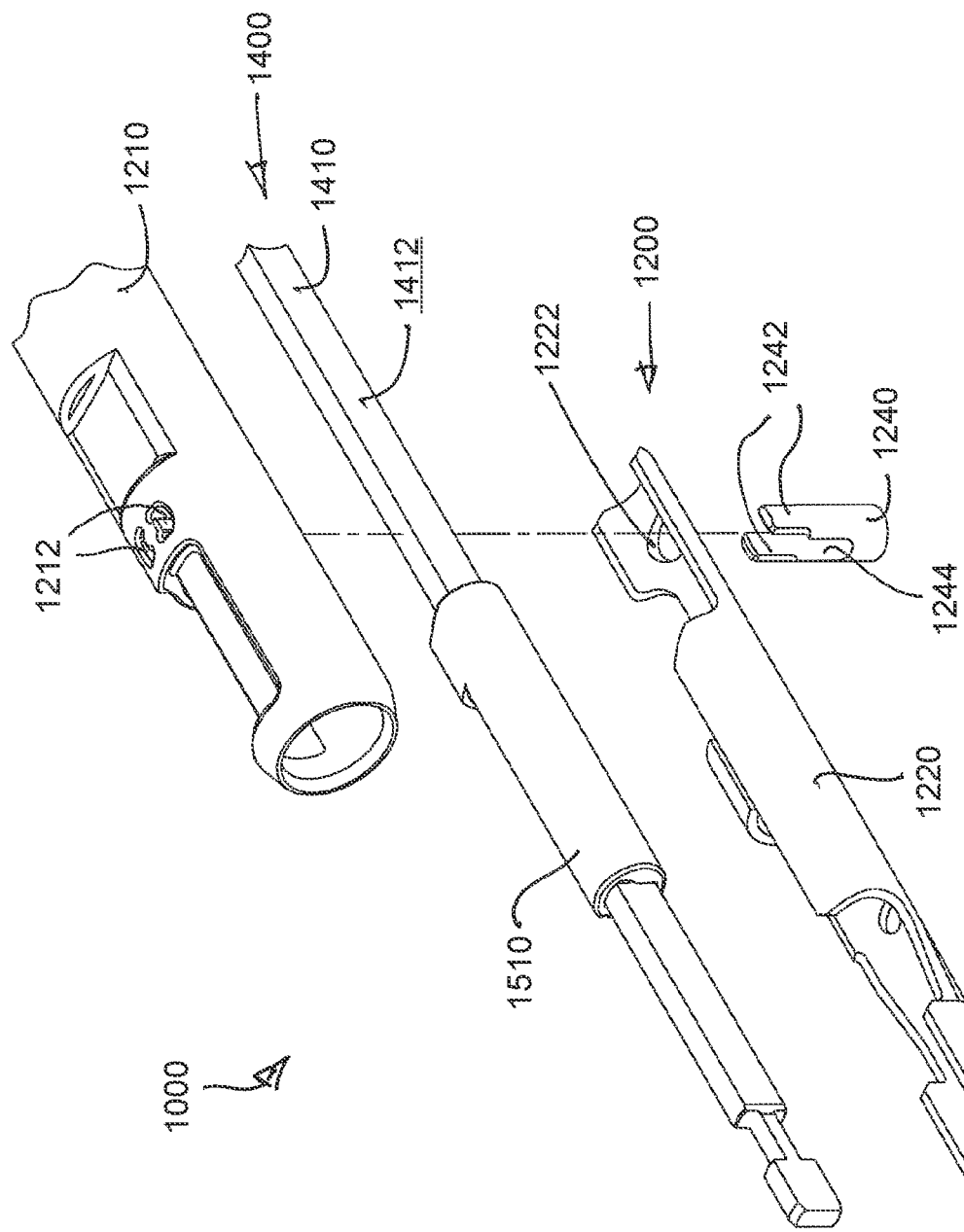

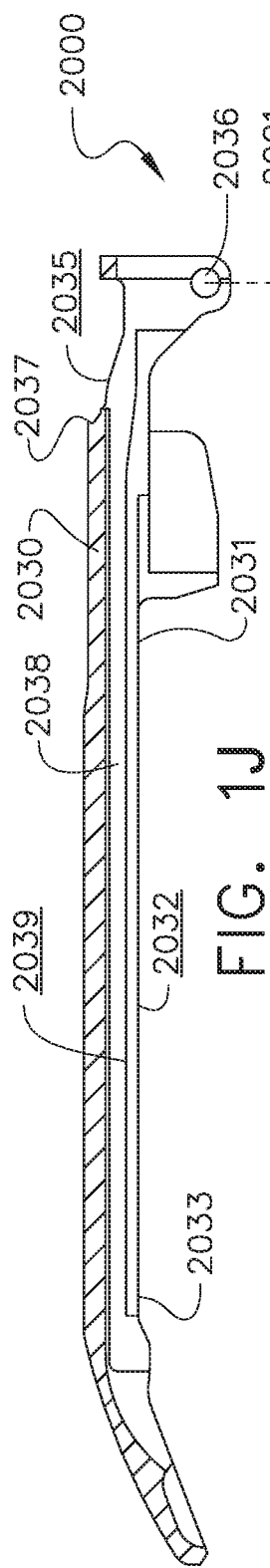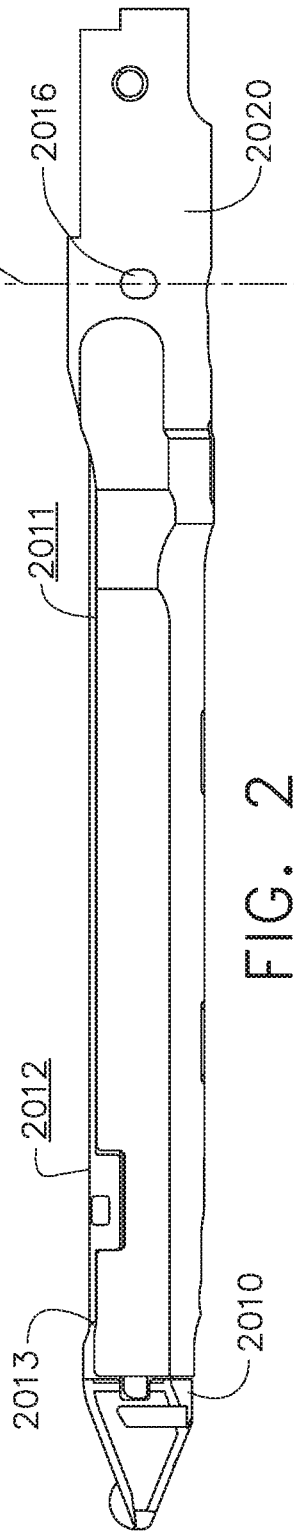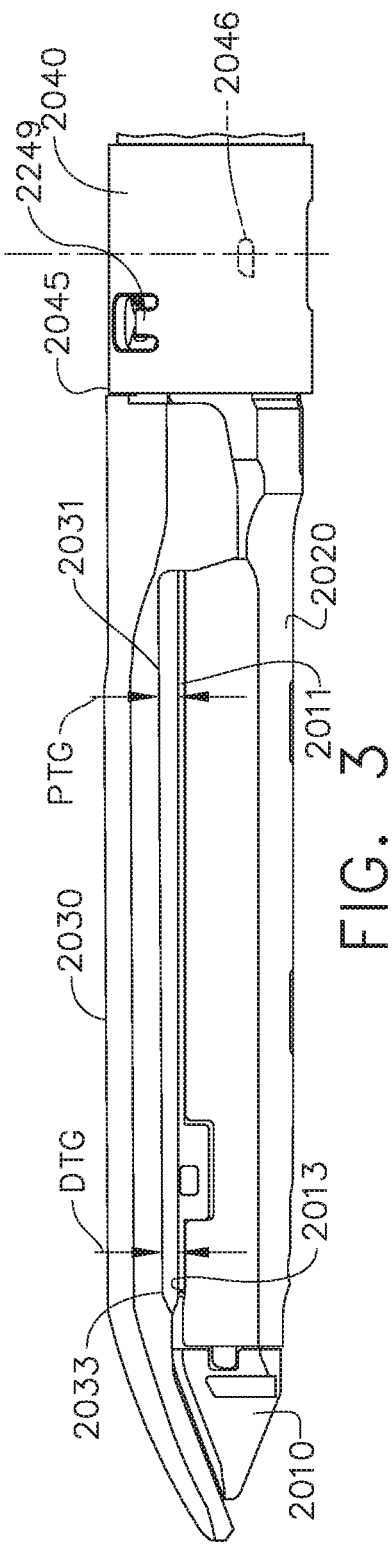

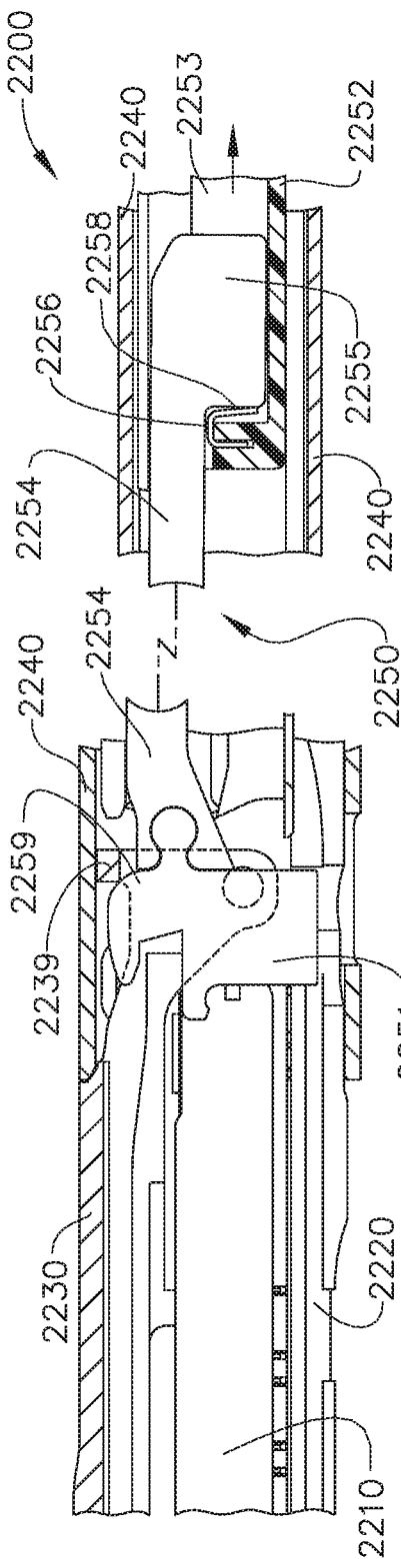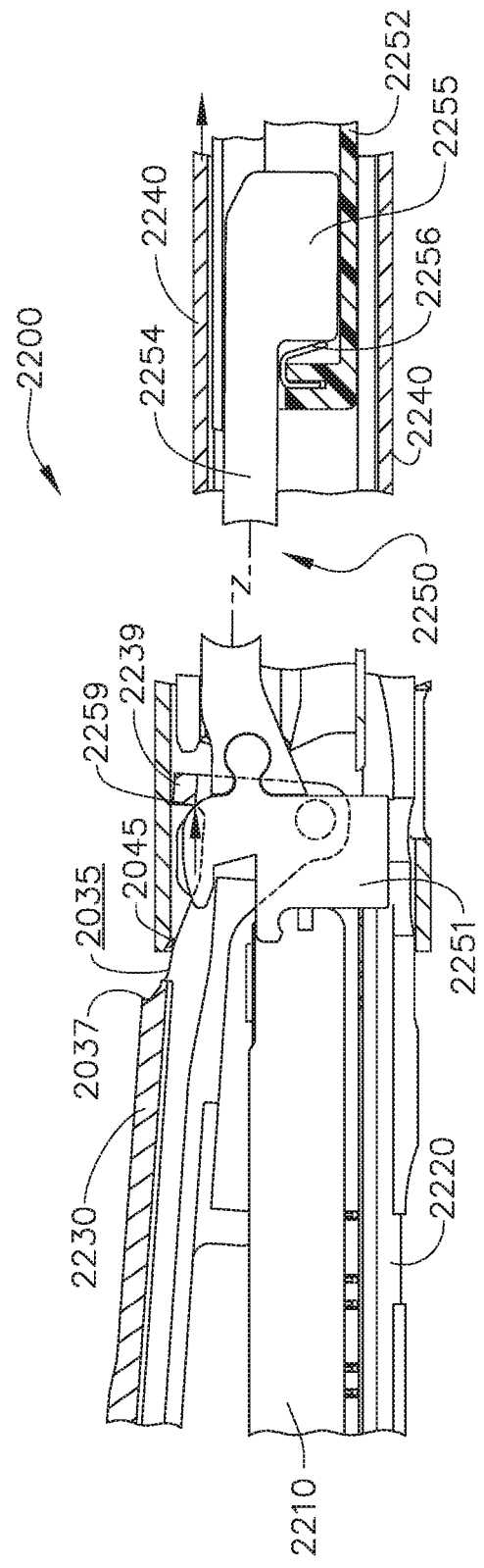
FIG. 7
FIG. 8

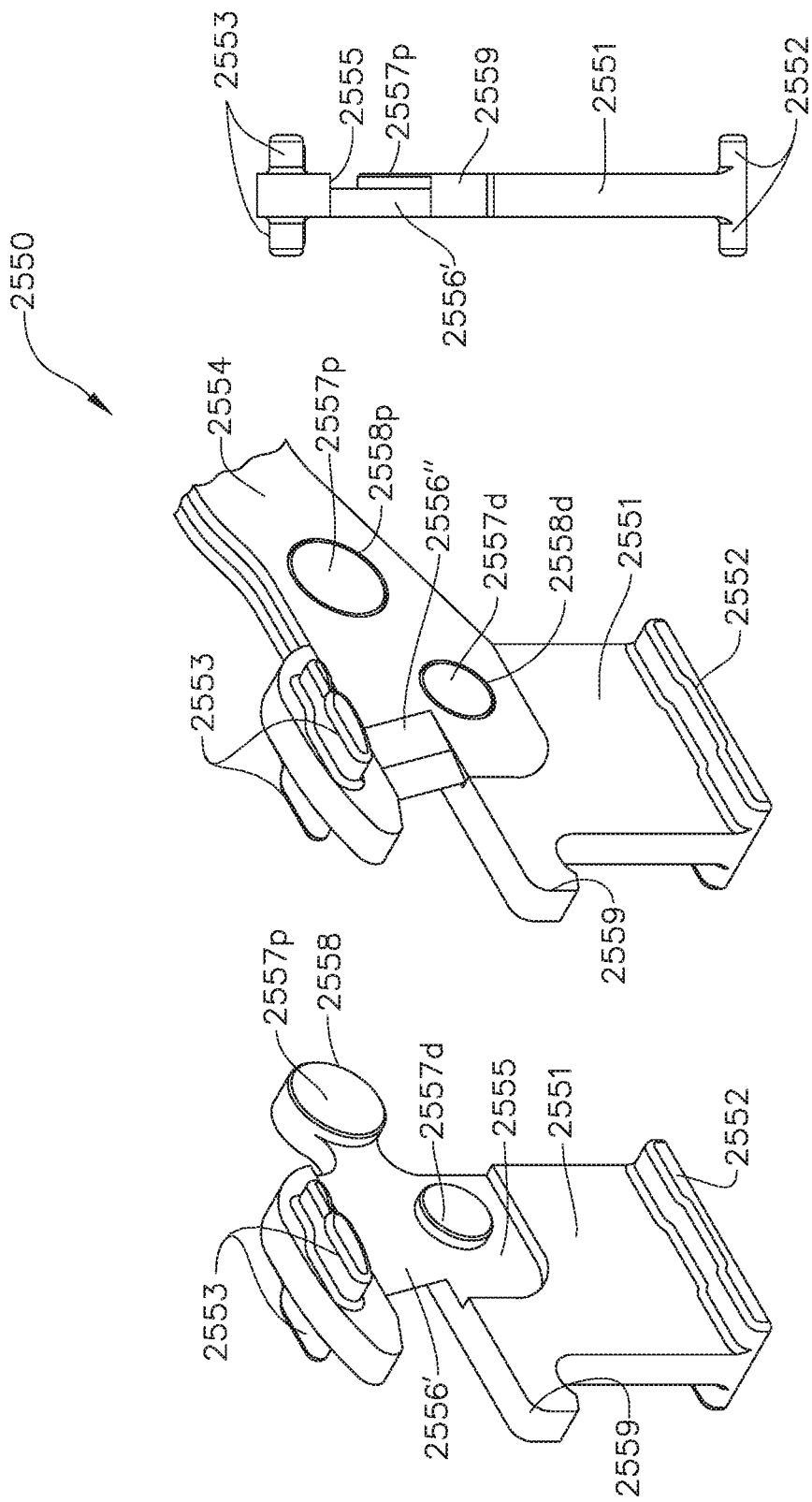

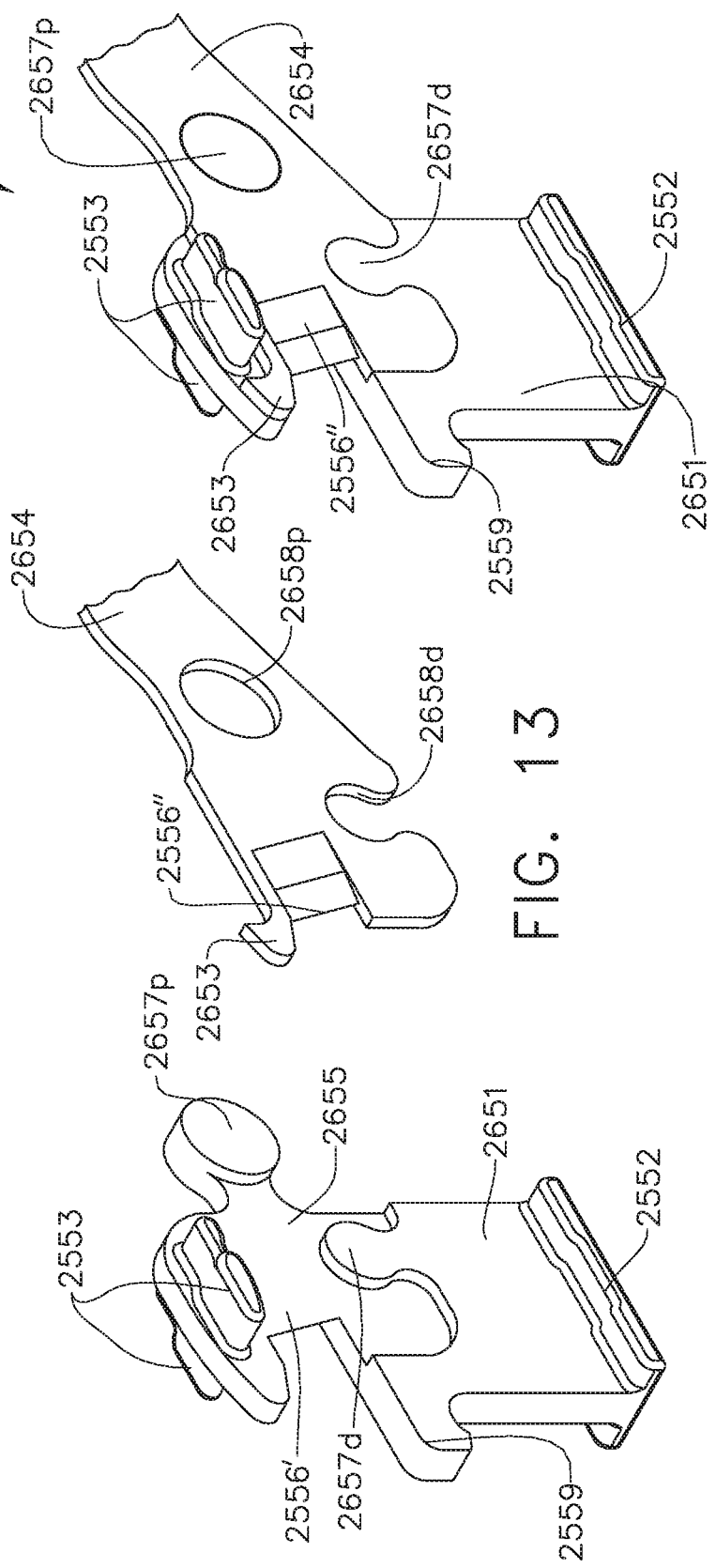

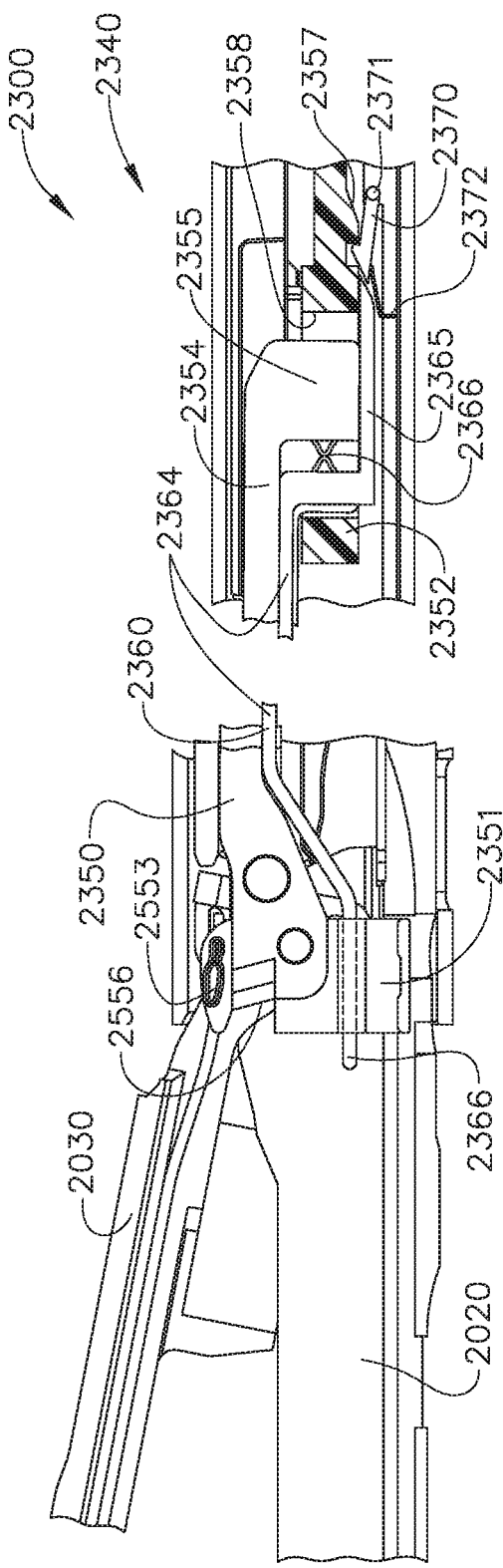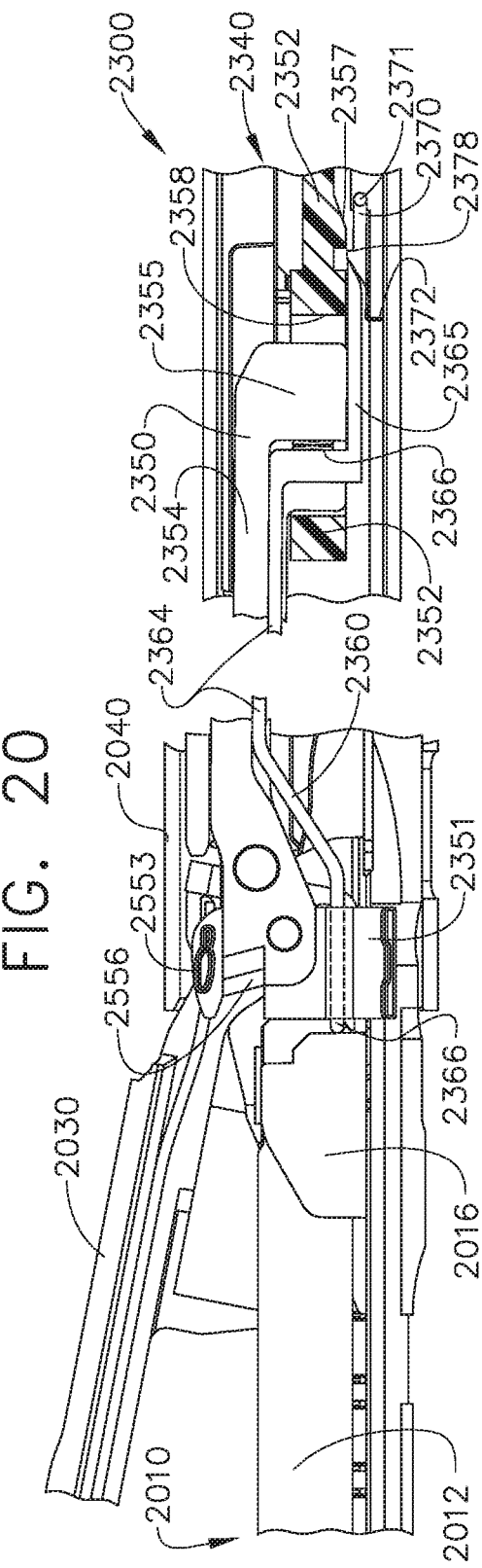

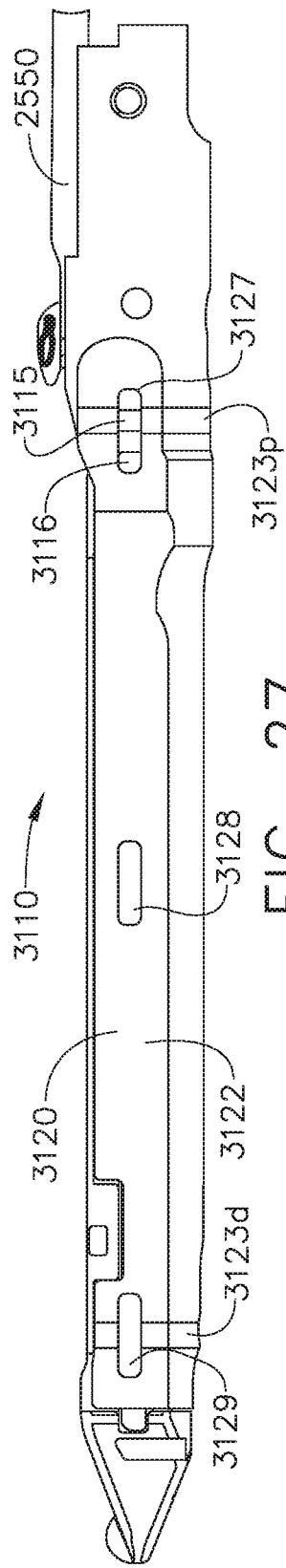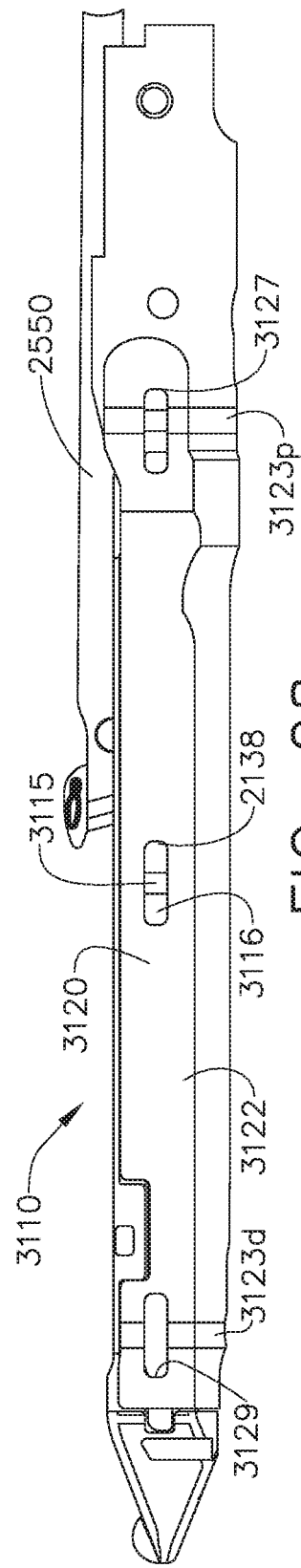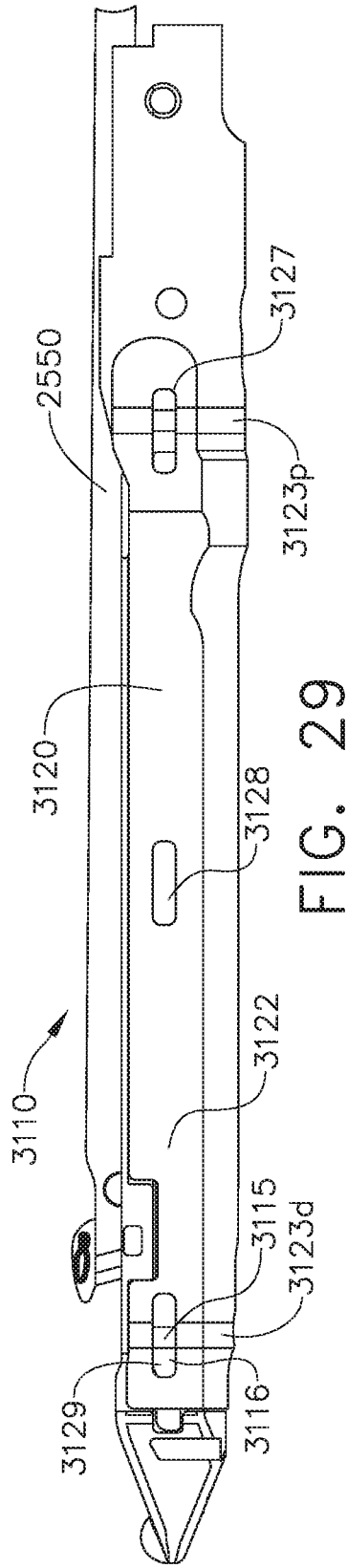

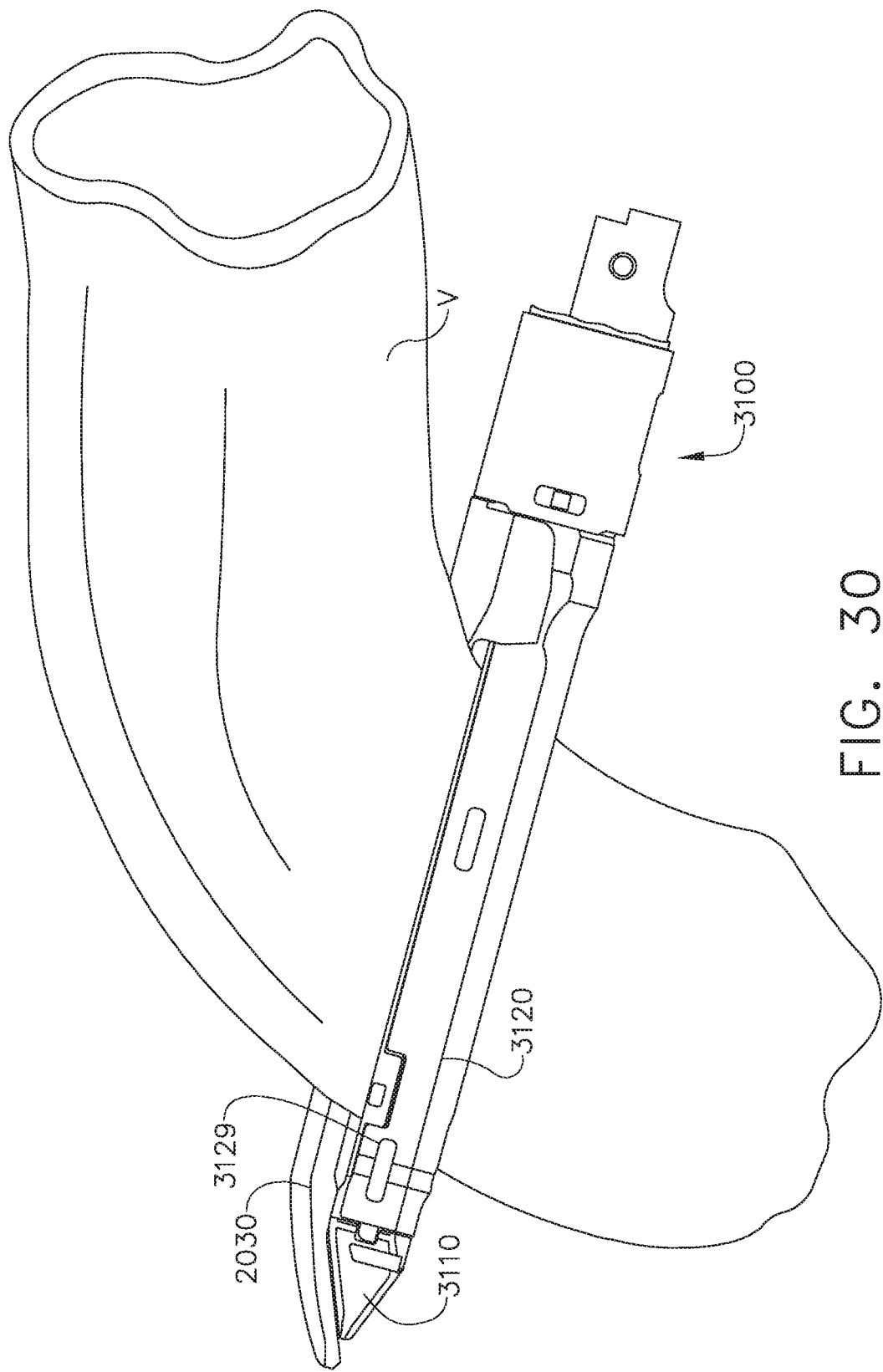

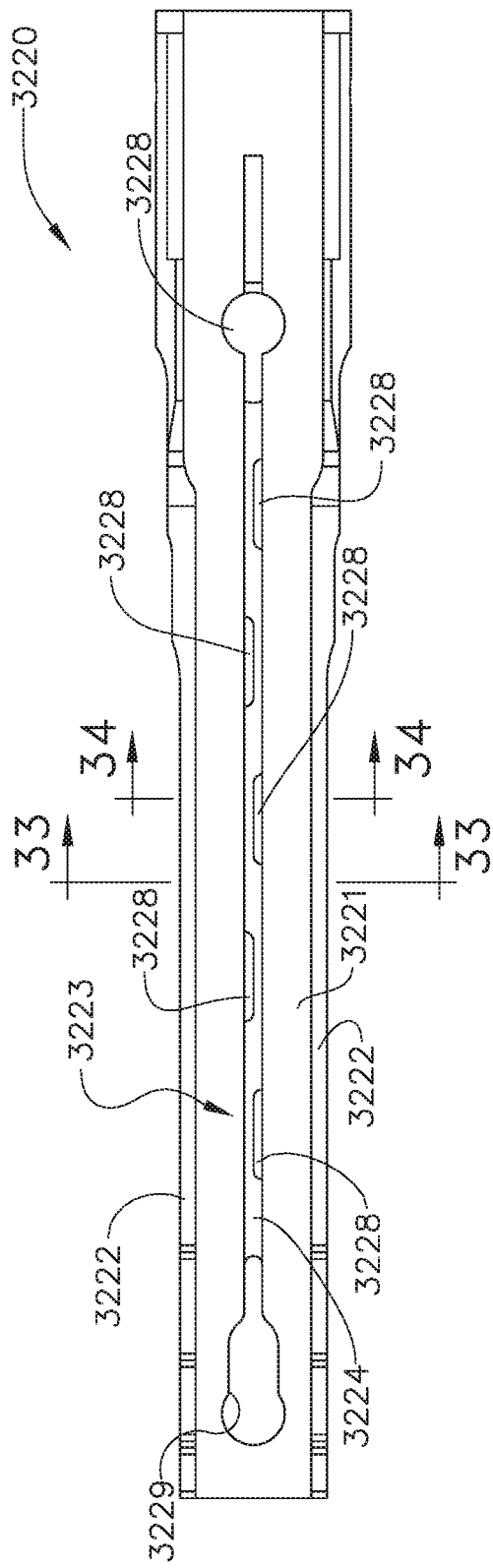
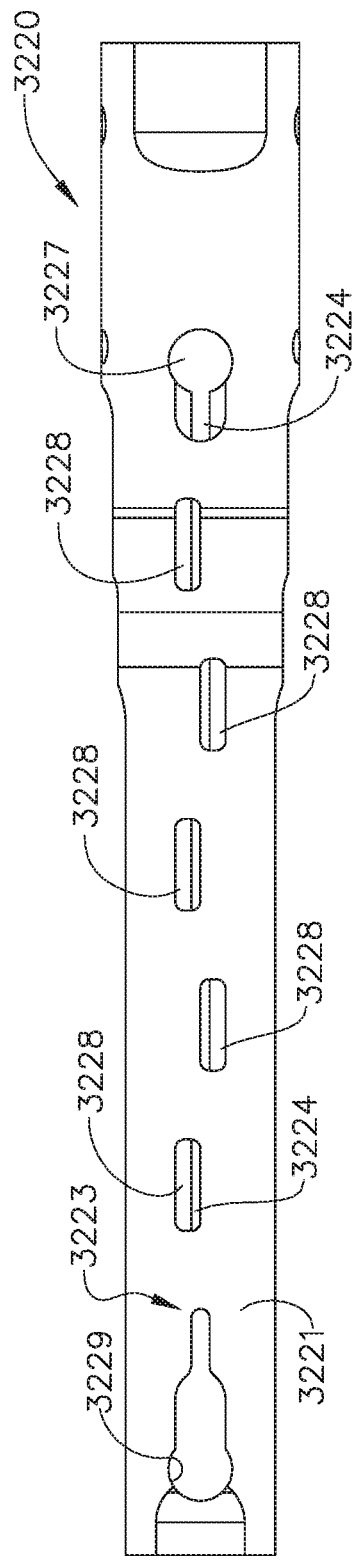
FIG. 31
FIG. 32

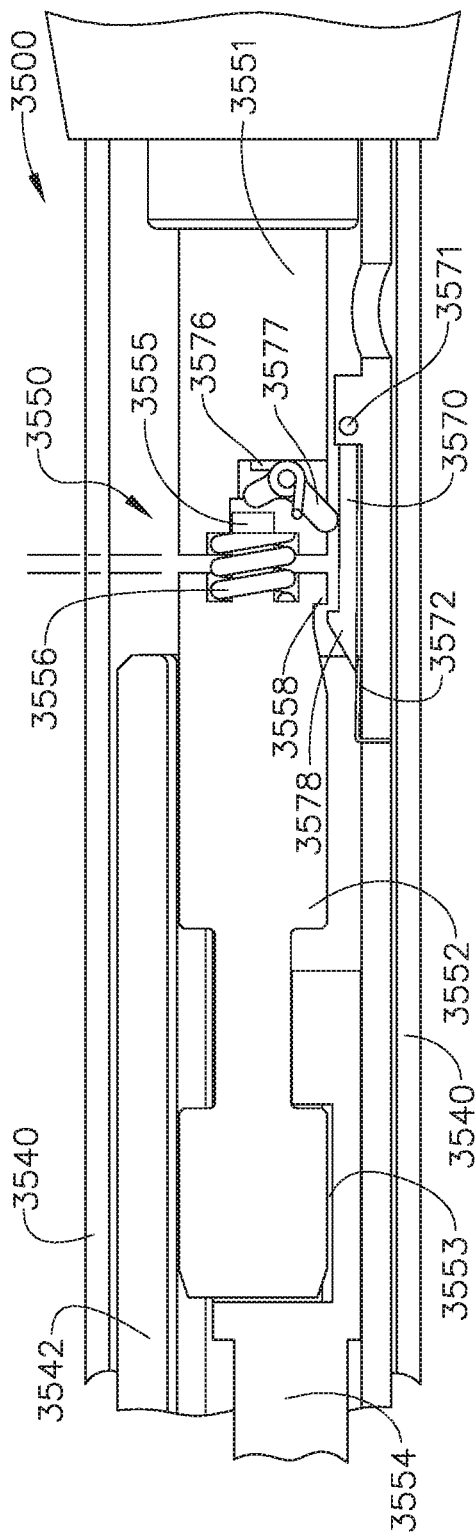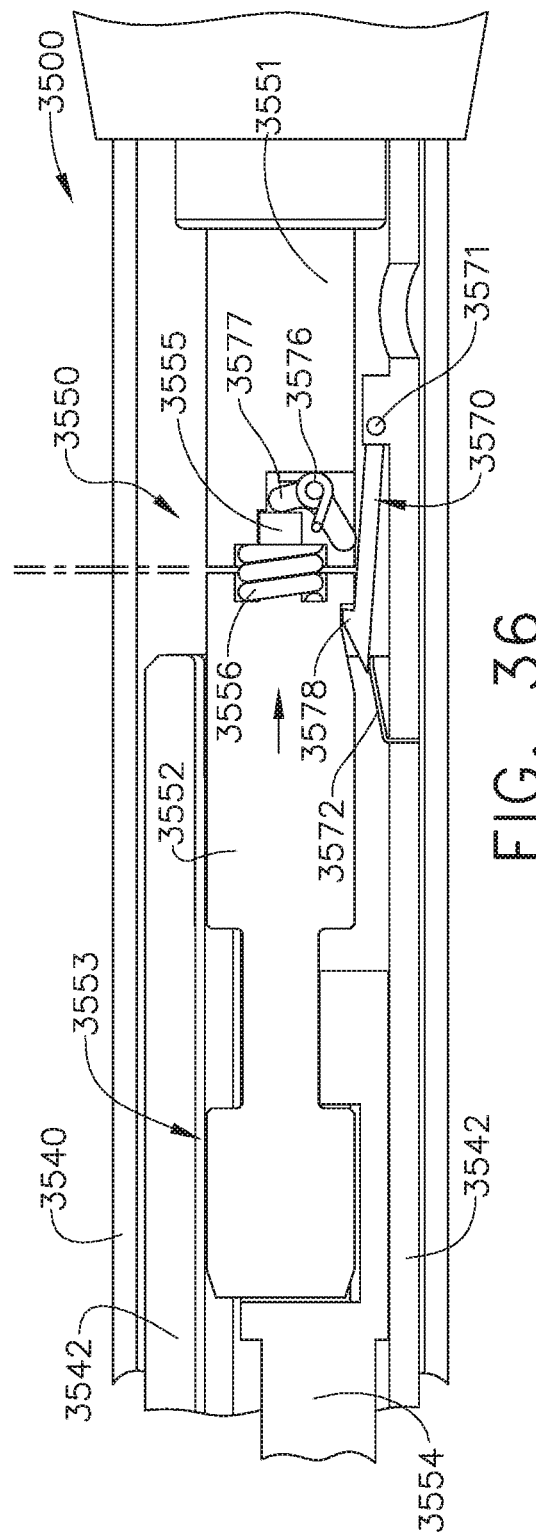

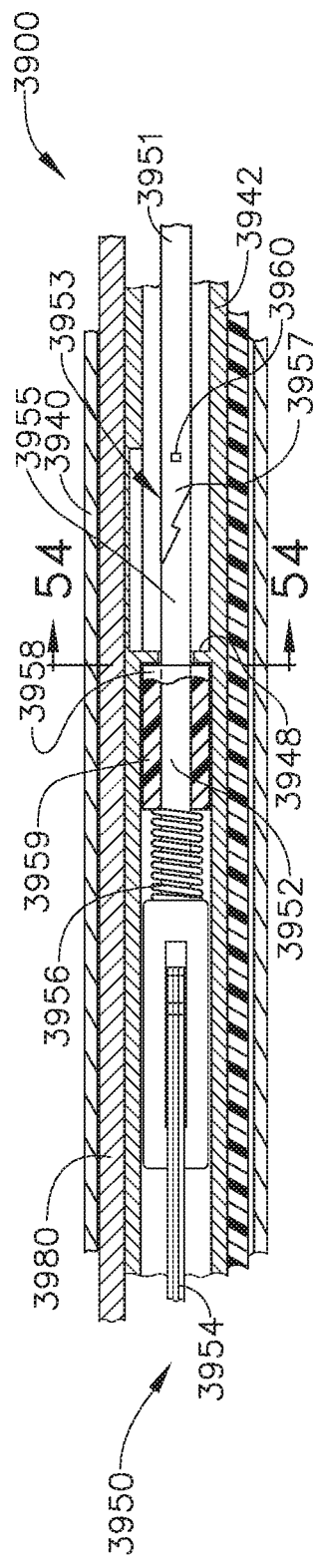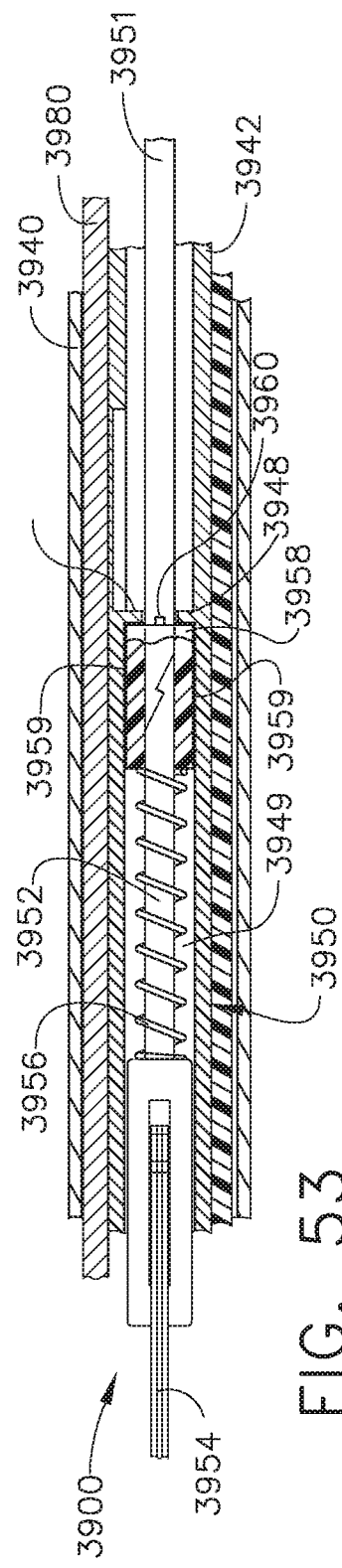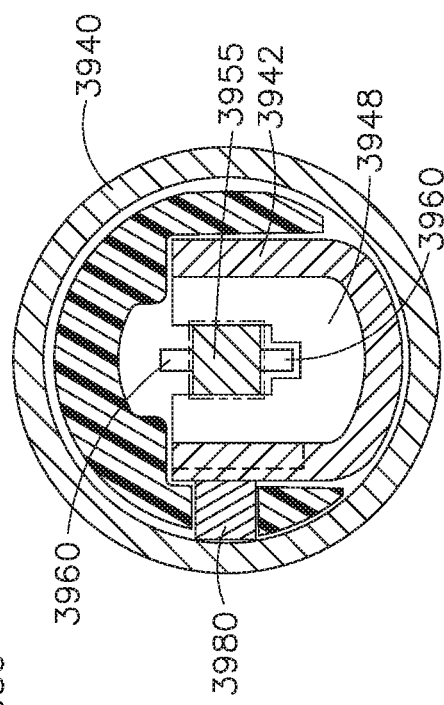
FIG. 52
FIG. 53
FIG. 54

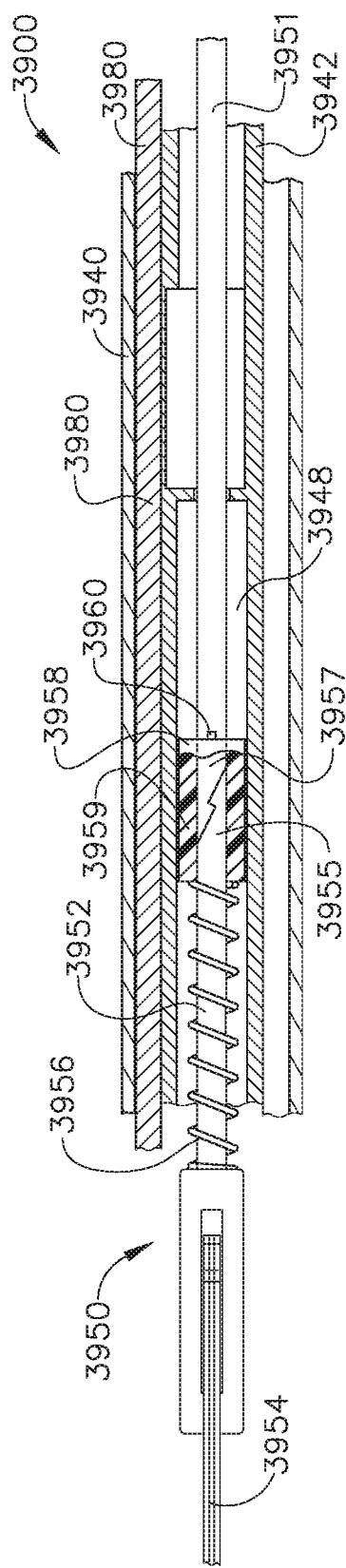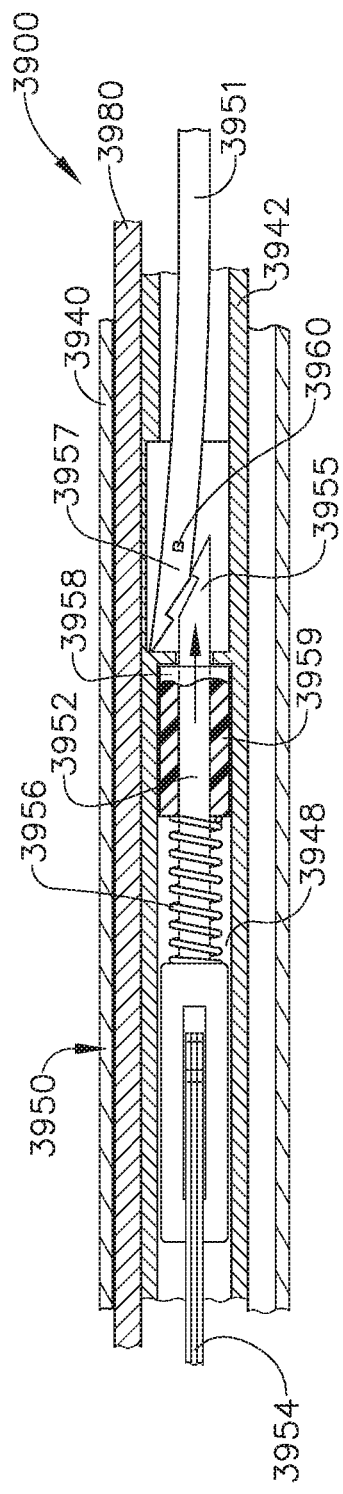

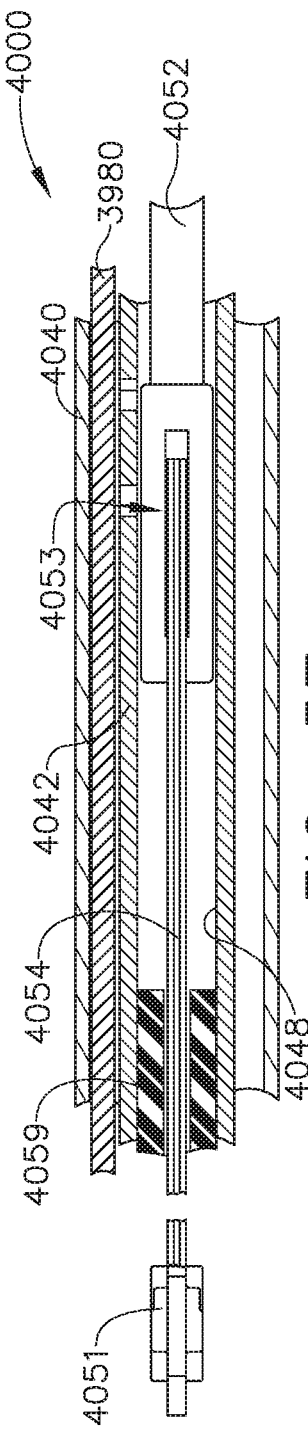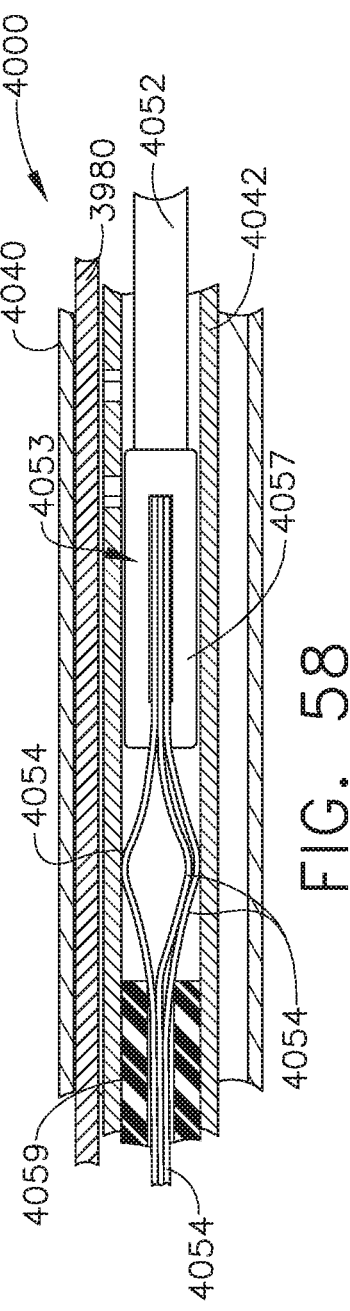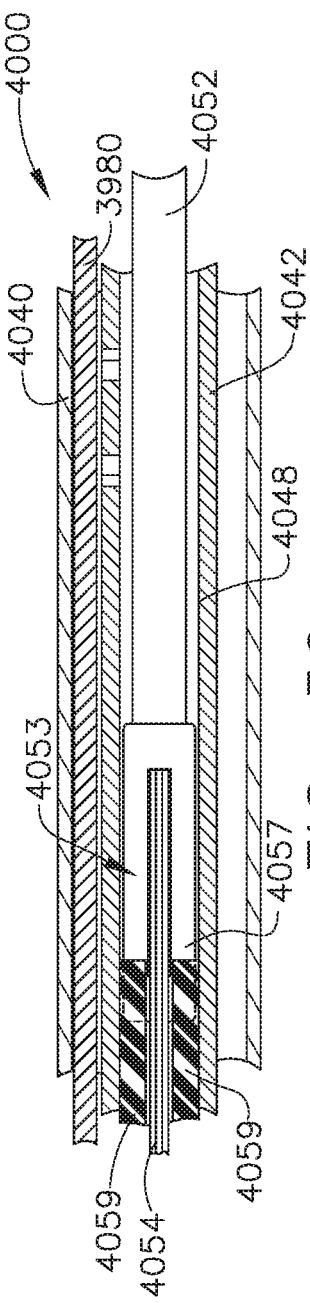

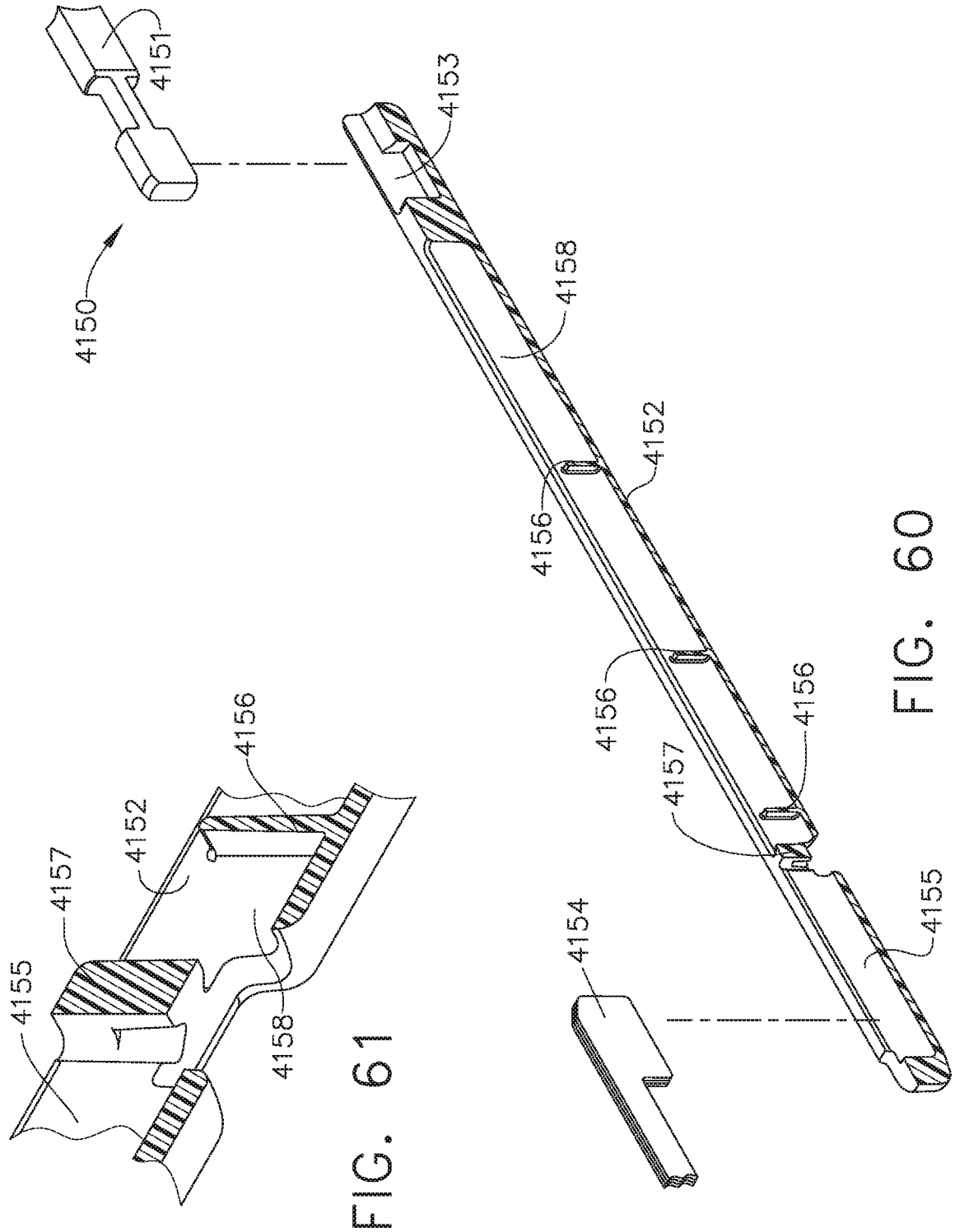

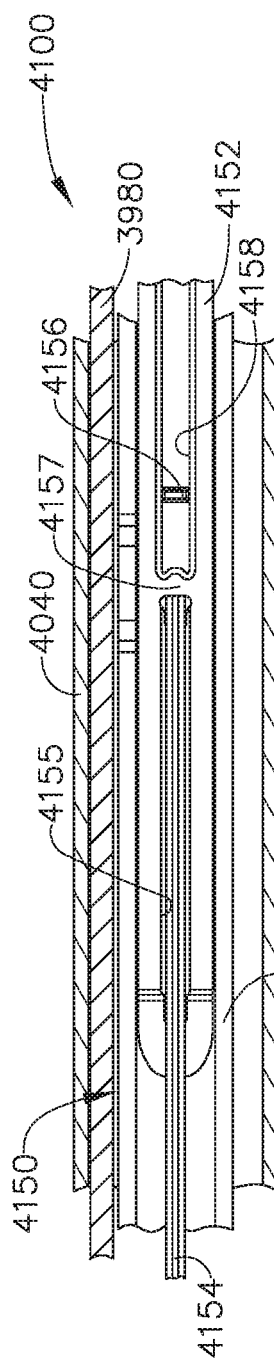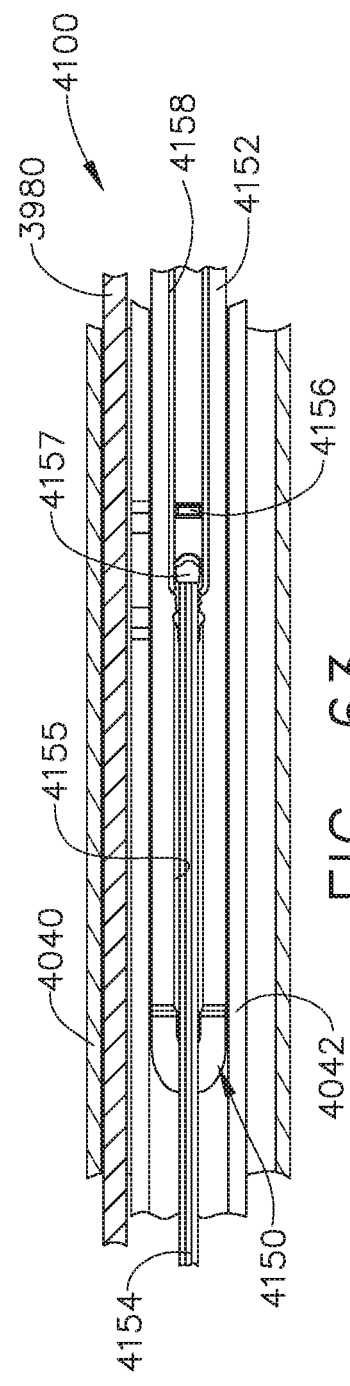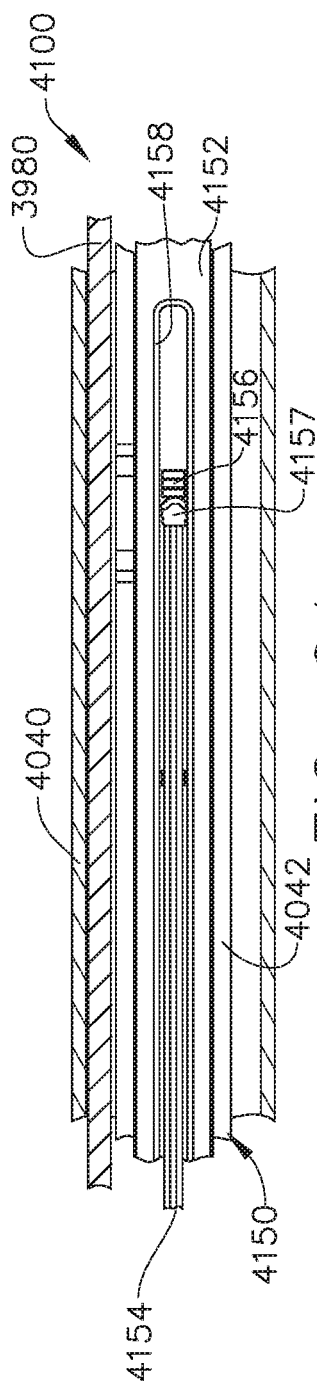

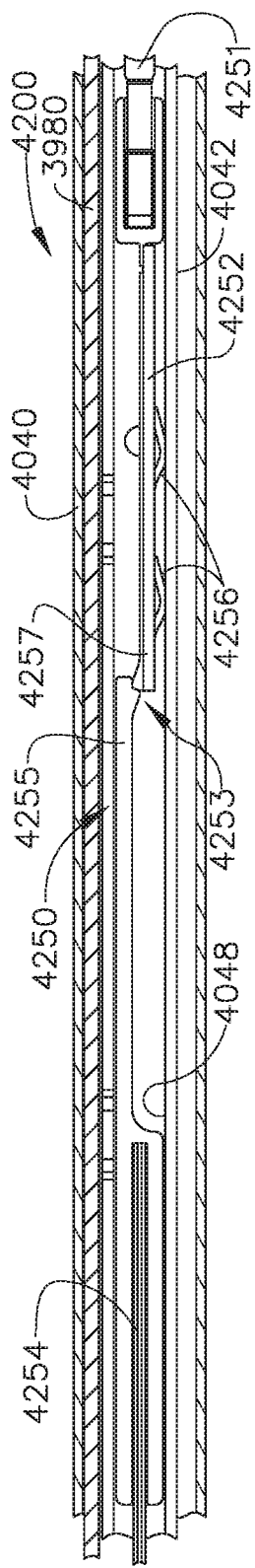
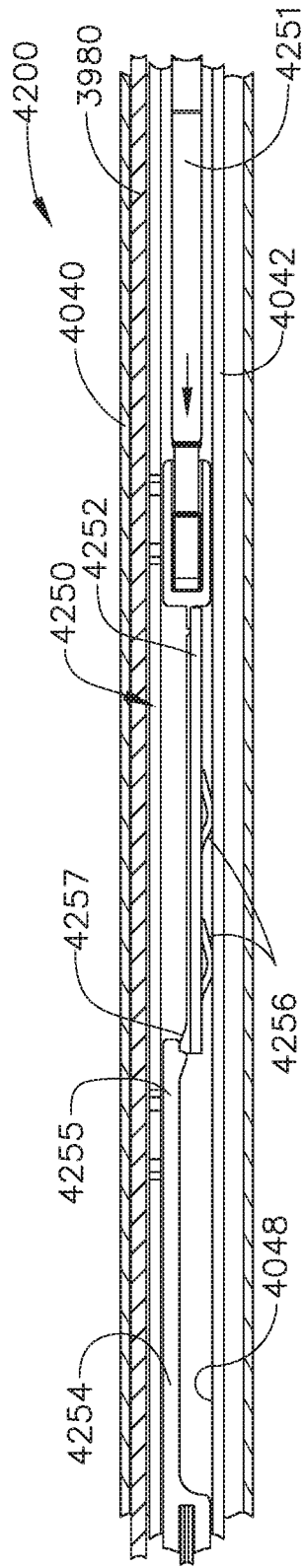
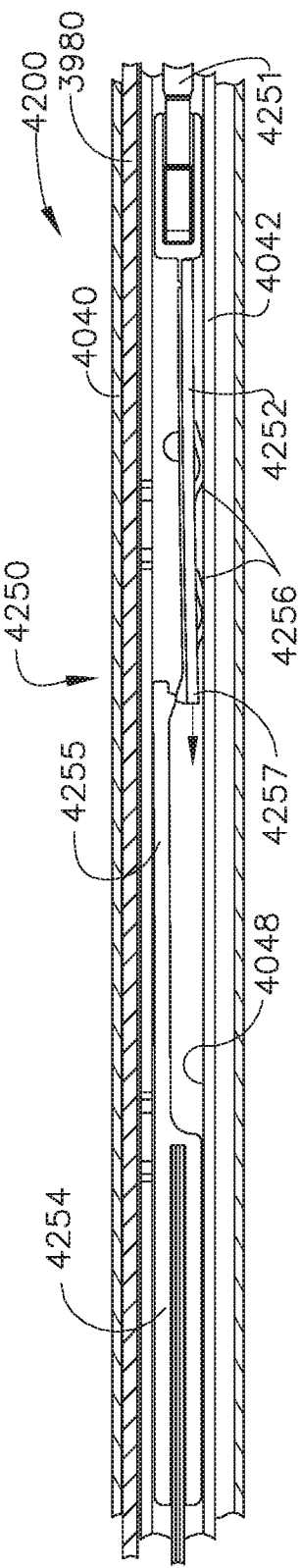

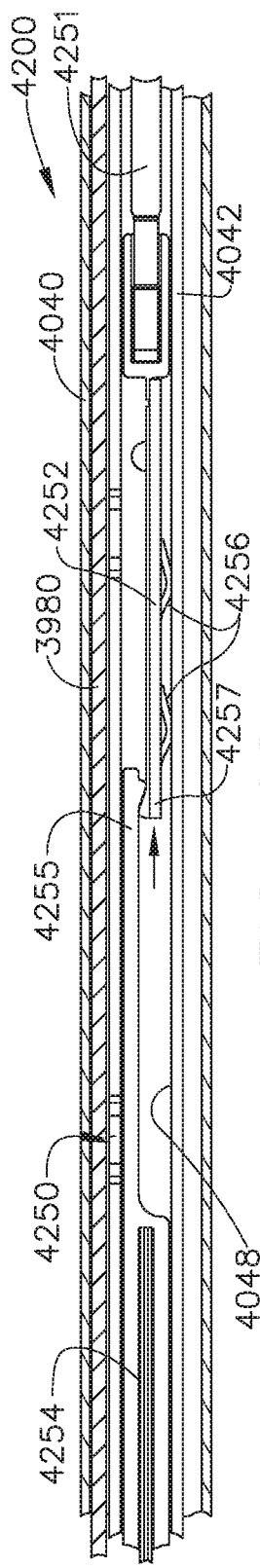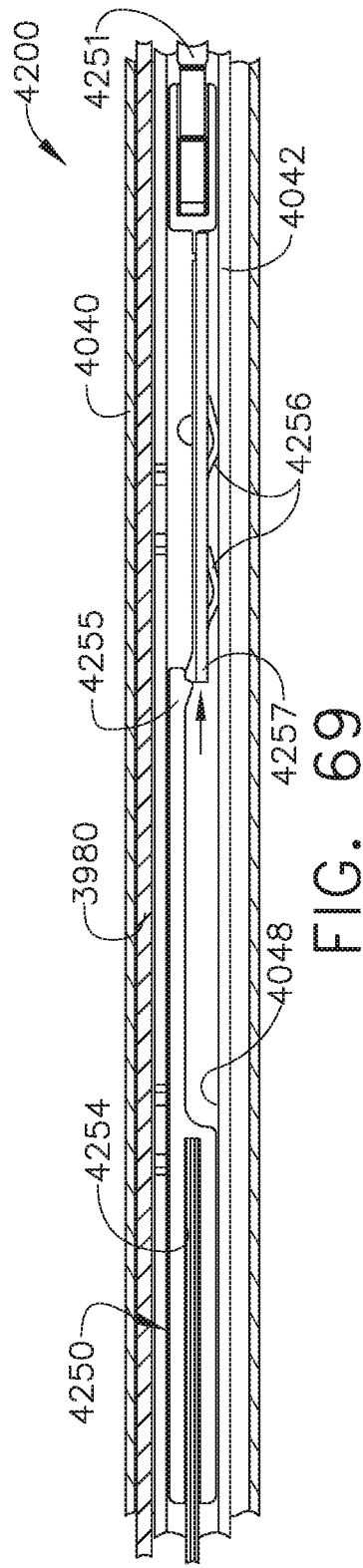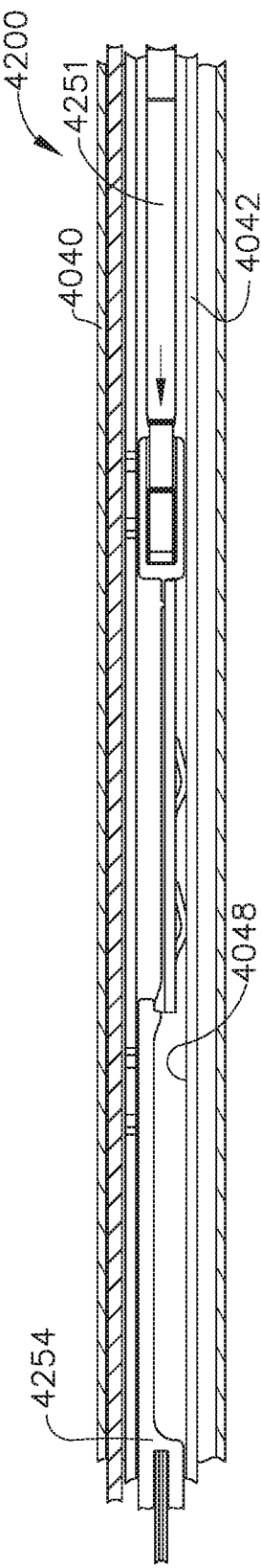

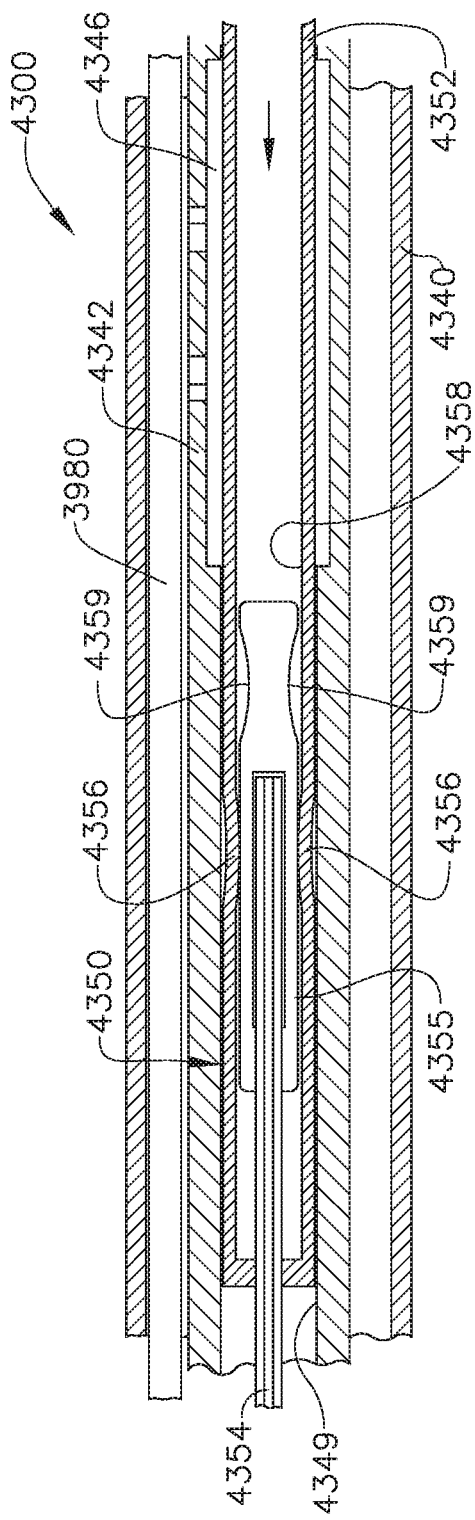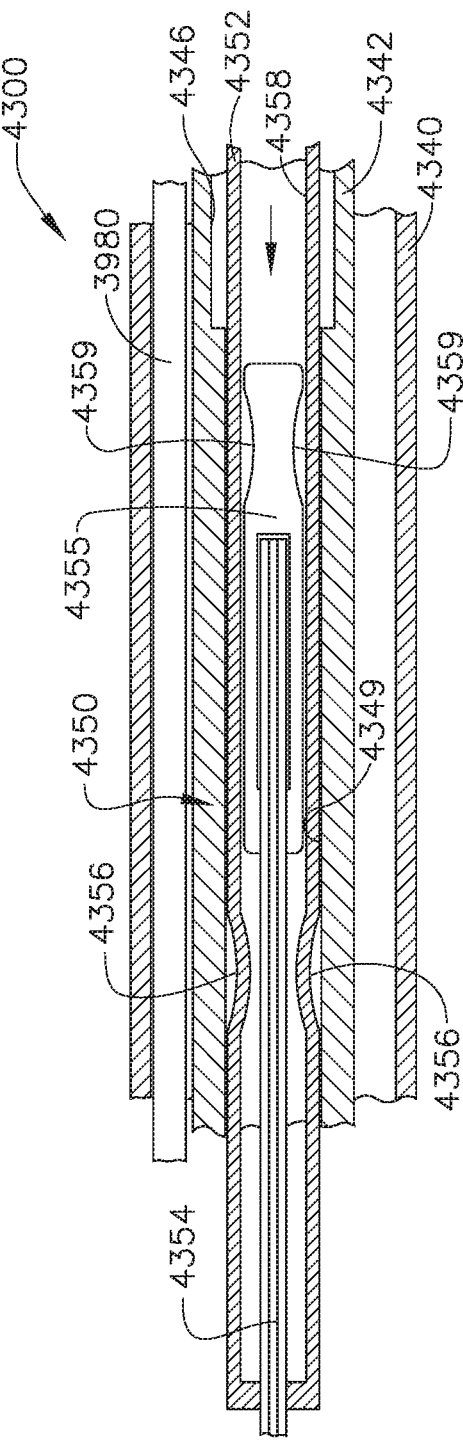

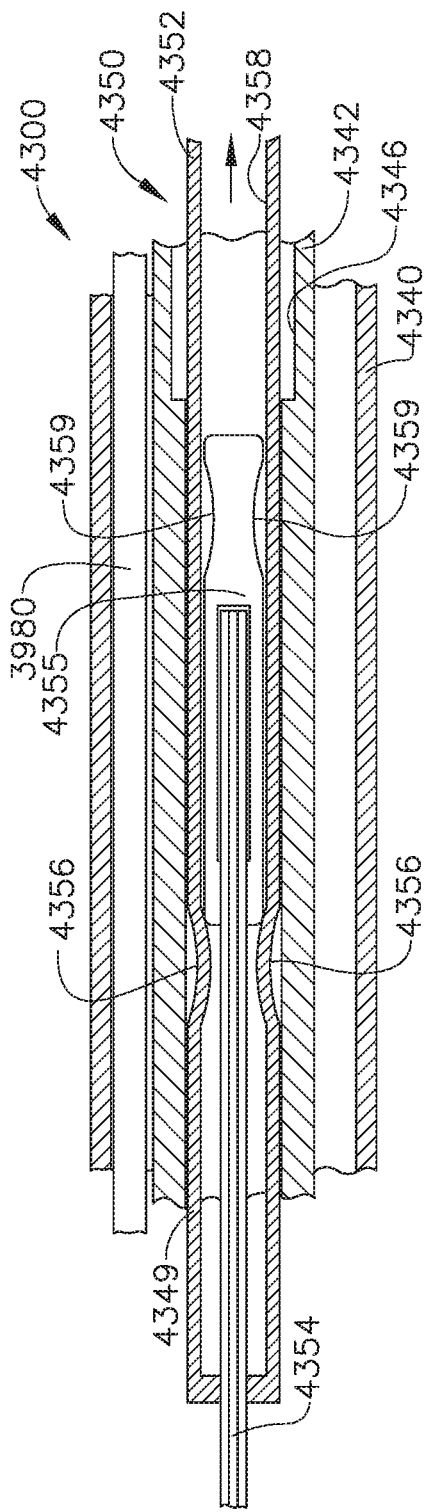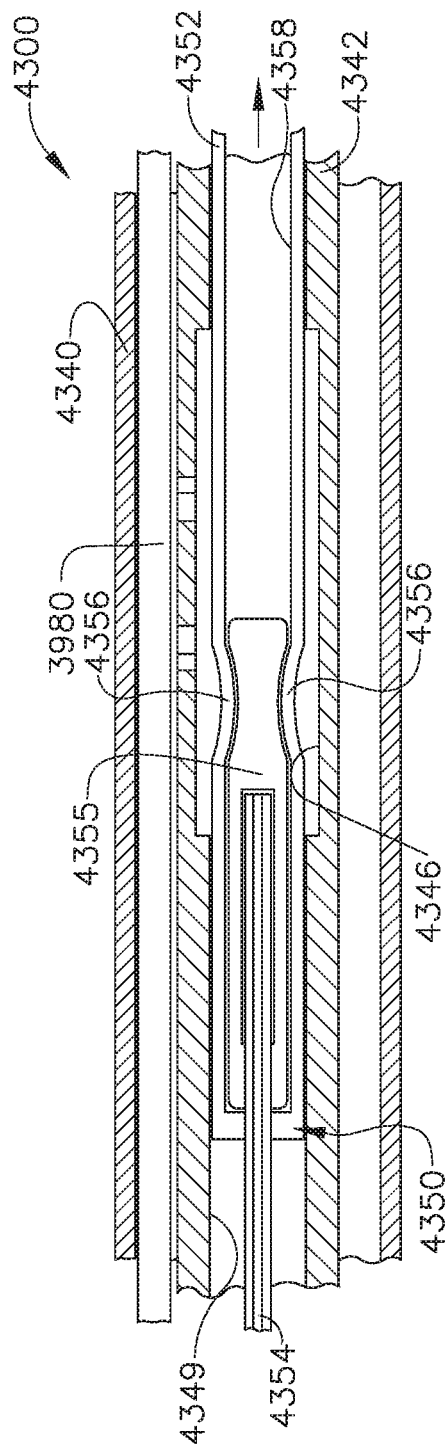

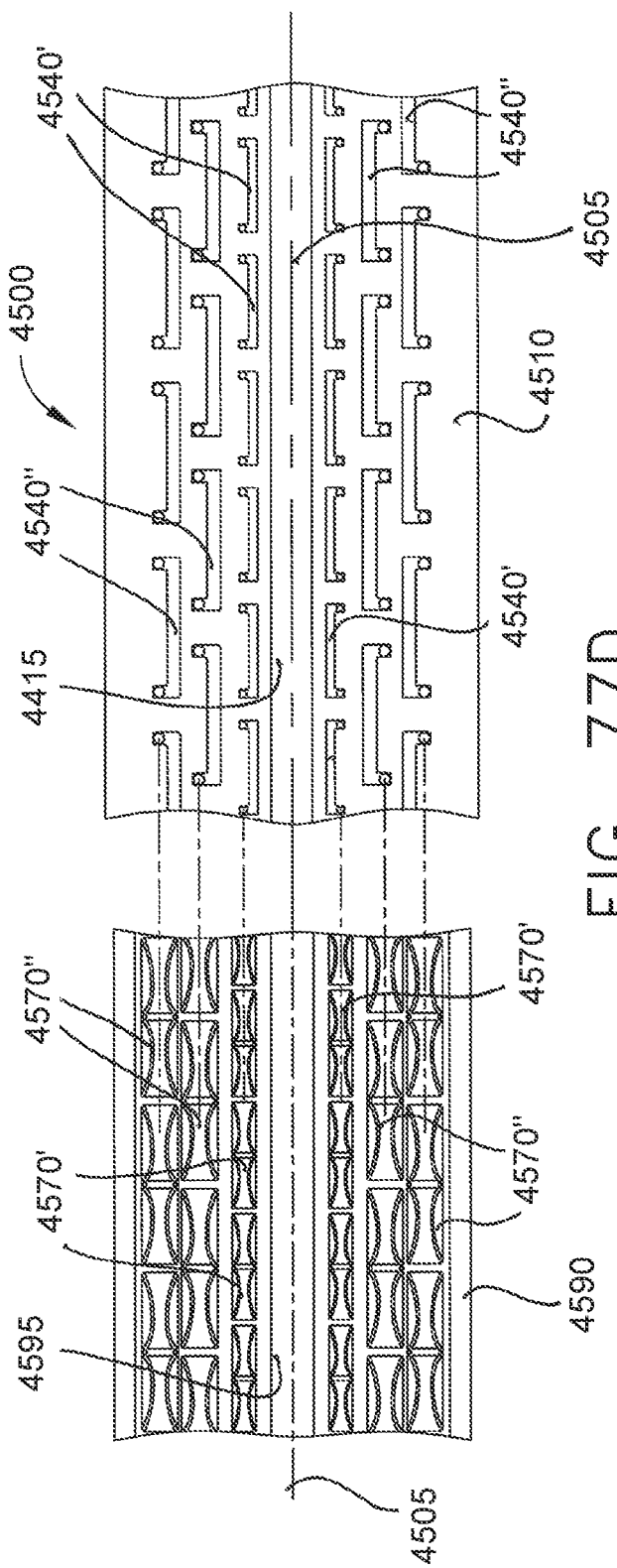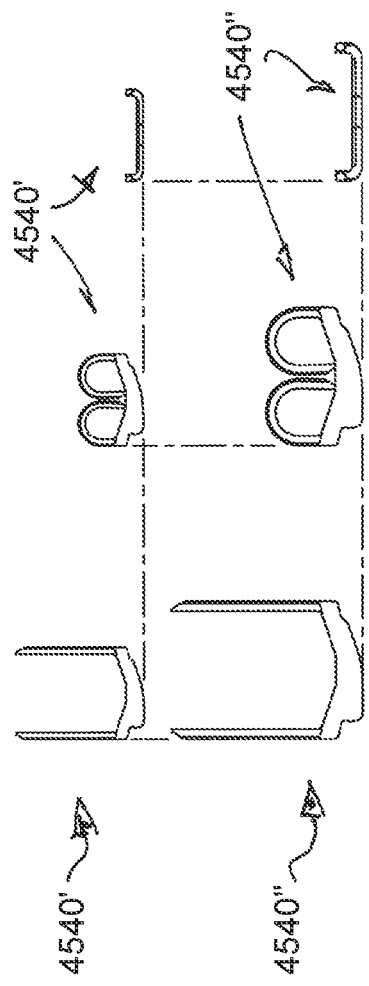
FIG. 77D
FIG. 77E

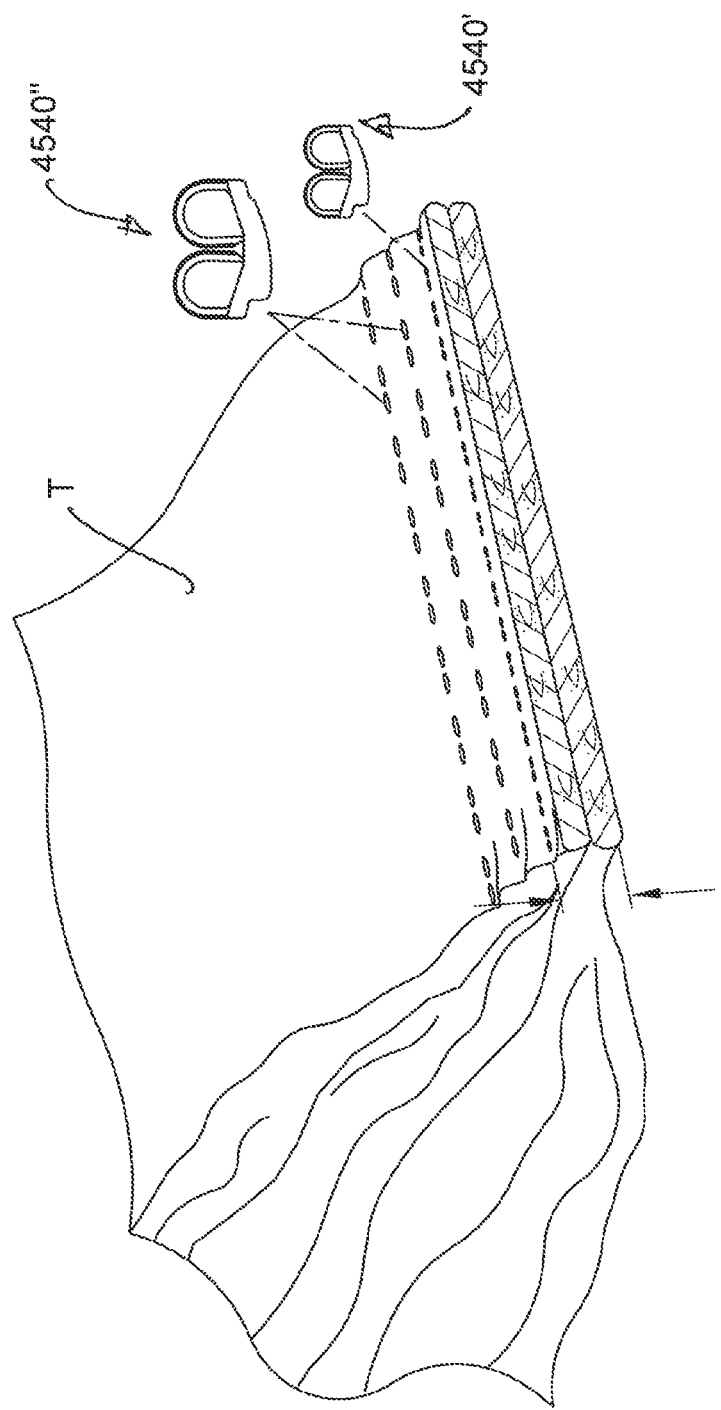

STAPLE FIRING MEMBER COMPRISING A MISSING CARTRIDGE AND/OR SPENT CARTRIDGE LOCKOUT

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 1G is a partial cross-sectional plan view of the surgical instrument of FIG. 1 illustrating the end effector in an unarticulated configuration;

FIG. 1H is a partial cross-sectional plan view of the surgical instrument of FIG. 1 illustrating the end effector in an articulated configuration;

FIG. 1I is a partial exploded view of the surgical instrument of FIG. 1;

FIG. 1J is a cross-sectional view of an anvil jaw of the surgical instrument of FIG. 1;

FIG. 2 is an elevational view of a cartridge jaw in accordance with at least one embodiment;

FIG. 3 is an elevational view of an end effector including the anvil jaw of FIG. 1 and the cartridge jaw of FIG. 2;

FIG. 7 is a partial cross-sectional view of a surgical instrument including the firing assembly of FIG. 6;

FIG. 8 is a partial cross-sectional view of the surgical instrument of FIG. 7 illustrated in a partially-opened configuration;

FIG. 9 is a perspective view of a coupling member of a firing member in accordance with at least one embodiment;

FIG. 10 is a partial perspective view of the firing member of FIG. 9 including a layered firing bar attached to the coupling member;

FIG. 11 is an end view of the firing member of FIG. 9;

FIG. 12 is a perspective view of a coupling member of a firing member in accordance with at least one embodiment;

FIG. 13 is a partial perspective view of a firing bar of the firing member of FIG. 12;

FIG. 14 is a partial perspective view of the firing member of FIG. 12;

FIG. 20 is a partial cross-sectional view of a surgical instrument including the firing assembly of FIG. 19 illustrated in a locked out configuration;

FIG. 21 is a partial cross-sectional view of the surgical instrument of FIG. 20 illustrated in an unlocked configuration;

FIG. 27 is an elevational view of the surgical instrument of FIG. 26 illustrated in an unfired configuration;

FIG. 28 is an elevational view of the surgical instrument of FIG. 26 illustrated in a partially-fired configuration;

FIG. 29 is an elevational view of the surgical instrument of FIG. 26 illustrated in a fully-fired configuration;

FIG. 30 illustrates the surgical instrument of FIG. 26 clamped onto a vessel;

FIG. 31 is a top plan view of a cartridge jaw in accordance with at least one embodiment;

FIG. 32 is a bottom plan view of the cartridge jaw of FIG. 31;

FIG. 35 is a partial cross-sectional view of a surgical instrument comprising a firing assembly including a firing force lockout illustrated in an unlocked condition;

FIG. 36 is a partial cross-sectional view of the surgical instrument of FIG. 35 illustrating the firing force lockout in a locked configuration;

FIG. 52 is a partial cross-sectional view of a surgical instrument comprising a firing member and a firing force lockout in accordance with at least one embodiment;

FIG. 53 is a partial cross-sectional view of the surgical instrument of FIG. 52 illustrating the firing member moved distally;

FIG. 54 is an end cross-sectional view of the surgical instrument of FIG. 52 taken along line 54-54 in FIG. 52;

FIG. 55 is a partial cross-sectional view of the surgical instrument of FIG. 52 illustrating the firing member in a fired position;

FIG. 56 is a partial cross-sectional view of the surgical instrument of FIG. 52 illustrating the firing force lockout in a locked condition;

FIG. 57 is a partial cross-sectional view of a surgical instrument comprising a firing member and a firing force lockout in accordance with at least one embodiment;

FIG. 58 is a partial cross-sectional view of the surgical instrument of FIG. 57 illustrating the firing force lockout in a locked condition;

FIG. 59 is a partial cross-sectional view of the surgical instrument of FIG. 57 illustrating the firing force lockout after it has been reset and the firing member advanced distally to perform a staple firing stroke;

FIG. 60 is a partial exploded view of a firing assembly of a surgical instrument in accordance with at least one embodiment;

FIG. 61 is a detail view of a fuse region of the firing assembly of FIG. 60 configured to fail when the firing load transmitted through the firing assembly exceeds a threshold;

FIG. 62 is a partial cross-sectional view of the surgical instrument of FIG. 60 illustrating the firing assembly in an unfired position and the fuse region in an intact state;

FIG. 63 is a partial cross-sectional view of the surgical instrument of FIG. 60 illustrating the fuse region in a failed state;

FIG. 64 is a partial cross-sectional view of the surgical instrument of FIG. 60 illustrating the firing assembly in a collapsed state;

FIG. 65 is a partial cross-sectional view of a surgical instrument comprising a firing assembly having a resettable fuse portion in accordance with at least one embodiment;

FIG. 66 is a partial cross-sectional view of the surgical instrument of FIG. 65 illustrating the firing assembly in a fired position;

FIG. 67 is a partial cross-sectional view of the surgical instrument of FIG. 65 illustrating the fuse portion in a failed state;

FIG. 68 is a partial cross-sectional view of the surgical instrument of FIG. 65 illustrating the fuse portion being retracted and reset;

FIG. 69 is a partial cross-sectional view of the surgical instrument of FIG. 65 illustrating the fuse portion in a reset state;

FIG. 70 is a partial cross-sectional view of the surgical instrument of FIG. 65 illustrating the firing assembly in a fired position;

FIG. 74 is a partial cross-sectional view of the surgical instrument of FIG. 71 illustrating the fuse portion in a first-stage failed state during the staple firing stroke of the firing assembly;

FIG. 75 is a partial cross-sectional view of the surgical instrument of FIG. 71 illustrating the fuse portion in a second-stage failed state during the staple firing stroke of the firing assembly;

FIG. 76 is a partial cross-sectional view of the surgical instrument of FIG. 71 illustrating the firing assembly being reset;

FIG. 77 is a partial cross-sectional view of the surgical instrument of FIG. 71 illustrating the firing assembly in a reset state;

FIG. 77D is a partial plan view of the staple cartridge of FIG. 77C and an anvil for use therewith;

FIG. 77E comprises elevational views of the staples of the staple cartridge of FIG. 77C in an unformed configuration, elevational views of the staples of the staple cartridge of FIG. 77C in a formed configuration, and plan views of the staples of the staple cartridge of FIG. 77C in an unformed configuration;

FIG. 77F illustrates the staples of FIG. 77E implanted into the tissue of a patient;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
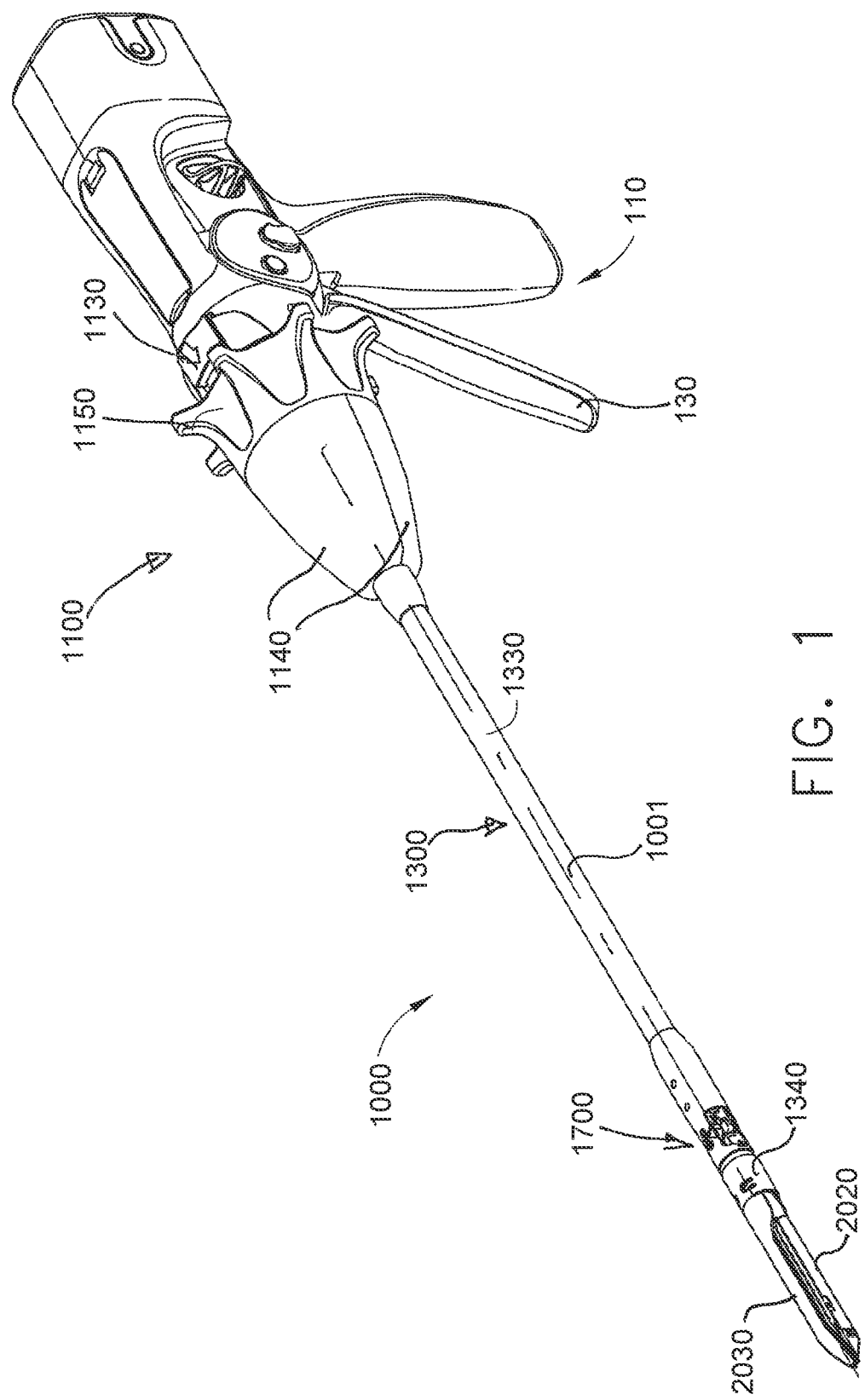
FIG. 1 is a perspective view of a surgical instrument including a handle and an interchangeable shaft assembly comprising an end effector in accordance with at least one embodiment.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,230, entitled ARTICULATABLE SURGICAL STAPLING INSTRUMENTS;

U.S. patent application Ser. No. 15/386,221, entitled LOCKOUT ARRANGEMENTS FOR SURGICAL END EFFECTORS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES; and U.S. patent application Ser. No. 15/386,240, entitled SURGICAL END EFFECTORS AND ADAPTABLE FIRING MEMBERS THEREFOR.

Applicant of the present application owns the following U.S. Patent Applications that were filed on Dec. 21, 2016 and which are each herein incorporated by reference in their respective entireties:

U.S. patent application Ser. No. 15/385,939, entitled STAPLE CARTRIDGES AND ARRANGEMENTS OF STAPLES AND STAPLE CAVITIES THEREIN;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TISSUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;

U.S. patent application Ser. No. 15/385,948, entitled SURGICAL STAPLING INSTRUMENTS AND STAPLE-FORMING ANVILS;

U.S. patent application Ser. No. 15/385,956, entitled SURGICAL INSTRUMENTS WITH POSITIVE JAW OPENING FEATURES;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT; and U.S. patent application Ser. No. 15/385,947, entitled STAPLE CARTRIDGES AND ARRANGEMENTS OF STAPLES AND STAPLE CAVITIES THEREIN.

Applicant of the present application owns the following U.S. Patent Applications that were filed on Dec. 21, 2016 and which are each herein incorporated by reference in their respective entireties:

U.S. patent application Ser. No. 15/385,896, entitled METHOD FOR RESETTING A FUSE OF A SURGICAL INSTRUMENT SHAFT;

U.S. patent application Ser. No. 15/385,898, entitled STAPLE FORMING POCKET ARRANGEMENT TO ACCOMMODATE DIFFERENT TYPES OF STAPLES;

U.S. patent application Ser. No. 15/385,899, entitled SURGICAL INSTRUMENT COMPRISING IMPROVED JAW CONTROL;

U.S. patent application Ser. No. 15/385,901, entitled STAPLE CARTRIDGE AND STAPLE CARTRIDGE CHANNEL COMPRISING WINDOWS DEFINED THEREIN;

U.S. patent application Ser. No. 15/385,902, entitled SURGICAL INSTRUMENT COMPRISING A CUTTING MEMBER;

U.S. patent application Ser. No. 15/385,905, entitled FIRING ASSEMBLY COMPRISING A LOCKOUT;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT;

U.S. patent application Ser. No. 15/385,908, entitled FIRING ASSEMBLY COMPRISING A FUSE; and U.S. patent application Ser. No. 15/385,909, entitled FIRING ASSEMBLY COMPRISING A MULTIPLE FAILED-STATE FUSE.

Applicant of the present application owns the following U.S. Patent Applications that were filed on Dec. 21, 2016 and which are each herein incorporated by reference in their respective entireties:

U.S. patent application Ser. No. 15/385,920, entitled STAPLE FORMING POCKET ARRANGEMENTS;

U.S. patent application Ser. No. 15/385,913, entitled ANVIL ARRANGEMENTS FOR SURGICAL STAPLERS;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;

U.S. patent application Ser. No. 15/385,893, entitled BILATERALLY ASYMMETRIC STAPLE FORMING POCKET PAIRS;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;

U.S. patent application Ser. No. 15/385,911, entitled SURGICAL STAPLERS WITH INDEPENDENTLY ACTUATABLE CLOSING AND FIRING SYSTEMS;

U.S. patent application Ser. No. 15/385,927, entitled SURGICAL STAPLING INSTRUMENTS WITH SMART STAPLE CARTRIDGES;

U.S. patent application Ser. No. 15/385,917, entitled STAPLE CARTRIDGE COMPRISING STAPLES WITH DIFFERENT CLAMPING BREADTHS;

U.S. patent application Ser. No. 15/385,900, entitled STAPLE FORMING POCKET ARRANGEMENTS COMPRISING PRIMARY SIDEWALLS AND POCKET SIDEWALLS;

U.S. patent application Ser. No. 15/385,931, entitled NO-CARTRIDGE AND SPENT CARTRIDGE LOCKOUT ARRANGEMENTS FOR SURGICAL STAPLERS;

U.S. patent application Ser. No. 15/385,915, entitled FIRING MEMBER PIN ANGLE;

U.S. patent application Ser. No. 15/385,897, entitled STAPLE FORMING POCKET ARRANGEMENTS COMPRISING ZONED FORMING SURFACE GROOVES;

U.S. patent application Ser. No. 15/385,922, entitled SURGICAL INSTRUMENT WITH MULTIPLE FAILURE RESPONSE MODES;

U.S. patent application Ser. No. 15/385,924, entitled SURGICAL INSTRUMENT WITH PRIMARY AND SAFETY PROCESSORS;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;

U.S. patent application Ser. No. 15/385,910, entitled ANVIL HAVING A KNIFE SLOT WIDTH;

U.S. patent application Ser. No. 15/385,903, entitled CLOSURE MEMBER ARRANGEMENTS FOR SURGICAL INSTRUMENTS; and U.S. patent application Ser. No. 15/385,906, entitled FIRING MEMBER PIN CONFIGURATIONS.

Applicant of the present application owns the following U.S. Patent Applications that were filed on Dec. 21, 2016 and which are each herein incorporated by reference in their respective entireties:

U.S. patent application Ser. No. 15/386,188, entitled STEPPED STAPLE CARTRIDGE WITH ASYMMETRICAL STAPLES;

U.S. patent application Ser. No. 15/386,192, entitled STEPPED STAPLE CARTRIDGE WITH TISSUE RETENTION AND GAP SETTING FEATURES;

U.S. patent application Ser. No. 15/386,206, entitled STAPLE CARTRIDGE WITH DEFORMABLE DRIVER RETENTION FEATURES;

U.S. patent application Ser. No. 15/386,226, entitled DURABILITY FEATURES FOR END EFFECTORS AND FIRING ASSEMBLIES OF SURGICAL STAPLING INSTRUMENTS;

U.S. patent application Ser. No. 15/386,222, entitled SURGICAL STAPLING INSTRUMENTS HAVING END EFFECTORS WITH POSITIVE OPENING FEATURES; and U.S. patent application Ser. No. 15/386,236, entitled CONNECTION PORTIONS FOR DISPOSABLE LOADING UNITS FOR SURGICAL STAPLING INSTRUMENTS.

Applicant of the present application owns the following U.S. Patent Applications that were filed on Dec. 21, 2016 and which are each herein incorporated by reference in their respective entireties:

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM;

U.S. patent application Ser. No. 15/385,890, entitled SHAFT ASSEMBLY COMPRISING SEPARATELY ACTUATABLE AND RETRACTABLE SYSTEMS;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;

U.S. patent application Ser. No. 15/385,894, entitled SHAFT ASSEMBLY COMPRISING A LOCKOUT; and U.S. patent application Ser. No. 15/385,895, entitled SHAFT ASSEMBLY COMPRISING FIRST AND SECOND ARTICULATION LOCKOUTS.

Applicant of the present application owns the following U.S. Patent Applications that were filed on Dec. 21, 2016 and which are each herein incorporated by reference in their respective entireties:

U.S. patent application Ser. No. 15/385,916, entitled SURGICAL STAPLING SYSTEMS;

U.S. patent application Ser. No. 15/385,918, entitled SURGICAL STAPLING SYSTEMS;

U.S. patent application Ser. No. 15/385,919, entitled SURGICAL STAPLING SYSTEMS;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES;

U.S. patent application Ser. No. 15/385,923, entitled SURGICAL STAPLING SYSTEMS;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;

U.S. patent application Ser. No. 15/385,932, entitled ARTICULATABLE SURGICAL END EFFECTOR WITH ASYMMETRIC SHAFT ARRANGEMENT;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVERDRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER;

U.S. Design patent application Ser. No. 29/569,227, entitled SURGICAL FASTENER;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS;

U.S. patent application Ser. No. 14/742,941, entitled SURGICAL END EFFECTORS WITH DUAL CAM ACTUATED JAW CLOSING FEATURES;

U.S. patent application Ser. No. 14/742,914, entitled MOVABLE FIRING BEAM SUPPORT ARRANGEMENTS FOR ARTICULATABLE SURGICAL INSTRUMENTS;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;

U.S. patent application Ser. No. 14/742,885, entitled DUAL ARTICULATION DRIVE SYSTEM ARRANGEMENTS FOR ARTICULATABLE SURGICAL INSTRUMENTS; and U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Patent Application Publication No. 2016/0256184;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;

U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Patent Application Publication No. 2016/0256155;

U.S. patent application Ser. No. 14/640,837, entitled SMART SENSORS WITH LOCAL SIGNAL PROCESSING, now U.S. Patent Application Publication No. 2016/0256163;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Patent Application Publication No. 2016/0256162; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Patent Application Publication No. 2016/0249919;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Patent Application Publication No. 2016/0249915;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Patent Application Publication No. 2016/0249908;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Patent Application Publication No. 2016/0249927; and U.S. patent application Ser. No. 14/633,562, entitled SURGICAL APPARATUS CONFIGURED TO TRACK AN END-OF-LIFE PARAMETER, now U.S. Patent Application Publication No. 2016/0249917.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Patent Application Publication No. 2016/0174977;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM, now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM, now U.S. Patent Application Publication No. 2016/0174971.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled POLARITY OF HALL MAGNET TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises,"

"has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

A surgical instrument comprising a handle 110 and a shaft assembly 1100 removably attachable to the handle 110 is illustrated in FIGS. 1-1J. The shaft assembly 1000 comprises an attachment portion 1100 configured to releasably attach the shaft assembly 1000 to the handle 110, a frame assembly 1200 extending distally from the attachment portion 1100, and an end effector rotatably coupled to the frame assembly 1200 about an articulation joint 1700. The end effector comprises a cartridge jaw 2020—which is configured to receive a staple cartridge 2010 therein—and an anvil jaw 2030. Referring primarily to FIG. 1E, the anvil jaw 2030 is rotatably coupled to the cartridge jaw 2020 about pins 2025. The shaft assembly 1000 further comprises a closure system 1300 configured to move the anvil jaw 2030 toward the cartridge jaw 2020, as discussed in greater detail further below. In addition, the shaft assembly 1000 further comprises a firing system 1400 configured to eject the staples removably stored in the staple cartridge 2010 and deform the staples against the anvil jaw 2030.

Figure 1A:
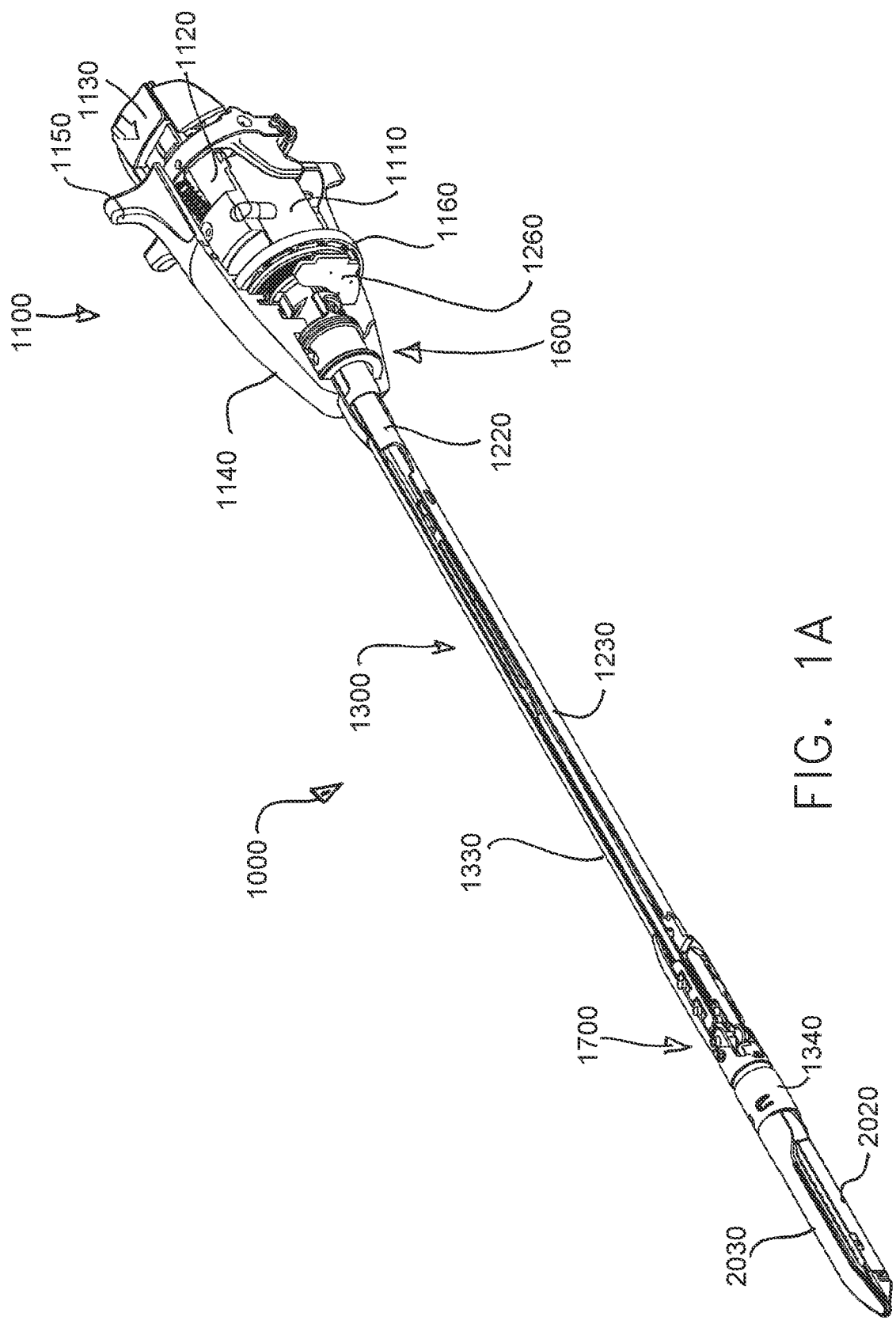
FIG. 1A is a perspective view of the surgical instrument of FIG. 1 illustrated with some components removed.
Figure 1B:
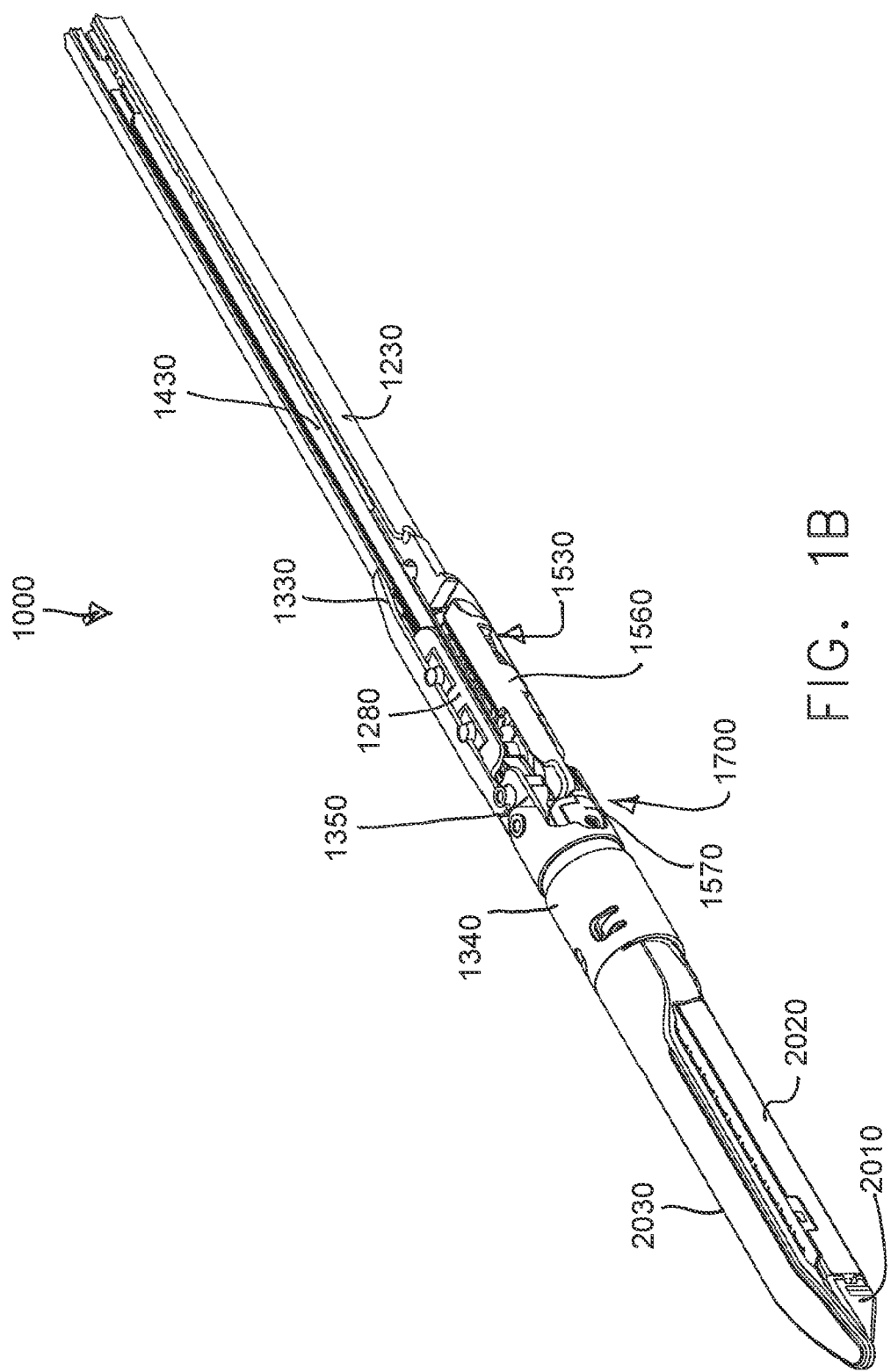
FIG. 1B is a perspective view of a distal portion of the surgical instrument of FIG. 1 illustrated with some components removed.
Figure 1C:
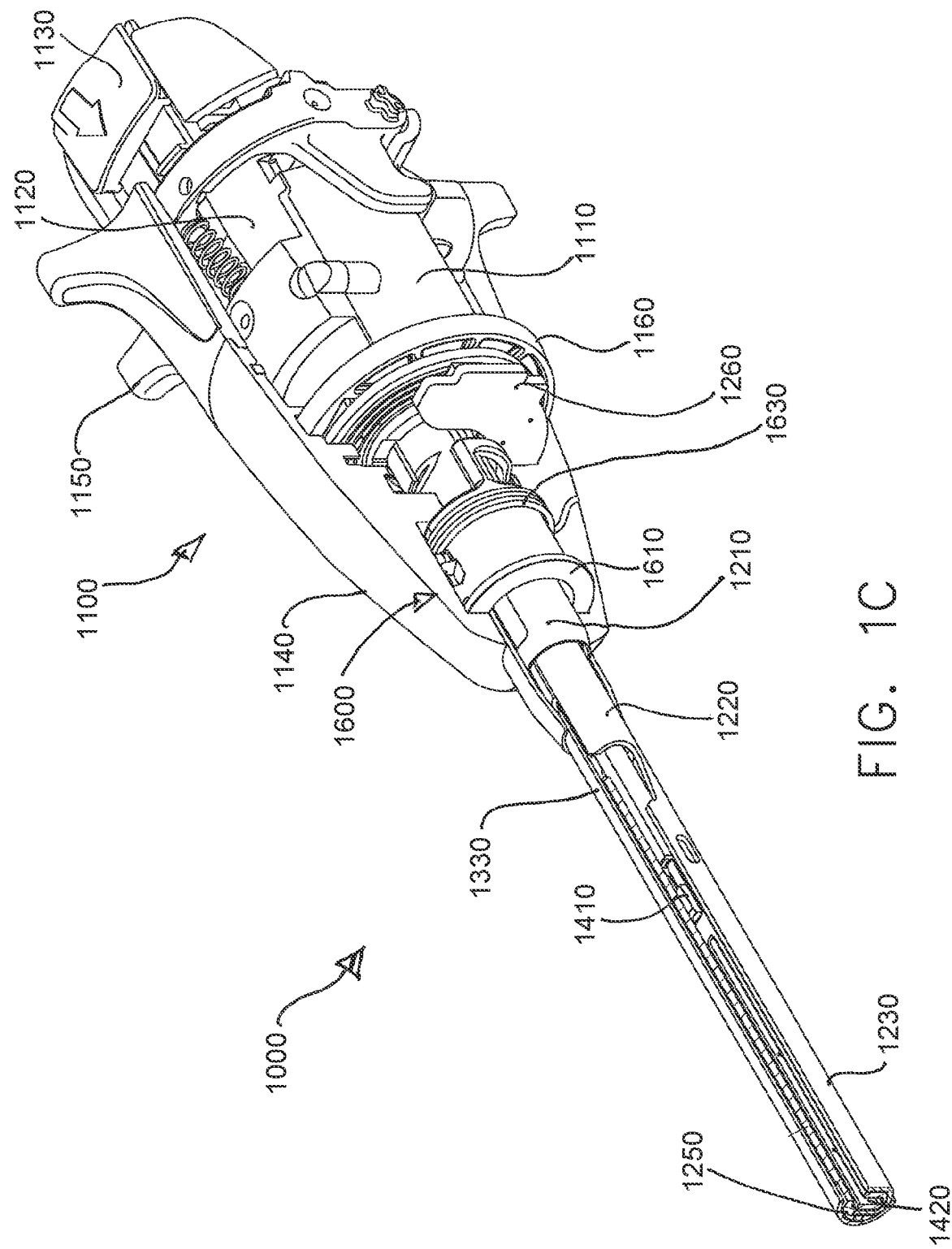
FIG. 1C is a perspective view of a proximal portion of the surgical instrument of FIG. 1 illustrated with some components removed.
Figure 1D:
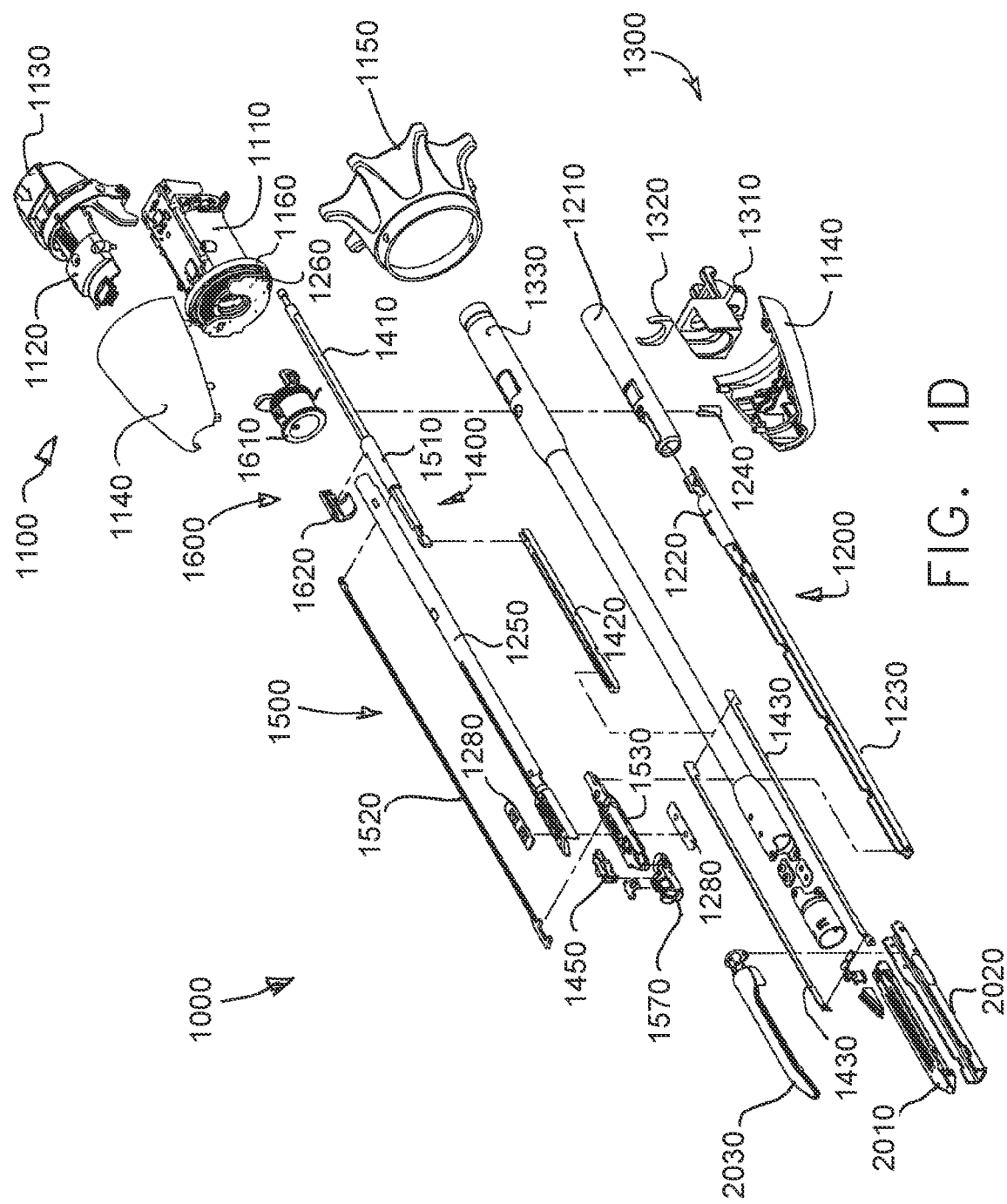
FIG. 1D is an exploded view of the surgical instrument of FIG. 1.
Figure 1E:
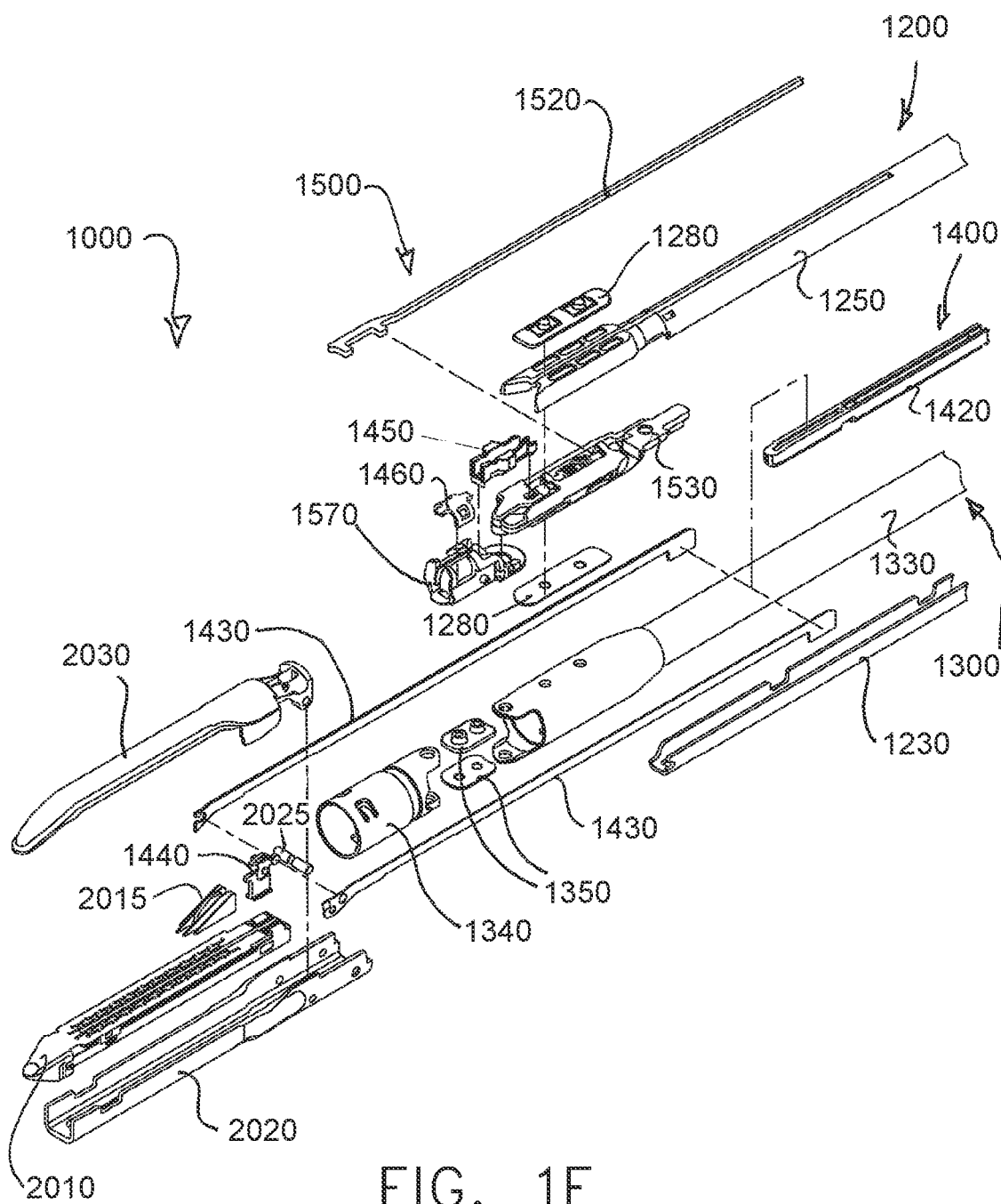
FIG. 1E is an exploded view of the distal end of the surgical instrument of FIG. 1.

Referring primarily to FIGS. 1A, 1C, and 1D, the attachment portion 1100 comprises a lower frame 1110 and, in addition, an upper frame 1120 attached to the lower frame 1110. The upper frame 1120 comprises a latch 1130 which is configured to releasably engage the frames 1110 and 1120 to a frame of the handle 110. The attachment portion 1100 further comprises housing portions 1140 and a nozzle 1150 attached to the housing portions 1140. The housing portions 1140 comprise one or more grooves and/or one or more walls defined therein which are configured to permit the housing portions 1140 and the nozzle 1150 to rotate—but not translate, or at least substantially translate—relative to the frames 1110 and 1120. Moreover, the housing portions 1140 comprise one or more grooves and/or one or more walls defined therein which are configured to mount the frame assembly 1200 thereto. The frame assembly 1200 is engaged with the housing portions 1140 such that the frame assembly 1200, the housing portions 1140, and the nozzle 1150 are rotatable together about a longitudinal axis 1001 of the shaft assembly 1000.

Figure 1F:
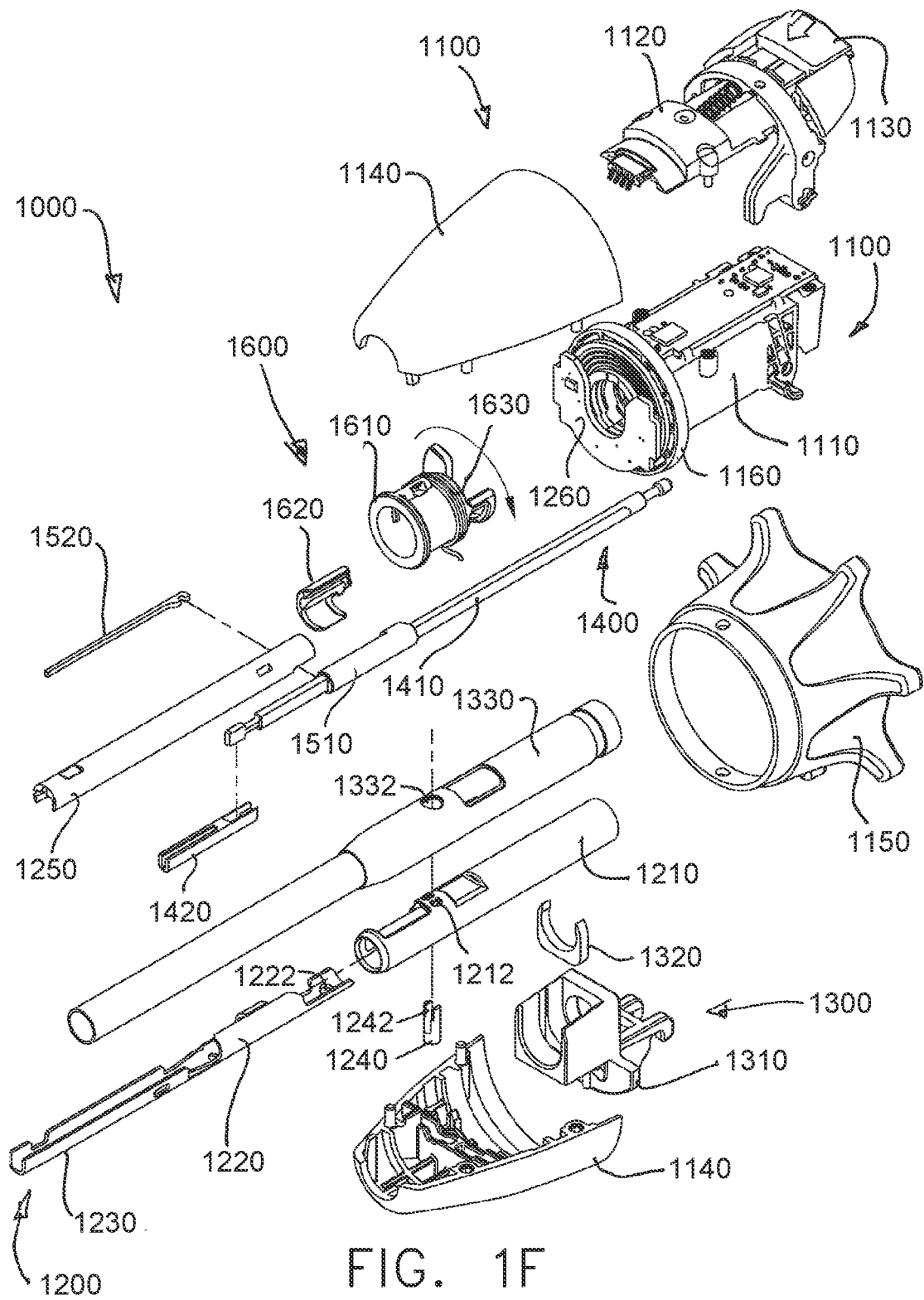
FIG. 1F is an exploded view of the proximal end of the surgical instrument of FIG. 1.

Referring primarily to FIGS. 1D, 1E, and 1F, the frame assembly 1200 comprises a proximal frame portion 1210, an intermediate frame portion 1220, and a distal frame portion 1230. The frame portions 1210, 1220, and 1230 comprise a rigid, or at least substantially rigid, spine of the shaft assembly 1100. The proximal end of the proximal frame portion 1210 is mounted to a slip joint interface 1260. The slip joint interface 1260 co-operates with a slip joint interface 1160 defined on the lower frame 1110 of the attachment portion 1100 which is configured to permit the frame assembly 1200 to rotate relative to the frames 1110 and 1120, as discussed above. In addition, the slip joint interfaces 1160 and 1260 co-operate to provide an electrical interface which can electrically couple sensors in the end effector, for example, and the attachment portion 1100. The attachment portion 1100 comprises one or more circuits in electrical communication with the slip joint interface 1160 which can be placed in electrical communication with a control module and/or microprocessor of the handle 110, for example, when the shaft assembly 1000 is attached to the handle 110.

Further to the above, referring primarily to FIGS. 1D, 1E, and 1F, the frame assembly 1200 further comprises a spine cover 1250. The spine cover 1250 co-operates with the frame portions 1210, 1220, and 1230 to enclose, or at least substantially enclose, the firing system 1400 therein. The frame assembly 1200 further comprises spacers 1280 which are configured to prevent, or at least limit, relative movement between the frame assembly 1200 and the closure system 1300. Each spacer 1280 comprises one or more pins extending therefrom which extend into apertures defined in the closure system 1300.

Referring primarily to FIGS. 1D, 1E, and 1F, the closure assembly 1300 comprises a closure actuator 1310 that is operably coupled with a closure trigger 130 of the handle 110 when the shaft assembly 1000 is assembled to the handle 110. The closure assembly 1300 further comprises a closure tube 1330 and, in addition, a tube retainer 1320 configured to mount the closure tube 1330 to the closure actuator 1310. More specifically, the tube retainer 1320 mounts the closure tube 1330 to the closure retainer 1310 such that the closure retainer 1310 can push the closure tube 1330 distally and pull the closure tube 1330 proximally. Referring primarily to FIG. 1E, the closure assembly 1300 further comprises a distal closure tube 1340 which is rotatably coupled to the closure tube 1330 via articulation links 1350. When the closure tube 1330 is pushed distally by the closure actuator 1310, the closure tube 1330 pushes the distal closure tube 1340 into engagement with the anvil jaw 2030 and moves the anvil jaw 2030 toward the cartridge jaw 2020. When the closure tube 1330 is pulled proximally by the closure actuator 1310, the distal closure tube 1340 can disengage from the anvil jaw 2030 which can allow the anvil jaw 2030 to be opened. In other instances, the distal closure tube 1340 can pull the anvil jaw 2030 into an open, or an at least partially open, position when the distal closure tube 1340 is retracted.

Referring primarily to FIGS. 1D, 1E, and 1F, the firing assembly 1400 comprises a proximal firing rod 1410 that is operably engaged with a firing system of the handle 110 when the shaft assembly 1000 is assembled to the handle 110. The firing assembly 1400 further comprises an intermediate firing rod 1420 coupled to the proximal firing rod 1410 and, in addition, a firing bar 1430 coupled to the intermediate firing rod 1420. The firing bar 1430 is comprised of a plurality of flexible layers, but can comprise any suitable configuration. The firing assembly 1400 further comprises a coupling member 1440 mounted to the firing bar 1430. When the firing assembly 1400 is advanced distally by the firing system of the handle 110, the coupling member 1440 pushes a sled 2015 of the staple cartridge 2010 distally to eject the staples from the staple cartridge 2010 and into tissue captured between the staple cartridge 2010 and the anvil jaw 2030. The coupling member 1440 also comprises a cutting edge which incises the tissue as the coupling member 1440 is advanced distally to eject the staples.

Further to the above, referring to FIGS. 1F and 1I, the shaft assembly 1000 further comprises a frame pin 1240. The frame pin 1240 couples the frame assembly 1200 and the firing assembly 1400 together such that they can rotate in unison about the longitudinal axis 1001 when the nozzle 1150 is rotated about the longitudinal axis 1001, as discussed above. Referring primarily to FIG. 1I, the frame pin 1240 extends through, and is snugly positioned within, an aperture 1222 defined in the intermediate frame portion 1220. The frame pin 1240 also comprises projections 1242 which extend into apertures 1212 defined in the proximal frame portion 1210. Similar to the above, the projections 1242 are snugly positioned in the apertures 1212. In addition, the frame pin 1240 also comprises a slot 1244 defined therein. The proximal firing rod 1410 extends through the slot 1244 and slides relative to the frame pin 1240 when the proximal firing rod 1410 is moved proximally and distally, as discussed above. The sidewalls of the slot 1244 are spaced apart from one another in order to closely receive the lateral sides 1412 of the proximal firing rod 1410 therebetween. As a result, the frame pin 1240 can transfer the rotation of the frame assembly 1200 to the firing assembly 1400 when the frame assembly 1200 is rotated about the longitudinal axis 1001, as discussed above. Referring primarily to FIG. 1F, the closure tube 1330 can also comprise a clearance aperture 1332 defined therein which is configured to receive a portion of the frame pin 1240 therein.

Referring primarily to FIGS. 1E, 1F, 1G, and 1H, the shaft assembly 1000 further comprises an articulation system 1500 configured to articulate the end effector about the articulation joint 1700. The articulation system 1500 comprises an articulation driver 1510 mounted to the proximal firing rod 1410 and, in addition, an articulation bar 1520 which is selectively engageable with the articulation driver 1510. When the articulation bar 1520 is engaged with the articulation driver 1510, the movement of the proximal firing rod 1410 is transmitted to the articulation bar 1520. In such instances, the shaft assembly 1000 is in an articulation operating mode. When the articulation bar 1520 is not engaged with the articulation driver 1510, the movement of the proximal firing rod 1410 is not transmitted to the articulation bar 1520. In such instances, the shaft assembly 1000 is in a firing operating mode. As a result of the above, the movement of the firing assembly 1400 is selectively transferable to the articulation system 1500. As discussed in greater detail below, the shaft assembly 1000 further comprises a switching system 1600 configured to switch the shaft assembly 1000 between its articulation operating mode and its firing operating mode.

Referring primarily to FIGS. 1C and 1F, the switching system 1600 comprises a shift collar 1610 and a shift plate 1620. The shift collar 1610 is rotatable about the longitudinal axis 1001 of the shaft assembly 1000 between an unactuated position and an actuated position. The closure assembly 1300 is configured to drive the switching system 1600 and rotate the shift collar 1610 from its unactuated position to its actuated position when the closure assembly 1300 is advanced distally to close the anvil jaw 2030. The shift collar 1610 is configured to drive the shift plate 1620 longitudinally from a first position to a second position when the shift collar 1610 is moved from its unactuated position to its actuated position. When the shift plate 1620 is in its first position, the articulation bar 1520 is operably engaged with the proximal firing rod 1410 and the shaft assembly 1000 is in its articulation operating mode. In such instances, the proximal and distal movement of the firing assembly 1400 is transferred to the articulation assembly 1500. When the shift plate 1620 is moved into its second position, the shift plate 1620 operably decouples the articulation bar 1520 from the proximal firing rod 1410 and the shaft assembly 1000 is in its firing operating mode. In such instances, the proximal and distal movement of the firing assembly 1400 is not transferred to the articulation assembly 1500.

When the closure assembly 1300 is pulled proximally to disengage the distal closure tube 1340 from the anvil jaw 2030, further to the above, the shift collar 1610 can be rotated back into its unactuated position. Referring again to FIG. 1F, the switching system 1600 further comprises a biasing member, or spring, 1630 configured to bias the shift collar 1610 into its unactuated position.

Referring primarily to FIGS. 1G and 1H, the articulation system 1500 further comprises an articulation assembly 1530 fixedly mounted to the distal frame portion 1230. The articulation assembly 1530 comprises an articulation frame 1540 and, in addition, a lock system 1550 slidably mounted to the articulation frame 1540. The lock system 1550 is slidable in a distal direction to allow the end effector to be rotated about the articulation joint 1700 in a first direction. The lock system 1550 is also slidable in a proximal direction to allow the end effector to be rotated about the articulation joint 1700 in a second direction. The articulation bar 1520 is operably engaged with the lock system 1550 such that the articulation bar 1520 can push the lock system 1550 distally when the articulation bar 1520 is pushed distally by the proximal firing rod 1410. Moreover, the articulation bar 1520 is operably engaged with the lock system 1550 such that the articulation bar 1520 can pull the lock system 1550 proximally when the articulation bar 1520 is pulled proximally by the proximal firing rod 1410.

Further to the above, the articulation assembly 1530 further comprises an articulation link 1560. Similar to the lock system 1550, the articulation bar 1520 is configured to push the articulation link 1560 distally when the articulation bar 1520 is pushed distally and, correspondingly, configured to pull the articulation link 1560 proximally when the articulation bar 1520 is pulled proximally. The distal end of the articulation link 1560 is engaged with a channel retainer 1570 fixedly mounted in the cartridge jaw 1220. More specifically, the channel retainer 1570 comprises a pin extending therefrom which is positioned within an aperture defined in the articulation link 1560. When the articulation link 1560 is pushed distally, further to the above, the articulation link 1560 drives the end effector in its first direction. When the articulation link 1560 is pulled proximally, the articulation link 1560 drives the end effector in a second, or opposite, direction, as illustrated in FIG. 1H.

The articulation assembly 1530, further to the above, is configured and arranged such that it prevents the rotation of the end effector about the articulation joint 1700 when the lock system 1550 is in a neutral, or unpushed, state. When the lock system 1550 is pushed distally or pulled proximally by the articulation bar 1520, the articulation assembly 1530 is unlocked so that the end effector can be rotated about the articulation joint 1700. In order to relock the end effector in position, the articulation bar 1520 can be used to re-position the lock system 1550 in its neutral state and/or allow a biasing member to re-position the lock system 1550 in its neutral state.

Referring again to FIGS. 1G and 1H, the shaft assembly 1000 further comprises a knife guide 1450 positioned within and/or adjacent to the articulation joint 1700. The knife guide 1450 is configured to support the firing bar 1430 when the end effector is in an articulated configuration, as illustrated in FIG. 1H, among other configurations. The knife guide 1450 comprises lateral sidewalls 1454 defined therein which are configured to support and/or guide the layers of the firing bar 1430—especially when the firing bar 1430 is moved proximally and distally, as described above. The knife guide 1450 is configured to rotate within the articulation joint 1700 when the end effector is rotated. More specifically, the knife guide 1450 rotates in a first direction when the end effector is rotated in a first direction and, correspondingly, the knife guide 1450 rotates in a second direction when the end effector is rotated in a second direction. The distal end 1456 of the knife guide 1450 comprises a post extending therefrom which is positioned in an aperture defined in the channel retainer 1570 which can serve as a pivot joint between the knife guide 1450 and the channel retainer 1570.

Referring primarily to FIGS. 1G and 1H, the shaft assembly 1000 further comprises a cap 1460 engaged with the channel retainer 1570. In at least one instance, the cap 1460 is engaged with the channel retainer 1570 in a snap-fit manner, for example. The cap 1460 is configured to limit the vertical movement of the firing bar 1430 and hold the firing bar 1430 in the knife guide 1450.

Referring again to FIG. 1H, the knife guide 1450 comprises lateral pushers 1452 extending therefrom. The lateral pushers 1452 are configured to push the tissue of a patient out of the articulation joint 1700 when the end effector and the knife guide 1450 are rotated, as described above. Stated another way, the lateral pushers 1452 are configured to push the tissue away from the pinch points between the cartridge jaw 2020 and the frame assembly 1200, for example. Moreover, the lateral pushers 1452 are configured to block, or close, gaps defined between the cartridge jaw 2020 and the frame assembly 1200.

A surgical instrument 2000 is illustrated in FIGS. 1-3. The surgical instrument 2000 comprises a cartridge jaw 2020 and an anvil jaw 2030. The cartridge jaw 2020 comprises a staple cartridge 2010 which includes a plurality of staples removably stored therein. The staple cartridge 2010 is replaceable and can be removed from the cartridge jaw 2020; however, other embodiments are envisioned in which the staple cartridge 2020 is not replaceable. The staple cartridge 2010 comprises a proximal end 2011, a distal end 2013, and a tissue compression surface 2012 extending between the proximal end 2011 and the distal end 2013. The staple cartridge 2010 further comprises staple cavities defined in the tissue compression surface 2012 and staples removably stored in the staple cavities. The anvil jaw 2030 comprises a proximal end 2031, a distal end 2033, and a tissue compression surface 2032 extending between the proximal end 2031 and the distal end 2033. The anvil jaw 2030 further comprises staple forming pockets defined in the tissue compression surface 2032.

The anvil jaw 2030 is rotatably coupled to the cartridge jaw 2020. Referring to FIG. 2, the cartridge jaw 2020 comprises apertures 2016 defined on opposite sides thereof.

Each aperture 2016 is elongate and extends along a vertical axis 2001. The anvil jaw 2030 comprises projections 2036 that extend laterally therefrom in opposite directions. The projections 2036 are slidably positioned within the apertures 2016. The apertures 2016 and the projections 2036 define a joint about which the anvil jaw 2030 can be rotated relative to the cartridge jaw 2020 between an open position and a closed position. The projections 2036 are closely received between the vertical sidewalls of the apertures 2016 such that proximal and/or distal longitudinal movement of the anvil jaw 2030 relative to the cartridge jaw 2020 is prevented, or at least inhibited. That said, the projections 2036 are movable vertically within the apertures 2016, as described in greater detail further below. In some embodiments, an anvil jaw may comprise a pivot pin about which the anvil jaw is rotatable relative to a cartridge jaw between an open position and a fully-closed position.

Further to the above, the surgical instrument 2000 comprises a closure member, or tube, 2040 configured to contact the anvil jaw 2030 and move the anvil jaw 2030 from its open position toward its closed position (FIG. 3) during a closure stroke. More specifically, the closure tube 2040 comprises a distal tube end 2045 configured to engage a cam surface 2035 defined on the anvil jaw 2030 and rotate the distal end 2033 of the anvil jaw 2030 toward the distal end 2013 of the staple cartridge 2010. The closure tube 2040 slides distally along the cam surface 2035 until the distal tube end 2045 comes into contact with a push shoulder 2037 defined on the anvil jaw 2030. In such instances, the projections 2036 rotate within the apertures 2016 as the anvil jaw 2030 is rotating relative to the cartridge jaw 2020.

Referring primarily to FIG. 3, the rotation of the anvil jaw 2030, without more, may result in the tissue gap between the distal end 2013 of the staple cartridge 2010 and the distal end 2033 of the anvil jaw 2030 (DTG) being larger than the tissue gap between the proximal end 2011 of the staple cartridge 2010 and the proximal end 2031 of the anvil jaw 2030 (PTG). When the distal tissue gap DTG is larger than the proximal tissue gap PTG, the tissue captured within the distal tissue gap DTG may experience less clamping force, or compression, than the tissue captured within the proximal tissue gap PTG. Moreover, in such instances, the tissue compression surface 2032 of the anvil jaw 2030 may not be parallel to the tissue compression surface 2012 of the staple cartridge 2010 and, as a result, the staples deformed by the distal end 2033 of the anvil jaw 2030 may be larger than the staples deformed by the proximal end 2031.

Further to the above, the closure tube 2040 further comprises one or more lift cams 2046 configured to move the distal end 2033 of the anvil jaw 2030 closer to the distal end 2013 of the staple cartridge 2010. The lift cams 2046 of the closure tube 2040 are configured to engage the projections 2036 of the anvil jaw 2030 and push the projections 2036 upwardly within the apertures 2016 during the closure stroke of the closure tube 2040. In such instances, the lift cams 2046 can drive the distal end 2033 of the anvil jaw 2030 toward the distal end 2013 of the staple cartridge 2010 and increase the clamping force applied to the tissue captured within the distal tissue gap DTG. In various instances, the lift cams 2046 can position the anvil jaw 2030 relative to the staple cartridge 2010 such that the distal tissue gap DTG is the same, or at least substantially the same, as the proximal tissue gap PTG; however, the reader should understand that the thickness of the tissue captured between the tissue compression surfaces 2012 and 2032 can affect the distal tissue gap DTG and the proximal tissue gap PTG. In any event, the clamping force applied to the tissue in distal tissue gap DTG can be the same, or at least substantially the same, as the clamping force applied to the tissue in the proximal tissue gap PTG.

In various instances, further to the above, the tissue captured within the distal tissue gap DTG can be pushed out of the distal tissue gap DTG when the tissue is being incised by a cutting member. In at least one instance, the lift cams 2046 can position the anvil jaw 2030 relative to the staple cartridge 2010 such that the distal tissue gap DTG is smaller than the proximal tissue gap PTG. In such instances, the clamping force applied to the tissue in distal tissue gap DTG can be larger than the clamping force applied to the tissue in the proximal tissue gap PTG. As a result, the tissue captured in the DTG is less likely to be pushed out of the distal tissue gap DTG.

In at least one sense, further to the above, the distal tube end 2045 of the closure tube 2040 comprises a first, or initial, cam and the lift cams 2046 of the closure tube 2040 comprise a second, or subsequent, cam. That said, the lift cams 2046 can be configured to engage the projections 2036 at any suitable point in the closure stroke. In at least one instance, the lift cams 2046 are configured to engage the projections 2036 at the same time that the distal tube end 2045 engages the push shoulder 2037. In such instances, the distal end 2033 of the anvil jaw 2030 can be pushed downwardly toward the distal end 2013 of the staple cartridge 2010 at the end of the closure stroke. In other instances, the lift cams 2046 are configured to engage the projections 2036 before the distal tube end 2045 engages the push shoulder 2037. In such instances, the distal end 2033 of the anvil jaw 2030 can be cambered downwardly as the anvil jaw 2030 is being closed. In some instances, the lift cams 2046 are configured to engage the projections 2036 after the distal tube end 2045 has engaged the push shoulder 2037. In such instances, the closure tube 2040 can apply a significant clamping force to the tissue at the very end of the closure stroke which includes, one, a push-to-close force component from the distal tube end 2045 and, two, a lift-to-close force component from the lift cams 2046.

As discussed above, referring again to FIG. 3, the lift cams 2046 are configured to affect, or close, the distal tissue gap DTG during the closure stroke of the closure tube 2040. The lift cams 2046 do not affect, or at least substantially affect, the proximal tissue gap PTG. In various instances, the tissue positioned in the proximal tissue gap PTG can act as a fulcrum about which the anvil jaw 2030 is rotated when the lift cams 2046 engage the anvil projections 2036. In certain instances, the proximal tissue gap PTG can adjust to the thickness of the tissue captured between the anvil compression surface 2032 and the cartridge compression surface 2012.

Referring again to FIG. 1, the anvil jaw 2030 comprises a longitudinal slot 2038 which is configured to receive a portion of a firing assembly, or a cutting member portion of the firing assembly, during a tissue cutting stroke. As described in greater detail below, a firing assembly can comprise a cam member configured to engage the anvil jaw 2030 and position the anvil jaw 2030 relative to the staple cartridge 2010 during the tissue cutting stroke. The longitudinal slot 2038 comprises a cam surface 2039 which is engaged by the firing assembly to compress the tissue, or control the compression of the tissue, captured between the cartridge compression surface 2012 and the anvil compression surface 2032. The cam surface 2039 of the anvil jaw 2030 is parallel to the tissue compression surface 2032. In other embodiments, the cam surface 2039 is not parallel to the tissue compression surface 2032. In at least one such embodiment, the cam surface 2039 extends along a plane which is not parallel to a plane including the tissue compression surface 2032. For instance, the distance between the cam surface 2039 and the tissue compression surface 2032 can be larger at the distal end 2033 of the anvil jaw 2030 as compared to the proximal end 2031. In such instances, the compression force applied to the tissue by the firing assembly can increase as the cutting member portion is progressed through its tissue cutting stroke which can prevent, or at least reduce the possibility of, the tissue being pushed out of the distal tissue gap DTG, for example.

In various instances, further to the above, the cam surface 2039 of the anvil jaw 2030 can be pointed downwardly toward the distal end 2013 of the cartridge jaw 2010 when the anvil jaw 2030 has reached its fully-closed position.

Figure 4:
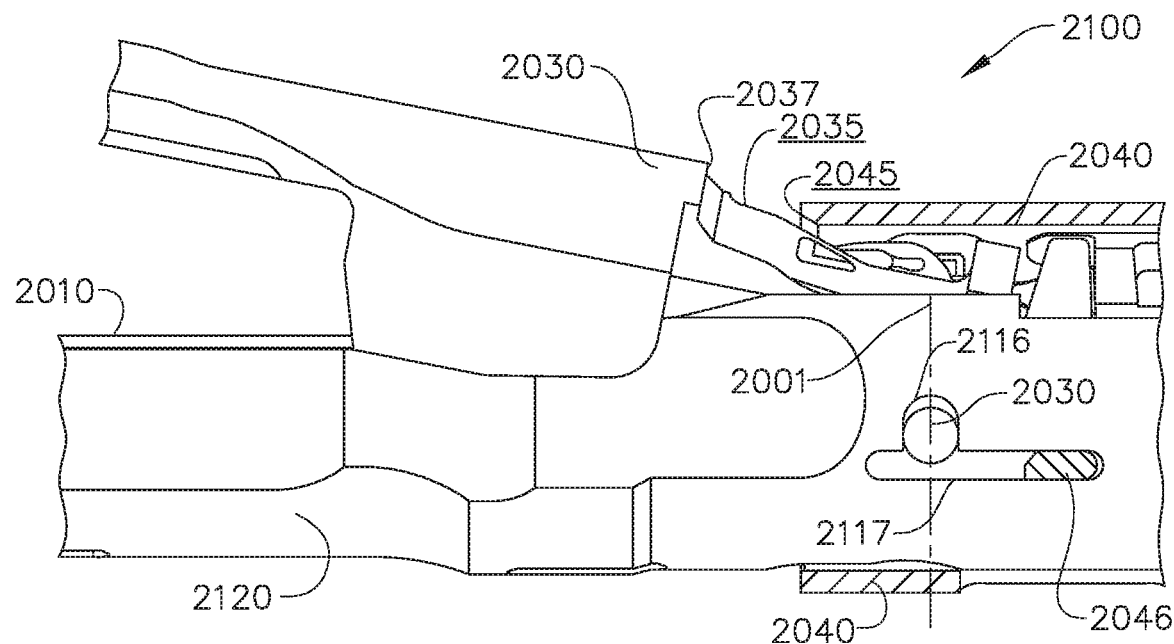
FIG. 4 is a partial elevational view of an end effector in accordance with at least one embodiment illustrated in an open configuration.
Figure 5:
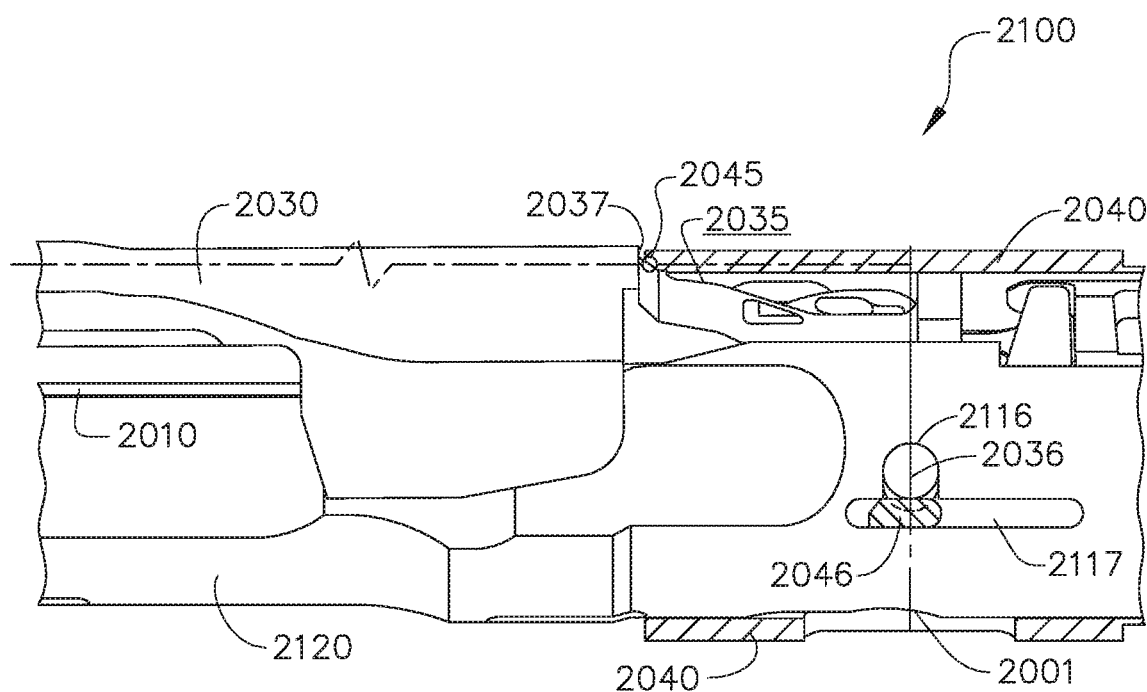
FIG. 5 is a partial elevational view of the end effector of FIG. 4 illustrated in a fully-closed configuration.

A surgical instrument 2100 is illustrated in FIGS. 4 and 5. The surgical instrument 2100 is similar to the surgical instrument 2000 in many respects. The surgical instrument 2100 comprises a cartridge jaw 2120 and an anvil jaw 2030. The cartridge jaw 2120 comprises a staple cartridge 2010 which includes a plurality of staples removably stored therein. The staple cartridge 2010 is replaceable and can be removed from the cartridge jaw 2120; however, other embodiments are envisioned in which the staple cartridge 2010 is not replaceable. Similar to the above, the anvil jaw 2030 is rotatably coupled to the cartridge jaw 2120. The cartridge jaw 2120 comprises apertures 2116 defined on opposite sides thereof. Each aperture 2116 is elongate and extends along a vertical axis 2001.

Also similar to the above, the anvil jaw 2030 comprises projections 2036 that extend laterally therefrom in opposite directions. The projections 2036 are slidably positioned within the apertures 2116. The apertures 2116 and the projections 2036 define a joint about which the anvil jaw 2030 can be rotated relative to the cartridge jaw 2120 between an open position and a closed position. The projections 2036 are closely received between the vertical sidewalls of the apertures 2116 such that longitudinal proximal and/or distal movement of the anvil jaw 2030 relative to the cartridge jaw 2120 is prevented, or at least inhibited. That said, the projections 2036 are movable vertically within the apertures 2116. As illustrated in FIGS. 4 and 5, the cartridge jaw 2120 further comprises longitudinal slots 2117 defined on opposite sides thereof. Each longitudinal slot 2117 intersects a bottom portion of an aperture 2116.

Further to the above, the surgical instrument 2100 comprises a closure member, or tube, 2040 configured to contact the anvil jaw 2030 and move the anvil jaw 2030 from its open position (FIG. 4) toward its closed position (FIG. 5) during a closure stroke. More specifically, further to the above, the distal tube end 2045 of the closure tube 2040 is configured to engage a cam surface 2035 defined on the anvil jaw 2030 and rotate the anvil jaw 2030 toward the cartridge jaw 2120. The closure tube 2040 slides distally along the cam surface 2035 until the distal tube end 2045 comes into contact with a push shoulder 2037 defined on the anvil jaw 2030. In such instances, the projections 2036 rotate within the apertures 2116 as the anvil jaw 2030 is rotating relative to the cartridge jaw 2120.

Further to the above, the lift cams 2046 of the closure tube 2040 are configured to engage the projections 2036 of the anvil jaw 2030 and push the projections 2036 upwardly within the apertures 2116 during the closure stroke of the closure tube 2040. In such instances, the lift cams 2046 can drive the distal tip of the anvil jaw 2030 toward the distal tip of the cartridge jaw 2120 and increase the clamping force applied to the tissue captured between the distal tips of the cartridge jaw 2120 and the anvil jaw 2030. The movement of the lift cams 2046 is limited to a longitudinal path defined by the longitudinal slots 2117. In at least one instance, the longitudinal path comprises a longitudinal axis which is orthogonal, or at least substantially orthogonal, to the vertical axis 2001, for example. The intersection of the longitudinal slots 2117 and the apertures 2116 allows the lift cams 2046 to engage the projections 2036 as the closure tube 2040 is advanced distally during its closure stroke.

As discussed above, the surgical instruments 2000 and 2100 comprise a fixed cartridge jaw and a movable anvil jaw. However, other embodiments are envisioned. For instance, a surgical instrument can comprise a fixed anvil jaw and a movable cartridge jaw. Such embodiments can be useful when the space between the targeted tissue and a body cavity wall is limited, for example. More specifically, in various instances, the anvil jaw 2030 is thinner than the staple cartridge jaw 2020 and, if the anvil jaw 2030 is fixed, the anvil jaw 2030 could provide a thin, but stiff, jaw that could be slid behind tissue in tight spaces.

Figure 6:
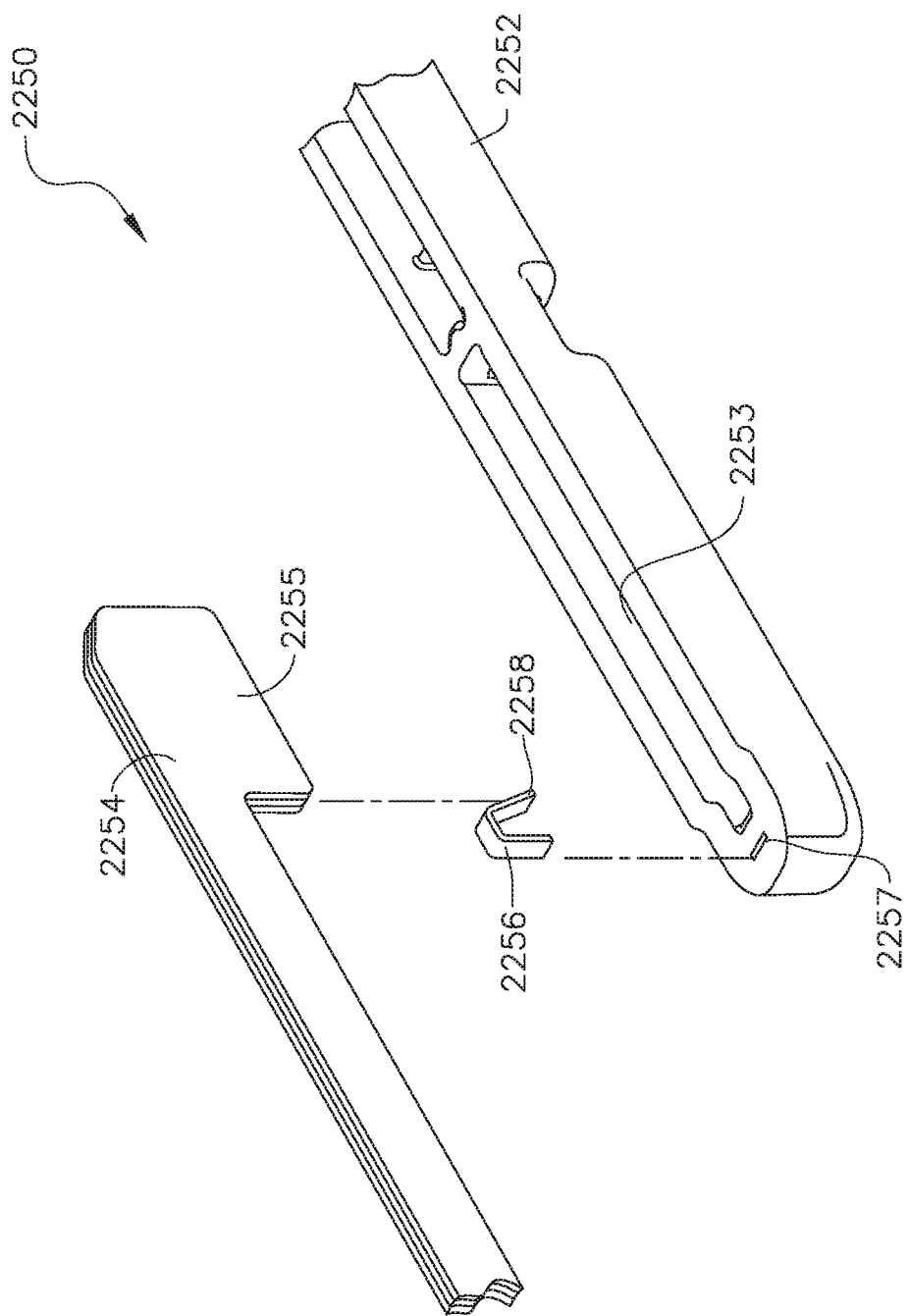
FIG. 6 is a partial perspective view of a firing assembly in accordance with at least one embodiment.

A surgical instrument 2200 is illustrated in FIGS. 6-8. The surgical instrument 2200 is similar to the surgical instruments 2000 and 2100 in many respects. The surgical instrument 2200 comprises a cartridge jaw 2220 and an anvil jaw 2230 rotatably coupled to the cartridge jaw 2220. The cartridge jaw 2220 comprises a replaceable staple cartridge 2210 including a plurality of staples removably stored therein. In other embodiments, the staple cartridge 2210 is not removable from the cartridge jaw 2220. The cartridge jaw 2220 and the anvil jaw 2230 are similar to the cartridge jaw 2020 and the anvil jaw 2030, respectively. The surgical instrument 2200 further comprises a closure tube 2240. The closure tube 2240 is similar to the closure tube 2040 in many respects. Among other things, the closure tube 2240 comprises a distal tube end 2245 configured to engage a cam surface 2035 and/or a push shoulder 2037 on the anvil jaw 2230 to rotate the anvil jaw 2230 toward the cartridge jaw 2220.

The surgical instrument 2200 further comprises a firing assembly 2250. The firing assembly 2250 comprises a coupling member 2251, a firing bar 2254 mounted to the coupling member 2251, and a firing rod 2252. The coupling member 2251 is configured to be advanced distally from a proximal unfired position to a distal fired position by the firing rod 2252 and the firing bar 2254 during a firing stroke of the firing assembly 2250 to eject the staples from the staple cartridge 2210. The coupling member 2251 comprises a first cam configured to engage the cartridge jaw 2220 and a second cam configured to engage the anvil jaw 2230 during the firing stroke. Among other things, the first and second cams lock the anvil jaw 2230 in a closed position during the firing stroke. After at least a portion of the firing stroke has been completed, the firing assembly 2250 can be retracted to disengage the first and second cams from the jaws 2220 and 2230, respectively. At such point, the closure tube 2240 can be retracted proximally to disengage the distal tube end 2245 from the cam surface 2035.

The closure tube 2240 further comprises at least one crimp tab 2249 (FIG. 3). The crimp tab 2249 is configured to positively open the anvil jaw 2230. As the closure tube 2240 is being retracted proximally, further to the above, the distal tube end 2245 slides proximally across the cam surface 2035 and, after the closure tube 2240 has been sufficiently retracted, the crimp tab 2249 contacts a cam tab 2239 defined on the anvil jaw 2230. Stated another way, the crimp tab 2249 does not initially engage the cam tab 2239 as the closure tube 2240 is being retracted; rather, the crimp tab 2249 comes into contact with the cam tab 2239 as the closure tube 2240 is being retracted. Once the crimp tab 2249 is engaged with the cam tab 2239, further retraction of the closure tube 2240 will open the anvil jaw 2230. the closure tube 2240 must be sufficiently retracted before the biasing member can open the anvil jaw 2230. As a result, the anvil jaw 2230 may not open immediately during the retraction stroke of the closure tube 2240 absent the use of a resilient biasing feature which can drive the anvil jaw 2230 into an at least partially open position while the closure tube 2240 is being retracted, as discussed in greater detail below.

Further to the above, the firing assembly 2250 comprises a biasing member, or spring, 2256, for example, positioned intermediate the firing rod 2252 and a proximal tail 2255 of the firing bar 2254. Referring primarily to FIG. 6, the spring 2256 comprises an end securely mounted in a recess 2257 defined in the distal end of the firing rod 2252 and, in addition, a cantilever end 2258 which extends into a longitudinal opening 2253 defined in the firing rod 2252. When the firing assembly 2250 is retracted, as illustrated in FIG. 7, the firing rod 2252 applies a retraction force to the firing bar 2254 via the spring 2256. This retraction force resiliently compresses the spring 2256, as also illustrated in FIG. 7. As the firing assembly 2250 is retracted, the coupling member 2251 comes into contact with the anvil jaw 2230. More specifically, a shoulder 2259 defined on the coupling member 2251 contacts the cam tab 2239 defined on the anvil jaw 2230. At such point, the spring 2256 is still in its compressed state and is applying a load to the anvil jaw 2230 through the coupling member 2251. This load, however, does not open the anvil jaw 2230 until the closure tube 2240 is moved proximally away from the push shoulder 2037. Once the closure tube 2240 begins its opening motion, however, the load can quickly open, or at least partially open, the anvil jaw 2230, as illustrated in FIG. 8. In various instances, as a result, very little, if any, lag exists between the opening motion of the closure tube 2240 and the opening motion of the anvil jaw 2230.

Further to the above, the spring 2256 will apply the quick-opening force to the anvil jaw 2230 so long as the spring 2256 is resiliently compressed between the firing rod 2252 and the firing bar 2254. Once the spring 2256 has returned to its uncompressed state, the firing assembly 2250 may no longer apply an opening force to the anvil jaw 2230. Further opening of the anvil jaw 2230 can be accomplished through retraction of the closure system so that the positive jaw opening crimp tab 2249 applies force to the cam tab 2239 to fully open the anvil jaw 2230.

A coupling member 2551 is illustrated in FIGS. 9-11 and a portion of a firing assembly 2550 is illustrated in FIG. 10. The coupling member 2551 comprises a first cam 2552 configured to engage a first jaw and second cams 2553 configured to engage a second jaw. The coupling member 2551 further comprises a recess 2555 defined therein. The recess 2555 is configured to receive a firing bar 2554 therein. In at least one instance, the lateral side of the firing bar 2554 is flush with the lateral side of the coupling member 2551 when the firing bar 2554 is fully seated in the coupling member 2551. In other instances, the lateral side of the firing bar 2554 is recessed with respect to the lateral side of the coupling member 2551.

Further to the above, the firing bar 2554 comprises a plurality of flexible layers. Each of the layers is mounted to the coupling member 2551. The coupling member 2551 comprises a first, or proximal, mounting post, or projection, 2557p and a second, or distal, mounting post, or projection, 2557d. Each layer of the firing bar 2554 comprises an aperture 2558p configured to closely receive the mounting post 2557p. In at least one instance, the mounting post 2557p is press fit into the apertures 2558p such that little, if any, relative movement is possible between the firing bar 2554 and the mounting post 2557p. Similarly, each layer of the firing bar 2554 comprises an aperture 2558d configured to closely receive the mounting post 2557d. In at least one instance, the mounting post 2557d is press fit into the apertures 2558d such that little, if any, relative movement is possible between the firing bar 2554 and the mounting post 2557d. Mounting posts 2557p and 2557d provide, one, a mechanical attachment of the coupling member 2551 to the firing bar 2554 and, two, surfaces which extend out to the exterior surface of the firing bar 2554 that provide significant exposed surface area that allows a welded connection to be made between the coupling member 2551 and the firing bar 2554. In various instances, the perimeters of the mounting posts 2557p and 2557d are welded to the layers, or at least the outer layer, of the firing bar 2554. In some instances, the ends of the mounting posts 2557p and 2557d are entirely welded over to make the connection between the coupling member 2551 and the firing bar 2554.

The mounting post 2557p and the mounting post 2557d are not aligned longitudinally. Referring primarily to FIG. 9, the mounting posts 2557p and 2557d are positioned on opposite sides of a longitudinal axis 2558. The longitudinal axis 2558 is collinear with and/or parallel to the longitudinal path of the firing assembly 2550. As a result of the above, the interconnection between the coupling member 2251 and the firing bar 2554 can withstand torque loads which act to rotate the coupling member 2551 upwardly and/or downwardly. In alternative embodiments, the mounting posts 2557p and 2557d are aligned longitudinally. In such instances, the mounting posts 2557p and 2557d can comprise an alignment datum for properly orienting the coupling member 2551 relative to the firing bar 2554.

Referring primarily to FIG. 10, the firing assembly 2550 comprises a cutting portion configured to cut the tissue of a patient as the firing assembly 2550 is advanced distally through a staple cartridge. The coupling member 2551 comprises a first cutting part 2556' of the cutting portion and the firing bar 2554 comprises a second cutting part 2556" of the cutting portion. The first cutting part 2556' is positioned laterally with respect to the second cutting part 2556". The face of the first cutting part 2556', however, is aligned with the face of the second cutting part 2556" such that these faces comprise a continuous, or at least substantially continuous, cutting edge, as illustrated in FIG. 10. In at least one instance, only one layer of the firing bar 2554 constitutes the second cutting part 2556"; however, alternative embodiments are envisioned in which more than one layer of the firing bar 2554 constitutes the second cutting part 2556". In certain embodiments, the coupling member 2551 does not constitute part of the cutting portion. In at least one such embodiment, the firing bar 2554 comprises the entirety of the cutting portion. In any event, the arrangements discussed above can reduce the cost of creating the firing assembly 2250 by eliminating the need to sharpen and hone the coupling member 2251, and transferring the sharpening operation to one of the flat layers of the firing bar 2554.

A coupling member 2651 is illustrated in FIG. 12, a portion of a firing bar 2654 is illustrated in FIG. 13, and a portion of a firing assembly 2650 comprising the coupling member 2651 and the firing bar 2654 is illustrated in FIG. 14. The coupling member 2651 comprises a first cam 2552 configured to engage a first jaw and second cams 2553 configured to engage a second jaw. Referring to FIG. 12, the coupling member 2651 further comprises a recess 2655 defined therein. The recess 2655 is configured to receive the firing bar 2654 therein, as illustrated in FIG. 14. In at least one instance, the lateral side of the firing bar 2654 is flush with the lateral side of the coupling member 2651 when the firing bar 2654 is fully seated in the recess 2655. In other instances, the lateral side of the firing bar 2654 is recessed with respect to the lateral side of the coupling member 2651.

Referring primarily to FIG. 12, the coupling member 2651 comprises a proximal mounting post 2657*p* and a distal mounting post 2657*d*. The firing bar 2654, referring to FIG. 13, comprises a proximal aperture 2658*p* configured to closely receive the mounting post 2657*p*. In at least one instance, the mounting post 2657*p* is press-fit within the proximal aperture 2658*p* of the firing bar 2654. The firing bar 2654 further comprises a distal aperture 2658*d* configured to closely receive the distal mounting post 2657*d* of the coupling member 2651. In at least one instance, the mounting post 2657*d* is press-fit within the distal aperture 2658*d* of the firing bar 2654. Mounting posts 2657*p* and 2657*d* provide, one, a mechanical attachment of the coupling member 2651 to the firing bar 2654 and, two, surfaces which extend out to the exterior surface of the firing bar 2654 that provide significant exposed surface area that allows a welded connection to be made between the coupling member 2651 and the firing bar 2654. In various instances, the perimeters of the mounting posts 2657*p* and 2657*d* are welded to the layers, or at least the outer layer, of the firing bar 2654. In some instances, the ends of the mounting posts 2657*p* and 2657*d* are entirely welded over to make the connection between the coupling member 2651 and the firing bar 2654.

Referring again to FIG. 13, the firing bar 2654 further comprises a hook, or catch, 2653. Referring now to FIG. 14, the hook 2653 is engaged with the coupling member 2651. More specifically, the hook 2653 is at least partially wrapped around the distal end of a second cam 2553. In various instances, the hook 2653 can be used to align the firing bar 2654 with the coupling member 2651 before seating the firing bar 2654 into the recess 2655 in the coupling member 2651. Moreover, the hook 2653 extends over the cutting part 2556" of the coupling member 2651 and can be configured to direct the flow of tissue toward the cutting edge of the cutting part 2556". The firing bar 2654 comprises a single layer and the hook 2653 is defined on that layer; however, the hook 2653 can be defined on multiple layers in other firing bars. In any event, the hook 2653, the distal aperture 2658*d*, and the proximal aperture 2658*p* are configured to retain the firing bar 2654 to the coupling member 2651.

As discussed above, the firing bar 2654 is positioned within a lateral recess 2655. Referring to FIG. 12, the second cam 2553 that extends over the recess 2655 is longer than the other second cam 2553. Moreover, the firing bar 2654 is offset laterally with respect to the center of the coupling member 2651. In use, as a result, the firing bar 2654 can experience a lateral twist when the firing assembly 2650 is being advanced distally during its firing stroke. To account for this twist, in various instances, the second cams 2553 can be closely received within a jaw, such as the anvil jaw 2030, for example. More specifically, referring again to FIG. 1, the sidewalls of the slot 2038 are configured such that there is little, if any, lateral gap between the sidewalls and the lateral sides of the second cams 2553. Other means can be used.

Figures 15, 16:
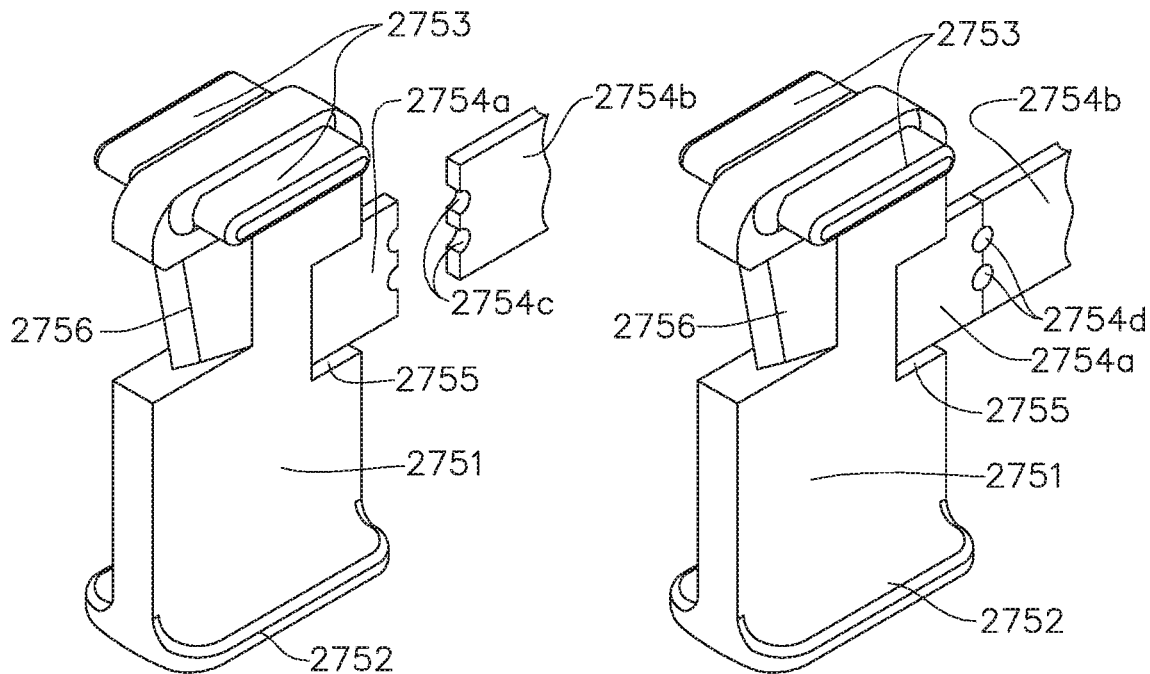
FIG. 15 is a partial perspective view of a coupling member and a firing bar layer of a firing member in accordance with at least one embodiment.
FIG. 16 is a partial perspective view of the firing bar layer attached to the coupling member of FIG. 15.

Turning now to FIGS. 15-18, a firing assembly 2750 comprises a coupling member 2751 and a firing bar 2754 including multiple layers attached to the coupling member 2751. The coupling member 2751 comprises a first cam 2752 configured to engage a first jaw, second cams 2753 configured to engage a second jaw, and a cutting edge 2756 configured to transect tissue during a firing stroke of the firing assembly 2750. The coupling member 2751 comprises a mounting tab 2754*a* extending proximally therefrom and lateral recesses 2755 defined on opposite sides of the mounting tab 2754*a*. Referring to FIG. 16, a center layer 2754*b* of the firing bar 2754 is attachable to the mounting tab 2754*a*. The mounting tab 2754*a* and the center layer 2754*b* define apertures 2754*c* therebetween which are configured to receive welds 2754*d* therein to retain the center layer 2754*b* to the mounting tab 2754*a*; however, any suitable joining method could be used to join the center layer 2754*b* to the mounting tab 2754*a*.

Figures 17, 18:
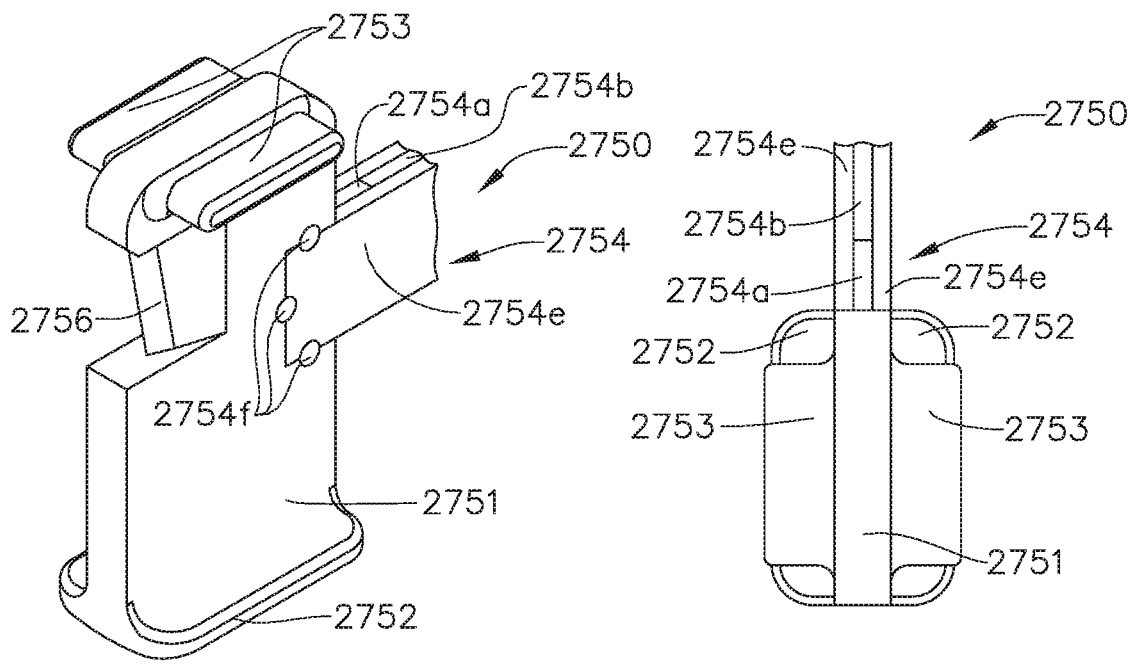
FIG. 17 is a partial perspective view of additional layers of the firing bar attached to the coupling member of FIG. 15.
FIG. 18 is a partial plan view of the coupling member and the firing bar of FIG. 15.

Further to the above, referring now to FIG. 17, the firing bar 2754 further comprises lateral layers 2754*e* which are mounted to the coupling member 2751 in the lateral recesses 2755. Each of the lateral layers 2754*e* is mounted to the coupling member 2751 via welds 2754*f*; however, other joining methods could be used. In various instances, the welds 2754*f* are located distally with respect to the welds 2754*d*. As a result, the attachment points of the lateral layers 2754*e* to the coupling member 2751 are positioned distally with respect to the attachment point of the center layer 2754*b*. Due to this longitudinal offset, the welds 2754*d* and 2754*f* can withstand and transmit torque loads. Moreover, the welds 2754*d* and 2754*f* are not in the same shear plane and the possibility of the coupling member 2751 becoming detached from the firing bar 2754 is reduced.

As discussed in greater detail below, a firing assembly, or cutting member, can be part of, and/or comprise, a lockout system configured to prevent or limit the distal advancement of the firing assembly in certain instances. Referring again to FIGS. 9 and 10, the coupling member 2551 of the firing assembly 2550 comprises a distal projection 2559. The distal projection 2559 is part of a lockout arrangement configured to prevent the firing assembly 2550 from being advanced distally in the event that an unspent staple cartridge is not properly positioned in front of the firing assembly 2550. In such instances, the firing assembly 2550 can be pushed downwardly into a locked out state by a biasing member when the firing assembly 2550 is advanced distally in order to prevent the firing assembly 2550 from performing a staple firing stroke. To the extent that an unspent staple cartridge is properly positioned in front of the firing assembly 2550, the distal projection 2559 can be supported by a sled in the staple cartridge which can allow the firing assembly 2550 to complete the staple firing stroke. The entire disclosures of:

U.S. Pat. No. 7,044,352, entitled SURGICAL STAPLING INSTRUMENT HAVING A SINGLE LOCKOUT MECHANISM FOR PREVENTION OF FIRING, which issued on May 16, 2006;

U.S. Pat. No. 7,143,923, entitled SURGICAL STAPLING INSTRUMENT HAVING A FIRING LOCKOUT FOR AN UNCLOSED ANVIL, which issued on Dec. 5, 2006;

U.S. Pat. No. 6,988,649, entitled SURGICAL STAPLING INSTRUMENT HAVING A SPENT CARTRIDGE LOCKOUT, which issued on Jan. 24, 2006;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006; and U.S. Pat. No. 6,978,921, entitled SURGICAL STAPLING INSTRUMENT INCORPORATING AN E-BEAM FIRING MECHANISM, which issued on Dec. 27, 2005, are incorporated by reference herein.

Figure 19:
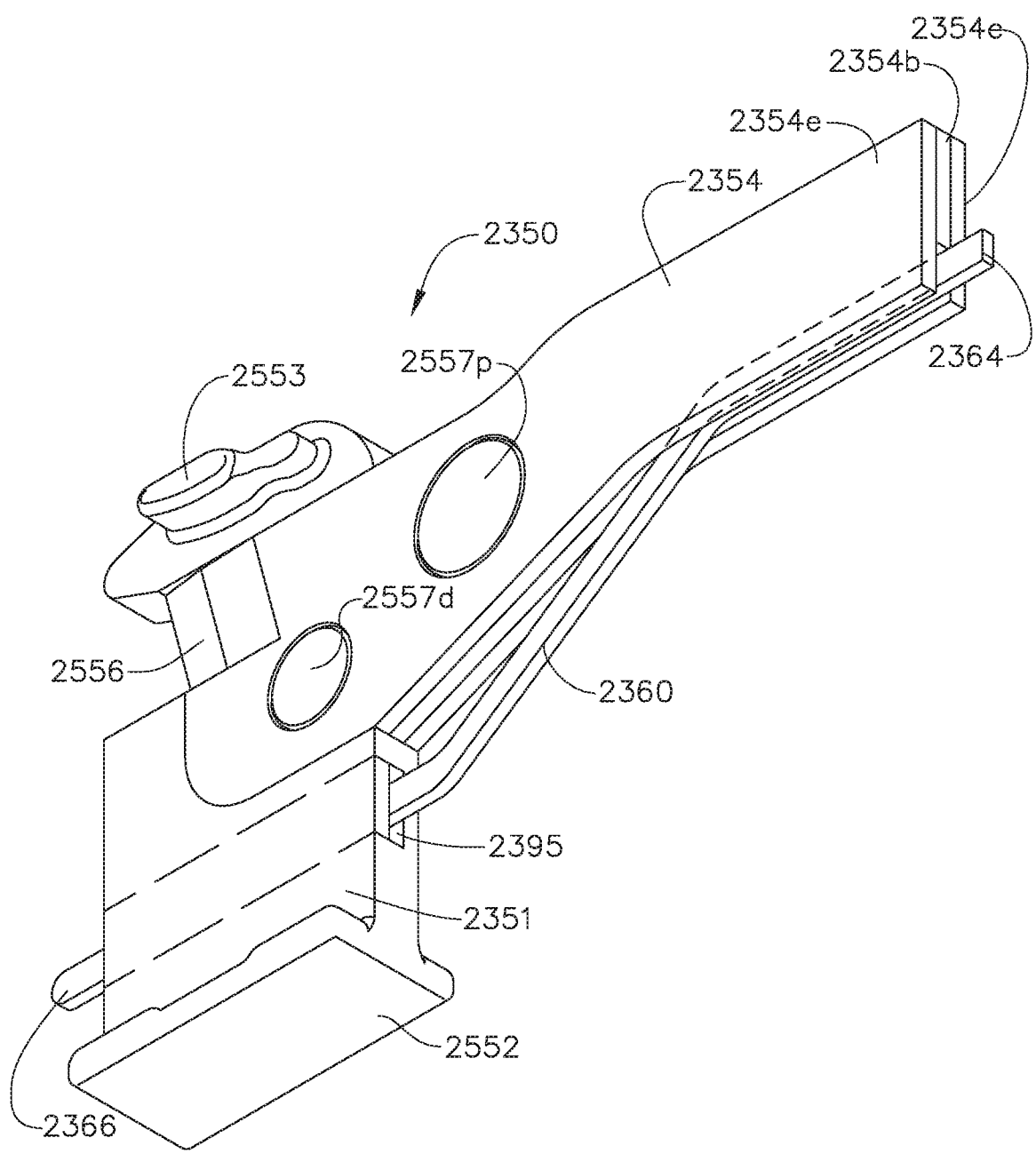
FIG. 19 is a partial perspective view of a firing assembly comprising a coupling member, a firing bar, and a lockout bar in accordance with at least one embodiment.

A firing assembly 2350 of a surgical instrument 2300 is illustrated in FIGS. 19-21. The firing assembly 2350 comprises a coupling member 2351 and a firing bar 2354 mounted to the coupling member 2351. The coupling member 2351 is similar to the coupling member 2551 in many respects. The firing bar 2354 comprises a plurality of layers including central layer 2354b and lateral layers 2354e. The surgical instrument 2300 is configured to receive a staple cartridge having a sled stored therein that, during a staple firing stroke, is advanced distally by the firing assembly 2350. The staple cartridge 2010, for example, comprises a cartridge body 2011 and, in addition, a sled 2014 which is movable through the cartridge body 2011 from a proximal, unfired position to a distal, fired position during the staple firing stroke. When the sled 2014 is in its proximal, unfired position, the staple cartridge 2010 is unspent. When the sled 2014 has been moved distally from its proximal, unfired position, the staple cartridge 2010 becomes spent.

The firing assembly 2350 further comprises a lockout system. The lockout system is configured to prevent the firing assembly 2350 from being advanced distally to perform a staple firing stroke if an unspent staple cartridge, such as staple cartridge 2010, for example, is not properly positioned in the surgical instrument 2300, as illustrated in FIG. 20. In fact, a staple cartridge is entirely missing from the surgical instrument 2300 in FIG. 20. Correspondingly, the lockout system is configured to permit the firing assembly 2350 to be advanced distally to perform a staple firing stroke if an unspent staple cartridge, such as staple cartridge 2010, for example, is properly positioned in the surgical instrument 2300, as illustrated in FIG. 21.

Referring primarily to FIG. 19, the firing assembly 2350 comprises a lockout bar 2360 slidably mounted to the firing bar 2354. The lockout bar 2360 comprises a longitudinal portion 2364 and a distal end 2366. The longitudinal portion 2364 of the lockout bar 2360 extends through a longitudinal clearance slot defined between the lateral layers 2354e of the firing bar 2354. The distal end 2366 of the lockout bar 2360 extends through an aperture 2359 defined in the coupling member 2351 and projects distally from the coupling member 2351. The lockout bar 2360 is slidable between a distal, or locked, position (FIG. 20) and a proximal, or unlocked, position (FIG. 21) when an unspent staple cartridge 2010 is properly positioned in the cartridge jaw 2020. More specifically, further to the above, an unspent staple cartridge 2010 comprises a sled 2014 in its proximal, unfired position which contacts the lockout bar 2360 and pushes the lockout bar 2360 proximally when the unspent staple cartridge 2010 is inserted into the cartridge jaw 2020. The sled 2014 is releasably retained to the cartridge body 2011 such that the sled 2014 remains in its proximal, unfired position while pushing the lockout bar 2360 proximally. In at least one instance, the cartridge body 2011 comprises one or more detents which releasably hold the sled 2014 in its proximal, unfired position.

The firing assembly 2350 further comprises a firing rod 2352 having a longitudinal slot 2358 defined therein. The firing bar 2354 comprises a proximal end 2355 positioned in the longitudinal slot 2358 and, similarly, the lockout bar 2360 comprises a proximal end 2365 which is also positioned in the longitudinal slot 2358. When the lockout bar 2360 is in its locked position, as illustrated in FIG. 20, a lock 2370 is engaged with the firing rod 2352 which prevents the firing rod 2352 from being advanced distally. Correspondingly, in such instances, the lock 2370 prevents the firing rod 2352 from advancing the firing bar 2354, and the coupling member 2351, through a staple firing stroke. The lock 2370 is rotatably mounted to a shaft 2340 of the surgical instrument 2300 about a pivot 2371 and comprises a lock shoulder engaged with a lock recess, or notch, 2378 defined in the firing rod 2352. The lock 2370 is biased into engagement with the firing rod 2352 by a spring 2372.

Upon comparing FIGS. 20 and 21, further to the above, it can be seen that the lockout bar 2360 moves relative to the firing bar 2354 when the lockout bar 2360 is moved between its locked position (FIG. 20) and its unlocked position (FIG. 21) when an unspent staple cartridge 2010 is loaded into the surgical instrument 2300. The firing assembly 2350 further comprises a biasing member, or spring, 2368 positioned intermediate the proximal end 2355 of the firing bar 2354 and the proximal end 2365 of the lockout bar 2360 which is compressed between the proximal ends 2355 and 2365 when the lockout bar 2360 is moved proximally. If the unspent staple cartridge 2010 were to be removed from the cartridge jaw 2020 before the staple cartridge 2010 is fired, the biasing member 2368 would resiliently expand and push the lockout bar 2360 distally into its locked position and allow the spring 2372 to return the lock 2370 into its locked position and re-engage the firing rod 2352. Stated another way, the spring 2368 biases the lockout bar 2360 into its locked position in the absence of an unspent staple cartridge in the cartridge jaw 2020.

When the lockout bar 2360 is moved proximally into its unlocked condition, as illustrated in FIG. 21, the proximal end 2365 of the lockout bar 2360 engages the lock 2370 and rotates the lock 2370 downwardly out of engagement with the firing rod 2352 against the bias of the spring 2372. At such point, the firing assembly 2350 can be advanced distally to perform the staple firing stroke. Notably, the firing rod 2352 pushes the firing bar 2354 distally. More specifically, the proximal sidewall of the longitudinal slot 2358 abuts the proximal end 2355 of the firing bar 2354 as the firing rod 2352 is advanced distally. Also, notably, the firing bar 2354 pushes the lockout bar 2360 distally via the spring 2368. As a result, the lockout bar 2360 travels with the firing bar 2354 when the firing bar 2354 is moved distally during the staple firing stroke.

Further to the above, the distal movement of the firing bar 2354 and the lockout bar 2360 during the staple firing stroke moves the proximal end 2365 of the lockout bar 2360 away from the lock 2370. In such instances, however, the lock recess 2378 defined in the firing rod 2352 is no longer in alignment with the lock 2370. As a result, the lock 2370 cannot re-engage the firing rod 2352 and lock the firing rod 2352 in position even though the lockout bar 2360 has been disengaged from the lock 2370. When the firing rod 2352 is retracted in order to reset the surgical instrument 2300, the firing rod 2352 can pull the firing bar 2354 and the lockout bar 2360 proximally to the position illustrated in FIG. 20. In such instances, the lock recess 2378 is re-aligned with the lock 2370 such that the spring 2372 can re-engage the lock 2370 with the firing rod 2352 and re-lock the firing assembly 2350 in position. In various instances, the firing rod 2352 further comprises a ramp 2375 configured to deflect the lock 2370 downwardly as the firing rod 2352 is being retracted.

Further to the above, the firing rod 2352 is pulled proximally after a staple firing stroke to retract the firing bar 2354, the lockout bar 2360, and the coupling member 2351 of the firing assembly 2350. Notably, the sled 2014 of the staple cartridge 2010 is not retracted by the firing rod 2352. Instead, the sled 2014 remains in its fired position. As a result, the lockout bar 2360 is pushed out of its locked position when the firing assembly 2350 is returned to its reset position and, as such, the firing assembly 2350 is prevented from being advanced distally once again until the spent staple cartridge 2010 is removed from the cartridge jaw 2020 and an unspent staple cartridge 2010, for example, is properly positioned in the cartridge jaw 2020.

Moreover, further to the above, it should be appreciated that the sled 2014 of a spent staple cartridge 2010 cannot contact the lockout bar 2360 when the spent staple cartridge 2010 is loaded into the cartridge jaw 2020 because the sled 2014 is not in its proximal position and, as a result, the sled 2014 cannot unlock the firing assembly 2350.

Figure 22:
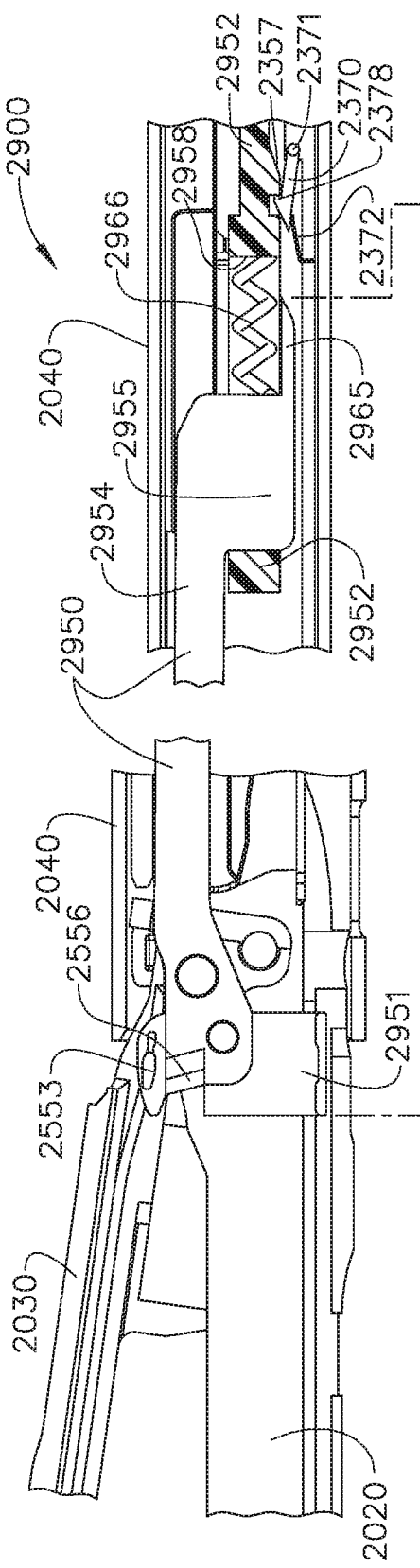
FIG. 22 is a partial cross-sectional view of a surgical instrument illustrated in a locked out configuration.
Figure 23:
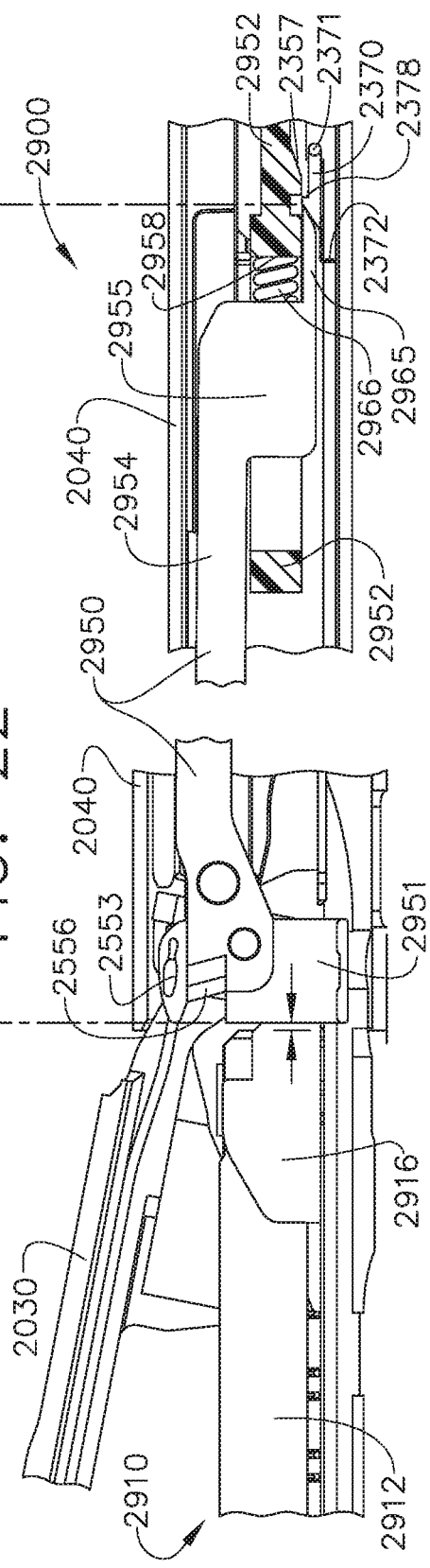
FIG. 23 is a partial cross-sectional view of the surgical instrument of FIG. 22 illustrated in an unlocked configuration.

A surgical instrument 2900 comprising a firing assembly 2950 is illustrated in FIGS. 22 and 23. Similar to the above, the firing assembly 2950 comprises a lockout system configured to prevent the firing assembly 2950 from being advanced distally to perform a staple firing stroke without an unspent staple cartridge 2910, for example, properly positioned in the cartridge jaw 2020. In at least one instance, the surgical instrument 2900 can comprise the lock 2370 and lock spring 2372 arrangement discussed above in connection with the surgical instrument 2300, for example, which can block the distal advancement of the firing assembly 2950 when an unspent staple cartridge is not properly seated in the cartridge jaw 2020, as illustrated in FIG. 22. When an unspent staple cartridge 2910 is properly seated in the cartridge jaw 2020, as illustrated in FIG. 23, the lockout system can permit the firing assembly 2950 to perform the staple firing stroke. The staple cartridge 2910 is similar to the staple cartridge 2010 in many respects and comprises a cartridge body 2912 and a sled 2916 movable from a proximal, unfired position (FIG. 23) to a distal, fired position by the firing assembly 2950 during the staple firing stroke.

The firing assembly 2950 comprises a firing rod 2952, a firing bar 2954, and a coupling member 2951 mounted to the firing bar 2954. The coupling member 2951 is similar to the coupling member 2551 in many respects. The firing bar 2954 comprises a proximal portion 2955 slidably positioned in a longitudinal slot 2958 defined in the firing rod 2952. The firing assembly 2950 further comprises a biasing member, or compression spring, 2966 positioned in the longitudinal slot 2958 intermediate the proximal portion 2955 of the firing bar 2954 and the firing rod 2952. When an unspent staple cartridge 2910 is not positioned in the cartridge jaw 2020, as illustrated in FIG. 22, the spring 2966 is configured to bias the firing bar 2954 forward. In this forward position of the firing bar 2954, a key 2965 of the firing bar 2954 is not engaged with the lock 2370 and, as a result, the spring 2372 biases the lock 2370 into the lock recess 2378 defined in the firing rod 2952 which prevents the firing rod 2952 from being advanced distally to perform a staple firing stroke.

When an unspent staple cartridge 2910 is properly positioned in the cartridge jaw 2020, as illustrated in FIG. 23, the sled 2916 directly contacts the coupling member 2951 and pushes the firing bar 2954 proximally into its unlocked position. In this proximal position of the firing bar 2954, the key 2965 of the firing bar 2954 is engaged with the lock 2370 and holds the lock 2370 out of the lock notch 2378 in the firing rod 2952. In such instances, as a result, the firing rod 2952 can be advanced distally to push the firing bar 2954, the coupling member 2951, and the sled 2916 through the staple firing stroke. Similar to the above, the firing rod 2952 can be retracted to pull the firing bar 2954 and the coupling member 2951 proximally to reset the surgical instrument 2900. Also similar to the above, the sled 2916 is not retracted with the firing assembly 2950 and, as a result, the firing bar 2954 is in its forward, or locked, position after the firing assembly 2950 has been retracted. The reader should appreciate that the spent staple cartridge 2910 must be replaced with an unspent staple cartridge 2910 to unlock the lock 2370 from the firing assembly 2950 and use the surgical instrument 2900 once again.

Figure 24:
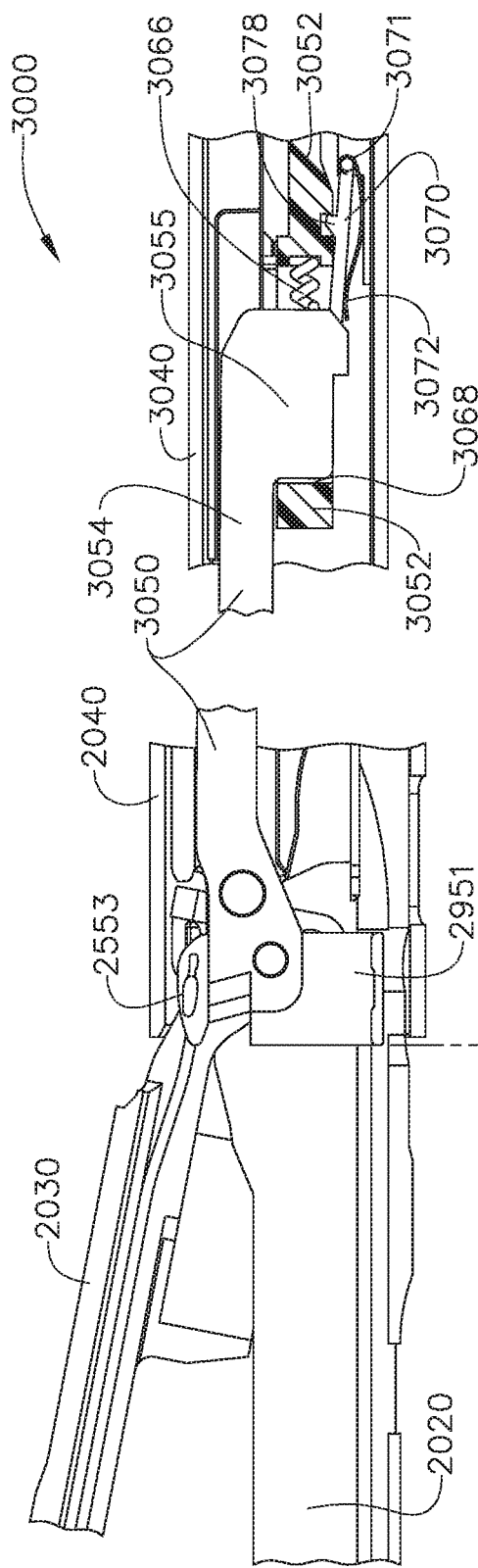
FIG. 24 is a partial cross-sectional view of a surgical instrument illustrated in a locked out configuration.
Figure 25:
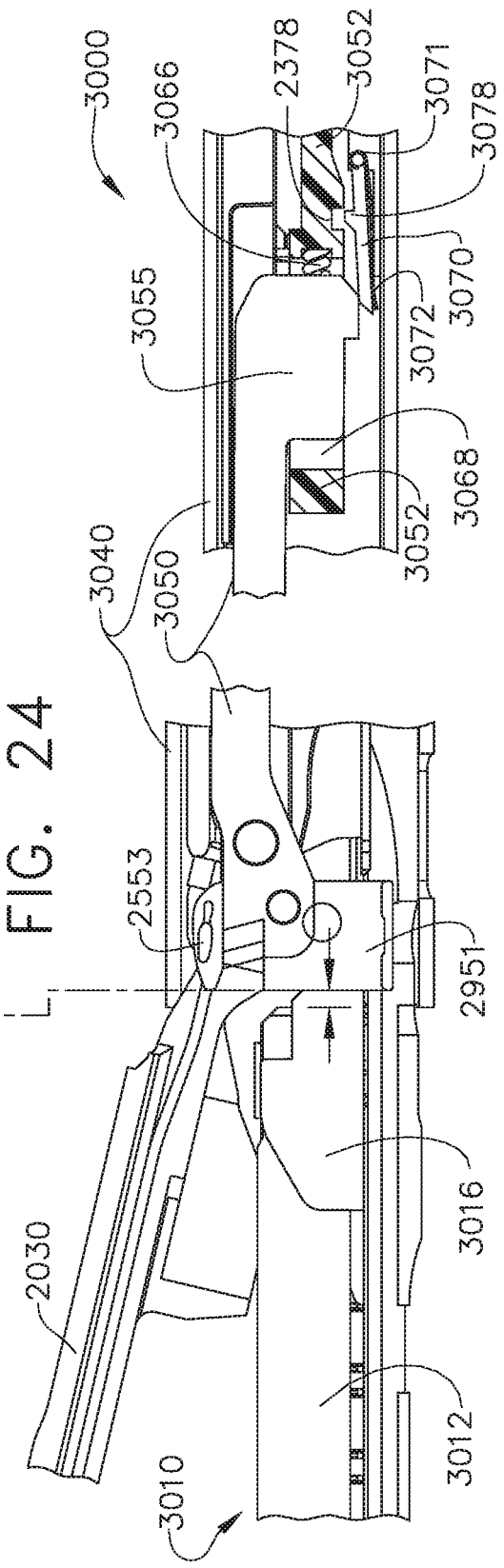
FIG. 25 is a partial cross-sectional view of the surgical instrument of FIG. 24 illustrated in an unlocked configuration.

A surgical instrument 3000 comprising a shaft 3040 and a firing assembly 3050 is illustrated in FIGS. 24 and 25. Similar to the above, the firing assembly 3050 comprises a lockout system configured to prevent the firing assembly 3050 from being advanced distally to perform a staple firing stroke without an unspent staple cartridge 3010, for example, properly positioned in the cartridge jaw 2020. The surgical instrument 3000 comprises a lock 3070 in the shaft 3040 which, similar to lock 2370, can block the distal advancement of the firing assembly 3050, as illustrated in FIG. 24. When an unspent staple cartridge 3010 is properly seated in the cartridge jaw 2020, as illustrated in FIG. 25, the lockout system can permit the firing assembly 3050 to perform the staple firing stroke. The staple cartridge 3010 is similar to the staple cartridge 2010 in many respects and comprises a cartridge body 3012 and a sled 3016 movable from a proximal, unfired position (FIG. 25) to a distal, fired position by the firing assembly 3050 during the staple firing stroke.

The firing assembly 3050 comprises a firing rod 3052, a firing bar 3054, and a coupling member 2951 mounted to the firing bar 3054. The firing bar 3054 comprises a proximal portion 3055 slidably positioned in a longitudinal slot 3058 defined in the firing rod 3052. The firing assembly 3050 further comprises a biasing member, or compression spring, 3066 positioned in the longitudinal slot 3058 intermediate the firing rod 3052 and proximal portion 3055 of the firing bar 3054. When an unspent staple cartridge 3010 is not positioned in the cartridge jaw 2020, as illustrated in FIG. 24, the spring 3066 is configured to bias the firing bar 3054 forward. In this forward position of the firing bar 3054, a leaf spring 3072 biases the lock 3070 into the lock notch 2378 defined in the firing rod 3052 which prevents the firing rod 3052 from being advanced distally to perform a staple firing stroke.

When an unspent staple cartridge 3010 is positioned in the cartridge jaw 2020, as illustrated in FIG. 25, the sled 3016 directly contacts the coupling member 2951 and pushes the firing bar 3054 proximally into its unlocked position. In this proximal position of the firing bar 3054, the proximal end 3055 of the firing bar 3054 is engaged with the lock 3070 and holds the lock 3070 out of the lock notch 2378 in the firing rod 3052 against the biasing force of the leaf spring 3072. In such instances, as a result, the firing rod 3052 can be advanced distally to push the firing bar 3054, the coupling member 2951, and the sled 3016 through the staple firing stroke. Similar to the above, the firing rod 3052 can be retracted to pull the firing bar 3054 and the coupling member 2951 proximally to reset the surgical instrument 3000. Also similar to the above, the sled 3016 is not retracted with the firing assembly 3050 and, as a result, the firing bar 3054 is in its forward, or locked, position after the firing assembly 3050 has been retracted. The reader should appreciate that the spent staple cartridge 3010 must be replaced with an unspent staple cartridge 3010 to unlock the lock 3070 from the firing assembly 3050 and use the surgical instrument 3000 once again.

As discussed above, the lock 2370 is positioned in the shafts of the surgical instruments 2900 and 3000; however, the lock 2370 can be placed in any suitable location. In various instances, the surgical instrument 2900 and/or 3000, for example, can comprise an articulation joint about which an end effector, including the jaws 2020 and 2030, can be articulated. In at least one instance, the lock 2370 is positioned distally with respect to the articulation joint. In such instances, the lockout system is unaffected by the articulation joint. In other instances, the lock 2370 is positioned proximally with respect to the articulation joint. Placing the lock 2370 in such a position can shorten the portion of the surgical instrument which is distal to the articulation joint and improve the accessibility of the surgical instrument into a small surgical site, for instance.

As discussed above, a firing assembly of a surgical instrument can be advanced distally through a staple cartridge to eject the staples from the staple cartridge during a staple firing stroke. As also discussed above, the staple cartridge can comprise a sled which is pushed distally by the firing assembly to drive the staples out of the staple cartridge during the staple firing stroke. In various instances, however, a clinician may not be able to observe the progress of the staple firing stroke. Absent such information, the clinician may not know whether the tissue captured within the surgical instrument has been sufficiently stapled.

Turning now to FIGS. 26-30, a surgical instrument 3100 comprises a cartridge jaw 3120 configured to receive a staple cartridge 3110 therein. The cartridge jaw 3120 comprises a bottom portion and lateral side walls 3122 extending from the bottom portion. The staple cartridge 3110 is positionable between the lateral side walls 3122 of the cartridge jaw 3120. The staple cartridge 3110 and the cartridge jaw 3120 comprise co-operating features configured to align and releasably hold the staple cartridge 3110 in a seated position (FIGS. 27-29). The staple cartridge 3110 further comprises a sled 3116 movable between a proximal, unfired position (FIGS. 26 and 27) and a distal, fired position (FIG. 29) by the firing assembly 2550 during a staple firing stroke.

The cartridge jaw 3120 comprises a series of openings, or windows, defined in a lateral side wall 3122. The windows of the cartridge jaw 3120 comprise a proximal window 3127, a distal window 3129, and an intermediate window 3128 positioned intermediate the proximal window 3127 and the distal window 3129. Each window 3127, 3128, and 3129 comprises an elongate longitudinal through hole positioned along a longitudinal axis 3121; however, the windows 3127, 3128, and 3129 can have any suitable arrangement. In at least one instance, the intermediate window 3128 is positioned at the midpoint between the proximal window 3127 and the distal window 3129. In other instances, the intermediate window 3128 can be positioned at any suitable location between the proximal window 3127 and the distal window 3129. In at least one instance, the cartridge jaw 3120 can comprise more than one intermediate window 3128.

The staple cartridge 3110 comprises a series of openings, or windows, defined in the lateral sides of the cartridge body 3112. The windows of the staple cartridge 3110 comprise a proximal window 3117, a distal window 3119, and an intermediate window 3118 positioned intermediate the proximal window 3117 and the distal window 3119. Each window 3117, 3118, and 3119 comprises an elongate longitudinal through hole positioned along a longitudinal axis 3111; however, the windows 3117, 3118, and 3119 can have any suitable arrangement. In at least one instance, the intermediate window 3118 is positioned at the midpoint between the proximal window 3117 and the distal window 3119. In other instances, the intermediate window 3118 can be positioned at any suitable location between the proximal window 3117 and the distal window 3119. In at least one instance, the staple cartridge 3110 can comprise more than one intermediate window 3118.

When the staple cartridge 3110 is fully seated in the cartridge jaw 3120, the windows in the staple cartridge 3110 are aligned with the windows in the cartridge jaw 3120. More specifically, the proximal cartridge window 3117 is aligned with the proximal jaw window 3127, the intermediate cartridge window 3118 is aligned with the intermediate jaw window 3128, and the distal cartridge window 3119 is aligned with the distal jaw window 3129. In such instances, the windows 3117 and 3127 form a first pair of aligned apertures, the windows 3118 and 3128 form a second pair of aligned apertures, and the windows 3119 and 3129 form a third pair of aligned apertures. As a result, a clinician can look into the staple cartridge 3110 through the cartridge jaw 3120 at three distinct locations.

Further to the above, the staple cartridge 3110 engages the cartridge jaw 3120 in a snap-fit connection when the staple cartridge 3110 is fully seated within the cartridge jaw 3120. In such instances, the longitudinal axis 3111 of the staple cartridge 3110 is aligned with the longitudinal axis 3121 of the cartridge jaw 3120. When the axes 3111 and 3121 are perfectly aligned, the edges of the cartridge windows 3118 and 3119 are not offset with respect to the jaw windows 3128 and 3129, respectively. To the extent that the axes 3111 and 3121 are somewhat aligned, but not perfectly aligned, the cartridge windows 3118 and 3119 may be offset with respect to the jaw windows 3128 and 3129. In either event, the at least substantially aligned windows can serve the purpose of observing the position of the sled 3116 during the firing stroke, as discussed below.

When the sled 3116 is in its proximal, unfired position, as illustrated in FIG. 27, the sled 3116 is visible through the aligned cartridge window 3117 and jaw window 3127. In such instances, a clinician can visually observe that the staple cartridge 3110 is unspent. If the sled 3116 is not visible through the aligned cartridge window 3117 and jaw window 3127 prior to the beginning of the staple firing stroke, then the clinician can assume that the staple cartridge 3110 has been at least partially spent and that a lockout of the stapling instrument 3100, such as those described herein, for example, may be actuated if the spent staple cartridge 3110 is not replaced with an unspent staple cartridge. Moreover, if the sled 3116 is not visible through the aligned cartridge window 3117 and jaw window 3127 during the staple firing stroke, then the clinician can assume that the staple firing stroke is in progress.

When the sled 3116 has been moved half-way through the staple firing stroke, referring now to FIG. 28, the sled 3116 is visible through the aligned cartridge window 3118 and jaw window 3128. In such instances, a clinician can visually observe that the staple cartridge 3110 has been partially spent. Although the windows 3118 and 3128 are aligned at the midpoint of the staple firing stroke, the windows 3118 and 3128 can be aligned at any suitable location. Moreover, any suitable number of window pairs 3118 and 3128 can be utilized to observe the sled 3116 during the staple firing stroke. When the sled 3116 is in its distal, fired position, as illustrated in FIG. 29, the sled 3116 is visible through the aligned cartridge window 3119 and jaw window 3129. In such instances, a clinician can visually observe that the staple cartridge 3110 has been completely spent. Understanding whether or not a staple cartridge has been completely, or at least sufficiently, spent is important for a clinician in determining whether or not to retract the firing assembly 2550. For instance, referring to FIG. 30, a clinician would know that the vessel V captured between the staple cartridge 3010 and the anvil jaw 2030 has been completely stapled when they can observe the sled 3116 in the distal window 3129.

Figure 26:
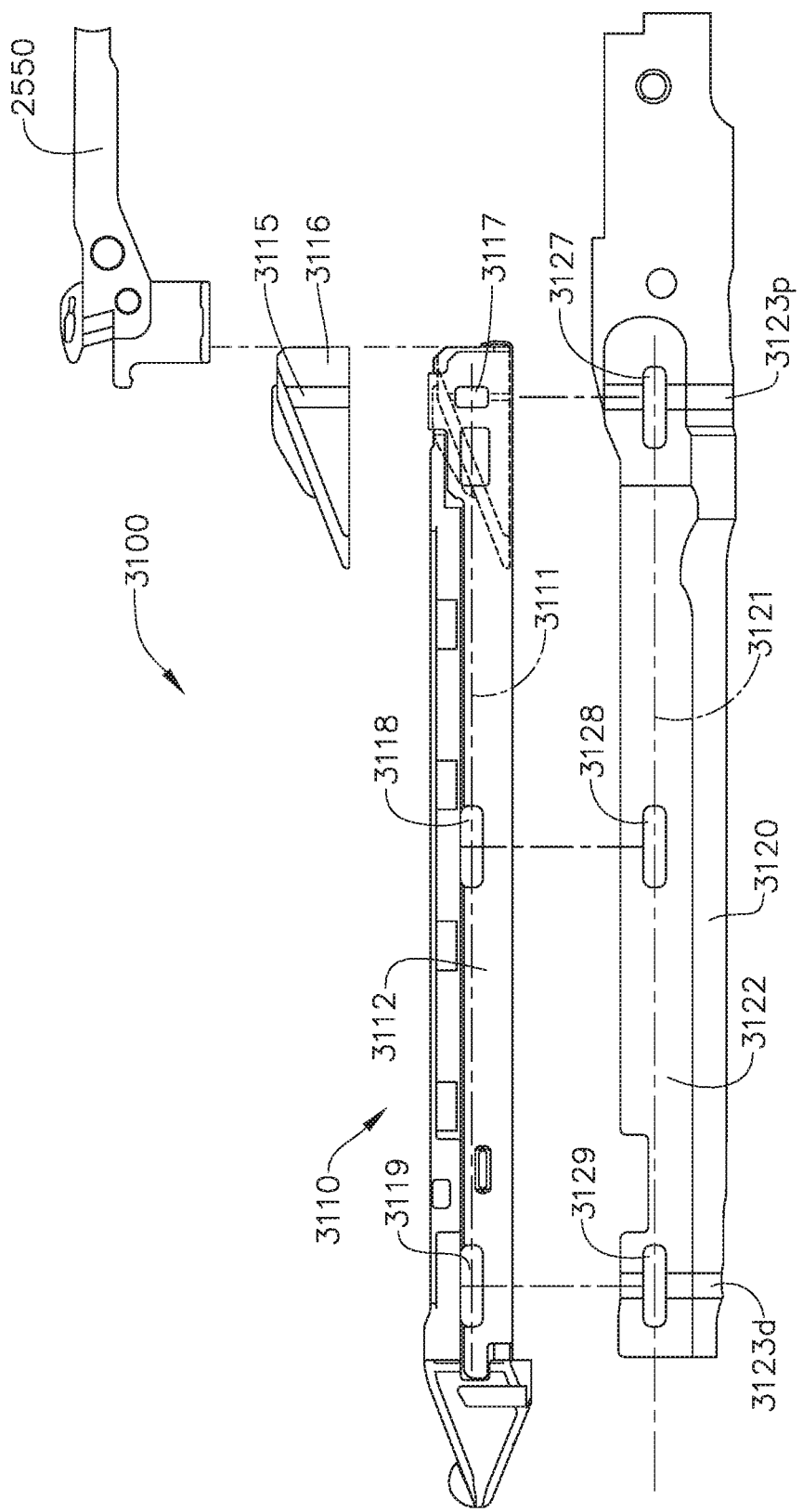
FIG. 26 is an exploded view of a cartridge jaw, a staple cartridge, and a firing member of a surgical instrument in accordance with at least one embodiment.

Referring primarily to FIG. 26, the sled 3116 comprises a demarcation 3115 which is observable through the aligned cartridge and jaw windows and can assist a clinician in understanding the position of the sled 3116 within the staple cartridge 3110. In at least one instance, the demarcation 3115 comprises a color which is different than the color of the cartridge jaw 3120 and/or the sled 3116, such as blue, for example. In certain instances, the demarcation can comprise a ridge, for example.

Referring primarily to FIG. 26, the cartridge jaw 3120 further comprises a proximal datum 3123p and a distal datum 3123d. When the sled 3116 is in its proximal, unfired position, the demarcation 3115 is aligned with the proximal datum 3123p. In such instances, the proximal datum 3123p can assist a clinician in determining whether the staple cartridge 3110 is unspent. When the sled 3116 is in its distal, completely fired position, the demarcation 3115 is aligned with the distal datum 3123d. In such instances, the proximal datum 3123p can assist a clinician in determining whether the staple cartridge 3110 has been completely spent. The datums 3123p and 3123d comprise narrow linear vertical markings on the cartridge jaw 3120; however, the datums 3123p and 3123d can comprise any suitable configuration. In at least one instance, the datums 3123p and 3123d are the same color as the demarcation 3115. In other instances, the datums 3123p and 3123d are a different color than the demarcation 3115.

Further to the above, the intermediate cartridge window 3118 is the same size as the intermediate jaw window 3128. Similarly, the distal cartridge window 3119 is the same size as the distal jaw window 3129. That said, the proximal cartridge window 3117 is not the same size as the proximal jaw window 3127. The proximal cartridge window 3117 is narrower than the proximal jaw window 3127 as measured along the longitudinal axes 3111 and 3121. In at least one instance, the proximal cartridge window 3117 has the same width as the demarcation 3115. In such instances, a clinician can accurately assess whether or not the sled 3116 has been advanced distally even the slightest amount.

As discussed above, the cartridge jaw 3120 is configured to receive a replaceable staple cartridge therein; however, the cartridge and jaw windows disclosed herein can be used with a stapling assembly that does not comprise a replaceable staple cartridge. Moreover, the cartridge and jaw windows disclosed herein can be adapted to either side or both sides of a stapling assembly.

Referring to FIGS. 31-34, a cartridge jaw 3220 comprises a bottom portion, or wall, 3221 and lateral side portions, or walls, 3222 extending from the bottom wall 3221. Similar to the above, the cartridge jaw 3220 is configured to receive a replaceable staple cartridge between the side walls 3222. The bottom wall 3221 comprises a longitudinal slot 3223 defined therein which is configured to receive the bottom cam of the firing assembly 2550, for example.

Figure 33:
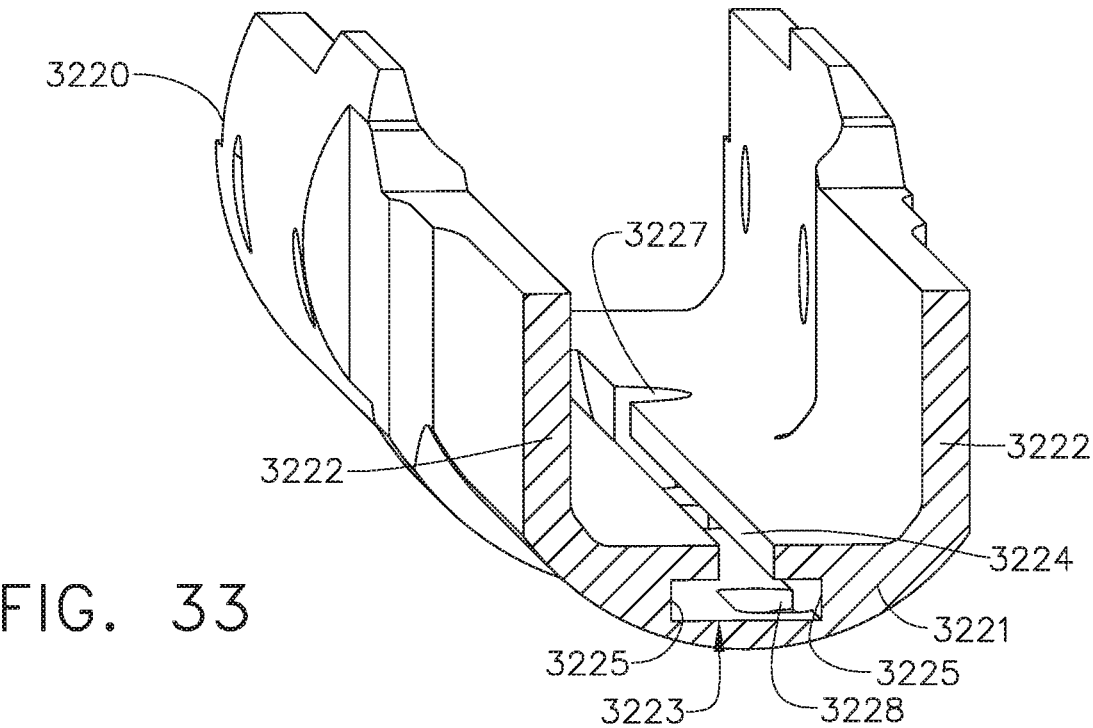
FIG. 33 is a cross-sectional view of the cartridge jaw of FIG. 31 taken along line 33-33 in FIG. 31.
Figure 34:
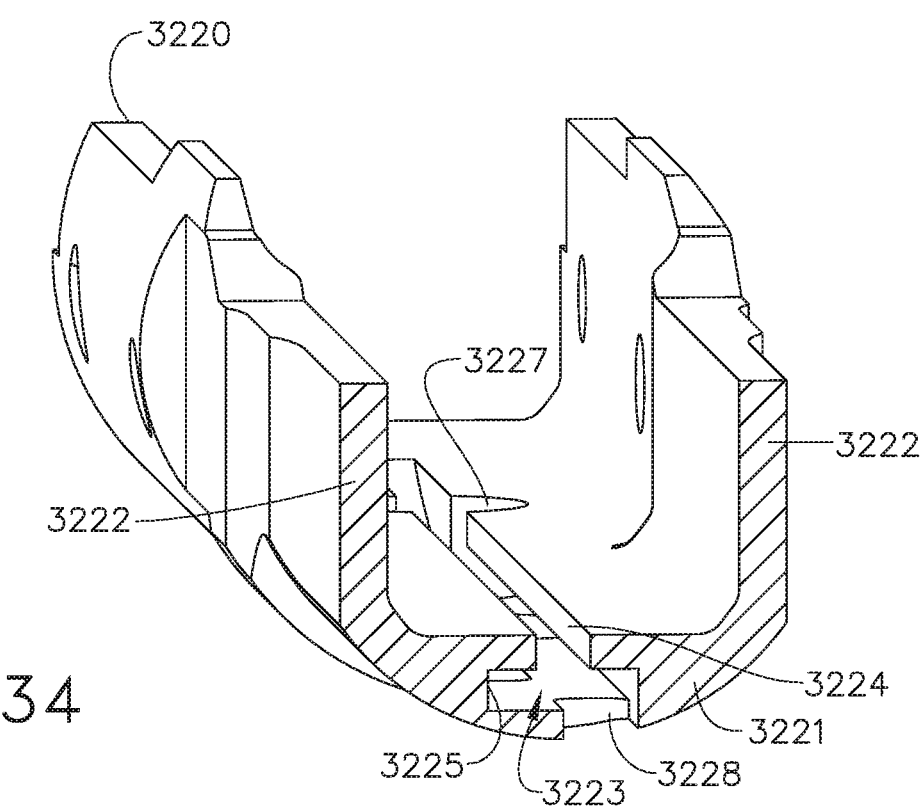
FIG. 34 is a cross-sectional view of the cartridge jaw of FIG. 31 taken along line 34-34 in FIG. 31.

Referring primarily to FIGS. 33 and 34, the longitudinal slot 3223 comprises a central portion 3224. The central portion 3224 is part of a T-shaped configuration that includes lateral portions 3225 which extend laterally from the central portion 3224. The longitudinal slot 3223 further comprises a proximal opening, or window, 3227 and a distal opening, or window, 3229 at the opposite ends of the central portion 3224. The sled of a staple cartridge is aligned with the proximal opening 3227 when the sled is in its proximal, unfired position. In such instances, a clinician can observe whether or not the staple cartridge has been spent. Similarly, the sled is aligned with the distal opening 3229 when the sled is in its distal, fully-fired position. In such instances, a clinician can observe whether or not the staple cartridge has been completely spent.

Referring again to FIGS. 31 and 32, the longitudinal slot 3223 further comprises intermediate openings, or windows, 3228 defined in the bottom wall 3221 between the proximal opening 3227 and the distal opening 3229. Similar to the above, the progression of the sled during the staple firing stroke can be observed through the openings 3228. The openings 3228 are elongate in the longitudinal direction; however, the openings 3228 can comprise any suitable configuration. The openings 3228 are spaced periodically such that the bottom wall 3221 is sufficiently stiff between the lateral side walls 3222. Moreover, any suitable number of openings 3228 can be used, although the bottom wall 3221 will be stiffer with less openings 3228.

Referring primarily to FIG. 32, the openings 3228 are offset with respect to the central portion 3224 of the longitudinal slot 3223. Stated another way, each opening 3228 comprises a longitudinal axis which is not collinear with a longitudinal axis of the central portion 3224. Moreover, the openings 3228 are staggered with respect the longitudinal axis of the central portion 3224 in an alternating manner. In at least one instance, a first opening 3228 is defined on one side of the longitudinal axis while a second opening 3228 is defined on the opposite side of the longitudinal axis. This pattern of the openings 3228 repeats along the length of the longitudinal slot 3223. Such an arrangement can increase the width of the walls between the openings 3228 and, as a result, increase the stiffness of the bottom wall 3221 as compared to embodiments where all of the openings 3228 are positioned along the longitudinal axis of the central portion. Other embodiments, however, are envisioned.

As discussed herein, a surgical instrument can comprise a firing assembly configured to apply a firing load, or force, to a sled of a staple cartridge during a firing stroke. The firing load is sufficient to push the staples out of the staple cartridge and into the tissue of a patient, deform the staples against an anvil, and incise the tissue. In certain instances, the firing load can increase significantly beyond a threshold which is deemed safe and/or suitable for the operation of the surgical instrument. In at least one such instance, the firing load can increase significantly when the firing assembly abuts a missing cartridge lockout and/or a spent cartridge lockout, for example.

Referring now to FIGS. 35-38, a surgical instrument 3500 comprises a shaft 3540 and a firing assembly 3550. The firing assembly 3550 comprises a first firing rod 3551, a second firing rod 3552, and a firing bar 3554. The firing assembly 3550 further comprises a biasing member, or spring, 3556 positioned intermediate the first firing rod 3551 and the second firing rod 3552. When the first firing rod 3551 is advanced distally, the first firing rod 3551 pushes the second firing rod 3552 distally via the spring 3556. The distal end of the second firing rod 3552 is connected to the firing bar 3554 at an interconnection 3553 and, when the second firing rod 3552 is advanced distally, the second firing rod 3552 pushes the firing bar 3554 distally. Stated another way, a firing load can be transmitted from the first firing rod 3551 to the second firing rod 3552 through the spring 3556 and ultimately to the firing bar 3554.

Further to the above, the spring 3556 is compressed between the first firing rod 3551 and the second firing rod 3552 in response to the firing load, or force, transmitted through the firing assembly 3550. When the firing load transmitted through the firing assembly 3550 is below a predetermined force threshold, the spring 3556 transmits the firing load to the second firing rod 3552 to perform the firing stroke, as illustrated in FIG. 35. When the firing load exceeds the threshold, the spring 3556 is compressed to a point in which a proximal end 3555 of the second firing rod 3552 actuates a lockout system which prevents the firing assembly 3550 from being advanced through its staple firing stroke, as illustrated in FIG. 36. At such point, the clinician can evaluate the surgical instrument 3500 as to why the firing force threshold of the surgical instrument 3500 was exceeded.

Further to the above, the spring 3556, when compressed, applies a biasing force to the second firing rod 3552 which opposes the proximal movement of the second firing rod 3552 relative to the first firing rod 3551. The threshold force of the firing assembly 3550 accounts for the firing force needed to staple and cut the tissue and, in addition, the biasing force created by the spring 3556. In various instances, the biasing force of the spring 3556 opposes the firing force transmitted through the second firing rod 3552. Moreover, the biasing force of the spring 3556 increases linearly, and proportionately, in response to the relative movement between the second firing rod 3552 and the first firing rod 3551. That said, once the force transmitted through the firing assembly 3550 exceeds the threshold force, the lockout system switches between an unlocked configuration and a locked configuration, as discussed in greater detail below.

Further to the above, and as also described in greater detail below, the lockout system of the firing assembly 3550 can be tripped, or actuated, into a locked stated when the compression of the spring 3556 has exceeded a threshold compression, or deflection. Stated another way, the lockout system does not actuate into a locked state while the compression of the spring 3556 is below the threshold compression of the spring 3556.

The lockout system comprises, further to the above, a lock 3570 rotatably mounted to a frame 3542 of the shaft 3540 about a pivot 3571 and, in addition, a lock actuator 3577 mounted to the first firing rod 3551. The lock 3570 is held in an unlocked position, or configuration, by the lock actuator 3577 when the lock actuator 3577 has not been actuated. The lock actuator 3577 is rotatably mounted to the first firing rod 3551 and is rotatable between an unactuated position (FIG. 35) and an actuated position (FIG. 36). When the spring 3556 of the firing assembly 3550 is not compressed more than its threshold compression, or above its force threshold, as illustrated in FIG. 35, the lock actuator 3577 is biased into its unactuated position by a torsion spring 3576 and the lock 3570 is held out of engagement with the firing assembly 3550.

When the spring 3556 is compressed more than its threshold compression, or above its force threshold, the proximal end 3555 of the second firing rod 3552 engages the lock actuator 3577 and rotates the lock actuator 3577 into its actuated position, as illustrated in FIG. 36. In such instances, the lock 3570 is released by the lock actuator 3577 and engages the second firing rod 3552. More specifically, the lockout system further comprises a biasing member, or spring, 3572 configured to push the lock 3570 into engagement with the second firing rod 3552 once the lock 3570 is released. The lock 3570 comprises a lock shoulder 3578 which is configured to be received within a lock recess, or notch, 3558 defined in the second firing rod 3552 which prevents the firing assembly 3550 from being advanced distally.

Figure 37:
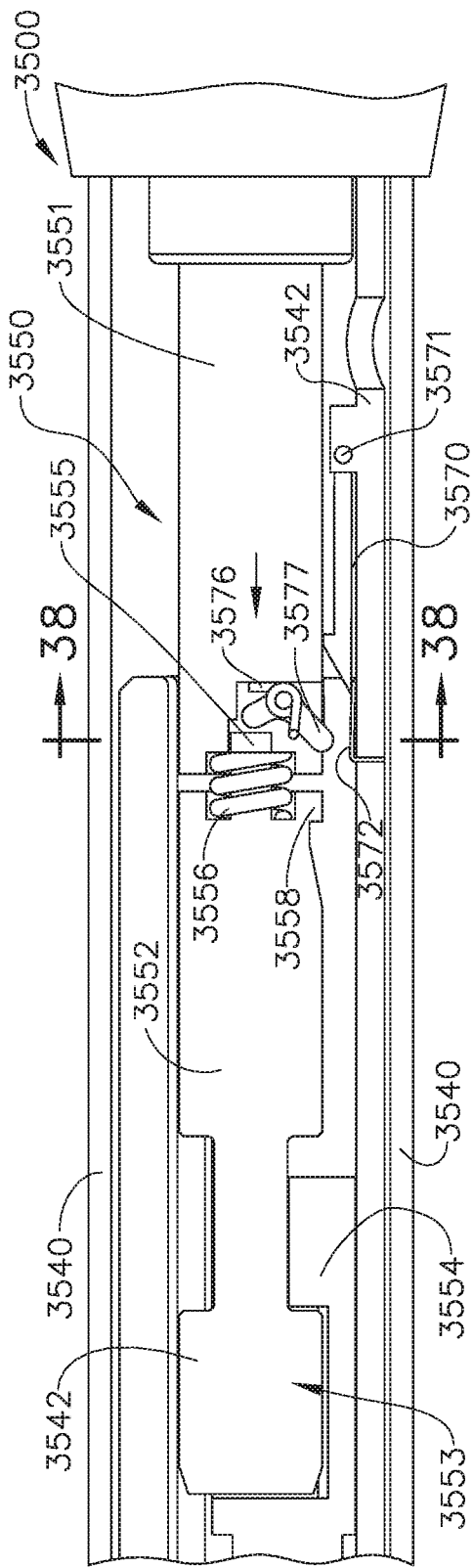
FIG. 37 is a partial cross-sectional view of the surgical instrument of FIG. 35 illustrating the firing force lockout in an unlocked configuration and the firing assembly in a fired position.
Figure 38:
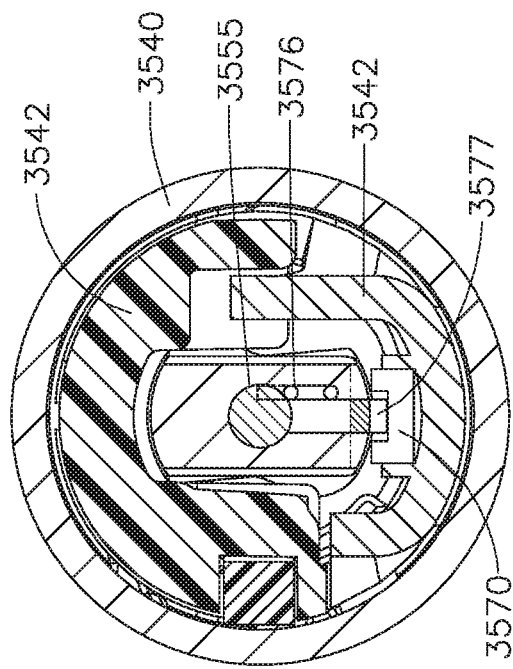
FIG. 38 is a cross-sectional view of the surgical instrument of FIG. 35 taken along line 38-38 in FIG. 37.

The reader should appreciate that the lock 3570 of the lockout system can only stop the advancement of the firing assembly 3550 when the lock notch 3558 defined in the second firing rod 3552 is aligned with the lock 3570. Once the firing assembly 3550 is advanced distally during the staple firing stroke and the lock notch 3558 is moved out of alignment with the lock shoulder 3578, as illustrated in FIG. 37, the lock 3570 is constrained in its unlocked position, or configuration, by the first firing rod 3551 throughout the firing stroke of the firing assembly 3550. As such, the lockout system of the firing assembly 3550 comprises a beginning-of-stroke lockout that stops the firing assembly 3550 from performing a staple firing stroke.

Further to the above, a missing cartridge lockout and/or a spent cartridge lockout in the end effector of the surgical instrument 3500, for example, can block the distal advancement of the firing assembly 3550 when a spent staple cartridge is seated in the end effector of the surgical instrument 3500 and/or an unspent staple cartridge is missing from the end effector altogether. In such instances, the force transmitted through the firing assembly 3550 will increase above the threshold force and the lockout system of the firing assembly 3550 can respond by also blocking the distal advancement of the firing assembly 3550. In various instances, the firing assembly lockout can bolster the missing cartridge and/or spent cartridge lockout. In such instances, as a result, the firing assembly 3550 cannot be used to cut tissue without an unspent staple cartridge properly seated in the end effector of the surgical instrument 3500.

In order to reset the firing assembly 3550, further to the above, the clinician can operate the surgical instrument 3500 to retract the firing assembly 3550 proximally. In at least one instance, the surgical instrument 3500 comprises an electric motor configured to drive the firing assembly 3550 through its staple firing stroke which can be operated in reverse to retract the firing assembly 3550. When the firing assembly 3550 is at least partially retracted, the spring 3556 can re-expand and push the second firing rod 3552 away from the first firing rod 3551 to disengage the second firing rod 3552 from the lock actuator 3577 of the lockout system. At such point, the firing assembly 3550 can be advanced distally to complete its staple firing stroke, as illustrated in FIG. 37.

Figure 39:
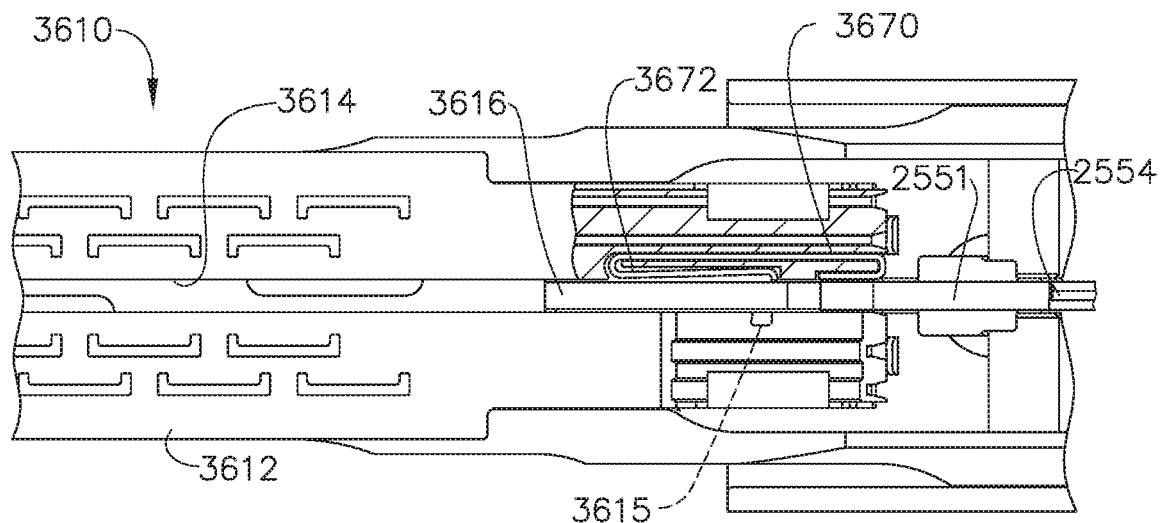
FIG. 39 is a partial plan view of a staple cartridge comprising a cartridge lockout in accordance with at least one embodiment.
Figure 40:
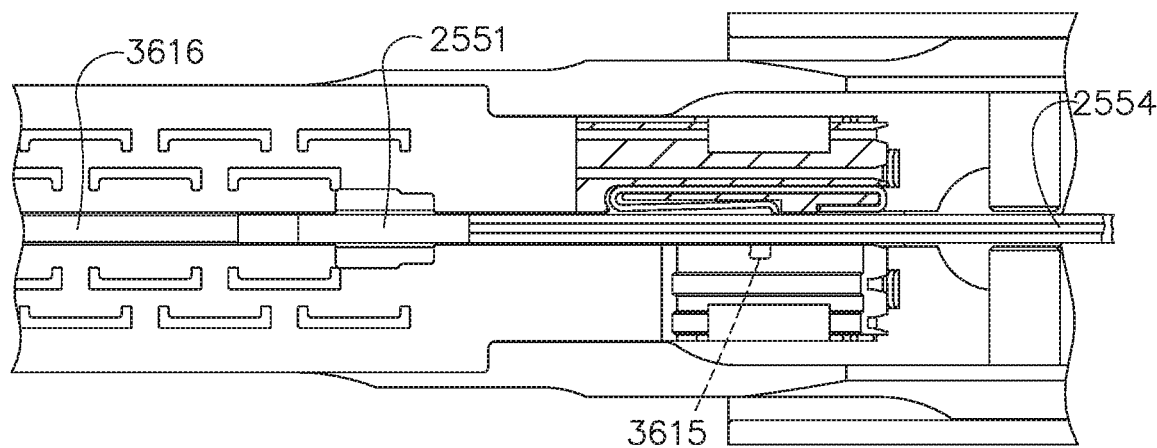
FIG. 40 is a partial plan view of the staple cartridge of FIG. 39 illustrating a firing member partially advanced through the staple cartridge.
Figure 41:
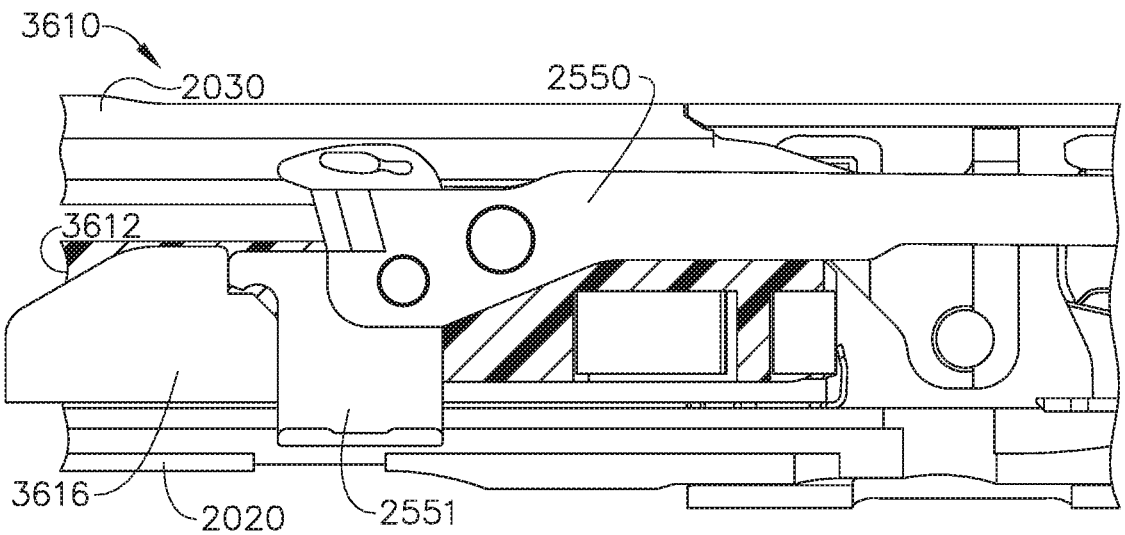
FIG. 41 is a partial cross-sectional elevational view of the staple cartridge of FIG. 39 illustrating the firing member in a partially-advanced position.

A staple cartridge 3610 comprising a spent cartridge lockout is illustrated in FIGS. 39-42. The staple cartridge 3610 comprises a cartridge body 3612 including staple cavities and a longitudinal slot 3614 defined therein. Referring primarily to FIG. 41, the staple cartridge 3610 further comprises a sled 3616 which is movable between a proximal, unfired position (FIG. 39) and a distal, fired position by a firing assembly, such as firing assembly 2550, for example, to eject staples removably stored in the staple cavities during a staple firing stroke. Referring now to FIG. 39, a portion of the sled 3616 travels within the longitudinal slot 3614 during the staple firing stroke. Moreover, referring to FIG. 40, a portion of the firing assembly 2550 also travels within the longitudinal slot 3614 during the staple firing stroke. More specifically, the firing assembly 2550 comprises a coupling member 2551 that travels within the slot 3614.

The staple cartridge 3610 further comprises a lock 3670. The lock 3670 comprises a first end mounted to the cartridge body 3612 and a second end 3672 that extends into the longitudinal slot 3614. When the staple cartridge 3610 is in an unfired condition and the sled 3616 is in its proximal, unfired position, referring again to FIG. 40, the second end 3672 of the lock 3670 is flexed into and held in an unlocked state by the sled 3616. In such instances, the lock 3670 cannot prevent the staple firing stroke from being initiated by the firing assembly 2550. As the sled 3616 is advanced distally by the firing assembly 2550, the sled 3616 is moved out of contact with the lock 3670. In such instances, the firing assembly 2550 continues to hold the lock 3670 in its unlocked configuration throughout the staple firing stroke.

After the staple firing stroke has been at least partially completed, the firing assembly 2550 can be retracted. In such instances, the sled 3616 is not retracted with the firing assembly 2550. Instead, the sled 3616 is left behind in a distal position within the cartridge body 3616. Thus, after the firing assembly 2550 has been completely retracted, referring to FIG. 42, the lock 3670 can unflex into a locked configuration such that the second end 3672 blocks the longitudinal slot 3614. Stated another way, the second end 3672 of the lock 3670 can block the firing assembly 2550 from being advanced through another staple firing stroke.

Further to the above, the lock 3670 comprises a spent cartridge lockout. After the sled 3616 has been advanced distally out of alignment with the lock 3670, the staple cartridge 3610 has become a spent staple cartridge whether or not all of, or any of, the staples have been ejected from the staple cartridge 3610. Retraction of the firing assembly 2550 into its unfired position, at such point, would cause the staple cartridge 3610 to lock itself out. Accordingly, the staple cartridge 3610 would have to be removed from the surgical instrument and replaced with an unspent staple cartridge before the surgical instrument could be used once again.

Figure 42:
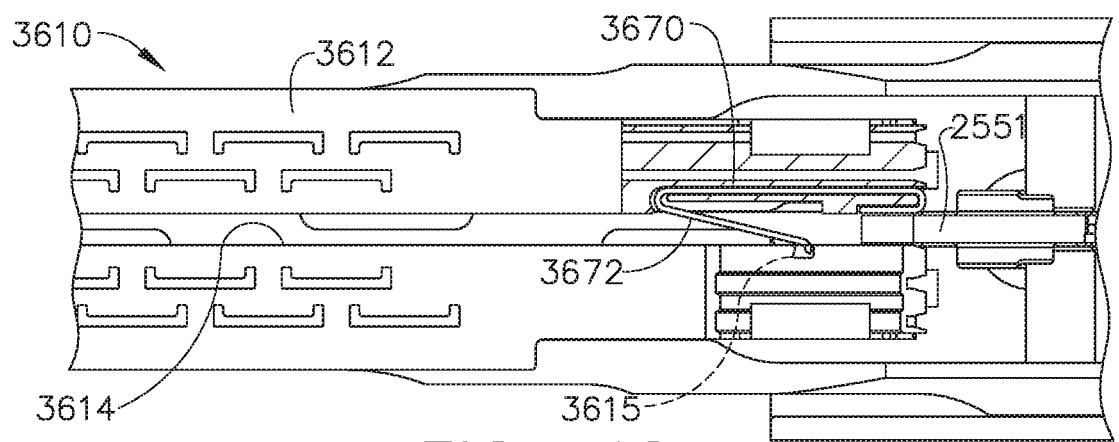
FIG. 42 is a partial plan view of the staple cartridge of FIG. 39 illustrating the firing member in a retracted position and the cartridge lockout in a locked configuration.
Figure 43:
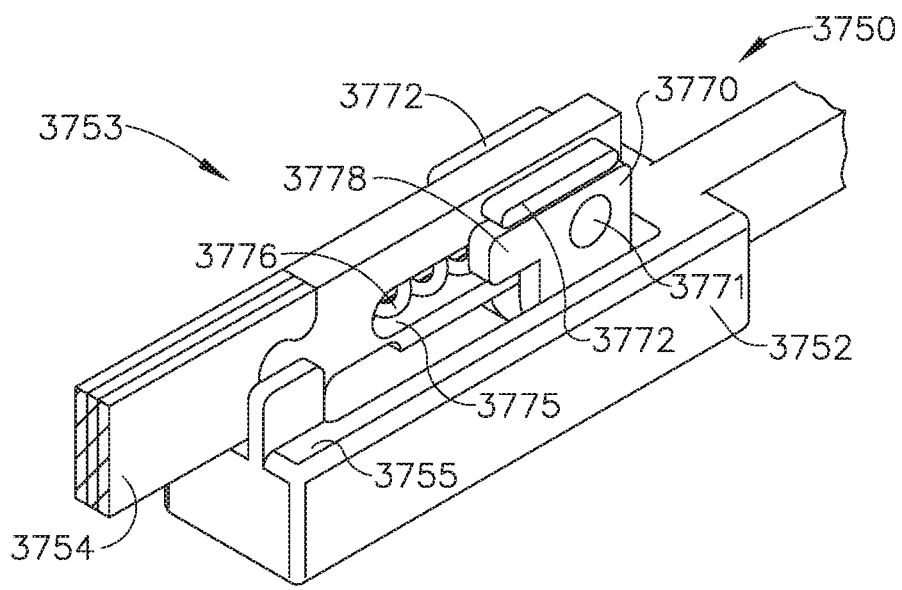
FIG. 43 is a partial perspective view of a firing lockout assembly of a surgical instrument illustrated in an unlocked configuration in accordance with at least one embodiment.
Figure 44:
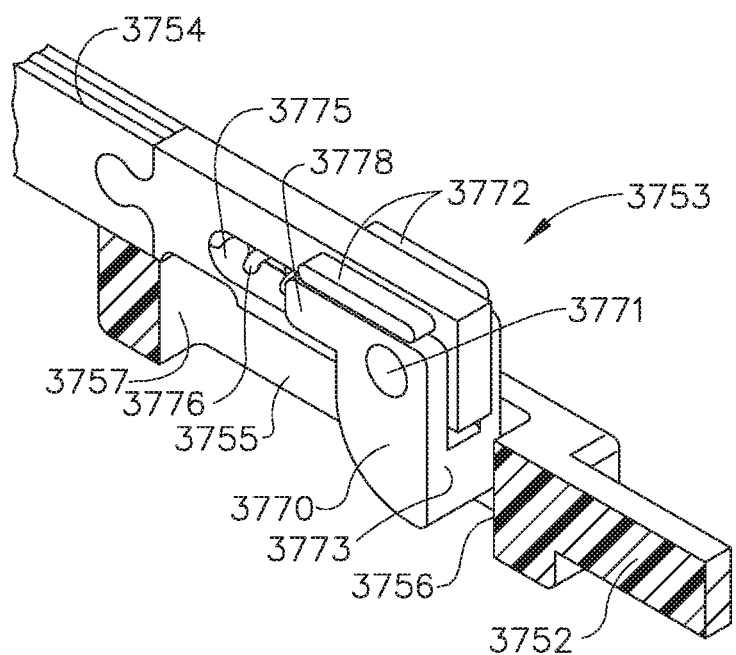
FIG. 44 is a partial cross-sectional perspective view of the firing lockout assembly of FIG. 43 illustrated in its unlocked configuration.
Figure 45:
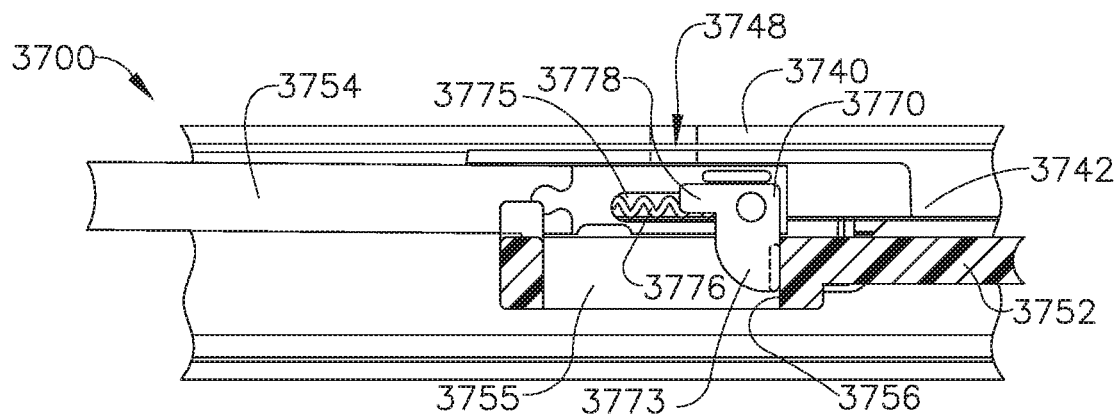
FIG. 45 is a partial cross-sectional elevational view of the surgical instrument of FIG. 43 illustrating the firing lockout in its unlocked configuration.

Further to the above, the cartridge body 3610 can include a notch 3615 configured to receive a portion of the lock 3670 when the lock 3670 moves into its locked configuration, as illustrated in FIG. 42. The notch 3615 is defined in a sidewall of the longitudinal slot 3614 and positioned opposite the first portion of the lock 3670 which is mounted to the cartridge body 3612. Interaction between the second end 3672 of the lock 3670 and the sidewalls of the notch 3615 can strengthen the lockout and reduce the possibility of the firing assembly 2550 being pushed by the lock 3670. In addition to or in lieu of the above, the firing assembly 2550 can comprise a lockout which is triggered, or actuated, when the firing assembly 2550 abuts the lock 3670.

Figure 46:
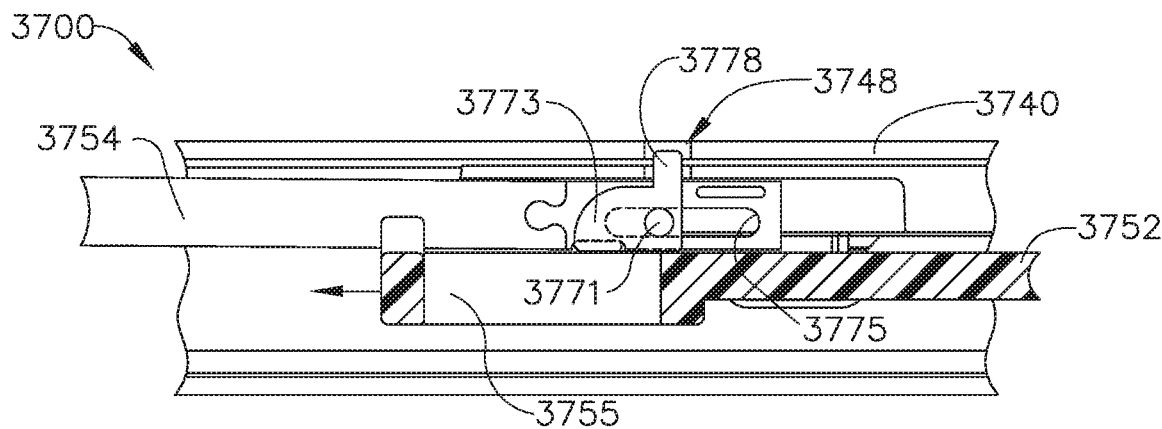
FIG. 46 is a partial cross-sectional elevational view of the surgical instrument of FIG. 43 illustrating the firing lockout in a locked configuration.

Turning now to FIGS. 43-47, a firing assembly 3750 of a surgical instrument 3700 comprises a firing rod 3752 and a firing bar 3754. The firing rod 3752 comprises an aperture 3755 defined in the distal end thereof. The aperture 3755 comprises a proximal endwall 3756 and a distal endwall 3757. The firing bar 3754 comprises a lockout 3770 positioned in the aperture 3755 at an interface 3753. When the firing rod 3752 is advanced distally during a staple firing stroke, the proximal endwall 3756 of the aperture 3755 contacts the lockout 3770 and pushes the firing bar 3754 distally. In the event that the force transmitted between the firing rod 3752 and the firing bar 3754 exceeds a predetermined force threshold, the lockout 3770 moves from an unlocked state (FIG. 45) into a locked state (FIG. 46). Similar to the above, the force threshold can be exceeded when the firing assembly 3750 abuts a spent cartridge lockout and/or a missing cartridge lockout, for example.

The lockout 3770 is rotatably and slidably mounted to the firing bar 3754. The firing bar 3754 comprises a longitudinal slot 3775 defined therein and the lockout 3770 comprises a pin 3771 slidably positioned within the slot 3775. The firing bar 3754 further comprises a spring 3776 positioned intermediate the pin 3771 and a distal end of the slot 3775. As a result, a firing force transmitted from the firing rod 3752 can flow through the lockout 3770 and the lockout pin 3771, through the spring 3776, and into the firing bar 3754—so long as the firing force is below the force threshold. In the event that the firing force exceeds the force threshold, the firing rod 3752 can push the lockout 3770 distally within the longitudinal slot 3775, as illustrated in FIG. 46. In such instances, the lockout 3770 can also rotate upwardly into engagement with a shaft 3740 of the surgical instrument 3700. More specifically, referring primarily to FIG. 44, the firing bar 3754 comprises ledges 3772 extending laterally therefrom which prevent the lockout 3770 from rotating upwardly when the firing force is below the threshold and the lockout 3770 is positioned in the proximal end of the longitudinal slot 3775; however, once the lockout 3770 is pushed distally away from the ledges 3772, the firing force acts to rotate the lockout 3770 upwardly as illustrated in FIG. 46.

Further to the above, the shaft 3740 comprises a frame 3742 including a lock aperture 3748 defined therein which is configured to receive a portion of the lockout 3770 when the lockout 3770 is rotated upwardly. The interaction between the lockout 3770 and the sidewalls of the lock aperture 3748 prevent the firing assembly 3750 from being advanced distally through its staple firing stroke. Similar to the above, the lock aperture 3748 is defined in the shaft 3740 at a location which corresponds to the initiation of the staple firing stroke. As a result, the lockout 3770 is configured and arranged to assist in locking out the surgical instrument 3700 in the event that a staple cartridge is missing from, or a spent staple cartridge is positioned within, the surgical instrument 3700. That said, the lock aperture 3748 can be positioned in any suitable location. Moreover, more than one lock aperture 3748 can be utilized to provide more than one location in which the firing assembly 3750 can be locked out.

Figure 47:
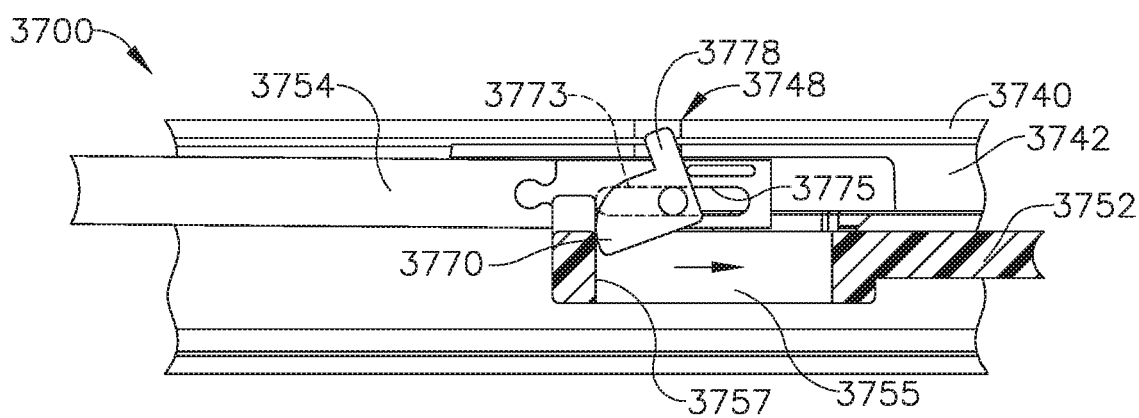
FIG. 47 is a partial cross-sectional elevational view of the surgical instrument of FIG. 43 illustrating the firing lockout being returned to its unlocked configuration.
Figure 48:
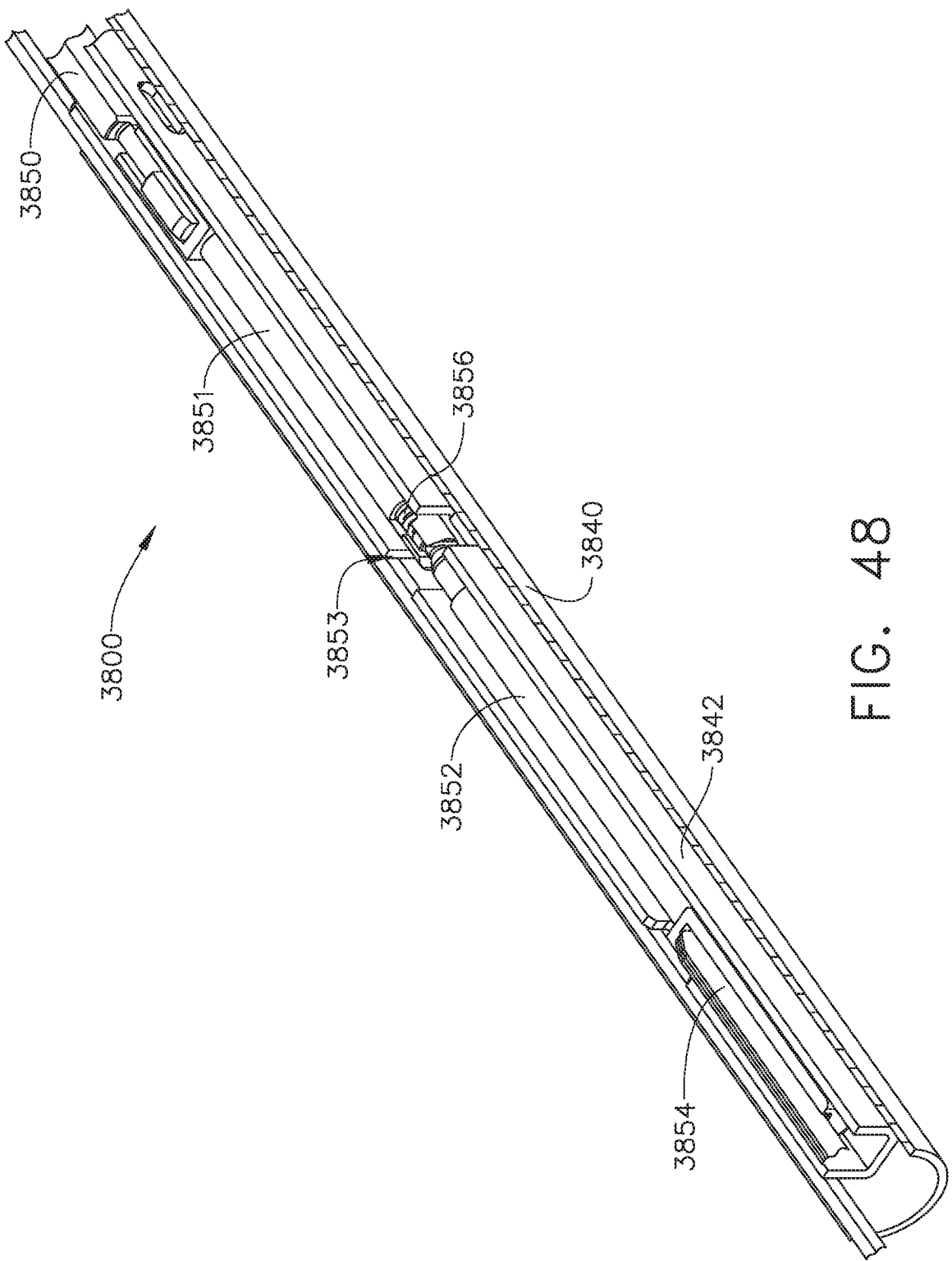
FIG. 48 is a partial perspective view of a surgical instrument comprising a firing lockout in accordance with at least one embodiment.
Figure 49:
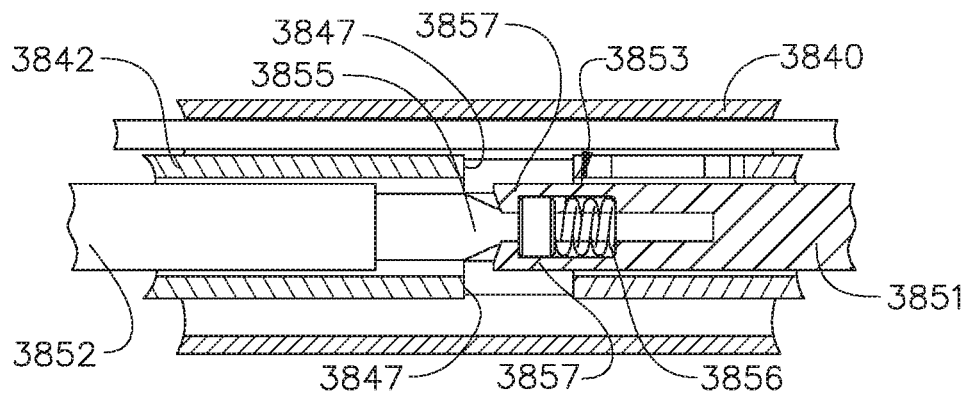
FIG. 49 is a partial cross-sectional view of the surgical instrument of FIG. 48 illustrating the firing lockout in an unlocked configuration.

The lockout 3770 can be reset after it has been moved into its locked configuration (FIG. 46). Turning now to FIG. 47, the firing rod 3752 can be moved proximally until the distal endwall 3757 of the aperture 3755 contacts the lockout 3770 and, at such point, the endwall 3757 can rotate the lockout 3770 downwardly and positively return the lockout 3770 to its unlocked configuration as the firing rod 3752 continues to move proximally. Moreover, the firing rod 3752 can pull the lockout 3770 back under the ledges 3772 (FIG. 44) as the firing rod 3752 is being retracted. At such point, the firing assembly 3750 is reset and can be re-advanced distally—assuming that the impediment which blocked the firing assembly 3750 has been addressed.

Turning now to FIGS. 48-51, a surgical instrument 3800 comprises a shaft 3840 and a firing assembly 3850. The shaft 3840 comprises a frame 3842 and a longitudinal passage configured to slidably receive the firing assembly 3850. The firing assembly 3850 comprises a first firing rod 3851, a second firing rod 3852, and a firing bar 3854. The first firing rod 3851 is coupled to the second firing rod 3852 at an interconnection 3853. In use, referring to FIG. 49, the interconnection 3853 is configured to transmit a force, or firing load, between the first firing rod 3851 and the second firing rod 3852. However, as discussed in greater detail below, the interconnection 3853 is configured to slip when the firing load transmitted through the firing assembly 3850 exceeds a predetermined force threshold.

Further to the above, the second firing rod 3852 comprises a proximal end 3855 positioned in a cavity defined in the distal end of the first firing rod 3851. The first firing rod 3851 further comprises lock arms 3857 engaged with the proximal end 3855 of the second firing rod 3852 which are configured to transmit the firing load from the first firing rod 3851 to the second firing rod 3852 when the firing load is below the force threshold. More specifically, the lock arms 3857 push on inclined surfaces 3859 defined on the proximal end 3855 of the second firing rod 3852. When the firing load exceeds the force threshold, the lock arms 3857 slide along the inclined surfaces 3859 causing the interconnection 3853 to slip, splay, and elastically flare outwardly to disrupt the firing stroke of the firing assembly 3850.

Figure 50:
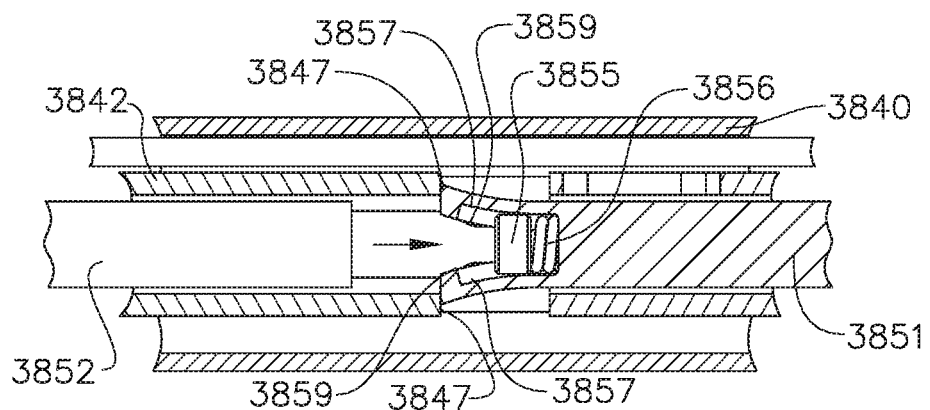
FIG. 50 is a partial cross-sectional view of the surgical instrument of FIG. 48 illustrating the firing lockout in a locked configuration.
Figure 51:
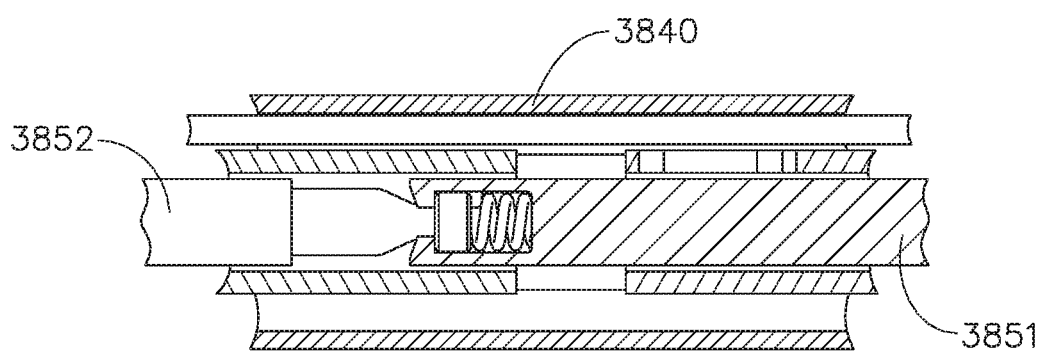
FIG. 51 is a partial cross-sectional view of the surgical instrument of FIG. 48 illustrating the firing lockout after it has been returned to its unlocked configuration.

Further to the above, referring to FIG. 50, the lock arms 3857 are configured to engage lock shoulders 3847 defined on the shaft frame 3842 when the lock arms 3857 slide relative to the inclined surfaces 3859 and flare outwardly. The interaction between the lock arms 3857 and the lock shoulders 3847 prevents the firing assembly 3850 from being advanced through its staple firing stroke. Similar to the above, the lock shoulders 3847 are positioned at the beginning of the staple firing stroke of the firing assembly 3850 such that the lockout feature of the firing assembly 3850 is responsive to a beginning-of-stroke lockout; however, the lock shoulders 3847 can be placed at any suitable location, or locations.

Further to the above, the firing assembly 3850 can be reset after it has been locked out. The first firing rod 3851 can be retracted proximally to operably re-engage the lock arms 3857 with the proximal end 3855 of the second firing rod 3852. In such instances, the lock arms 3857 can resiliently move inwardly to grasp the proximal end 3855. The firing assembly 3850 further comprises a biasing member, or spring, 3856 configured to bias a head of the proximal end 3855 against the lock arms 3857. Once the interconnection 3853 has been reset, referring to FIG. 51, the firing assembly 3850 can be advanced through its staple firing stroke—assuming that the force threshold is not exceeded once again. Notably, the shaft frame 3842 prevents the lock arms 3857 from disengaging from the second firing rod 3852 during the staple firing stroke.

Turning now to FIGS. 52-56, a surgical instrument 3900 comprises a shaft 3940, an end effector positioned at a distal end of the shaft 3940, an articulation actuator 3980 configured to articulate the end effector relative to the shaft 3940, and a firing assembly 3950. The shaft 3940 comprises a shaft frame 3942 which has a longitudinal cavity 3949 defined therein. The firing assembly 3950 comprises a first firing rod 3951, a second firing rod 3952, and a firing bar 3954. The first firing rod 3951 comprises a distal end 3957 operably engaged with a proximal end 3955 of the second firing rod 3952 at an interface 3953. When the firing load transmitted through the firing assembly 3950 is below a predetermined force threshold, referring to FIGS. 52-55, the firing assembly 3950 can be pushed through a staple firing stroke. When the firing load exceeds the predetermined threshold within, and only within, a lockout zone that is prior to or at the beginning of the staple firing stroke, referring to FIG. 56, the distal end 3957 of the first firing rod 3951 can slip relative to the proximal end 3955 of the second firing rod 3952 and stop the distal advancement of the second firing rod 3952.

Further to the above, in at least one embodiment, the distal end 3957 of the first firing rod 3951 comprises a barb and the proximal end 3955 of the second firing rod 3952 comprises a barb catch configured to be coupled with the barb of the distal end 3957. When the distal end 3957 decouples from the proximal end 3955, the barb of the distal end 3957 can engage a wall 3948 in the shaft 3940 and stop the distal advancement of the first firing rod 3951, and the firing assembly 3950, when the first firing rod 3951 slips relative to the second firing rod 3952.

Referring again to FIGS. 52 and 53, the firing assembly 3950 further comprises a firing collar 3959 slidably positioned in the longitudinal cavity 3949 of the shaft 3940. The firing collar 3959 is comprises of a resilient material which is frictionally-engaged with the sidewalls of the longitudinal cavity 3949, for example. Upon comparing FIGS. 52 and 53, it can be seen that the second firing rod 3952 slides within the firing collar 3959 while the firing collar 3959 remains stationary during the initial distal movement of the firing assembly 3950. This initial distal movement of the firing assembly 3950 is not part of the staple firing stroke. Such initial distal movement of the firing assembly 3950, however, can be used to perform a different function within the end effector, such as closing the end effector, for example.

Further to the above, the first firing rod 3951 comprises a projection 3960 defined thereon configured to engage the firing collar 3959 to initiate the staple firing stroke. At such point, the interface 3953 is positioned within the firing collar 3959 which prevents the distal end 3957 of the first firing rod 3951 from slipping relative to the proximal end 3955 of the second firing rod 3952 during the staple firing stroke. As a result of the above, the interface 3953 can decouple prior to or at the beginning of the staple firing stroke but, on the other hand, remain intact throughout the staple firing stroke. The firing collar 3959 comprises a rigid proximal end 3958 that is engaged by the projection 3960 and is pushed distally by the projection 3960 during the staple firing stroke, as illustrated in FIG. 56. The firing assembly 3950 further comprises a spring 3956 positioned intermediate and compressed between the firing bar 3954 and the firing collar 3959 which can assist in controlling the relative position between the firing bar 3954 and the firing collar 3959.

Turning now to FIGS. 57-59, a surgical instrument 4000 comprises a shaft 4040 and a firing assembly 4050. The shaft 4040 comprises a frame 4042 including a longitudinal aperture 4048 defined therein. The firing assembly 4050 comprises a firing rod 4052 and a plurality of flexible firing bars, or layers, 4054 that are operably coupled to a distal end 4057 of the firing rod 4052 at an interface 4053. The layers 4054 are configured to transmit a firing force from the firing rod 4052 to a coupling member 4051 of the firing assembly 4050 when the firing force is below a predetermined force threshold, as illustrated in FIG. 57. In the event that the firing force exceeds the force threshold, the layers 4054 can flex outwardly, as illustrated in FIG. 58, which can prevent the firing assembly 4050 from performing the staple firing stroke. In order to reset the firing assembly 4050, the firing rod 4052 can be retracted proximally to permit the layers 4054 to resiliently flex inwardly to their unflexed state. As illustrated in FIG. 59, the firing assembly 4050 further comprises a firing collar 4059 configured to bolster the layers 4054 and prevent the layers 4054 from flexing outwardly during the staple firing stroke. Similar to the above, the firing collar 4059 is comprised of a flexible material that is frictionally-engaged with the sidewalls of the longitudinal shaft aperture 4048 and does not initially move with the layers 4054. Stated another way, the firing collar 4059 does not travel with the layers 4054 until the distal end 4057 of the firing rod 4052 contacts the firing collar 4059.

Turning now to FIGS. 60-64, a surgical instrument 4100 comprises a shaft 4040 and a firing assembly 4150. The firing assembly 4150 comprises a first firing rod 4151, a second firing rod 4152, and a firing bar 4154. The first firing rod 4151 comprises a distal end positioned within an aperture 4153 defined in a proximal end of the second firing rod 4152. The second firing rod 4152 comprises a distal end comprising a longitudinal slot 4155 defined therein configured to receive a proximal end of the firing bar 4154. Referring primarily to FIGS. 60 and 61, the second firing rod 4152 comprises a wall 4157 configured to transmit a firing force from the second firing rod 4152 to the firing bar 4154. The wall 4157 comprises a fuse. When the firing force is below a predetermined force threshold, the wall 4157 is configured to remain intact, as illustrated in FIG. 62. In at least one instance, the force threshold is 80 lbf, for example. The wall 4157, however, is configured to fail when the firing force exceeds the force threshold, as illustrated in FIG. 63. At such point, the firing bar 4154 slidable within a longitudinal slot 4158 defined in the second firing rod 4152 and the distal movement of the second firing rod 4152 is not transmitted to the firing bar 4154. The fuse, or wall, 4157 is not resettable.

The firing assembly 4150 can comprise other fuses in addition to or in lieu of the above. For instance, the second firing rod 4152 further comprises fuses 4156 positioned proximally with respect to the wall 4157. Fuses 4156 comprise displaceable elements positioned within and frictionally-engaged with the sidewalls of the longitudinal slot 4158. In certain embodiments, the fuses 4156 comprise walls integrally formed with the sidewalls of the slot 4158. In at least one instance, the fuses 4156 are each configured to fail at the same force threshold as the wall 4157, such as 80 lbf, for example. In such instances, a fuse 4156 can push the firing bar 4154 distally and the staple firing stroke can be completed in the event that the firing force exceeded the force threshold for only a moment. In the event that the firing force exceeds the force threshold for more than a moment, the fuses 4156 can fail sequentially, as illustrated in FIG. 64. Alternatively, the fuses 4156 can be configured to fail at a threshold, or thresholds, that are larger than the force threshold of the wall 4157. For instance, the wall 4157 can have a force threshold of 60 lbf while the fuses can have a force threshold of 80 lbf. In at least one embodiment, the fuses 4156 can be configured to fail at increasingly higher force thresholds. For instance, the distal-most fuse 4156 can comprise the weakest fuse 4156, the fuse 4156 adjacent to the distal-most fuse 4156 can be stronger than the distal-most fuse 4156, and so forth. In other embodiments, the fuses 4156 fail at a lower force threshold than the wall 4157. In at least one such instance, the wall 4157 has a force threshold of 80 lbf and the fuses 4156 each have a force threshold of 60 lbf, for example.

Further to the above, the longitudinal slot 4158 has a length which is equal to or greater than the firing stroke of the firing assembly 4150. As a result, the second firing rod 4152 can be moved through its entire firing stroke after the wall 4157 and fuses 4156 fail without the firing bar 4154 abutting the proximal end of the longitudinal slot 4158. In order to retract the firing bar 4154 after the wall 4157 and/or the fuses 4156 have failed, the second firing rod 4152 can be retracted until the distal end of the longitudinal slot 4158 engages the firing bar 4154 and pulls the firing bar 4154 proximally. In certain instances, the firing bar 4154 is frictionally-engaged with the sidewalls of the longitudinal slot 4158 such that the firing bar 4154 can be retracted by the second firing rod 4152 if the wall 4157 and/or the fuses 4156 have failed.

Turning now to FIGS. 65-70, a surgical instrument 4200 comprises a shaft 4040 and a firing assembly 4250. The firing assembly 4250 comprises a first firing rod 4251, a second firing rod 4252 mounted to the first firing rod 4251, and a firing bar 4254. The second firing rod 4252 comprises a distal end shoulder 4257 operably engaged with a proximal end shoulder 4255 of the firing bar 4254 at an interface 4253 to transmit a firing load through the firing assembly 4250 during a staple firing stroke when the firing load is below a predetermined force threshold, as illustrated in FIGS. 65 and 66. The second firing rod 4252 further comprises one or more biasing members 4256 extending laterally therefrom. The biasing members 4256 are slidably engaged with the sidewalls of the longitudinal aperture 4048 in the shaft frame 4042. The biasing members 4256 are configured to bias the second firing rod 4252 into engagement with the firing bar 4254. When the firing load exceeds the force threshold, as illustrated in FIG. 67, the biasing members 4256 can compress or deflect and permit the second firing rod 4252 to deflect laterally and operably disengage from the firing bar 4254. At such point, the second firing rod 4252 can slide relative to the firing bar 4254 without transmitting the firing force to the second firing rod 4252.

Further to the above, the firing assembly 4250 is resettable. Referring now to FIG. 68, the first firing rod 4251 can be retracted proximally to retract the second firing rod 4252 such that, referring to FIG. 69, the distal end shoulder 4257 of the second firing rod 4252 is realigned and operably re-coupled with the proximal end shoulder 4255 of the firing bar 4254. In such instances, the biasing members 4256 can unflex and re-expand to re-align the second firing rod 4252 with the firing bar 4254. At such point, referring now to FIG. 70, the firing assembly 4250 can be advanced distally once again to complete the staple firing stroke. The reader should note that the interface 4253 of the firing assembly 4250 can decouple, and be recoupled, at any point before and/or during the staple firing stroke. Thus, the interface 4253 can decouple when the firing assembly 4250 engages a missing cartridge lockout, a spent cartridge lockout, and/or at any other moment in which the firing force becomes excessive.

Turning now to FIGS. 71-77, a surgical instrument 4300 comprises a shaft 4340 and a firing assembly 4350. The shaft 4340 comprises a frame 4342. The frame 4342 comprises a proximal longitudinal aperture 4346 and a distal longitudinal aperture 4349 configured to receive the firing assembly 4350. The firing assembly 4350 comprises a first firing rod 4351, a second firing rod 4352 operably coupled to the first firing rod 4351, and a firing bar 4354 operably coupled to the second firing rod 4352 at an interface 4353. The interface 4353 comprises a multi-stage fuse, as described in greater detail below.

Figure 71:
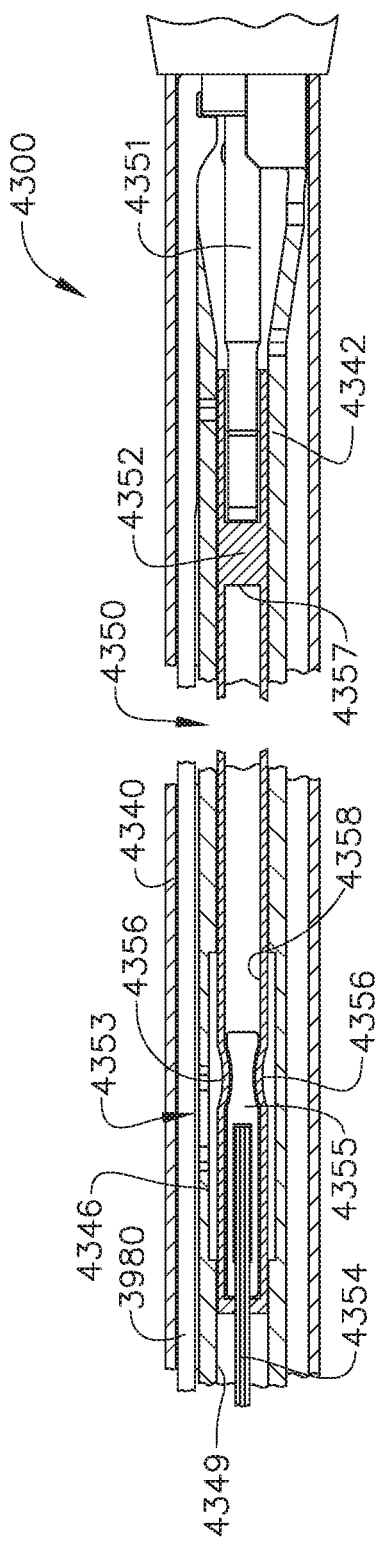
FIG. 71 is a partial cross-sectional view of a surgical instrument comprising a firing assembly having a fuse portion in accordance with at least one embodiment.
Figure 72:
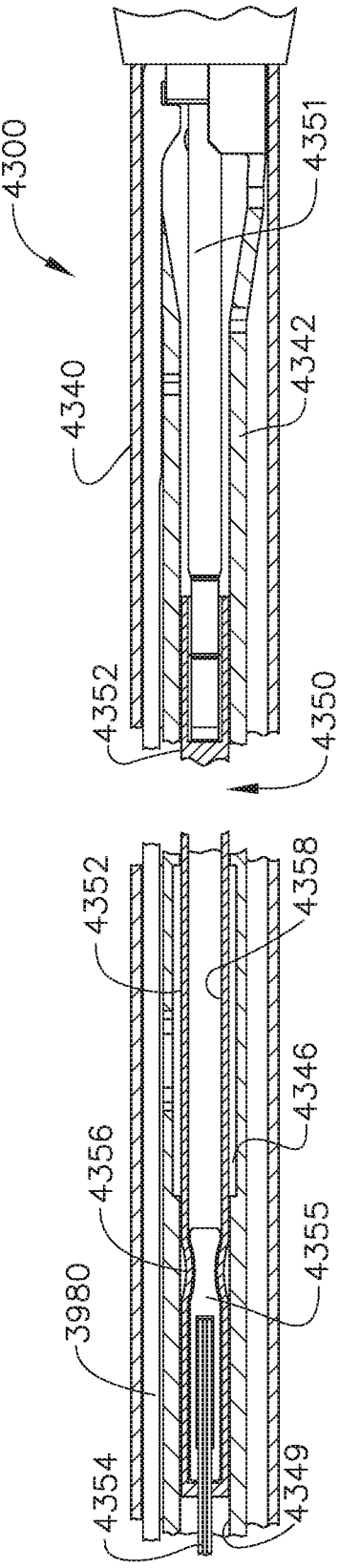
FIG. 72 is a partial cross-sectional view of the surgical instrument of FIG. 71 illustrating the firing assembly in a fired position.

Further to the above, the firing bar 4354 comprises a proximal connector 4355 including drive recesses 4359 defined on opposite sides thereof. The proximal connector 4355 is positioned in a longitudinal slot 4358 defined in the second firing rod 4352 and is operably, and releasably, coupled to the second firing rod 4352 via projections 4356 which extend inwardly from the sidewalls of the second firing rod 4352 to engage the drive recesses 4359. In use, a firing load is transmitted from the first firing rod 4351, through the second firing rod 4352, and into the firing bar 4354 to perform a staple firing stroke when the firing load is below a predetermined force threshold, as illustrated in FIGS. 71 and 72.

Figure 73:
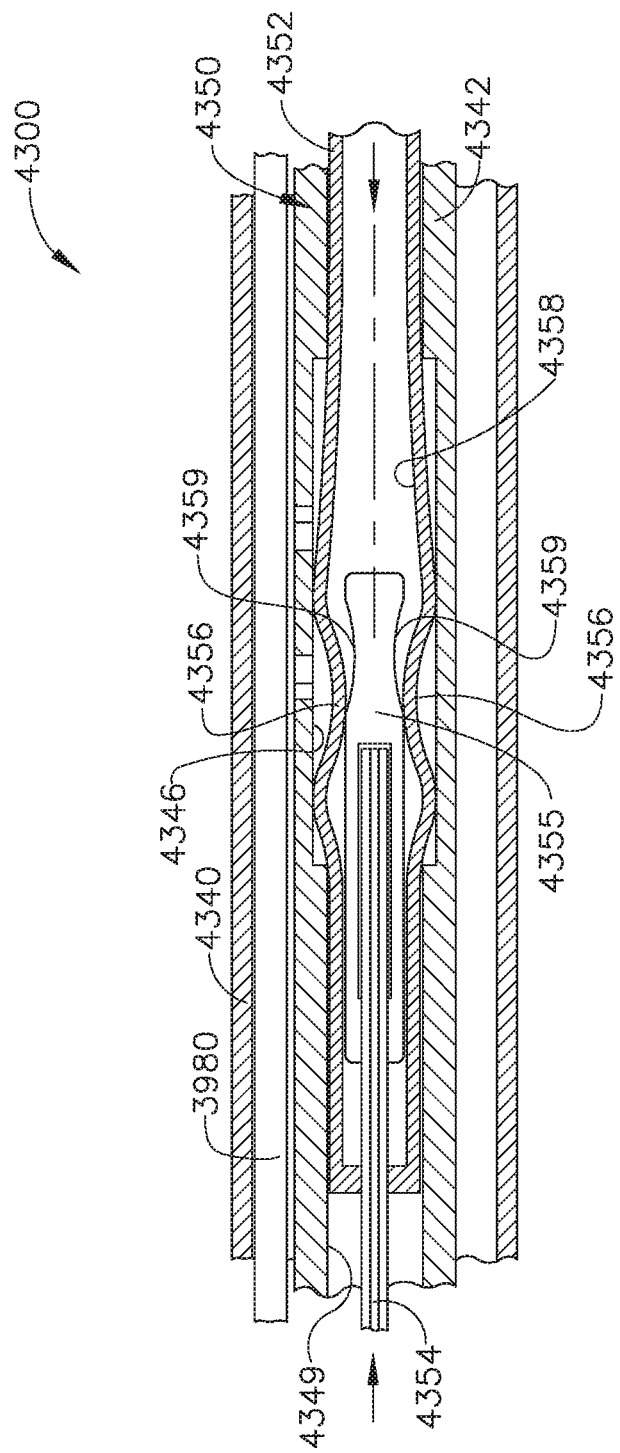
FIG. 73 is a partial cross-sectional view of the surgical instrument of FIG. 71 illustrating the fuse portion in a failed state prior to the firing assembly being advanced distally to perform a staple firing stroke, wherein the fuse portion is also acting as a firing force lockout preventing the staple firing stroke.

When the firing load transmitted through the firing assembly 4350 exceeds the force threshold, referring now to FIG. 73, the sidewalls of the second firing rod 4352 can flex outwardly such that the projections 4356 can disengage from the drive recesses 4359 defined in the connector 4355. At such point, the firing bar 4354 is operably disengaged from the second firing rod 4352 and the staple firing stroke has been interrupted. When the interface 4353 decouples at the initiation of the staple firing stroke, referring again to FIG. 73, the deflected sidewalls of the second firing rod 4352 can flex outwardly into the longitudinal aperture 4346 and engage the shaft frame 4342 to prevent the staple firing stroke of the firing assembly 4350. Stated another way, the deflected sidewalls of the second firing rod 4352 cannot enter the longitudinal aperture 4349 when the firing load exceeds the force threshold which prevents the second firing rod 4352 from being advanced distally.

When the firing load exceeds the force threshold during the staple firing stroke, however, the sidewalls of the second firing rod 4352 cannot deflect outwardly, or substantially outwardly, owing to their close proximity to the sidewalls of the longitudinal aperture 4349. As a result, a complete decoupling of the interface 4353 does not immediately occur if the force threshold is exceeded. Instead, referring to FIG. 74, the firing assembly 4350 can enter into a first failed state. In the first failed state of the firing assembly 4350, the projections 4356 of the second firing rod 4352 have decoupled from the drive recesses 4359 defined in the proximal connector 4355 of the firing bar 4354, however, the projections 4356 are still engaged with the proximal connector 4355. More specifically, the projections 4356 are compressed against the lateral sides of the proximal connector 4355 by the sidewalls of the longitudinal aperture 4349 such that a firing force, and/or a retraction force, can still be transmitted from the second firing rod 4352 to the firing bar 4354. In such instances, the staple firing stroke can be completed and/or the clinician can decide to retract the firing assembly 4350.

Further to the above, referring now to FIG. 75, the interface 4353 between the second firing rod 4352 and the firing bar 4354 can completely decouple and enter into a second failed state. In the second failed state, the projections 4356 are no longer engaged with the proximal connector 4355 of the firing bar 4354 and, as a result, the second firing rod 4352 can no longer deliver a firing motion and/or firing force to the firing bar 4354. Instead, the second firing rod 4352 will move relative to the firing bar 4354 as the second firing rod 4352 is moved distally. As illustrated in FIG. 71, the second firing rod 4352 comprises a longitudinal slot 4358 configured to accommodate relative movement between the second firing rod 4352 and the firing bar 4354. The longitudinal slot 4358 is long enough such that the firing bar 4354 does not contact the proximal end 4357 of the slot 4358.

In various instances, further to the above, the force threshold for the firing assembly 4350 to enter into its first failed state and the force threshold for the firing assembly 4350 to enter into is second failed state are the same. In such instances, the firing assembly 4350 can switch into its first failed state if a momentary pulse, or increase, in the firing force occurs and, yet, still operate in the first failed state. If, however, the increase in the firing force is not momentary, the firing assembly 4350 can then quickly enter into its second failed state. In at least one instance, the first and second force thresholds are 80 lbf, for example. In other instances, the force threshold for the firing assembly 4350 to enter into its first failed state and the force threshold for the firing assembly 4350 to enter into is second failed state are different. For instance, the first force threshold is 60 lbf and the second force threshold is 80 lbf, for example. Alternatively, the first force threshold is 80 lbf and the second force threshold is 60 lbf, for example. In either event, the firing assembly 4350 may be able to push through high firing force conditions and still be functional.

In either event, referring now to FIGS. 71 and 72, the firing assembly 4350 can be reset by retracting the second firing rod 4352. In at least one instance, the firing assembly 4350 can be reset into its first failed state and then re-operated. In other instances, the second firing rod 4352 is retracted until the projections 4356 resiliently re-engage the drive recesses 4359 defined in the proximal connector 4355 of the firing bar 4354 to completely reset the interface 4353 of the firing assembly 4350 before the firing assembly 4350 is re-operated. In either event, the retraction force applied to the second firing rod 4352 can be less than first force threshold and/or the second force threshold, for example.

Figure 77A:
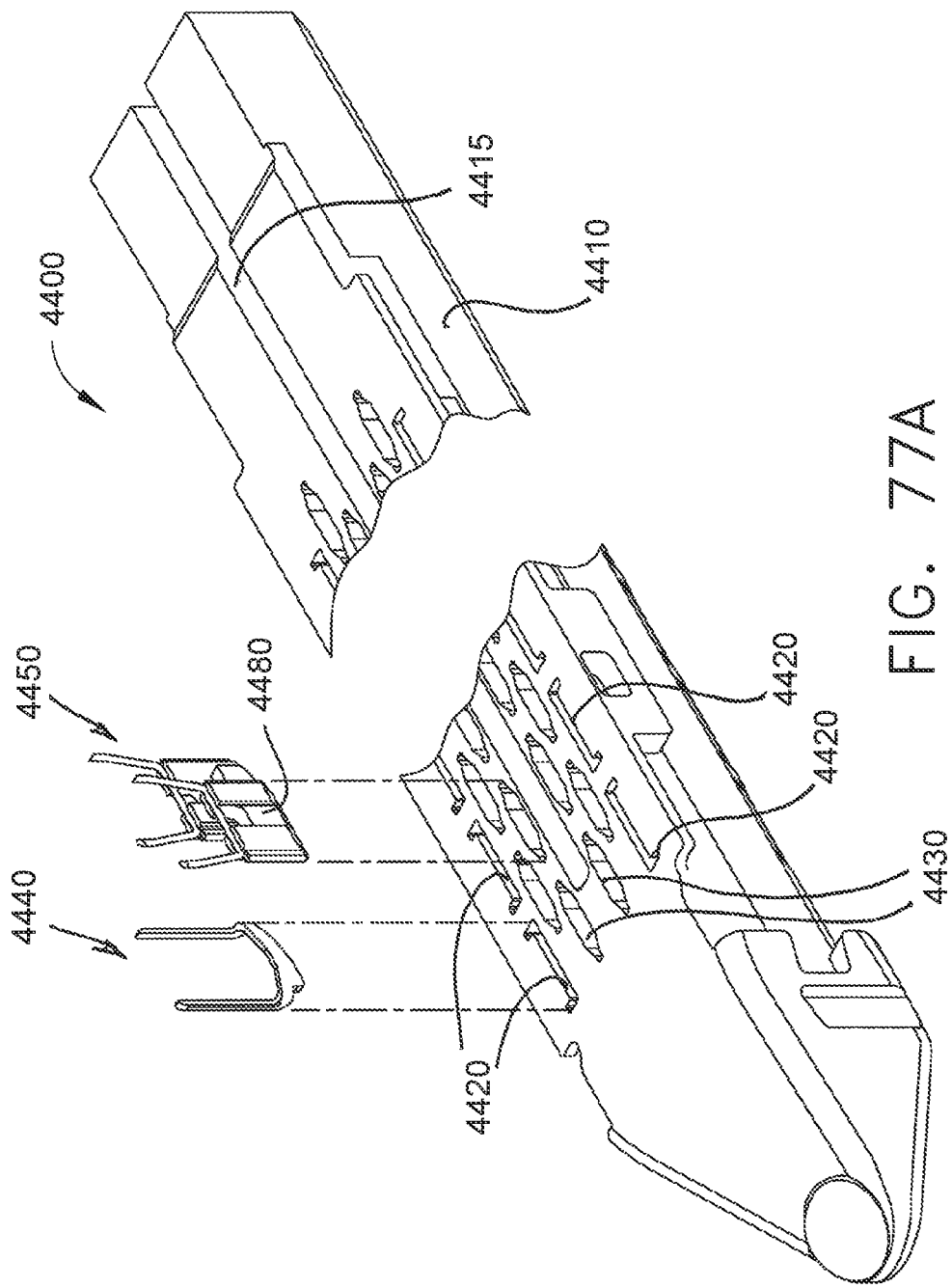
FIG. 77A is a perspective view of a staple cartridge in accordance with at least one embodiment.
Figure 77B:
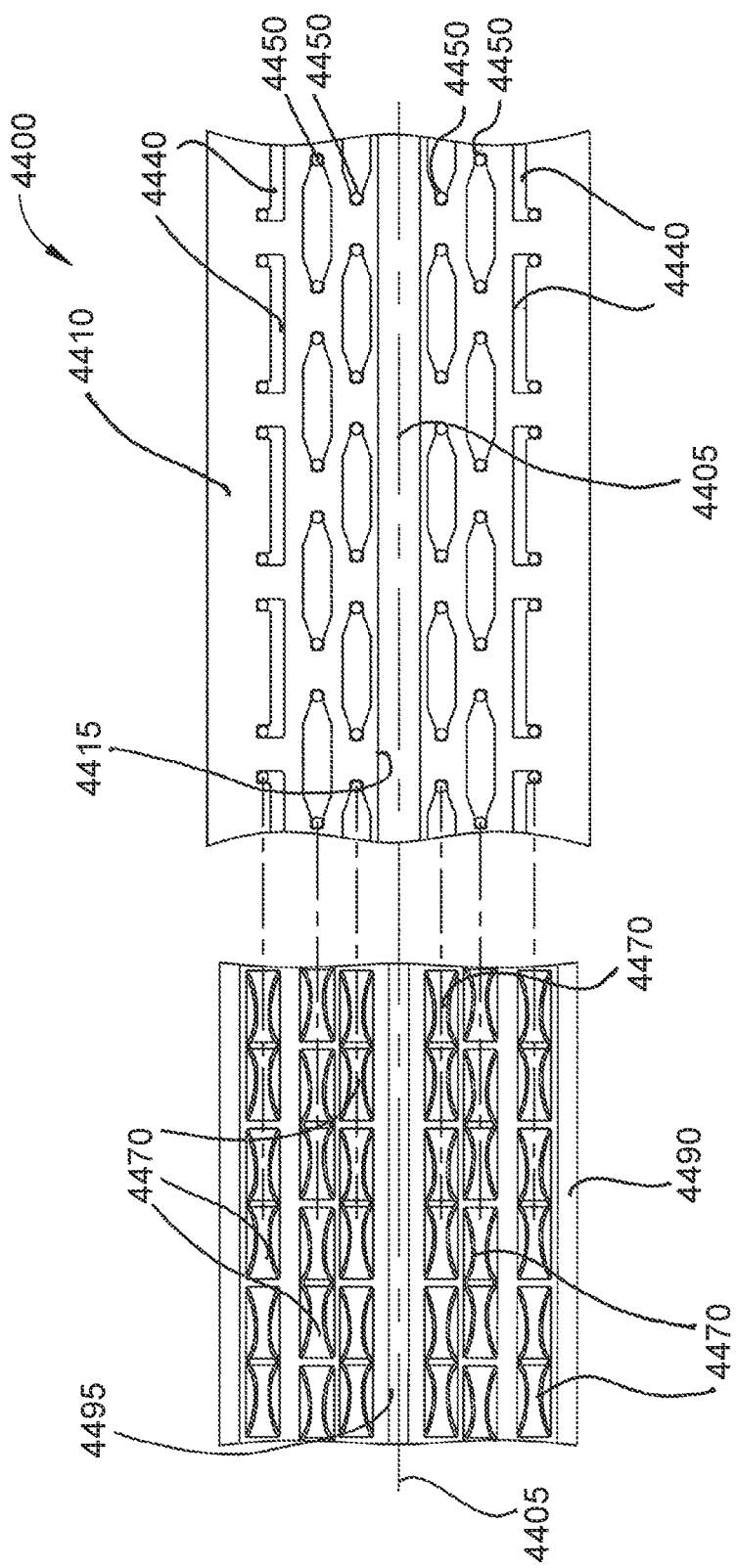
FIG. 77B is a partial plan view of the staple cartridge of FIG. 77A and an anvil for use therewith.

A staple cartridge 4400 is illustrated in FIGS. 77A and 77B. The staple cartridge 4400 is similar to the staple cartridges disclosed herein in many respects—most of which are not discussed herein for the sake of brevity. Moreover, the staple cartridge 4400 is usable with any of the surgical instruments disclosed herein. The staple cartridge 4400 comprises a cartridge body 4410 and a sled movable through the cartridge body 4410 by a firing member during a firing stroke. The cartridge body 4410 comprises a longitudinal slot 4415 defined therein which is configured to receive the firing member. The cartridge body 4410 further comprises longitudinal rows of staple cavities 4420 and longitudinal rows of staple cavities 4430. More specifically, the cartridge body 4410 comprises two inner rows of staple cavities 4420 positioned on each side of the longitudinal slot 4415 and an outer row of staple cavities 4430 positioned on each side of the rows of staple cavities 4420. That said, the staple cartridge 4400 can comprise any suitable number and arrangement of staple cavities 4420 and 4430. The longitudinal rows of staple cavities 4420 and 4430 are parallel, or at least substantially parallel, to one another; however, other embodiments are envisioned in which the longitudinal rows of staple cavities 4420 and 4430 are not parallel to one another.

The staple cartridge 4400 further comprises staples 4440 removably stored in the staple cavities 4420 and staples 4450 stored in the staple cavities 4430. The staples 4440 comprise stamped staples which have been stamped from one or more sheets of material. The staples 4450 comprise wire staples which have been bent into a substantially V-shaped configuration, for example. The V-shaped configuration is an unformed, or unfired, configuration. That said, the staples 4450 can have any suitable unfired configuration. In any event, the staple cartridge 4400 further comprises staple drivers 4480 configured to eject the staples 4450 from the staple cavities 4430. During the firing stroke, the sled is configured to engage the staple drivers 4480 and push the staples 4450 upwardly out of the staple cavities 4430. Concurrently, the sled directly engages the staples 4440 to eject the staples 4440 from the staple cavities 4420. Referring to FIG. 77B, the staples 4440 and 4450 contact an anvil 4490, or any other suitable anvil, positioned opposite the staple cartridge 4400 as the staples 4440 and 4450 are being ejected from the staple cartridge 4400. The anvil 4490 comprises forming pockets 4470 defined therein which are aligned with the legs of the staples 4440 and 4450 and are configured to deform the staples 4440 and 4450 during the firing stroke. In alternative embodiments, an anvil can comprise a first type of forming pocket aligned with each staple 4440 and a second, or different, type of forming pocket aligned with each staple 4450.

Further to the above, the anvil 4490 is configured to deform the staples 4440 to a first formed height and the staples 4450 to a second, or different, formed height. In at least one such instance, the first formed height of the staples 4440 is taller than the second formed height of the staples 4450. In alternative embodiments, the anvil 4490 is configured to deform the staples 4440 and the staples 4450 to the same formed height. In any event, the anvil 4490 further comprises a longitudinal slot 4495 defined therein which is configured to receive the firing member during the firing stroke. The longitudinal anvil slot 4495 is aligned, or centered, with the longitudinal cartridge slot 4415 along a longitudinal axis 4405.

Figure 77C:
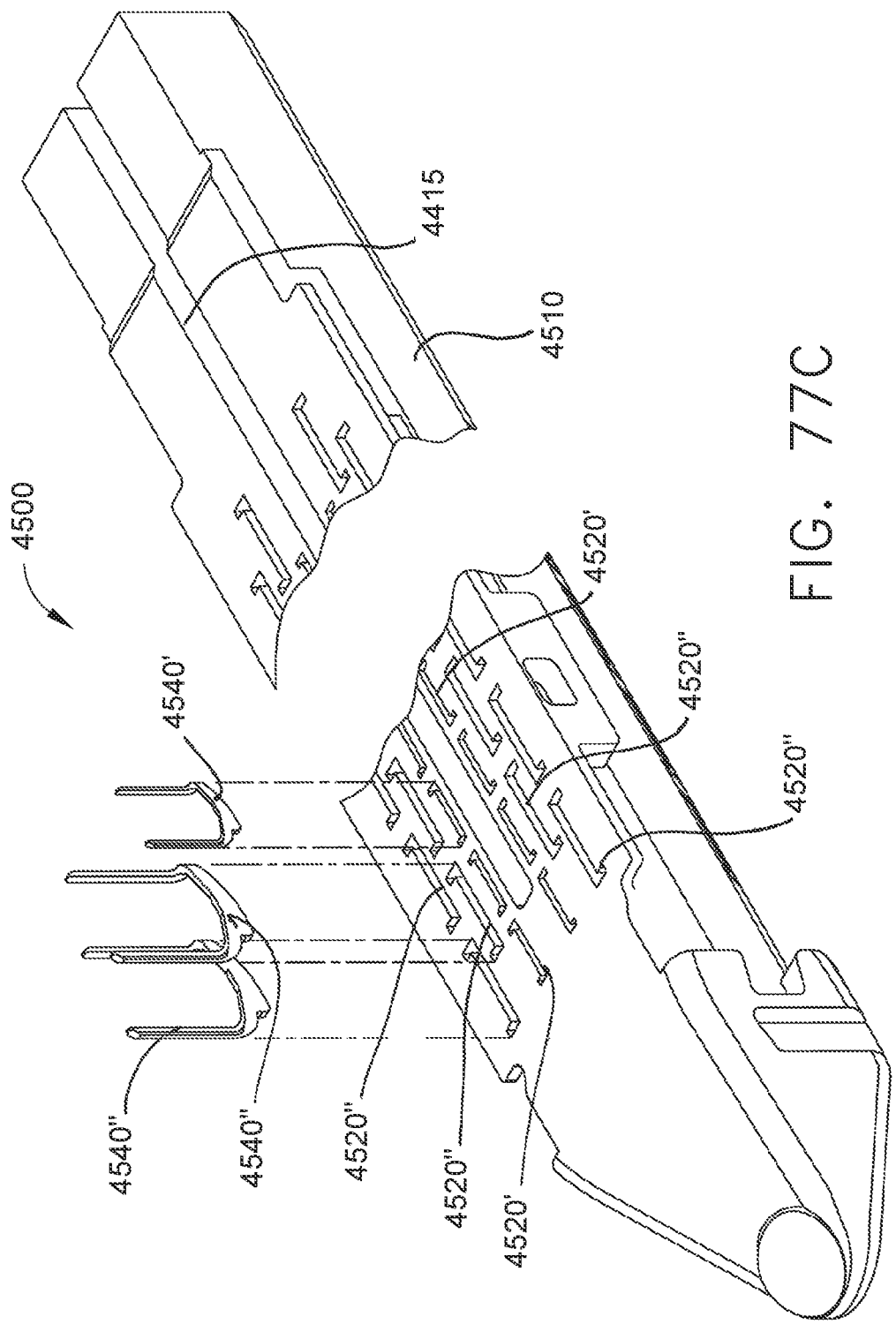
FIG. 77C is a perspective view of a staple cartridge in accordance with at least one embodiment.

A staple cartridge 4500 is illustrated in FIGS. 77C and 77D. The staple cartridge 4500 is similar to the staple cartridges disclosed herein in many respects—most of which are not discussed herein for the sake of brevity. Moreover, the staple cartridge 4500 is usable with any of the surgical instruments disclosed herein. The staple cartridge 4500 comprises a cartridge body 4510 and a sled movable through the cartridge body 4510 by a firing member during a firing stroke. The cartridge body 4510 comprises a longitudinal slot 4415 defined therein which is configured to receive the firing member. The cartridge body 4510 further comprises longitudinal rows of staple cavities 4520' and longitudinal rows of staple cavities 4520". More specifically, the cartridge body 4510 comprises an inner row of staple cavities 4520' positioned on each side of the longitudinal slot 4415 and two outer rows of staple cavities 4520" positioned on each side of the rows of staple cavities 4520'. That said, the staple cartridge 4500 can comprise any suitable number and arrangement of staple cavities 4520' and 4520". The longitudinal rows of staple cavities 4520' and 4520" are parallel, or at least substantially parallel, to one another; however, other embodiments are envisioned in which the longitudinal rows of staple cavities 4520' and 4520' are not parallel to one another.

The staple cartridge 4500 further comprises staples 4540' removably stored in the staple cavities 4520' and staples 4540" stored in the staple cavities 4520". The staples 4540' comprise stamped staples which have been stamped from one or more sheets of material. The staples 4540" also comprise stamped staples which have been stamped from one or more sheets of material. As illustrated in FIG. 77E, the staples 4540" are larger than the staples 4540'. More specifically, the staples 4540" are taller than the staples 4540'. In addition, the staples 4540" are wider than the staples 4540'. During the firing stroke, the sled directly engages the staples 4540' and 4540" to eject the staples 4540' from the staple cavities 4520' and the staples 4540" from the staple cavities 4520". Referring to FIG. 77D, the staples 4540' and 4540" contact an anvil 4590, or any other suitable anvil, positioned opposite the staple cartridge 4500 as the staples 4540' and 4540" are being ejected from the staple cartridge 4500. The anvil 4590 comprises forming pockets 4570' defined therein which are aligned with the legs of the staples 4540' and, in addition, forming pockets 4570" defined therein which are aligned with the legs of the staples 4540". The forming pockets 4570' and 4570" are configured to deform the staples 4540' and 4540", respectively, during the firing stroke.

Referring to FIGS. 77E and 77F, the anvil 4590 is configured to deform the staples 4540' to a first formed height and the staples 4540" to a second, or different, formed height. In at least one instance, the second formed height of the staples 4540" is taller than the first formed height of the staples 4540'. In use, the innermost row of staples 4540' in the staple cartridge 4500 are configured to apply a sufficiently-hemostatic seal in the incised tissue T, referring to FIG. 72F, and the outer row of larger staples 4540" are configured to provide a certain amount of flexibility in the staple line. In alternative embodiments, the staples 4540' and 4540" are deformed to the same formed height. In any event, the anvil 4590 further comprises a longitudinal slot 4595 defined therein which is configured to receive the firing member during the firing stroke. The longitudinal anvil slot 4595 is aligned, or centered, with the longitudinal cartridge slot 4415 along a longitudinal axis 4505.

Figure 78:
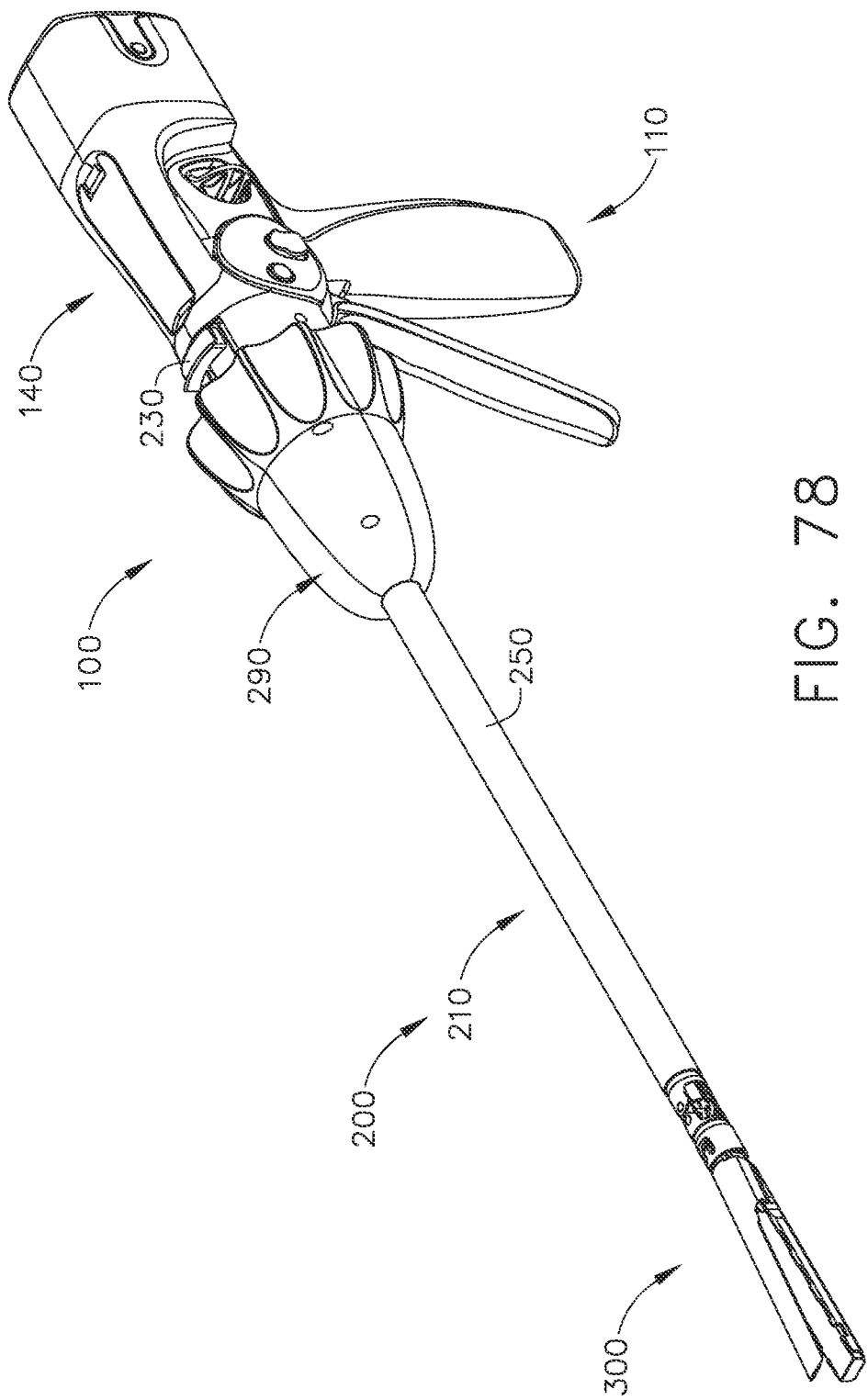
FIG. 78 is a perspective view of a surgical instrument including a handle and an interchangeable shaft assembly in accordance with at least one embodiment.

FIG. 78 illustrates an exemplary surgical instrument 100 comprising a handle 110 and an interchangeable shaft assembly 200 operably coupled thereto. The handle 110 comprises a housing 140 that is configured to be grasped, manipulated, and/or actuated by a clinician. The shaft assembly 200 comprises a shaft 210 and an end effector 300. The shaft 210 comprises a shaft frame (not shown in FIG. 78), and a hollow outer sleeve or closure tube 250 through which the shaft frame extends. The shaft assembly 200 further includes a nozzle assembly 290 configured to interface with the outer sleeve 250 and enable the clinician to selectively rotate the shaft 210 about a longitudinal axis. The shaft assembly 200 also includes a latch 230 which is a part of a lock system that releasably locks the shaft assembly 200 to the handle 110. In various circumstances, the latch 230 can close an electrical circuit in the handle 110, for example, when the latch 230 is engaged with the handle 110. The entire disclosure of U.S. patent application Ser. No. 13/803,086, entitled ARTICULATABLE SURGICAL INSTRUMENT COMPRISING AN ARTICULATION LOCK, which was filed on Mar. 14, 2013, is incorporated by reference herein. All of the embodiments disclosed herein are usable with the handle 110.

Figure 79:
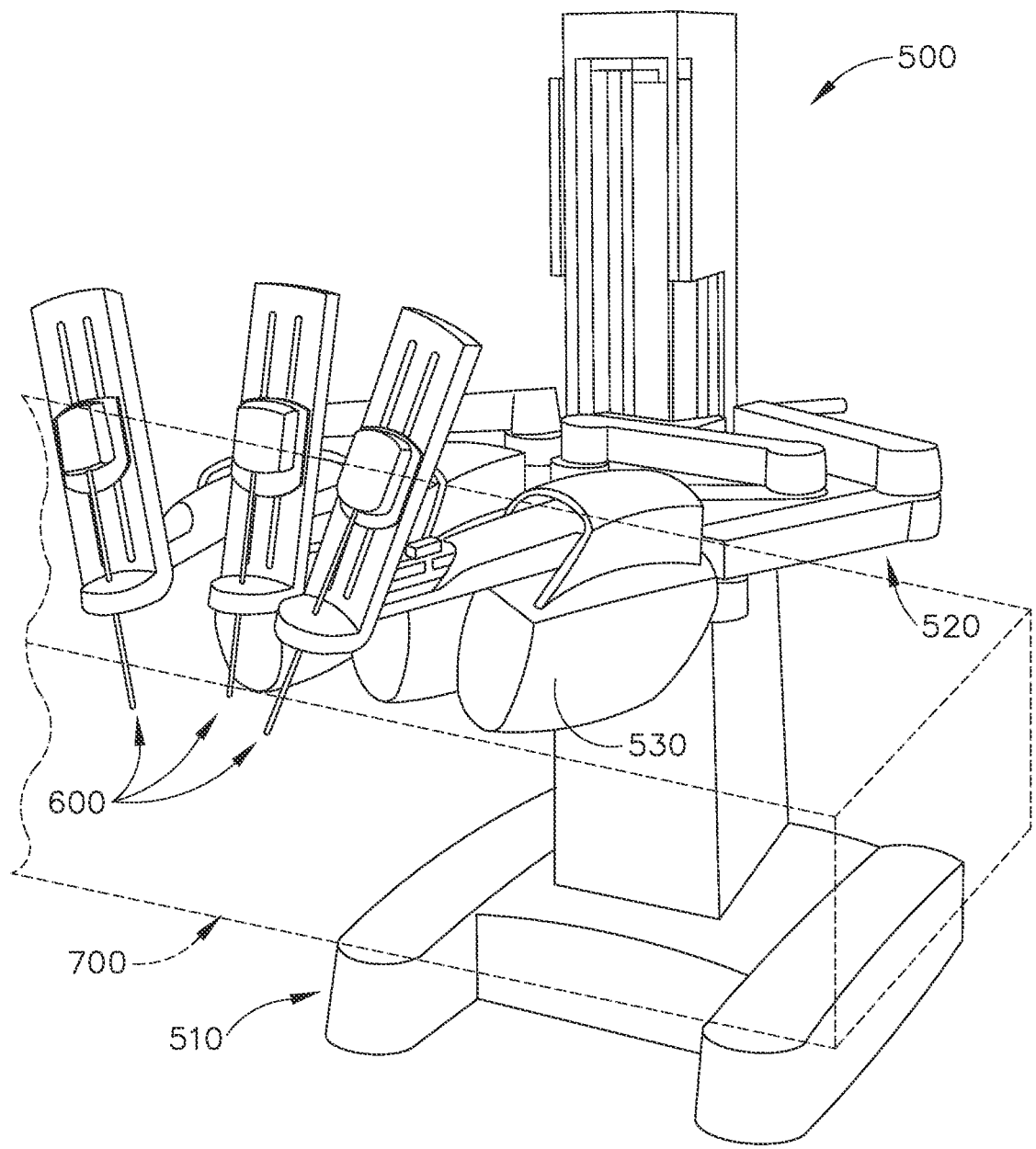
FIG. 79 is a perspective view of a robotic surgical system operably supporting a plurality of surgical tools in accordance with at least one embodiment.

FIG. 79 depicts an exemplary surgical robot 500 configured to actuate a plurality of surgical tools, generally designated as 600, for example. The surgical robot 500 may be used in connection with a master controller, not shown, configured to allow a surgeon to control and view a surgical procedure being performed by the surgical robot 500. In various forms, the surgical robot 500 includes a base 510 from which, in the illustrated embodiment, three surgical tools 600 are supported, for example. In various forms, the surgical tools 600 are each supported by a series of articulatable linkages, generally referred to as arms 520, and are operably coupled with one or more drive systems 530. These structures are illustrated with protective covers which obscure much of the movable components thereof. These protective covers may be optional, and may be limited in size or entirely eliminated in some embodiments to minimize the inertia that is encountered by servo mechanisms used to manipulate the arms 520. In various forms, the surgical robot 500 has wheels that allow the surgical robot 500 to be positioned adjacent an operating table by a single attendant. FIG. 79 further illustrates a work envelope 700 of the surgical robot 500. The work envelope 700 refers to the range of movement of the surgical tools 600 of the surgical robot 500. The shape and size of the work envelope 700 depicted in FIG. 79 is merely illustrative. Thus, a work envelope is not limited to the specific size and shape of the sample work envelope depicted in FIG. 79. The entire disclosure of U.S. Pat. No. 9,060,770, entitled ROBOTICALLY-DRIVEN SURGICAL INSTRUMENT WITH E-BEAM DRIVER, which issued on Jun. 23, 2015, is incorporated by reference herein. All of the embodiments disclosed herein are usable with the surgical robot 500.

EXAMPLES

Example 1

A surgical instrument comprising a first jaw, a second jaw, and a closure tube. The first jaw comprises a first proximal end and a first distal end. The second jaw comprises a second proximal end, a second distal end, a pivot pin about which the second jaw is rotatable relative to the first jaw between an open and a fully-closed position, and a cam surface. The closure tube is movable toward the first distal end of the first jaw during a closure stroke. The closure tube comprises a distal tube end configured to engage the cam surface and move the second distal end of the second jaw toward the first distal end of the first jaw during the closure stroke. The closure tube further comprises a wedge configured to engage the pivot pin and tilt the second distal end of the second jaw toward the first distal end during the closure stroke.

Example 2

The surgical instrument of Example 1, wherein a distal tissue gap is defined between the first distal end and the second distal end when the second jaw is in the fully-closed position, wherein a proximal tissue gap is defined between the first proximal end and the second proximal end when the second jaw is in the fully-closed position, and wherein the second jaw applies a larger clamping force to the tissue captured in the distal tissue gap than the proximal tissue gap.

Example 3

The surgical instrument of Examples 1 or 2, wherein the surgical instrument further comprises a staple cartridge including staples removably stored therein.

Example 4

The surgical instrument of Example 3, wherein the surgical instrument further comprises a firing member configured to eject the staples from the staple cartridge, wherein the firing member comprises a first cam configured to engage the first jaw and a second cam configured to engage the second jaw during a firing stroke, and wherein the first cam and the second cam are configured to co-operatively control a tissue gap between the first jaw and the second jaw.

Example 5

The surgical instrument of Example 4, wherein the second jaw further comprises a tissue compression surface, staple forming pockets defined in the tissue compression surface, and a second cam surface, wherein the second cam is configured to engage the second cam surface during the firing stroke to control the position, and wherein the tissue compression surface is not parallel to the second cam surface.

Example 6

The surgical instrument of Example 5, wherein a first distance is defined between the tissue compression surface and the second cam surface at the second proximal end of the second jaw, wherein a second distance is defined between the tissue compression surface and the second cam surface at the second distal end of the second jaw, and wherein the second distance is larger than the first distance.

Example 7

The surgical instrument of Examples 1, 2, 3, 4, 5, or 6, wherein the distal tube end is configured to engage the cam surface of the second jaw before the wedge engages the pivot pin during the closure stroke.

Example 8

The surgical instrument of Examples 1, 2, 3, 4, 5, 6, or 7, wherein the first jaw comprises a vertical slot, and wherein the pivot pin is slidably positioned in the vertical slot.

Example 9

The surgical instrument of Example 8, wherein the first jaw comprises a longitudinal slot, wherein the wedge is slidably positioned in the longitudinal slot, and wherein the longitudinal slot is in communication with the vertical slot.

Example 10

The surgical instrument of Examples 1, 2, 3, 4, 5, 6, 7, or 8, wherein the wedge does not move the second proximal end relative to the first proximal end.

Example 11

A surgical instrument comprising a first jaw, a second jaw, and a closure tube. The first jaw comprises a first proximal end and a first distal end. The second jaw comprises a second proximal end, a second distal end, a pivot pin about which the second jaw is rotatable relative to the first jaw between an open position and a fully-closed position, and a cam surface. The closure tube is movable toward the first distal end of the first jaw during a closure stroke. The closure tube comprises a distal tube end configured to engaged the cam surface and move the second distal end of the second jaw toward the first distal end of the first jaw during the closure stroke and a wedge configured to engage the pivot pin and push the second distal end of the second jaw toward the first distal end of the first jaw during the closure stroke to achieve the fully-closed position.

Example 12

The surgical instrument of Example 11, wherein the wedge does not move the second proximal end relative to the first proximal end.

Example 13

A surgical instrument comprising a first jaw, a second jaw, a closure tube, and a cutting member. The first jaw comprises a distal jaw end. The second jaw is movable relative to the first jaw between an open position and a closed position. The second jaw comprises a closure cam surface and an opening cam surface. The closure tube is movable toward the distal jaw end during a closure stroke. The closure tube comprises a distal tube end configured to engage the closure cam surface and move the second jaw into the closed position during the closure stroke. The cutting member is movable toward the distal jaw end during a cutting stroke and movable away from the distal jaw end during a retraction stroke. The cutting member comprises a proximal portion, a distal portion, and a biasing member positioned intermediate the proximal portion and the distal portion, wherein the biasing member is configured to bias the distal portion into engagement with the opening cam surface of the second jaw to at least partially open the second jaw after the retraction stroke.

Example 14

The surgical instrument of Example 13, wherein the closure tube is movable away from the distal jaw end during an opening stroke, and wherein the closure tube holds the second jaw in the closed position against the bias of the biasing member until the distal tube end is disengaged from the closure cam surface.

Example 15

The surgical instrument of Examples 13 or 14, wherein the surgical instrument further comprises a staple cartridge comprising staples removably stored therein, and wherein the cutting member is configured to eject the staples from the staple cartridge during the cutting stroke.

Example 16

The surgical instrument of Examples 13, 14, or 15, wherein the cutting member comprises a first cam configured to engage the first jaw and a second cam configured to engage the second jaw, and wherein the first jaw and the second jaw co-operatively control the position of the second jaw relative to the first jaw during the cutting stroke.

Example 17

A surgical instrument comprising a first jaw comprising a distal jaw end, a second jaw, and a cutting member. The second jaw is movable relative the first jaw to capture the tissue of a patient between the first jaw and the second jaw. The cutting member is movable toward the distal jaw end during a cutting stroke. The cutting member comprises a coupling portion comprising a first cam configured to engage the first jaw and a second cam configured to engage the second jaw during the cutting stroke and a bar comprising a plurality of layers attached to the coupling portion, wherein the bar comprises a cutting edge configured to cut the patient tissue during the cutting stroke.

Example 18

The surgical instrument of Example 17, wherein the surgical instrument further comprises a staple cartridge including staples removably stored therein, and wherein the cutting member is configured to eject the staples from the staple cartridge during the cutting stroke to staple the patient tissue.

Example 19

The surgical instrument of Examples 17 or 18, wherein the coupling portion further comprises a mounting recess, and wherein the bar comprises a distal bar end positioned in the mounting recess.

Example 20

The surgical instrument of Example 19, wherein the coupling portion further comprises a mounting projection within the mounting recess, and wherein the bar comprises a mounting aperture configured to closely receive the mounting projection.

Example 21

The surgical instrument of Examples 17, 18, 19, or 20, wherein the coupling portion further comprises a plurality of mounting projections, and wherein the bar comprises a plurality of mounting apertures configured to receive the mounting projections.

Example 22

The surgical instrument of Example 21, wherein the cutting member is movable along a longitudinal axis during the cutting stroke, and wherein the plurality of mounting projections comprises a first projection positioned along the longitudinal axis and a second projection positioned offset from the longitudinal axis.

Example 23

The surgical instrument of Examples 21 or 22, wherein the cutting member is movable along a longitudinal axis during the cutting stroke, and wherein the plurality of mounting projections comprises a first projection positioned on a first side of the longitudinal axis and a second projection positioned on a second side of the longitudinal axis.

Example 24

The surgical instrument of Examples 21, 22, or 23, wherein the plurality of mounting projections comprises a proximal projection and a distal projection, and wherein the distal projection is positioned distally with respect to the proximal projection.

Example 25

The surgical instrument of Examples 17, 18, 19, 20, 21, 22, 23, or 24, wherein the coupling portion comprises a shoulder, and wherein the bar comprises a hook engaged with the shoulder.

Example 26

The surgical instrument of Examples 17, 18, 19, 20, 21, 22, 23, 24, or 25, wherein the plurality of layers comprises a first layer and a second layer, and wherein the cutting edge is defined on the first layer and not defined on the second layer.

Example 27

The surgical instrument of Examples 17, 18, 19, 20, 21, 22, 23, 24, 25, or 26, wherein the plurality of layers comprises a first layer and a second layer, and wherein the cutting edge is defined on the first layer and the second layer.

Example 28

The surgical instrument of Examples 17, 18, 19, 20, 21, 22, 23, 24, 25, 26, or 27, wherein the plurality of layers comprises a first layer, a second layer, and an intermediate layer positioned intermediate the first layer and the second layer. The coupling portion comprises a first lateral recess, a second lateral recess, and a mounting tab. The first layer is mounted to the coupling portion in the first lateral recess, the second layer is mounted to the coupling portion in the second lateral recess, and the intermediate layer is attached to the mounting tab.

Example 29

A surgical stapler comprising a first jaw comprising a distal jaw end, a second jaw, a staple cartridge comprising a plurality of staples removably stored therein, and a firing member movable toward the distal jaw end during a firing stroke to eject the staples from the staple cartridge. The second jaw is movable relative to the first jaw to capture the tissue of a patient between the first jaw and the second jaw. The firing member comprises a coupling portion comprising a first cam configured to engage the first jaw and a second cam configured to engage the second jaw during the firing stroke and a bar attached to the coupling portion, wherein the bar comprises a cutting edge configured to cut the patient tissue during the firing stroke.

Example 30

A surgical instrument comprising a first jaw comprising a distal jaw end, a second jaw movable relative to the first jaw to capture the tissue of a patient between the first jaw and the second jaw, and a cutting member movable toward the distal jaw end during a cutting stroke. The cutting member comprises a coupling portion and a bar. The coupling portion comprises a first cam configured to engage the first jaw during the cutting stroke, a second cam configured to engage the second jaw during the cutting stroke, a first lateral recess, a second lateral recess, and a mounting tab. The bar comprises a first layer mounted to the coupling portion in the first lateral recess, a second layer mounted to the coupling portion in the second lateral recess, and an intermediate layer positioned intermediate the first layer and the second layer, wherein the intermediate layer is attached to the mounting tab.

Example 31

The surgical instrument of Example 30, wherein the surgical instrument further comprises a staple cartridge including staples removably stored therein, and wherein the cutting member is configured to eject the staples from the staple cartridge during the cutting stroke to staple the patient tissue.

Example 32

The surgical instrument of Examples 30 or 31, wherein the mounting tab extends distally with respect to the first lateral recess and the second lateral recess.

Example 33

The surgical instrument of Examples 30, 31, or 32, wherein the coupling portion comprises a cutting edge configured to cut the patient tissue.

Example 34

The surgical instrument of Examples 30, 31, 32, or 33, wherein the bar comprises a cutting edge configured to cut the patient tissue.

Example 35

A surgical instrument comprising a first jaw comprising a distal jaw end, a second jaw movable relative to the first jaw to capture the tissue of a patient between the first jaw and the second jaw, and a firing member movable toward the distal jaw end during a firing stroke. The firing member comprises a coupling portion comprising a lateral recess and a mounting tab and a bar comprising a first layer mounted to the coupling portion in the lateral recess and a second layer attached to the mounting tab.

Example 36

The surgical instrument of Example 35, wherein the surgical instrument further comprises a staple cartridge including staples removably stored therein, and wherein the firing member is configured to eject the staples from the staple cartridge during the firing stroke to staple the patient tissue.

Example 37

A surgical stapling instrument comprising a shaft, an end effector extending from the shaft, a firing assembly, a lock in the shaft, and a staple cartridge. The end effector comprises a first jaw comprises a distal jaw end and a second jaw movable relative to the first jaw between an open position and a closed position. The firing assembly is movable toward the distal jaw end during a firing stroke, and the firing assembly comprises a coupling portion configured to engage the first jaw and the second jaw during the firing stroke and a lockout bar comprising a distal lockout end, wherein the lockout bar is movable between a distal locked position and a proximal unlocked position. The lock in the shaft is engaged with the firing bar prior to the firing stroke when the lockout bar is in the distal locked position, and the lock is disengaged from the firing bar prior to the firing stroke when the lockout bar is in the proximal unlocked position. The staple cartridge is positionable in the first jaw and the staple cartridge comprises a cartridge body, a plurality of staples removably stored in the cartridge body, and a sled movable from a proximal unfired position and a distal fired position to eject the staples from the cartridge body during the firing stroke, wherein the sled is configured to push the lockout bar into the proximal unlocked position when the staple cartridge is loaded into the first jaw and the sled is in the proximal unfired position.

Example 38

The surgical stapling instrument of Example 37, wherein the coupling portion comprises an aperture, and wherein the distal lockout end extends through the aperture.

Example 39

The surgical stapling instrument of Examples 37 or 38, wherein the lockout bar is slidable within the firing bar.

Example 40

The surgical stapling instrument of Examples 37, 38, or 39, wherein the surgical stapling instrument further comprises a spring configured to bias the lockout bar into the distal locked position.

Example 41

The surgical stapling instrument of Examples 37, 38, 39, or 40, wherein the surgical stapling instrument further comprises a spring configured to bias said lock into engagement with the firing bar.

Example 42

The surgical stapling instrument of Example 41, wherein the lockout bar comprises a key configured to engage the lock and disengage the lock from the firing bar against the bias of the spring.

Example 43

The surgical stapling instrument of Examples 37, 38, 39, 40, 41, or 42, wherein the cartridge body comprises a detent configured to releasably hold the sled in the proximal unfired position when the sled engages the lockout bar.

Example 44

The surgical stapling instrument of Examples 37, 38, 39, 40, 41, 42, or 43, wherein the lockout bar travels with the firing bar during the firing stroke.

Example 45

The surgical stapling instrument of Example 44, wherein the firing bar is retractable after the firing stroke, and wherein the lockout bar travels with the firing bar when the firing bar is retracted.

Example 46

The surgical stapling instrument of Example 45, wherein the sled is not retracted with the firing bar and the lockout bar.

Example 47

The surgical stapling instrument of Example 46, wherein the lockout bar cannot be reset into its proximal unlocked position until the staple cartridge is removed from the first jaw and an unspent staple cartridge is positioned in the first jaw.

Example 48

A surgical stapling instrument comprising an end effector, a firing assembly, a lock, and a staple cartridge loadable into the end effector. The end effector comprises a first jaw comprising a distal jaw end and a second jaw movable relative to the first jaw between an open position and a closed position. The firing assembly is movable toward the distal jaw end during a firing stroke, and the firing assembly comprises a firing bar and a lockout bar, wherein the lockout bar is movable between a distal locked position and a proximal unlocked position relative to the firing bar. The lock is engaged with the firing bar prior to the firing stroke when the lockout bar is in the distal locked position, and the lock is disengaged from the firing bar prior to the firing stroke when the lockout bar is in the proximal unlocked position. The staple cartridge comprises a cartridge body, a plurality of staples removably stored in the cartridge body, and a sled movable from a proximal unfired position and a distal fired position to eject the staples from the cartridge body during the firing stroke, wherein the sled is configured to push the lockout bar into the proximal unlocked position when the staple cartridge is loaded into the end effector and the sled is in the proximal unfired position.

Example 49

A surgical stapling instrument comprising an end effector, a firing bar, a lock, and a staple cartridge loadable into the end effector. The end effector comprises a first jaw comprises a distal jaw end and a second jaw movable relative to the first jaw between an open position and a closed position. The firing bar is movable away from the distal jaw end between a distal unlocked position and a proximal unlocked position, and the firing bar is then movable toward the distal jaw end during a firing stroke. The lock is engaged with the firing bar when the firing bar is in the distal locked position to prevent the firing stroke, and the lock is disengaged from the firing bar when the firing bar is in the proximal unlocked position. The staple cartridge comprises a cartridge body, a plurality of staples removably stored in the cartridge body, and a sled movable from a proximal unfired position and a distal fired position to eject the staples from the cartridge body during the firing stroke, wherein the sled is configured to push the firing bar into the proximal unlocked position when the staple cartridge is loaded into the end effector and the sled is in the proximal unfired position.

Example 50

The surgical stapling instrument of Example 49, wherein the surgical stapling instrument further comprises a biasing member configured to bias the firing bar into the distal locked position.

Example 51

The surgical stapling instrument of Examples 49 or 50, wherein the surgical stapling instrument further comprises a biasing member configured to bias the lock into engagement with the firing bar.

Example 52

The surgical stapling instrument of Examples 49, 50, or 51, wherein the firing bar comprises a key configured to engage the lock and disengage the lock from the firing bar against the bias of the firing bar.

Example 53

The surgical stapling instrument of Examples 49, 50, 51, or 52, wherein the firing bar is retractable after the firing stroke, and wherein the sled is not retracted with the firing bar.

Example 54

The surgical stapling instrument of Example 53, wherein the firing bar cannot be reset into the proximal unlocked position until the staple cartridge is removed from the end effector and an unspent staple cartridge is loaded in the end effector.

Example 55

The surgical stapling instrument of Examples 49, 50, 51, 52, 53, or 54, wherein the cartridge body comprises a detent configured to releasably hold the sled in the proximal unfired position when the sled engages the firing bar to move the firing bar into the proximal unlocked position and permit the firing bar to move the sled through the firing stroke.

Example 56

The surgical stapling instrument of Examples 49, 50, 51, 52, 53, 54, or 55, wherein the surgical stapling instrument further comprises a shaft, wherein the end effector extends from the shaft, and wherein the lock is positioned in the shaft.

Example 57

A surgical stapling assembly comprising a cartridge jaw, a firing member, and a staple cartridge removably positionable in the cartridge jaw. The cartridge jaw comprises a proximal end, a distal end positioned opposite the proximal end, a bottom wall, a lateral side wall extending from the bottom wall, and a plurality of jaw windows defined in the lateral side wall. The firing member is movable toward the distal end during a firing stroke. The staple cartridge comprises a cartridge body, a plurality of cartridge windows defined in the cartridge body, wherein the cartridge windows are aligned with the jaw windows when the staple cartridge is positioned in the cartridge jaw, staples removably stored in the cartridge body, and a sled movable toward the distal end during the firing stroke to eject the staples from the cartridge body, wherein the progress of the sled during the firing stroke is observable through the cartridge windows and the jaw windows.

Example 58

The surgical stapling assembly of Example 57, wherein the sled comprises a datum observable through the cartridge windows and the jaw windows.

Example 59

The surgical stapling assembly of Example 58, wherein the sled is moved along a longitudinal axis during the firing stroke, and wherein the datum comprises a vertical line orthogonal to the longitudinal axis.

Example 60

The surgical stapling assembly of Examples 57, 58, or 59, wherein the plurality of jaw windows comprises a proximal jaw window and a distal jaw window, wherein the plurality of cartridge windows comprises a proximal cartridge window aligned with the proximal jaw window and a distal cartridge window aligned with the distal jaw window, wherein the sled is movable between a proximal unfired position and a distal fired position during the firing stroke, wherein the sled is observable through the proximal jaw window and the proximal cartridge window when the sled is in the proximal unfired position, and wherein the sled is observable through the distal jaw window and the distal cartridge window when the sled is in the distal fired position.

Example 61

The surgical stapling assembly of Example 60, wherein the plurality of jaw windows comprises an intermediate jaw window positioned intermediate the proximal jaw window and the distal jaw window, wherein the plurality of cartridge windows comprises an intermediate cartridge window positioned intermediate the proximal cartridge window and the distal cartridge window aligned with the intermediate jaw window, and wherein the sled is observable through the intermediate jaw window and the intermediate cartridge window during the firing stroke.

Example 62

The surgical stapling assembly of Examples 57, 58, 59, 60, or 61, wherein the jaw windows are positioned along a longitudinal jaw window axis, wherein the cartridge windows are positioned along a longitudinal cartridge window axis, and wherein the longitudinal jaw window axis is aligned with the longitudinal cartridge window axis when the staple cartridge is positioned in the cartridge jaw.

Example 63

The surgical stapling assembly of Examples 57, 58, 59, 60, 61, or 62, wherein the bottom wall comprises a longitudinal slot configured to receive the firing member during the firing stroke.

Example 64

The surgical stapling assembly of Example 63, wherein the sled is movable between a proximal unfired position and a distal fired position during the firing stroke, wherein the longitudinal slot comprises a proximal bottom window, and wherein the sled is observable through the proximal bottom window when the sled is in the proximal unfired position.

Example 65

The surgical stapling assembly of Examples 63 or 64, wherein the sled is movable between a proximal unfired position and a distal fired position during the firing stroke, wherein the longitudinal slot comprises a distal bottom window, and wherein the sled is observable through the distal bottom window when the sled is in the distal fired position.

Example 66

The surgical stapling assembly of Examples 63, 64, or 65, wherein the longitudinal slot comprises a plurality of bottom windows defined in the bottom wall, and wherein the progress of the sled during the firing stroke is observable through the bottom windows.

Example 67

The surgical stapling assembly of Example 66, wherein the longitudinal slot defines a longitudinal axis, and wherein the bottom windows are offset with respect to the longitudinal axis.

Example 68

The surgical stapling assembly of Example 67, wherein bottom windows are staggered on opposite sides of the longitudinal axis in an alternating manner.

Example 69

A surgical stapling assembly including a firing member, the surgical stapling assembly comprising a cartridge jaw and a staple cartridge positioned in the cartridge jaw. The cartridge jaw comprises a proximal end, a distal end positioned opposite the proximal end, a bottom portion, a lateral side portion extending from the bottom portion, and a plurality of jaw windows defined in the lateral side portion. The staple cartridge comprises a cartridge body comprising staple cavities, a plurality of cartridge windows defined in the cartridge body, wherein the cartridge windows are aligned with the jaw windows, staples removably stored in the staple cavities, and a sled movable toward the distal end by the firing member to eject the staples from the cartridge body, wherein the progress of the sled toward the distal end is observable through the cartridge windows and the jaw windows.

Example 70

A surgical stapling assembly comprising a cartridge jaw, a firing member, and a staple cartridge. The cartridge jaw comprises a proximal end, a distal end positioned opposite the proximal end, a bottom wall, lateral side walls extending from the bottom wall, and a longitudinal slot defined in the bottom wall, wherein the longitudinal slot comprises a plurality of jaw windows defined in the bottom wall. The firing member is movable toward the distal end through the longitudinal slot during a firing stroke. The staple cartridge is positionable between the lateral side walls in the cartridge jaw. The staple cartridge comprises a cartridge body, staples removably stored in the cartridge body, and a sled movable toward the distal end during the firing stroke to eject the staples from the cartridge body, wherein the progress of the sled during the firing stroke is observable through the jaw windows.

Example 71

The surgical stapling assembly of Example 70, wherein the sled is movable between a proximal unfired position and a distal fired position during the firing stroke, wherein the jaw windows comprise a proximal bottom window, and wherein the sled is observable through the proximal bottom window when the sled is in the proximal unfired position.

Example 72

The surgical stapling assembly of Examples 70 or 71, wherein the sled is movable between a proximal unfired position and a distal fired position during the firing stroke, wherein the jaw windows comprise a distal bottom window, and wherein the sled is observable through the distal bottom window when the sled is in the distal fired position.

Example 73

The surgical stapling assembly of Examples 70, 71, or 72, wherein the longitudinal slot defines a longitudinal axis, and wherein the jaw windows are offset with respect to the longitudinal axis.

Example 74

A surgical stapling assembly comprising a cartridge jaw and a staple cartridge. The cartridge jaw comprises a proximal end, a distal end positioned opposite said proximal end, a bottom wall, lateral side walls extending from the bottom wall, and a longitudinal slot defined in the bottom wall, wherein the longitudinal slot comprises a plurality of jaw windows defined in the bottom wall. The staple cartridge is positioned between the lateral side walls in the cartridge jaw. The staple cartridge comprises a cartridge body, staples removably stored in the cartridge body, and a sled movable toward the distal end during a firing stroke to eject the staples from the cartridge body, wherein the progress of the sled during the firing stroke is observable through the jaw windows.

Example 75

A surgical instrument comprising a shaft, an end effector comprising a staple cartridge, and a firing assembly. The staple cartridge comprises a cartridge body, staples removably stored in the cartridge body, and a sled configured to eject the staples from the cartridge body during a staple firing stroke. The firing assembly is configured to apply a pushing force to the sled during the staple firing stroke. The firing assembly comprises a first portion, a second portion, wherein the second portion is displaceable relative to the first portion, and a pushing force lockout system at least partially positioned intermediate the first portion and the second portion, wherein the pushing force lockout system is configured to engage the shaft and stop the staple firing stroke if the pushing force exceeds a threshold.

Example 76

The surgical instrument of Example 75, wherein the surgical instrument further comprises a biasing member positioned intermediate the first portion and the second portion, and wherein the biasing member is configured to apply a biasing force to the second portion which opposes the pushing force.

Example 77

The surgical instrument of Example 76, wherein the threshold comprises a pre-selected difference between the pushing force and the biasing force.

Example 78

The surgical instrument of Example 77, wherein the pushing force lockout system comprises a lock mounted to the shaft, a spring, and an actuator rotatably mounted to the firing assembly. The lock is displaceable between an unlocked position and a locked position, and the lock is configured to prevent the firing assembly from performing the staple firing stroke when the lock is in the locked position. The spring is configured to bias the lock into the locked position. The second portion is configured to rotate the actuator toward the lock and displace the lock into the unlocked position when the threshold is exceeded.

Example 79

The surgical instrument of Example 78, wherein the actuator is rotatably mounted to the first portion and the lock is configured to engage the second portion.

Example 80

The surgical instrument of Examples 78 or 79, wherein the surgical instrument further comprises an actuator spring configured to bias the actuator out of engagement with the lock, wherein the second portion overcomes the actuator spring when the second portion is moved toward the first portion.

Example 81

The surgical instrument of Examples 75, 76, 77, 78, 79, or 80, wherein the staple cartridge comprises a replaceable staple cartridge.

Example 82

The surgical instrument of Examples 75, 76, 77, 78, 79, 80, or 81, wherein the staple cartridge comprises a spent cartridge lockout configured to block the firing assembly from performing the staple firing stroke if the staple cartridge has been at least partially spent.

Example 83

The surgical instrument of Examples 75, 76, 77, 78, 79, 80, 81, or 82, wherein the surgical instrument further comprises an electric motor configured to drive the firing assembly through the staple firing stroke.

Example 84

A surgical instrument comprising a frame, an end effector comprising a staple cartridge, a firing assembly, and a firing force lockout system. The staple cartridge comprises a cartridge body, staples removably stored in the cartridge body, and a sled configured to eject the staples from the cartridge body during a firing stroke. The firing assembly is configured to apply a firing force to the sled during the firing stroke. The firing assembly comprises a first portion and a second portion, wherein the second portion is displaceable relative to the first portion. The firing force lockout system is configured to engage the frame and prevent the staple firing stroke if the firing force exceeds a threshold.

Example 85

The surgical instrument of Example 84, wherein the surgical instrument further comprises a biasing member positioned intermediate the first portion and the second portion, wherein the biasing member is configured to apply a biasing force to the second portion which opposes the firing force.

Example 86

The surgical instrument of Example 85, wherein the threshold comprises a pre-selected difference between the firing force and the biasing force.

Example 87

The surgical instrument of Example 86, wherein the firing force lockout system comprises a lock mounted to the frame, a spring, and an actuator rotatably mounted to the firing assembly. The lock is displaceable between an unlocked position and a locked position, and the lock is configured to prevent the firing assembly from performing the staple firing stroke when the lock is in the locked position. The spring is configured to bias the lock into the locked position. The second portion is configured to rotate the actuator toward the lock and displace the lock into the unlocked position when the threshold is exceeded.

Example 88

The surgical instrument of Example 87, wherein the actuator is rotatably mounted to the first portion and the lock is configured to engage the second portion.

Example 89

The surgical instrument of Examples 87 or 88, wherein the surgical instrument further comprises an actuator spring configured to bias the actuator out of engagement with the lock, and wherein the second portion overcomes the actuator spring when the second portion is moved toward the first portion.

Example 90

The surgical instrument of Examples 84, 85, 86, 87, 88, or 89, wherein the staple cartridge comprises a replaceable staple cartridge.

Example 91

The surgical instrument of Examples 84, 85, 86, 87, 88, 89, or 90, wherein the staple cartridge comprises a spent cartridge lockout configured to block the firing assembly from performing the staple firing stroke if the staple cartridge has been at least partially spent.

Example 92

A surgical instrument comprising an end effector comprising a staple cartridge, wherein the staple cartridge comprises a cartridge body, staples removably stored in the cartridge body, and a sled configured to eject the staples from the cartridge body during a firing stroke. The surgical instrument further comprises a firing assembly configured to apply a firing force to the sled during the firing stroke and means for stopping the staple firing stroke if the firing force exceeds a threshold.

Example 93

The surgical instrument of Example 92, wherein the means is resettable.

Example 94

A surgical instrument comprising a firing assembly movable through a firing stroke, an end effector comprising a staple cartridge, and a firing force lockout system. The staple cartridge comprises a cartridge body, staples removably stored in the cartridge body, a sled movable between a proximal unfired position and a distal fired position to eject the staples from the cartridge body during the firing stroke, and a spent cartridge lockout configured to block the firing assembly from performing the firing strong if the sled is not in the proximal unfired position at the initiation of the firing stroke. The firing force lockout system is configured to assist in preventing the firing assembly from performing the firing stroke when the firing assembly is blocked by the spent cartridge lockout.

Example 95

The surgical instrument of Example 94, wherein the firing assembly comprises a first portion and a second portion, and wherein the firing force lockout system is at least partially positioned intermediate the first portion and the second portion of the firing assembly.

Example 96

The surgical instrument of Example 95, wherein the second portion is movable relative to the first portion, and wherein the second portion is configured to deploy the firing force lockout system into a locked configuration when the second portion is moved toward the first portion.

Example 97

The surgical instrument of Example 96, wherein the surgical instrument further comprises a biasing member positioned intermediate the first portion and the second portion, and wherein the biasing member is configured to push the second portion away from the first portion.

Example 98

The surgical instrument of Example 97, wherein the firing force lockout system is biased into an unlocked configuration.

Example 99

The surgical instrument of Examples 94, 95, 96, 97, or 98, wherein the surgical instrument further comprises a frame, wherein the firing force lockout system is mounted to the firing assembly, and wherein the firing force lockout system is configured to engage the frame in response to the spent cartridge lockout blocking the firing assembly.

Example 100

The surgical instrument of Example 99, wherein the surgical instrument further comprises a longitudinal shaft, and wherein the frame is positioned within the longitudinal shaft.

Example 101

The surgical instrument of Examples 94, 95, 96, 97, 98, 99, or 100, wherein the surgical instrument further comprises an electric motor configured to move the firing assembly through the firing stroke.

Example 102

The surgical instrument of Example 101, wherein the firing force lockout system is deployable into a locked configuration when the firing assembly is blocked by the spent cartridge lockout, and wherein the electric motor is operable to retract the firing assembly to reset the firing force lockout system into an unlocked configuration.

Example 103

The surgical instrument of Examples 94, 95, 96, 97, 98, 99, 100, 101, or 102, wherein the cartridge body comprises a longitudinal slot configured to receive the firing assembly, and wherein the spent cartridge lockout comprises a metal clip. The metal clip comprises a mounting portion mounted to the cartridge body and a lock portion deflectable between a locked configuration and an unlocked configuration, wherein the lock portion extends into the longitudinal slot to block the firing assembly when the lock portion is in the locked configuration.

Example 104

The surgical instrument of Example 103, wherein the sled is configured to hold the lock portion in the unlocked configuration when the sled is in the proximal unfired position.

Example 105

The surgical instrument of Example 104, wherein the lock portion is biased toward the locked configuration, and wherein the sled is configured to release the lock portion when the sled is advanced distally during the firing stroke.

Example 106

The surgical instrument of Example 94, 95, 96, 97, 98, 99, 100, 101, 102, 103, 104, or 105, wherein the staple cartridge is a replaceable staple cartridge.

Example 107

The surgical instrument of Example 94, 95, 96, 97, 98, 99, 100, 101, 102, 103, 104, or 105, wherein the staple cartridge is not a replaceable staple cartridge.

Example 108

A surgical instrument comprising a firing assembly movable through a firing stroke, an end effector comprising a staple cartridge, and a firing lockout. The staple cartridge comprises a cartridge body, staple removably stored in the cartridge body, a sled movable between a proximal unfired position and a distal fired position to eject the staples from the cartridge body during the firing stroke, and a cartridge lockout configured to block the firing assembly if the sled is not in the proximal unfired position at the initiation of the firing stroke. The firing lockout is configured to prevent the firing assembly from performing the firing stroke when the firing assembly is blocked by the cartridge lockout.

Example 109

A surgical instrument comprising a shaft, a firing assembly movable through an actuation stroke, an end effector, and a firing lockout in the shaft. The end effector comprises a first jaw, a second jaw movable relative to the first jaw, wherein the firing assembly comprises a first cam configured to engage the first jaw and a second cam configured to engage the second jaw to control the position of the second jaw relative to the first jaw during the actuation stroke, and a staple cartridge. The staple cartridge comprises a cartridge body, staples removably stored in the cartridge body, a sled movable between a proximal unfired position and a distal fired position to eject the staples from the cartridge body, and a cartridge lockout configured to block the firing assembly if the sled is not in the proximal unfired position at the beginning of the actuation stroke. The firing lockout is configured to block the firing assembly if the firing assembly is blocked by the cartridge lockout.

Example 110

A surgical instrument comprising an end effector and a firing assembly configured to transmit a firing load to the end effector during a firing stroke. The firing assembly comprises a first portion, a second portion, and a fuse portion, wherein the fuse portion is configured to transmit the firing load from the first portion to the second portion when the fuse portion is intact, wherein the fuse portion is configured to fail when the firing load exceeds a threshold, and wherein the first portion cannot transmit the firing load to the second portion once the fuse portion has failed.

Example 111

The surgical instrument of Example 110, wherein the fuse portion is resettable.

Example 112

The surgical instrument of Example 111, wherein the end effector comprises a distal end, wherein the firing assembly is advanced toward the distal end during the firing stroke, and wherein the firing assembly is advanced away from the distal end to reset the fuse portion.

Example 113

The surgical instrument of Examples 110, 111, or 112, wherein the first portion comprises a flexible first rod, wherein the second portion comprises a second rod, and wherein the flexible first rod is configured to bend and disengage from the second rod when the firing load exceeds the threshold.

Example 114

The surgical instrument of Example 113, wherein the flexible rod resiliently bends out of engagement with the second rod when the firing load exceeds the threshold, and wherein the flexible first rod is configured to snap back into engagement with the second rod when the flexible first rod is realigned with the second rod.

Example 115

The surgical instrument of Examples 113 or 114, wherein the firing assembly further comprises a collar, wherein the second rod is slidably positioned in the collar, wherein the flexible first rod is not positioned in the collar when the firing stroke is initiated, wherein the flexible first rod enters into the collar during the firing stroke, and wherein the collar prevents the flexible first rod from disengaging from the second rod.

Example 116

The surgical instrument of Example 113, 114, or 115, wherein the surgical instrument further comprises a frame, wherein the flexible first rod is configured to engage the frame and block the firing assembly from performing the firing stroke when the flexible first rod disengages from the second rod.

Example 117

The surgical instrument of Examples 113, 114, 115, or 116, wherein the surgical instrument further comprises a biasing member configured to bias the flexible first rod into engagement with the second rod.

Example 118

The surgical instrument of Examples 110, 111, 112, 113, 114, 115, 116, or 117, wherein the fuse portion comprises a first barb defined on the first portion and a second barb defined on the second portion engaged with the first barb, and wherein the first barb disengages from the second barb when the firing force exceeds the threshold.

Example 119

The surgical instrument of Examples 110, 111, 112, 113, 114, 115, 116, 117, or 118, wherein fuse portion comprises a first foot defined on the first portion and a second foot defined on the second portion engaged with the first foot, and wherein the first foot slips relative to the second foot when the firing force exceeds the threshold.

Example 120

The surgical instrument of Example 119, wherein the surgical instrument further comprises a frame, wherein said first portion comprises a biasing member engaged with said frame, and wherein said biasing member is configured to bias said first foot into engagement with said second foot.

Example 121

The surgical instrument of Examples 110, 111, 112, 113, 114, 115, 116, 117, 118, 119, or 120, wherein the second portion comprises a plurality of layers, wherein the fuse portion comprises a proximal portion of the layers which splays outwardly when the firing force exceeds the threshold.

Example 122

The surgical instrument of Example 121, wherein the surgical instrument further comprises a frame, wherein the splayed layers are configured to engage the frame and block the firing assembly from performing the firing stroke when the firing load exceeds the threshold.

Example 123

The surgical instrument of Examples 121 or 122, wherein the layers resiliently splay outwardly when the firing load exceeds the threshold, and wherein the layers are configured to flex inwardly to reset the fuse portion when the firing assembly is retracted.

Example 124

The surgical instrument of Examples 110, 111, 112, 113, 114, 115, 116, 117, 118, 119, 120, 121, or 122, wherein the fuse portion is not resettable.

Example 125

The surgical instrument of Example 124, wherein the fuse portion comprises a wall defined in the first portion, and wherein the wall is configured to break away from the first portion when the firing load exceeds the threshold.

Example 126

The surgical instrument of Examples 124 or 125, wherein the fuse portion comprises a series of collapsible walls arranged along a longitudinal axis in the first portion, and wherein the collapsible walls are configured to fail sequentially when the firing force exceeds the threshold.

Example 127

The surgical instrument of Examples 110, 111, 112, 113, 114, 115, 116, 117, 118, 119, 120, 121, 122, 123, 124, 125, or 126, wherein the end effector comprises a staple cartridge.

Example 128

A surgical instrument comprising an end effector comprising a staple cartridge and a firing assembly. The staple cartridge comprises a cartridge body, staples removably stored in the cartridge body, and a sled configured to eject the staples from the cartridge body. The firing assembly is configured to apply a firing load to the sled during a staple firing stroke. The firing assembly comprises a first portion, a second portion, and a fuse configured to transmit the firing load from the first portion to the second portion when the fuse is intact, wherein the fuse is configured to fail when the firing load exceeds a threshold, and wherein the firing assembly cannot transmit the firing stroke to the sled once the fuse has failed.

Example 129

A surgical instrument comprising an end effector comprising a staple cartridge and a firing assembly. The staple cartridge comprises a cartridge body, staples removably stored in the cartridge body, and a sled configured to eject the staples from the cartridge body. The firing assembly is configured to apply a firing load to the sled during a staple firing stroke. The firing assembly comprises a fuse configured to transmit the firing load to the sled when the fuse is intact, wherein the fuse is configured to fail when the firing load exceeds a threshold, and wherein the firing assembly cannot transmit the firing load to the sled once the fuse has failed.

Example 130

A surgical instrument comprising an end effector comprising a staple cartridge and a firing assembly comprising a fuse. The staple cartridge comprises a cartridge body, staples removably stored in the cartridge body, and a sled configured to eject the staples from the cartridge body. The fuse comprises an intact state, wherein the firing assembly is configured to transmit a firing load to the sled during a firing stroke when the fuse is in the intact state, a first failed state, wherein the firing assembly is configured to transmit a load to the sled when the fuse is in the first failed state, and a second failed state, wherein the firing assembly cannot transmit a load to the sled when the fuse is in the second failed state.

Example 131

The surgical instrument of Example 130, wherein the fuse is resettable from the first failed state to the intact state.

Example 132

The surgical instrument of Example 131, wherein the end effector comprises a distal end, and wherein the firing assembly is retractable away from the distal end to reset the fuse into the intact state.

Example 133

The surgical instrument of Examples 130, 131, or 132, wherein the fuse is resettable from the second failed state to the first failed state.

Example 134

The surgical instrument of Example 133, wherein the end effector comprises a distal end, and wherein the firing assembly is retractable away from the distal end to reset said fuse into said intact state.

Example 135

The surgical instrument of Example 130, wherein the fuse is not resettable from the first failed state to the intact state.

Example 136

The surgical instrument of Example 130, wherein the fuse is not resettable from the second failed state to the first failed state.

Example 137

The surgical instrument of Examples 130, 131, 132, 133, 134, 135, or 136, wherein the firing assembly can be used to finish the firing stroke in the first failed state of the fuse.

Example 138

The surgical instrument of Examples 130, 131, 132, 133, 134, 135, or 136, wherein the firing assembly cannot be used to finish the firing stroke in the first failed state of the fuse.

Example 139

The surgical instrument of Examples 130, 131, 132, 133, 134, 135, 136, 137, or 138, wherein the fuse is configured to stop the firing stroke in the second failed state.

Example 140

The surgical instrument of Example 139, wherein the surgical instrument further comprises a frame, wherein the fuse is configured to engage the frame to stop the firing stroke in the second failed state.

Example 141

The surgical instrument of Examples 130, 131, 132, 133, 134, 135, 136, 137, 138, 139, or 140, wherein the firing assembly further comprises a first portion and a second portion, and wherein the fuse is positioned intermediate the first portion and the second portion.

Example 142

The surgical instrument of Example 141, wherein the second portion partially collapses relative to the first portion when the fuse is in the first failed state.

Example 143

The surgical instrument of Example 141, wherein the second portion completely collapses relative to the first portion when the fuse is in the second failed state.

Example 144

The surgical instrument of Examples 130, 131, 132, 133, 134, 135, 136, 137, 138, 139, 140, 141, 142, or 143, wherein the firing load is greater than the load.

Example 145

The surgical instrument of Examples 130, 131, 132, 133, 134, 135, 136, 137, 138, 139, 140, 141, 142, or 143, wherein the firing load is equal to the load.

Example 146

The surgical instrument of Examples 130, 131, 132, 133, 134, 135, 136, 137, 138, 139, 140, 141, 142, 143, 144, or 145, wherein the fuse comprises a biasing portion configured to bias the fuse into the intact state.

Example 147

The surgical instrument of Examples 130, 131, 132, 133, 134, 135, 136, 137, 138, 139, 140, 141, 142, 143, 144, 145, or 146, wherein the biasing portion is configured to bias the fuse into the first failed state once the fuse has left the intact state.

Example 148

A surgical instrument comprising an electric motor, an end effector comprising a staple cartridge, and a firing assembly comprising a fuse. The staple cartridge comprises a cartridge body, staples removably stored in the cartridge body, and a sled configured to eject the staples from the cartridge body. The fuse comprises an intact state, wherein the fuse is configured to transmit a firing load from the electric motor to the sled during a firing stroke when the fuse is in the intact state, a slipped state, wherein the fuse is configured to transmit a load from the electric motor to the sled when the fuse is in the slipped state, and a failed state, wherein the fuse cannot transmit a load to the sled when the fuse is in the second failed state.

Example 149

A surgical instrument comprising an end effector comprising a staple cartridge, wherein the staple cartridge comprises a cartridge body including a distal end, staples removably stored in the cartridge body, and a sled configured to eject the staples from the cartridge body. The surgical instrument further comprises a firing assembly configured to apply a firing force to and advance the sled toward the distal end during a firing stroke and means for limiting the functionality of the firing assembly in a plurality of operating states if the firing force exceeds a threshold.

Example 150

A method for operating a surgical instrument comprising a firing assembly including a fuse, wherein the method comprises the steps of advancing the firing assembly to perform a staple firing stroke and apply a firing load to a staple cartridge assembly, stopping the firing assembly if the fuse in the firing assembly fails from an excessive firing load, and retracting the firing assembly to reset the fuse.

Example 151

The method of Example 150, wherein the method further comprises the step of completing the staple firing stroke after the retracting step.

Example 152

The method of Examples 150 or 151, wherein the method further comprises the step of retracting the firing assembly to an unfired position instead of completing the staple firing stroke.

Example 153

The method of Examples 150, 151, or 152, wherein the surgical instrument comprises an end effector, wherein the end effector comprises a missing staple cartridge lockout, and wherein the firing load becomes an excessive firing load when the firing assembly abuts the missing staple cartridge lockout

Example 154

The method of Examples 150, 151, 152, or 153, wherein the surgical instrument comprises an end effector, wherein the end effector comprises a spent staple cartridge lockout, and wherein the firing load becomes an excessive firing load when the firing assembly abuts the spent staple cartridge lockout.

Example 155

The method of Examples 150, 151, 152, 153, or 154, wherein the surgical instrument comprises a lockout configured to perform the stopping step.

Example 156

The method of Examples 150, 151, 152, 153, 154, or 155, wherein the method further comprises the steps of replacing the staple cartridge assembly with an unspent staple cartridge assembly and completing the staple firing stroke after the stopping step.

Example 157

A method for operating a surgical instrument comprising a firing assembly including a fuse, wherein the method comprises the steps of advancing the firing assembly within a staple cartridge assembly to perform a staple firing stroke and apply a firing load to the staple cartridge assembly, completing the staple firing stroke if the fuse in the firing assembly enters into a first failed state, and stopping the staple firing stroke if the fuse in the firing assembly enters into a second failed state after entering into the first failed state.

Example 158

The method of Example 157, wherein the method further comprises the step of resetting the fuse after the stopping step.

Example 159

The method of Example 158, wherein the resetting step comprises the step of retracting the firing assembly.

Example 160

The method of Examples 157, 158, or 159, wherein the completing step comprises the steps of retracting the firing assembly and then advancing the firing assembly.

Example 161

The method of Examples 157, 158, 159, or 160, wherein the fuse enters into the first failed state when the firing load exceeds a first force threshold, and wherein the fuse enters into the second failed state when the firing load exceeds a second force threshold.

Example 162

The method of Example 161, wherein the first force threshold is different than the second force threshold.

Example 163

The method of Examples 161 or 162, wherein the second force threshold is higher than the first force threshold.

Example 164

The method of Examples 157, 158, 159, 160, 161, 162, or 163, wherein the surgical instrument comprises a lockout configured to perform the stopping step.

Example 165

The method of Examples 157, 158, 159, 160, 161, 162, 163, or 164, wherein the method further comprises the steps of replacing the staple cartridge assembly with an unspent staple cartridge assembly and completing the staple firing stroke after the stopping step.

Example 166

The method of Examples 157, 158, 159, 160, 161, 162, 163, 164, or 165, wherein the method further comprises the step of resetting the fuse from the second failed state to the first failed state after the stopping step.

Example 167

The method of Examples 157, 158, 159, 160, 161, 162, 163, 164, 165, or 166, wherein the method further comprises the step of resetting the fuse from second failed state to an unfailed state after the stopping step.

Example 168

A method for operating a surgical instrument comprising a firing assembly including a fuse, wherein the method comprises the steps of advancing the firing assembly to perform a staple firing stroke and apply a firing load to a staple cartridge assembly, stopping the firing assembly if the fuse in the firing assembly changes state, and resetting the fuse to an unfailed state.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapling instrument, comprising:
    a shaft;
    an end effector extending from said shaft, said end effector comprising:
        a first jaw comprising a distal jaw end; and
        a second jaw movable relative to said first jaw between an open position and a closed position;
    a firing assembly movable toward said distal jaw end during a firing stroke, wherein said firing assembly comprises:
        a coupling portion configured to engage said first jaw and said second jaw during said firing stroke;
        a firing bar configured to push said coupling portion; and
        a lockout bar comprising a distal lockout end, wherein said lockout bar is translatable between a distal locked position and a proximal unlocked position;
    a lock in said shaft, wherein said lock is engaged with said firing bar prior to said firing stroke when said lockout bar is in said distal locked position, and wherein said lock is disengaged from said firing bar prior to said firing stroke when said lockout bar is in said proximal unlocked position; and
    a staple cartridge positionable in said first jaw, wherein said staple cartridge comprises:
        a cartridge body;
        a plurality of staples removably stored in said cartridge body; and a sled movable between a proximal unfired position and a distal fired position to eject said staples from said cartridge body during said firing stroke, wherein said sled is configured to push said lockout bar into said proximal unlocked position when said staple cartridge is loaded into said first jaw and said sled is in said proximal unfired position.

2. The surgical stapling instrument of claim 1, further comprising a spring configured to bias said lockout bar into said distal locked position.

3. The surgical stapling instrument of claim 1, further comprising a spring configured to bias said lock into engagement with said firing bar.

4. The surgical stapling instrument of claim 3, wherein said lockout bar comprises a key configured to engage said lock and disengage said lock from said firing bar against said bias of said spring.

5. The surgical stapling instrument of claim 1, wherein said cartridge body comprises a detent configured to releasably hold said sled in said proximal unfired position when said sled engages said lockout bar.

6. A surgical stapling instrument, comprising:
a shaft;
an end effector extending from said shaft, said end effector comprising:
　a first jaw comprising a distal jaw end; and
　a second jaw movable relative to said first jaw between an open position and a closed position;
a firing assembly movable toward said distal jaw end during a firing stroke, wherein said firing assembly comprises:
　a coupling portion configured to engage said first jaw and said second jaw during said firing stroke;
　a firing bar configured to push said coupling portion; and
　a lockout bar comprising a distal lockout end, wherein said lockout bar is movable between a distal locked position and a proximal unlocked position;
a lock in said shaft, wherein said lock is engaged with said firing bar prior to said firing stroke when said lockout bar is in said distal locked position, and wherein said lock is disengaged from said firing bar prior to said firing stroke when said lockout bar is in said proximal unlocked position; and
a staple cartridge positionable in said first jaw, wherein said staple cartridge comprises:
　a cartridge body;
　a plurality of staples removably stored in said cartridge body; and
　a sled movable between a proximal unfired position and a distal fired position to eject said staples from said cartridge body during said firing stroke, wherein said sled is configured to push said lockout bar into said proximal unlocked position when said staple cartridge is loaded into said first jaw and said sled is in said proximal unfired position;
wherein said coupling portion comprises an aperture, and wherein said distal lockout end extends through said aperture.

7. A surgical stapling instrument, comprising:
a shaft;
an end effector extending from said shaft, said end effector comprising:
　a first jaw comprising a distal jaw end; and
　a second jaw movable relative to said first jaw between an open position and a closed position;
a firing assembly movable toward said distal jaw end during a firing stroke, wherein said firing assembly comprises:
　a coupling portion configured to engage said first jaw and said second jaw during said firing stroke;
　a firing bar configured to push said coupling portion; and
　a lockout bar comprising a distal lockout end, wherein said lockout bar is movable between a distal locked position and a proximal unlocked position;
a lock in said shaft, wherein said lock is engaged with said firing bar prior to said firing stroke when said lockout bar is in said distal locked position, and wherein said lock is disengaged from said firing bar prior to said firing stroke when said lockout bar is in said proximal unlocked position; and
a staple cartridge positionable in said first jaw, wherein said staple cartridge comprises:
　a cartridge body;
　a plurality of staples removably stored in said cartridge body; and
　a sled movable between a proximal unfired position and a distal fired position to eject said staples from said cartridge body during said firing stroke, wherein said sled is configured to push said lockout bar into said proximal unlocked position when said staple cartridge is loaded into said first jaw and said sled is in said proximal unfired position;
wherein said lockout bar is slidable within said firing bar.

8. A surgical stapling instrument, comprising:
a shaft;
an end effector extending from said shaft, said end effector comprising:
　a first jaw comprising a distal jaw end; and
　a second jaw movable relative to said first jaw between an open position and a closed position;
a firing assembly movable toward said distal jaw end during a firing stroke, wherein said firing assembly comprises:
　a coupling portion configured to engage said first jaw and said second jaw during said firing stroke;
　a firing bar configured to push said coupling portion; and
　a lockout bar comprising a distal lockout end, wherein said lockout bar is movable between a distal locked position and a proximal unlocked position;
a lock in said shaft, wherein said lock is engaged with said firing bar prior to said firing stroke when said lockout bar is in said distal locked position, and wherein said lock is disengaged from said firing bar prior to said firing stroke when said lockout bar is in said proximal unlocked position; and
a staple cartridge positionable in said first jaw, wherein said staple cartridge comprises:
　a cartridge body;
　a plurality of staples removably stored in said cartridge body; and
　a sled movable between a proximal unfired position and a distal fired position to eject said staples from said cartridge body during said firing stroke, wherein said sled is configured to push said lockout bar into said proximal unlocked position when said staple cartridge is loaded into said first jaw and said sled is in said proximal unfired position;
wherein said lockout bar travels with said firing bar during said firing stroke.

9. The surgical stapling instrument of claim 8, wherein said firing bar is retractable after said firing stroke, and wherein said lockout bar travels with said firing bar when said firing bar is retracted.

10. The surgical stapling instrument of claim 9, wherein said sled is not retracted with said firing bar and said lockout bar.

11. The surgical stapling instrument of claim 10, wherein said lockout bar cannot be reset into its proximal unlocked position until said staple cartridge is removed from said first jaw and an unspent staple cartridge is positioned in said first jaw.

12. A surgical stapling instrument, comprising:
an end effector, comprising:
a first jaw comprising a distal jaw end; and
a second jaw movable relative to said first jaw between an open position and a closed position;
a firing assembly movable toward said distal jaw end during a firing stroke, wherein said firing assembly comprises:
a firing bar; and
a lockout bar, wherein said lockout bar is translatable between a distal locked position and a proximal unlocked position relative to said firing bar;
a lock, wherein said lock is engaged with said firing bar prior to said firing stroke when said lockout bar is in said distal locked position, and wherein said lock is disengaged from said firing bar prior to said firing stroke when said lockout bar is in said proximal unlocked position; and
a staple cartridge loadable into said end effector, wherein said staple cartridge comprises:
a cartridge body;
a plurality of staples removably stored in said cartridge body; and
a sled movable between a proximal unfired position and a distal fired position to eject said staples from said cartridge body during said firing stroke, wherein said sled is configured to push said lockout bar into said proximal unlocked position when said staple cartridge is loaded into said end effector and said sled is in said proximal unfired position.

13. A surgical stapling instrument, comprising:
an end effector, comprising:
a first jaw comprising a distal jaw end; and
a second jaw movable relative to said first jaw between an open position and a closed position;
a firing bar translatable away from said distal jaw end between a distal unlocked position and a proximal unlocked position, wherein said firing bar is then movable toward said distal jaw end during a firing stroke;
a lock, wherein said lock is engaged with said firing bar when said firing bar is in said distal locked position to prevent said firing stroke, and wherein said lock is disengaged from said firing bar when said firing bar is in said proximal unlocked position; and
a staple cartridge loadable into said end effector, wherein said staple cartridge comprises:
a cartridge body;
a plurality of staples removably stored in said cartridge body; and
a sled movable between a proximal unfired position and a distal fired position to eject said staples from said cartridge body during said firing stroke, wherein said sled is configured to push said firing bar into said proximal unlocked position when said staple cartridge is loaded into said end effector and said sled is in said proximal unfired position.

14. The surgical stapling instrument of claim 13, further comprising a biasing member configured to bias said firing bar into said distal locked position.

15. The surgical stapling instrument of claim 13, further comprising a biasing member configured to bias said lock into engagement with said firing bar.

16. The surgical stapling instrument of claim 13, wherein said firing bar is retractable after said firing stroke, and wherein said sled is not retracted with said firing bar.

17. The surgical stapling instrument of claim 13, wherein said cartridge body comprises a detent configured to:
releasably hold said sled in said proximal unfired position when said sled engages said firing bar to move said firing bar into said proximal unlocked position; and
permit said firing bar to move said sled through said firing stroke.

18. The surgical stapling instrument of claim 13, further comprising a shaft, wherein said end effector extends from said shaft, and wherein said lock is positioned in said shaft.

19. A surgical stapling instrument, comprising:
an end effector, comprising:
a first jaw comprising a distal jaw end; and
a second jaw movable relative to said first jaw between an open position and a closed position;
a firing bar movable away from said distal jaw end between a distal unlocked position and a proximal unlocked position, wherein said firing bar is then movable toward said distal jaw end during a firing stroke;
a lock, wherein said lock is engaged with said firing bar when said firing bar is in said distal locked position to prevent said firing stroke, and wherein said lock is disengaged from said firing bar when said firing bar is in said proximal unlocked position; and
a staple cartridge loadable into said end effector, wherein said staple cartridge comprises:
a cartridge body;
a plurality of staples removably stored in said cartridge body; and
a sled movable between a proximal unfired position and a distal fired position to eject said staples from said cartridge body during said firing stroke, wherein said sled is configured to push said firing bar into said proximal unlocked position when said staple cartridge is loaded into said end effector and said sled is in said proximal unfired position;
wherein said firing bar comprises a key configured to engage said lock and disengage said lock from said firing bar against a bias of said firing bar.

* * * * *